United States Patent [19]
Paoletti et al.

[11] Patent Number: 5,843,456
[45] Date of Patent: *Dec. 1, 1998

[54] ALVAC POXVIRUS-RABIES COMPOSITIONS AND COMBINATION COMPOSITIONS AND USES

[75] Inventors: Enzo Paoletti, Delmar, N.Y.; Joanne Maki, Colbert, Ga.

[73] Assignee: Virogenetics Corporation, Troy, N.Y.

[ * ] Notice: The term of this patent shall not extend beyond the expiration date of Pat. Nos. 5,759,841, 5,756,103 and 5,756,102.

[21] Appl. No.: 486,969

[22] Filed: Jun. 7, 1995

Related U.S. Application Data

[63] Continuation-in-part of Ser. No. 105,483, Aug. 13, 1993, Pat. No. 5,494,807, which is a continuation of Ser. No. 847,951, Mar. 6, 1992, abandoned, which is a continuation-in-part of Ser. No. 713,967, Jun. 11, 1991, abandoned, which is a continuation-in-part of Ser. No. 666,056, Mar. 7, 1991, abandoned, which is a continuation of Ser. No. 36,217, Mar. 24, 1993, Pat. No. 5,364,773.

[51] Int. Cl.$^6$ ............... A61K 39/275; A61K 39/295; A61K 39/205
[52] U.S. Cl. ............... 424/199.1; 424/204.1; 424/201.1; 424/202.1; 424/205.1; 424/218.1; 424/224.1; 435/320.1; 435/69.3; 435/172.3; 435/235.1; 435/252.3; 530/350; 530/826; 514/2
[58] Field of Search ............... 424/199.1, 201.1, 424/204.1, 205.1, 202.1, 218.1, 224.1; 435/320.1, 64.3, 172.3, 235.1, 252.3; 530/350, 826; 514/2

[56] References Cited

U.S. PATENT DOCUMENTS 5,494,807  2/1996  Paoletti et al. ............... 435/69.3

OTHER PUBLICATIONS

Benmansour A, 1985, Annales del'Instistu Pasteur–virologie, vol. 136 E, No. 2, pp. 167–173. (Abstract only).

Wiktor, T. et al, 1984, PNAS, vol. 81, pp. 7194–7198.

Taylor, J. et al, 1991, Vaccine, vol. 9, pp. 190–193.

Tartaglia, J. et al, 1992, Virology, vol. 188, pp. 217–232.

Cooper, P. et al., 1991, Obiettivie Documenti Veterinari, vol. 12 (10), pp. 25–30. (Abstract is enclosed).

*Primary Examiner*—Mary E. Mosher
*Assistant Examiner*—Ali R. Salimi
*Attorney, Agent, or Firm*—Frommer Lawrence & Haug LLP; William S. Frommer; Thomas J. Kowalski

[57] ABSTRACT

Attenuated recombinant viruses containing DNA encoding a rabies virus antigen in a "cocktail" or combination or multivalent compositions well as methods for making and using the compositions, expression products therefrom, and antibodies generated, are disclosed and claimed. The recombinant viruses can be NYVAC or ALVAC recombinant viruses. The compositions and products therefrom and antibodies generated have several preventive, therapeutic and diagnostic uses.

35 Claims, 13 Drawing Sheets

```
   1 TGAATGTTAA ATGTTATACT TTGGATGAAG CTATAAATAT GCATTGGAAA AATAATCCAT
  61 TTAAAGAAAG GATTCAAATA CTACAAAACC TAAGCGATAA TATGTTAACT AAGCTTATTC
 121 TTAACGACGC TTTAAATATA CACAAATAAA CATAATTTTT GTATAACCTA ACAAATAACT
 181 AAAACATAAA AATAATAAAA GGAAATGTAA TATCGTAATT ATTTTACTCA GGAATGGGGT
 241 TAAATATTTA TATCACGTGT ATATCTATAC TGTTATCGTA TACTCTTTAC AATTACTATT
 301 ACGAATATGC AAGAGATAAT AAGATTACGT ATTTAAGAGA ATCTTGTCAT GATAATTGGG
 361 TACGACATAG TGATAAATGC TATTTCGCAT CGTTACATAA AGTCAGTTGG AAAGATGGAT
 421 TTGACAGATG TAACTTAATA GGTGCAAAAA TGTTAAATAA CAGCATTCTA TCGGAAGATA
 481 GGATACCAGT TATATTATAC AAAAATCACT GGTTGGATAA AACAGATTCT GCAATATTCG
 541 TAAAAGATGA AGATTACTGC GAATTTGTAA ACTATGACAA TAAAAGCCA TTTATCTCAA
 601 CGACATCGTG TAATTCTTCC ATGTTTTATG TATGTGTTTC AGATATTATG AGATTACTAT
 661 AAACTTTTTG TATACTTATA TTCCGTAAAC TATATTAATC ATGAAGAAAA TGAAAAAGTA
 721 TAGAAGCTGT TCACGAGCGG TTGTTGAAAA CAACAAAATT ATACATTCAA GATGGCTTAC
 781 ATATACGTCT GTGAGGCTAT CATGGATAAT GACAATGCAT CTCTAAATAG GTTTTTGGAC
 841 AATGGATTCG ACCCTAACAC GGAATATGGT ACTCTACAAT CTCCTCTTGA AATGGCTGTA
 901 ATGTTCAAGA ATACCGAGGC TATAAAAATC TTGATGAGGT ATGGAGCTAA ACCTGTAGTT
 961 ACTGAATGCA CAACTTCTTG TCTGCATGAT GCGGTGTTGA GAGACGACTA CAAAATAGTG
1021 AAAGATCTGT TGAAGAATAA CTATGTAAAC AATGTTCTTT ACAGCGGAGG CTTTACTCCT
1081 TTGTGTTTGG CAGCTTACCT TAACAAAGTT AATTTGGTTA AACTTCTATT GGCTCATTCG
1141 GCGGATGTAG ATATTTCAAA CACGGATCGG TTAACTCCTC TACATATAGC CGTATCAAAT
1201 AAAAATTTAA CAATGGTTAA ACTTCTATTG AACAAAGGTG CTGATACTGA CTTGCTGGAT
1261 AACATGGGAC GTACTCCTTT AATGATCGCT GTACAATCTG GAAATATTGA AATATGTAGC
1321 ACACTACTTA AAAAAAATAA AATGTCCAGA ACTGGGAAAA ATTGATCTTG CCAGCTGTAA
1381 TTCATGGTAG AAAAGAAGTG CTCAGGCTAC TTTTCAACAA AGGAGCAGAT GTAAACTACA
1441 TCTTTGAAAG AAATGGAAAA TCATATACTG TTTTGGAATT GATTAAAGAA AGTTACTCTG
1501 AGACACAAAA GAGGTAGCTG AAGTGGTACT CTCAAAATGC AGAACGATGA CTGCGAAGCA
1561 AGAAGTAGAG AAATAACACT TTATGACTTT CTTAGTTGTA GAAAAGATAG AGATATAATG
1621 ATGGTCATAA ATAACTCTGA TATTGCAAGT AAATGCAATA ATAAGTTAGA TTTATTTAAA
1681 AGGATAGTTA AAAATAGAAA AAAAGAGTTA ATTTGTAGGG TTAAAATAAT ACATAAGATC
1741 TTAAAATTTA TAAATACGCA TAATAATAAA AATAGATTAT ACTTATTACC TTCAGAGATA
1801 AAATTTAAGA TATTTACTTA TTTAACTTAT AAAGATCTAA AATGCATAAT TTCTAAATAA
1861 TGAAAAAAAA GTACATCATG AGCAACGCGT TAGTATATTT TACAATGGAG ATTAACGCTC
1921 TATACCGTTC TATGTTTATT GATTCAGATG ATGTTTTAGA AAAGAAAGTT ATTGAATATG
1981 AAAACTTTAA TGAAGATGAA GATGACGACG ATGATTATTG TTGTAAATCT GTTTTAGATG
2041 AAGAAGATGA CGCGCTAAAG TATACTATGG TTACAAAGTA TAAGTCTATA CTACTAATGG
2101 CGACTTGTGC AAGAAGGTAT AGTATAGTGA AAATGTTGTT AGATTATGAT TATGAAAAAC
2161 CAAATAAATC AGATCCATAT CTAAAGGTAT CTCCTTTGCA CATAATTTCA TCTATTCCTA
2221 GTTTAGAATA CTTTTCATTA TATTTGTTTA CAGCTGAAGA CGAAAAAAAT ATATCGATAA
2281 TAGAAGATTA TGTTAACTCT GCTAATAAGA TGAAATTGAA TGAGTCTGTG ATAATAGCTA
2341 TAATCAGAGA AGTTCTAAAA GGAAATAAAA ATCTAACTGA TCAGGATATA AAAACATTGG
2401 CTGATGAAAT CAACAAGGAG GAACTGAATA TAGCTAAACT ATTGTTAGAT AGAGGGGCCA
2461 AAGTAAATTA CAAGGATGTT TACGGTTCTT CAGCTCTCCA TAGAGCTGCT ATTGGTAGGA
2521 AACAGGATAT GATAAGCTG TTAATCGATC ATGGAGCTGA TGTAAACTCT TTAACTATTG
2581 CTAAAGATAA TCTTATTAAA AAAAAATAAT ATCACGTTTA GTAATATTAA AATATATTAA
2641 TAACTCTATT ACTAATAACT CCAGTGGATA TGAACATAAT ACGAAGTTTA TACATTCTCA
2701 TCAAAATCTT ATTGACATCA AGTTAGATTG TGAAAATGAG ATTATGAAAT TAAGGAATAC
2761 AAAAATAGGA TGTAAGAACT TACTAGAATG TTTTATCAAT AATGATATGA ATACAGTATC
2821 TAGGGCTATA AACAATGAAA CGATTAAAAA TTATAAAAAT CATTTCCCTA TATATAATAC
2881 GCTCATAGAA AAATTCATTT CTGAAAGTAT ACTAAGACAC GAATTATTGG ATGGAGTTAT
2941 AAATTCTTTT CAAGGATTCA ATAATAAATT GCCTTACGAG ATTCAGTACA TTATACTGGA
3001 GAATCTTAAT AACCATGAAC TAAAAAAAAT TTAGATAAT ATACATTAAA AAGGTAAATA
3061 GATCATCTGT TATTATAAGC AAAGATGCTT GTTGCCAATA ATATACAACA GGTATTTGTT
3121 TTTATTTTTA ACTACATATT TGATGTTCAT TCTCTTTATA TAGTATACAC AGAAAATTCA
3181 TAATCCACTT AGAATTTCTA GTTATCTAG
```

FIG.8

SEQUENCE LISTING ( 1 ) GENERAL INFORMATION:

( i i i ) NUMBER OF SEQUENCES: 55

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
TAATTAACTA GCTACCCGGG                                              20
```

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
GTACATTAAT TGATCGATGG GCCCTTAA                                     28
```

( 2 ) INFORMATION FOR SEQ ID NO:3:

( i ) SEQUENCE CHARACTERISTICS:
- ( A ) LENGTH: 73 base pairs
- ( B ) TYPE: nucleic acid
- ( C ) STRANDEDNESS: single
- ( D ) TOPOLOGY: linear ( i i ) MOLECULE TYPE: cDNA ( x i ) SEQUENCE DESCRIPTION: SEQ ID NO:3:

AGCTTCCCGG GTAAGTAATA CGTCAAGGAG AAAACGAAAC GATCTGTAGT TAGCGGCCGC     60

CTAATTAACT AAT     73

( 2 ) INFORMATION FOR SEQ ID NO:4:

( i ) SEQUENCE CHARACTERISTICS:
- ( A ) LENGTH: 69 base pairs
- ( B ) TYPE: nucleic acid
- ( C ) STRANDEDNESS: single
- ( D ) TOPOLOGY: linear ( i i ) MOLECULE TYPE: cDNA ( x i ) SEQUENCE DESCRIPTION: SEQ ID NO:4:

AGGGCCCATT CATTATGCAG TTCCTCTTTT GCTTTGCTAG ACATCAATCG CCGGCGGATT     60

AATTGATTA     69

( 2 ) INFORMATION FOR SEQ ID NO:5:

( i ) SEQUENCE CHARACTERISTICS:
- ( A ) LENGTH: 20 base pairs
- ( B ) TYPE: nucleic acid
- ( C ) STRANDEDNESS: single
- ( D ) TOPOLOGY: linear ( i i ) MOLECULE TYPE: cDNA ( x i ) SEQUENCE DESCRIPTION: SEQ ID NO:5:

TTAGTTAATT AGGCGGCCGC     20

( 2 ) INFORMATION FOR SEQ ID NO:6:

( i ) SEQUENCE CHARACTERISTICS:
- ( A ) LENGTH: 22 base pairs
- ( B ) TYPE: nucleic acid
- ( C ) STRANDEDNESS: single
- ( D ) TOPOLOGY: linear ( i i ) MOLECULE TYPE: cDNA ( x i ) SEQUENCE DESCRIPTION: SEQ ID NO:6:

CGATTACTAT GAAGGATCCG TT     22

( 2 ) INFORMATION FOR SEQ ID NO:7:

( i ) SEQUENCE CHARACTERISTICS:
- ( A ) LENGTH: 20 base pairs
- ( B ) TYPE: nucleic acid
- ( C ) STRANDEDNESS: single
- ( D ) TOPOLOGY: linear ( i i ) MOLECULE TYPE: cDNA ( x i ) SEQUENCE DESCRIPTION: SEQ ID NO:7:

TAATGATACT TCCTAGGCAA     20

( 2 ) INFORMATION FOR SEQ ID NO:8:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:8:

CGATTACTAG ATCTGAGCTC CCCGGGCTCG AGGGATCCGT T    41

( 2 ) INFORMATION FOR SEQ ID NO:9:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:9:

TAATGATCTA GACTCGAGGG GCCCGAGCTC CCTAGGCAA    39

( 2 ) INFORMATION FOR SEQ ID NO:10:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:10:

GATCCGAATT CTAGCT    16

( 2 ) INFORMATION FOR SEQ ID NO:11:

( i ) SEQUENCE CHARACTERISTICS:
  ( A ) LENGTH: 12 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:11:

GCTTAAGATC GA    12

( 2 ) INFORMATION FOR SEQ ID NO:12:

( i ) SEQUENCE CHARACTERISTICS:
  ( A ) LENGTH: 75 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:12:

TATGAGTAAC TTAACTCTTT TGTTAATTAA AAGTATATTC AAAAAATAAG TTATATAAAT    60

AGATCTGAAT TCGTT    75

( 2 ) INFORMATION FOR SEQ ID NO:13:

( i ) SEQUENCE CHARACTERISTICS:
  ( A ) LENGTH: 73 base pairs
  ( B ) TYPE: nucleic acid ( C ) STRANDEDNESS: single
    ( D ) TOPOLOGY: linear ( i i ) MOLECULE TYPE: cDNA ( x i ) SEQUENCE DESCRIPTION: SEQ ID NO:13:

ACTCATTGAA TTGAGAAAAC AATTAATTTT CATATAAGTT TTTTATTCAA TATATTTATC 60

TAGACTTAAG CAA 73

( 2 ) INFORMATION FOR SEQ ID NO:14:

( i ) SEQUENCE CHARACTERISTICS:
    ( A ) LENGTH: 49 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:14:

AAAATGGGCG TGGATTGTTA ACTTTATATA ACTTATTTTT TGAATATAC 49

( 2 ) INFORMATION FOR SEQ ID NO:15:

( i ) SEQUENCE CHARACTERISTICS:
    ( A ) LENGTH: 67 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:15:

ACACGAATGA TTTTCTAAAG TATTGGAAA GTTTATAGG TAGTTGATAG AACAAAATAC 60

ATAATTT 67

( 2 ) INFORMATION FOR SEQ ID NO:16:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:16:

TGTGCTTACT AAAAGATTTC ATAAACCTTT CAAAATATCC ATCAACTATC T 51

( 2 ) INFORMATION FOR SEQ ID NO:17:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:17:

TGTAAAAATA AATCACTTTT TATACTAAGA TCTCCCGGGC TGCAGC 46

( 2 ) INFORMATION FOR SEQ ID NO:18:

( i ) SEQUENCE CHARACTERISTICS:
    ( A ) LENGTH: 66 base pairs
    ( B ) TYPE: nucleic acid
    ( C ) STRANDEDNESS: single (D) TOPOLOGY: linear (ii) MOLECULE TYPE: cDNA (xi) SEQUENCE DESCRIPTION: SEQ ID NO:18:

TGTTTTATGT ATTAAAACAT TTTTATTTAG TGAAAAATAT GATTCTAGAG GGCCCGACGT    60

CGCCGG    66

(2) INFORMATION FOR SEQ ID NO:19:

(i) SEQUENCE CHARACTERISTICS:
  (A) LENGTH: 50 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:19:

TTTCTGTATA TTTGCACCAA TTTAGATCTT ACTCAAAATA TGTAACAATA    50

(2) INFORMATION FOR SEQ ID NO:20:

(i) SEQUENCE CHARACTERISTICS:
  (A) LENGTH: 44 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:20:

TGTCATTTAA CACTATACTC ATATTAATAA AAATAATATT TATT    44

(2) INFORMATION FOR SEQ ID NO:21:

(i) SEQUENCE CHARACTERISTICS:
  (A) LENGTH: 72 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:21:

GATCCTGAGT ACTTTGTAAT ATAATGATAT ATATTTTCAC TTTATCTCAT TGAGAATAA    60

AAAGATCTTA GG    72

(2) INFORMATION FOR SEQ ID NO:22:

(i) SEQUENCE CHARACTERISTICS:
  (A) LENGTH: 72 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:22:

GACTCATGAA ACATTATATT ACTATATATA AAAGTGAAAT AGAGTAAACT CTTATTTTTC    60

TAGAATCCTT AA    72

(2) INFORMATION FOR SEQ ID NO:23:

(i) SEQUENCE CHARACTERISTICS:
  (A) LENGTH: 72 base pairs
  (B) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:23:

```
GATCCAGATC TCCCGGGAAA AAAATTATTT AACTTTTCAT TAATAGGGAT TTGACGTATG        60
TAGCGTACTA GG                                                            72
```

( 2 ) INFORMATION FOR SEQ ID NO:24:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

```
GTCTAGAGGG CCCTTTTTTT AATAAATTGA AAAGTAATTA TCCCTAAACT GCATACTACG        60
CATGATCCTT AA                                                            72
```

( 2 ) INFORMATION FOR SEQ ID NO:25:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

```
GGGAGATCTC TCGAGCTGCA GGGCGCCGGA TCCTTTTTCT                              40
```

( 2 ) INFORMATION FOR SEQ ID NO:26:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

```
CCCTCTAGAG AGCTCGACGT CCCGCGGCCT AGGAAAAAGA                              40
```

( 2 ) INFORMATION FOR SEQ ID NO:27:

( i ) SEQUENCE CHARACTERISTICS:
        ( A ) LENGTH: 3209 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

```
TGAATGTTAA ATGTTATACT TTGGATGAAG CTATAAATAT GCATTGGAAA AATAATCCAT        60
TTAAAGAAAG GATTCAAATA CTACAAAACC TAAGCGATAA TATGTTAACT AAGCTTATTC       120
TTAACGACGC TTTAAATATA CACAAATAAA CATAATTTTT GTATAACCTA ACAAATAACT       180
AAAACATAAA AATAATAAAA GGAAATGTAA TATCGTAATT ATTTTACTCA GGAATGGGGT       240
TAAATATTTA TATCACGTGT ATATCTATAC TGTTATCGTA TACTCTTTAC AATTACTATT       300
```

```
ACGAATATGC AAGAGATAAT AAGATTACGT ATTTAAGAGA ATCTTGTCAT GATAATTGGG      360

TACGACATAG TGATAAATGC TATTTCGCAT CGTTACATAA AGTCAGTTGG AAAGATGGAT      420

TTGACAGATG TAACTTAATA GGTGCAAAAA TGTTAAATAA CAGCATTCTA TCGGAAGATA      480

GGATACCAGT TATATTATAC AAAAATCACT GGTTGGATAA AACAGATTCT GCAATATTCG      540

TAAAAGATGA AGATTACTGC GAATTTGTAA ACTATGACAA TAAAAGCCA TTTATCTCAA       600

CGACATCGTG TAATTCTTCC ATGTTTTATG TATGTGTTTC AGATATTATG AGATTACTAT      660

AAACTTTTTG TATACTTATA TTCCGTAAAC TATATTAATC ATGAAGAAAA TGAAAAGTA       720

TAGAAGCTGT TCACGAGCGG TTGTTGAAAA CAACAAAATT ATACATTCAA GATGGCTTAC      780

ATATACGTCT GTGAGGCTAT CATGGATAAT GACAATGCAT CTCTAAATAG GTTTTGGAC       840

AATGGATTCG ACCCTAACAC GGAATATGGT ACTCTACAAT CTCCTCTTGA AATGGCTGTA      900

ATGTTCAAGA ATACCGAGGC TATAAAAATC TTGATGAGGT ATGGAGCTAA ACCTGTAGTT      960

ACTGAATGCA CAACTTCTTG TCTGCATGAT GCGGTGTTGA GAGACGACTA CAAAATAGTG     1020

AAAGATCTGT TGAAGAATAA CTATGTAAAC AATGTTCTTT ACAGCGGAGG CTTTACTCCT     1080

TTGTGTTTGG CAGCTTACCT TAACAAAGTT AATTTGGTTA AACTTCTATT GGCTCATTCG     1140

GCGGATGTAG ATATTTCAAA CACGGATCGG TTAACTCCTC TACATATAGC CGTATCAAAT     1200

AAAATTTAA CAATGGTTAA ACTTCTATTG AACAAGGTG CTGATACTGA CTTGCTGGAT       1260

AACATGGGAC GTACTCCTTT AATGATCGCT GTACAATCTG GAAATATTGA ATATGTAGC      1320

ACACTACTTA AAAAAATAA AATGTCCAGA ACTGGGAAAA ATTGATCTTG CCAGCTGTAA      1380

TTCATGGTAG AAAAGAAGTG CTCAGGCTAC TTTTCAACAA AGGAGCAGAT GTAAACTACA     1440

TCTTTGAAAG AAATGGAAAA TCATATACTG TTTTGGAATT GATTAAAGAA AGTTACTCTG     1500

AGACACAAAA GAGGTAGCTG AAGTGGTACT CTCAAAATGC AGAACGATGA CTGCGAAGCA     1560

AGAAGTAGAG AAATAACACT TTATGACTTT CTTAGTTGTA GAAAAGATAG AGATATAATG     1620

ATGGTCATAA ATAACTCTGA TATTGCAAGT AAATGCAATA ATAAGTTAGA TTTATTTAAA     1680

AGGATAGTTA AAAATAGAAA AAAAGAGTTA ATTTGTAGGG TTAAAATAAT ACATAAGATC     1740

TTAAAATTTA TAAATACGCA TAATAATAAA AATAGATTAT ACTTATTACC TTCAGAGATA     1800

AAATTTAAGA TATTTACTTA TTTAACTTAT AAAGATCTAA AATGCATAAT TTCTAAATAA     1860

TGAAAAAAAA GTACATCATG AGCAACGCGT TAGTATATTT TACAATGGAG ATTAACGCTC     1920

TATACCGTTC TATGTTTATT GATTCAGATG ATGTTTTAGA AAAGAAAGTT ATTGAATATG     1980

AAAACTTTAA TGAAGATGAA GATGACGACG ATGATTATTG TTGTAAATCT GTTTTAGATG     2040

AAGAAGATGA CGCGCTAAAG TATACTATGG TTACAAAGTA TAAGTCTATA CTACTAATGG     2100

CGACTTGTGC AAGAAGGTAT AGTATAGTGA AAATGTTGTT AGATTATGAT TATGAAAAC     2160

CAAATAAATC AGATCCATAT CTAAAGGTAT CTCCTTTGCA CATAATTTCA TCTATTCCTA     2220

GTTAGAATA CTTTTCATTA TATTTGTTTA CAGCTGAAGA CGAAAAAAAT ATATCGATAA      2280

TAGAAGATTA TGTTAACTCT GCTAATAAGA TGAAATTGAA TGAGTCTGTG ATAATAGCTA     2340

TAATCAGAGA AGTTCTAAAA GGAAATAAAA ATCTAACTGA TCAGGATATA AAAACATTGG     2400

CTGATGAAAT CAACAAGGAG GAACTGAATA TAGCTAAACT ATTGTTAGAT AGAGGGGCCA     2460

AAGTAAATTA CAAGGATGTT TACGGTTCTT CAGCTCTCCA TAGAGCTGCT ATTGGTAGGA     2520

AACAGGATAT GATAAAGCTG TTAATCGATC ATGGAGCTGA TGTAAACTCT TTAACTATTG     2580

CTAAAGATAA TCTTATTAAA AAAAATAAT ATCACGTTTA GTAATATTAA AATATATTAA      2640

TAACTCTATT ACTAATAACT CCAGTGGATA TGAACATAAT ACGAAGTTTA TACATTCTCA     2700
```

```
TCAAAATCTT    ATTGACATCA    AGTTAGATTG    TGAAAATGAG    ATTATGAAAT    TAAGGAATAC       2760

AAAAATAGGA    TGTAAGAACT    TACTAGAATG    TTTTATCAAT    AATGATATGA    ATACAGTATC       2820

TAGGGCTATA    AACAATGAAA    CGATTAAAAA    TTATAAAAAT    CATTTCCCTA    TATATAATAC       2880

GCTCATAGAA    AAATTCATTT    CTGAAAGTAT    ACTAAGACAC    GAATTATTGG    ATGGAGTTAT       2940

AAATTCTTTT    CAAGGATTCA    ATAATAAATT    GCCTTACGAG    ATTCAGTACA    TTATACTGGA       3000

GAATCTTAAT    AACCATGAAC    TAAAAAAAAT    TTTAGATAAT    ATACATTAAA    AAGGTAAATA       3060

GATCATCTGT    TATTATAAGC    AAAGATGCTT    GTTGCCAATA    ATATACAACA    GGTATTTGTT       3120

TTTATTTTTA    ACTACATATT    TGATGTTCAT    TCTCTTTATA    TAGTATACAC    AGAAAATTCA       3180

TAATCCACTT    AGAATTTCTA    GTTATCTAG                                                  3209
```

( 2 ) INFORMATION FOR SEQ ID NO:28:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

```
GCTTCCCGGG    AATTCTAGCT    AGCTAGTTT                                                    29
```

( 2 ) INFORMATION FOR SEQ ID NO:29:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

```
ACTCTCAAAA    GCTTCCCGGG    AATTCTAGCT    AGCTAGTTTT    TATAAA                           46
```

( 2 ) INFORMATION FOR SEQ ID NO:30:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

```
GATCTTTATA    AAAACTAGCT    AGCTAGAATT    CCCGGGAAGC    TTTTGAGAGT                       50
```

( 2 ) INFORMATION FOR SEQ ID NO:31:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

```
CTGAAATTAT    TTCATTATCG    CGATATCCGT    TAAGTTTGTA    TCGTAATGGT    TCCTCAGGCT       60

CTCCTGTTTG    T                                                                          71
```

( 2 ) INFORMATION FOR SEQ ID NO:32:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

CATTACGATA CAAACTTAAC GGATATCGCG ATAATGAAAT AATTTCAG 48

( 2 ) INFORMATION FOR SEQ ID NO:33:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

ACCCCTTCTG GTTTTTCCGT TGTGTTTTGG GAAATTCCCT ATTTACACGA TCCCAGACAA 60

GCTTAGATCT CAG 73

( 2 ) INFORMATION FOR SEQ ID NO:34:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

CTGAGATCTA AGCTTGTCTG GGATCGTGTA AATAGGGAAT TTCCCAAAAC A 51

( 2 ) INFORMATION FOR SEQ ID NO:35:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

CAACGGAAAA ACCAGAAGGG GTACAAACAG GAGAGCCTGA GGAAC 45

( 2 ) INFORMATION FOR SEQ ID NO:36:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

GGATCCCCGG G 11

( 2 ) INFORMATION FOR SEQ ID NO:37:

( i ) SEQUENCE CHARACTERISTICS:
   ( A ) LENGTH: 42 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:37:

TTTTTCTAGA CTGCAGCCCG GGACATCATG CAGTGGTTAA AC 42

( 2 ) INFORMATION FOR SEQ ID NO:38:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:38:

CACCTTCAGG ATCTACTGTC G 21

( 2 ) INFORMATION FOR SEQ ID NO:39:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:39:

GGGTTTCAGA GGCAGTTC 18

( 2 ) INFORMATION FOR SEQ ID NO:40:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:40:

GATTAAACCT AAATAATTGT 20

( 2 ) INFORMATION FOR SEQ ID NO:41:

( i ) SEQUENCE CHARACTERISTICS:
      ( A ) LENGTH: 42 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:41:

TTTTTCTAGA CTGCAGCCCG GGACATCATG CAGTGGTTAA AC 42

( 2 ) INFORMATION FOR SEQ ID NO:42:

( i ) SEQUENCE CHARACTERISTICS:
      ( A ) LENGTH: 18 base pairs
      ( B ) TYPE: nucleic acid
      ( C ) STRANDEDNESS: single (D) TOPOLOGY: linear (ii) MOLECULE TYPE: cDNA (xi) SEQUENCE DESCRIPTION: SEQ ID NO:42:

GGGTTTCAGA GGCAGTTC 18

(2) INFORMATION FOR SEQ ID NO:43:

(i) SEQUENCE CHARACTERISTICS:
 (A) LENGTH: 21 base pairs
 (B) TYPE: nucleic acid
 (C) STRANDEDNESS: single
 (D) TOPOLOGY: linear (ii) MOLECULE TYPE: cDNA (xi) SEQUENCE DESCRIPTION: SEQ ID NO:43:

ATGTCCACTC GTGGCGATCT T 21

(2) INFORMATION FOR SEQ ID NO:44:

(i) SEQUENCE CHARACTERISTICS:
 (A) LENGTH: 24 base pairs
 (B) TYPE: nucleic acid
 (C) STRANDEDNESS: single
 (D) TOPOLOGY: linear (ii) MOLECULE TYPE: cDNA (xi) SEQUENCE DESCRIPTION: SEQ ID NO:44:

ACGCATGATG ACAAGATTAT TATC 24

(2) INFORMATION FOR SEQ ID NO:45:

(i) SEQUENCE CHARACTERISTICS:
 (A) LENGTH: 18 base pairs
 (B) TYPE: nucleic acid
 (C) STRANDEDNESS: single
 (D) TOPOLOGY: linear (ii) MOLECULE TYPE: cDNA (xi) SEQUENCE DESCRIPTION: SEQ ID NO:45:

CTGTGGAATT CGCAATGC 18

(2) INFORMATION FOR SEQ ID NO:46:

(i) SEQUENCE CHARACTERISTICS:
 (A) LENGTH: 53 base pairs
 (B) TYPE: nucleic acid
 (C) STRANDEDNESS: single
 (D) TOPOLOGY: linear (ii) MOLECULE TYPE: cDNA (xi) SEQUENCE DESCRIPTION: SEQ ID NO:46:

AAAACTGCAG CCCGGGAAGC TTACAAAAAT TAGACAAGAT TTGTTTCAGT ATC 53

(2) INFORMATION FOR SEQ ID NO:47:

(i) SEQUENCE CHARACTERISTICS:
 (A) LENGTH: 36 base pairs
 (B) TYPE: nucleic acid
 (C) STRANDEDNESS: single
 (D) TOPOLOGY: linear (ii) MOLECULE TYPE: cDNA (xi) SEQUENCE DESCRIPTION: SEQ ID NO:47:

GGTATGGCAA ATTTCTTTCA GGGACTCGGG GATGTG                                                                36

( 2 ) INFORMATION FOR SEQ ID NO:48:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:48:

CATTATCGCG ATATCCGTTA AGTTTGTATC GTAATGAGAC GATATAGGAT GGGAC          55

( 2 ) INFORMATION FOR SEQ ID NO:49:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:49:

ACTATTTTCA ATACTGAC                                                                                    18

( 2 ) INFORMATION FOR SEQ ID NO:50:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:50:

AAATGTGTAC CACGGGAC                                                                                    18

( 2 ) INFORMATION FOR SEQ ID NO:51:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:51:

AAGAAGCTTC TGCAGAATTC GTTAACAAAA ATCATTATAA TCGCCGGGGA TGAG           54

( 2 ) INFORMATION FOR SEQ ID NO:52:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:52:

TTTATATTGT AATTATA                                                                                     17

( 2 ) INFORMATION FOR SEQ ID NO:53:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:53:

GTAAACGAC GGCCAGT                                     17

( 2 ) INFORMATION FOR SEQ ID NO:54:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:54:

ATGATGACAC GTCTACATTT T                               21

( 2 ) INFORMATION FOR SEQ ID NO:55:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:55:

TGTTACATAA CGTACTTCAG C                               21

ALVAC POXVIRUS-RABIES COMPOSITIONS AND COMBINATION COMPOSITIONS AND USES

RELATED APPLICATIONS

This application is a continuation-in-part of application Ser. No. 08/105,483, filed Aug. 13, 1993, now U.S. Pat. No. 5,494,807, which in turn is a continuation of application Ser. No. 07/847,951, filed Mar. 6, 1992, now abandoned, which in turn is a continuation-in-part of application Ser. No. 07/713,967, filed Jun. 11, 1991, now abandoned, which in turn is a continuation-in-part of application Ser. No. 07/666,056, filed Mar. 7, 1991, now abandoned, which in turn is a continuation of application Ser. No. 08/036,217, filed Mar. 24, 1993, and issued Nov. 15, 1994 as U.S. Pat. No. 5,364,773. Each of the aforementioned and above-referenced applications and patent are hereby incorporated herein by reference.

FIELD OF THE INVENTION

The present invention relates to a modified recombinant poxvirus compositions and combination composition and to methods of making and using the same; for instance, a vaccinia virus or avipox (e.g. canarypox or fowlpox), e.g., modified poxvirus-rabies virus recombinants, compositions thereof, combination compositions thereof and uses thereof, such as an attenuated recombinant, especially a NYVAC or ALVAC-rabies virus recombinant, compositions thereof and combination compositions thereof, and uses thereof. Thus, the invention relates to a recombinant poxvirus-rabies virus, which virus expresses gene products of rabies virus in a composition; the composition can include any one of: canine distemper virus antigen, e.g., CDV HA and/or F glycoproteins, canine adenovirus type 2 antigen, canine coronavirus antigen, canine parainfluenza antigen, canine parvovirus antigen, Leptospira Canicola-Icterohaemorrhagiae Bacterin antigen, any combination of these antigens, or a feline leukemia virus antigen or feline herpesvirus antigen or any combination of these antigens. Such a composition can induce an immunological response against rabies virus infections, as well as against any other antigen in the composition, when administered to a host; and, the composition can elicit long-term immunity (response) against rabies in dogs and can afford protection or elicit an immunological response in pups having maternal immunity. The invention further relates to methods for making and using such compositions. The invention additionally relates to the products of expression of the poxvirus which by themselves are useful for eliciting an immune response e.g., raising antibodies, which antibodies are useful against rabies infection, or which expression products or antibodies elicited thereby, isolated from an animal or human or cell culture as the case may be, are useful for preparing a diagnostic kit, test or assay for the detection of the rabies, and the recombinant virus, or of infected cells, or, of the expression of the antigens or products in other systems. The isolated expression products and antibodies elicited by the recombinant virus are especially useful in kits, tests or assays for detection of antibodies or antigens in a system, host, serum or sample; and the expression products are useful for generation of antibodies.

Several publications are referenced in this application. Full citation to these references is found at the end of the specification immediately preceding the claims or where the publication is mentioned; and each of these publications is hereby incorporated herein by reference.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of poxviruses such as the vaccinia virus and avipox virus described in U.S. Pat. Nos. 4,769,330, 4,772,848, 4,603,112, 5,100,587, and 5,179,993, the disclosures of which are incorporated herein by reference.

First, the DNA gene sequence to be inserted into the virus, particularly an open reading frame from a non-pox source, is placed into an E. coli plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within E. coli bacteria (Clewell, 1972) and isolated (Clewell et al., 1969; Maniatis et al., 1982).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome. Additional strategies have recently been reported for generating recombinant vaccinia virus.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Vaccinia virus has been used successfully to immunize against smallpox, culminating in the worldwide eradication of smallpox in 1980. In the course of its history, many strains of vaccinia have arisen. These different strains demonstrate varying immunogenicity and are implicated to varying degrees with potential complications, the most serious of which are post-vaccinial encephalitis and generalized vaccinia (Behbehani, 1983).

With the eradication of smallpox, a new role for vaccinia became important, that of a genetically engineered vector for the expression of foreign genes. Genes encoding a vast number of heterologous antigens have been expressed in vaccinia, often resulting in protective immunity against challenge by the corresponding pathogen (reviewed in Tartaglia et al., 1990).

The genetic background of the vaccinia vector has been shown to affect the protective efficacy of the expressed foreign immunogen. For example, expression of Epstein Barr Virus (EBV) gp340 in the Wyeth vaccine strain of vaccinia virus did not protect cottontop tamarins against EBV virus induced lymphoma, while expression of the same gene in the WR laboratory strain of vaccinia virus was protective (Morgan et al., 1988).

A fine balance between the efficacy and the safety of a vaccinia virus-based recombinant vaccine candidate is extremely important. The recombinant virus must present the immunogen(s) in a manner that elicits a protective immune response in the vaccinated animal but lacks any significant pathogenic properties. Therefore attenuation of the vector strain would be a highly desirable advance over the current state of technology.

A number of vaccinia genes have been identified which are non-essential for growth of the virus in tissue culture and whose deletion or inactivation reduces virulence in a variety of animal systems.

The gene encoding the vaccinia virus thymidine kinase (TK) has been mapped (Hruby et al., 1982) and sequenced (Hruby et al., 1983; Weir et al., 1983). Inactivation or complete deletion of the thymidine kinase gene does not prevent growth of vaccinia virus in a wide variety of cells in tissue culture. $TK^-$ vaccinia virus is also capable of replication in vivo at the site of inoculation in a variety of hosts and administered by a variety of routes.

It has been shown for herpes simplex virus type 2 that intravaginal inoculation of guinea pigs with $TK^-$ virus resulted in significantly lower virus titers in the spinal cord than did inoculation with $TK^+$ virus (Stanberry et al., 1985). It has been demonstrated that herpesvirus encoded TK activity in vitro was not important for virus growth in actively metabolizing cells, but was required for virus growth in quiescent cells (Jamieson et al., 1974).

Attenuation of $TK^-$ vaccinia has been shown in mice inoculated by the intracerebral and intraperitoneal routes (Buller et al., 1985). Attenuation was observed both for the WR neurovirulent laboratory strain and for the Wyeth vaccine strain. In mice inoculated by the intradermal route, $TK^-$ recombinant vaccinia generated equivalent anti-vaccinia neutralizing antibodies as compared with the parental $TK^+$ vaccinia virus, indicating that in this test system the loss of TK function does not significantly decrease immunogenicity of the vaccinia virus vector. Following intranasal inoculation of mice with $TK^-$ and $TK^+$ recombinant vaccinia virus (WR strain), significantly less dissemination of virus to other locations, including the brain, has been found (Taylor et al., 1991a).

Another enzyme involved with nucleotide metabolism is ribonucleotide reductase. Loss of virally encoded ribonucleotide reductase activity in herpes simplex virus (HSV) by deletion of the gene encoding the large subunit was shown to have no effect on viral growth and DNA synthesis in dividing cells in vitro, but severely compromised the ability of the virus to grow on serum starved cells (Goldstein et al., 1988). Using a mouse model for acute HSV infection of the eye and reactivatable latent infection in the trigeminal ganglia, reduced virulence was demonstrated for HSV deleted of the large subunit of ribonucleotide reductase, compared to the virulence exhibited by wild type HSV (Jacobson et al., 1989).

Both the small (Slabaugh et al., 1988) and large (Schmidtt et al., 1988) subunits of ribonucleotide reductase have been identified in vaccinia virus. Insertional inactivation of the large subunit of ribonucleotide reductase in the WR strain of vaccinia virus leads to attenuation of the virus as measured by intracranial inoculation of mice (Child et al., 1990).

The vaccinia virus hemagglutinin gene (HA) has been mapped and sequenced (Shida, 1986). The HA gene of vaccinia virus is nonessential for growth in tissue culture (Ichihashi et al., 1971). Inactivation of the HA gene of vaccinia virus results in reduced neurovirulence in rabbits inoculated by the intracranial route and smaller lesions in rabbits at the site of intradermal inoculation (Shida et al., 1988). The HA locus was used for the insertion of foreign genes in the WR strain (Shida et al., 1987), derivatives of the Lister strain (Shida et al., 1988) and the Copenhagen strain (Guo et al., 1989) of vaccinia virus. Recombinant $HA^-$ vaccinia virus expressing foreign genes have been shown to be immunogenic (Guo et al., 1989; Itamura et al., 1990; Shida et al., 1988; Shida et al., 1987) and protective against challenge by the relevant pathogen (Guo et al., 1989; Shida et al., 1987).

Cowpox virus (Brighton red strain) produces red (hemorrhagic) pocks on the chorioallantoic membrane of chicken eggs. Spontaneous deletions within the cowpox genome generate mutants which produce white pocks (Pickup et al., 1984). The hemorrhagic function (u) maps to a 38 kDa protein encoded by an early gene (Pickup et al., 1986). This gene, which has homology to serine protease inhibitors, has been shown to inhibit the host inflammatory response to cowpox virus (Palumbo et al., 1989) and is an inhibitor of blood coagulation.

The u gene is present in WR strain of vaccinia virus (Kotwal et al., 1989b). Mice inoculated with a WR vaccinia virus recombinant in which the u region has been inactivated by insertion of a foreign gene produce higher antibody levels to the foreign gene product compared to mice inoculated with a similar recombinant vaccinia virus in which the u gene is intact (Zhou et al., 1990). The u region is present in a defective nonfunctional form in Copenhagen strain of vaccinia virus (open reading frames B13 and B14 by the terminology reported in Goebel et al., 1990a,b).

Cowpox virus is localized in infected cells in cytoplasmic A type inclusion bodies (ATI) (Kato et al., 1959). The function of ATI is thought to be the protection of cowpox virus virions during dissemination from animal to animal (Bergoin et al., 1971). The ATI region of the cowpox genome encodes a 160 kDa protein which forms the matrix of the ATI bodies (Funahashi et al., 1988; Patel et al., 1987). Vaccinia virus, though containing a homologous region in its genome, generally does not produce ATI. In WR strain of vaccinia, the ATI region of the genome is translated as a 94 kDa protein (Patel et al., 1988). In Copenhagen strain of vaccinia virus, most of the DNA sequences corresponding to the ATI region are deleted, with the remaining 3' end of the region fused with sequences upstream from the ATI region to form open reading frame (ORF) A26L (Goebel et al., 1990a,b).

A variety of spontaneous (Altenburger et al., 1989; Drillien et al., 1981; Lai et al., 1989; Moss et al., 1981; Paez et al., 1985; Panicali et al., 1981) and engineered (Perkus et al., 1991; Perkus et al., 1989; Perkus et al., 1986) deletions have been reported near the left end of the vaccinia virus genome. A WR strain of vaccinia virus with a 10 kb spontaneous deletion (Moss et al., 1981; Panicali et al., 1981) was shown to be attenuated by intracranial inoculation in mice (Buller et al., 1985). This deletion was later shown to include 17 potential ORFs (Kotwal et al., 1988b). Specific genes within the deleted region include the virokine N1L and a 35 kDa protein (C3L, by the terminology reported in Goebel et al., 1990a,b). Insertional inactivation of N1L reduces virulence by intracranial inoculation for both normal and nude mice (Kotwal et al., 1989a). The 35 kDa protein is secreted like N1L into the medium of vaccinia virus infected cells. The protein contains homology to the family of complement control proteins, particularly the complement 4B binding protein (C4bp) (Kotwal et al., 1988a). Like the cellular C4bp, the vaccinia 35 kDa protein binds the fourth component of complement and inhibits the classical complement cascade (Kotwal et al., 1990). Thus the vaccinia 35 kDa protein appears to be involved in aiding the virus in evading host defense mechanisms.

The left end of the vaccinia genome includes two genes which have been identified as host range genes, K1L (Gillard et al., 1986) and C7L (Perkus et al., 1990). Deletion of both of these genes reduces the ability of vaccinia virus to grow on a variety of human cell lines (Perkus et al., 1990).

Two additional vaccine vector systems involve the use of naturally host-restricted poxviruses, avipox viruses. Both fowlpoxvirus (FPV) and canarypoxvirus (CPV) have been engineered to express foreign gene products. Fowlpox virus (FPV) is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982) and there are no reports in the literature of avipoxvirus causing a productive infection in any non-avian species including man. This host restriction provides an inherent safety barrier to transmission of the virus to other species and makes use of avipoxvirus based vaccine vectors in veterinary and human applications an attractive proposition.

FPV has been used advantageously as a vector expressing antigens from poultry pathogens. The hemagglutinin protein of a virulent avian influenza virus was expressed in an FPV recombinant (Taylor et al., 1988a). After inoculation of the recombinant into chickens and turkeys, an immune response was induced which was protective against either a homologous or a heterologous virulent influenza virus challenge (Taylor et al., 1988a). FPV recombinants expressing the surface glycoproteins of Newcastle Disease Virus have also been developed (Taylor et al., 1990; Edbauer et al., 1990).

Despite the host-restriction for replication of FPV and CPV to avian systems, recombinants derived from these viruses were found to express extrinsic proteins in cells of nonavian origin. Further, such recombinant viruses were shown to elicit immunological responses directed towards the foreign gene product and where appropriate were shown to afford protection from challenge against the corresponding pathogen (Tartaglia et al., 1993a,b; Taylor et al., 1992; 1991b; 1988b).

Particularly in the U.S. a rabies combination or multivalent or "cocktail" vaccine or immunological composition (rabies antigen in combination with additional antigen or antigens in a composition), particularly for canines, is not presently available due to the inability of any previous combinations to pass efficacy testing. Such prior combinations exhibit what is known as "efficacy interference", namely a failure of one or more antigens, such as the rabies antigen, or the additional antigen(s) in the combination composition to maintain or achieve efficacy. This is believed due to interference on that antigen stimulating an immunological, antigenic, antibody, or protective response in the host, e.g., dog, when administered, because of the presence of the additional antigen(s) other or the rabies antigens. For instance, rabies antigens in a combination with additional antigens suffer interference from or interfere with the stimulation of an immunological, antigenic, antibody or protective response by those additional antigens in such a composition, when that composition is administered to dogs. More particularly, rabies antigens, when administered with one or more, or all, of canine distemper virus antigens, canine adenovirus antigens, canine coronavirus antigens, canine parainfluenza antigens, canine parvovirus antigens, and Leptospira bacterin antigens, can interfere with the response elicited by those antigens, and vice versa. However, for other hosts, such as cats, combination vaccines are known. Perhaps, without wishing to be bound by any one theory, the "efficacy interference" is due to (i) some peculiarity of the host, e.g., canine, biological system or, (ii) to the reaction with the host, e.g., canine, biological system by presently known rabies antigens or, (iii) to the reaction with the host, e.g., canine biological system by the presently known additional antigens in such previous combination compositions or, (iv) to some combination of the factors (i) to (iii). Any known combination compositions containing rabies antigen are not by recombinants and have an adjuvant.

Regardless of the theory, it is believed that there is presently no known rabies combination-with-additional-antigens composition, especially for canine use, which does not exhibit efficacy interference. There is thus a need for a rabies combination composition, especially for canine use. Accordingly, in pups and dogs, rabies antigens are usually separately administered and not in a combination composition with antigen(s), for protection. It would indeed be surprising, unexpected and non-obvious to be able to formulate a rabies combination (with other antigens) composition, i.e., a rabies multivalent composition, which exhibits a lack of efficacy interference, especially in canines, particularly, because as shown by the present knowledge and efficacy interference, one cannot simply combine antigen compositions to prepare a useful combination or multivalent or "cocktail" composition. In this instance (of the foregoing sentence), "antigen compositions" can mean recombinant poxviruses which code for and express an antigen themselves or a combination of such recombinants and antigens. It would also be desirable if a rabies antigen which can indeed be used in a combination or "cocktail" composition for canines can also be used in such a composition for other hosts, such as felines. In this manner, the rabies antigen for various veterinary combination or multivalent or "cocktail"

compositions need not vary, thereby providing an economic advantage in the manufacture thereof.

Additionally, it would be advantageous if such a rabies antigen provided long term protection or elicited a long term response for canines, as well as protection or elicited a response for pups with maternal immunity to rabies. As the skilled artisan is aware, maternal immunity is immunity that a newborn acquires from its mother upon birth and/or from nursing, which immunity, after a period of time, lapses in the newborn, thereby leaving the newborn susceptible. Furthermore, the presence of maternal antibodies in the newborn can prevent the newborn from obtaining a protective or immunological response when administered an antigen composition, e.g., a vaccine, thus meaning that the newborn must enter a period of no or little immunity, i.e., susceptibility, to the danger of the newborn before administration of an antigen or vaccine composition can be considered. In regard to maternal immunity, reference is made to U.S. Pat. No. 5,338,683, issued Aug. 16, 1994 and incorporated herein by reference.

It would even be more advantageous, surprising and unexpected if the rabies antigen which can be used in a combination, "cocktail" or multivalent composition, which lacks efficacy interference in canines, which can be used in such a composition for other hosts such as felines, and, which provides long-term response or protection in dogs as well as a response or protection in pups, in spite of maternal immunity was a recombinant virus, such as a recombinant poxvirus-rabies virus. And, moreover, it would be especially surprising and unexpected if this poxvirus-rabies virus recombinant was modified so as to be attenuated, e.g., an attenuated vaccinia virus-rabies virus recombinant or an attenuated avipox-rabies virus recombinant, such as a NYVAC-rabies or ALVAC-rabies recombinant; because, for instance, from attenuation and, diminished or lack of productive replication of the poxvirus in the host, one skilled in the art would have especially not expected and would be surprised by the usefulness of the attenuated recombinant for a "cocktail", multivalent or combination composition for canines and other hosts, especially in such a composition which provides long-term response or protection in canines and response or protection in pups in spite of protective immunity.

Attenuated poxvirus vectors would also be especially advantageous for antigenic or vaccine compositions, especially combination or "cocktail" or multivalent compositions, particularly in view of attenuated vectors providing diminished or little or no pathogenic properties with regard to the intended host or, to unintended, possibly accidental hosts, such as those who work with the vector in formulating or administering the vector or antigen, or who may otherwise come into contact with it. That is, attenuated poxvirus vectors provide diminished or little or no pathogenic properties to intended hosts such as dogs, pups, cats, kittens and the like and to unintended, possibly accidental hosts, such as humans engaged in formulating the vector into a composition for administration or in administering the composition (e.g., veterinarians, technicians, other workers) or, who may otherwise come into contact with the vector (e.g., pet owners).

It can thus be appreciated that provision of a rabies virus recombinant poxvirus, and of compositions and products therefrom, particularly NYVAC or ALVAC based rabies recombinants and compositions and products therefrom, especially such compositions containing other antigens, e.g., "cocktail" or multivalent or combination compositions and products therefrom which lack efficacy interference in canines, can be administered to other hosts, such as felines (either as a poxvirus rabies recombinant composition or as a component in the "cocktail" or combination or multivalent composition) and, which can induce long-term response or protection in dogs and response or protection in pups in spite of maternal immunity, would be a highly desirable advance over the current state of technology.

OBJECTS AND SUMMARY OF THE INVENTION

It is therefore an object of this invention to provide modified recombinant viruses, which viruses have enhanced safety, and to provide a method of making such recombinant viruses.

Additional objects of this invention include: to provide a recombinant poxvirus composition or an antigen composition, preferably a poxvirus-rabies recombinant composition, which is an antigenic, or vaccine or immunological composition (i.e., a composition containing a recombinant which expresses a rabies antigen, or the product from expression of the antigen), more preferably, such a composition having an increased level of safety and/or efficacy as compared to known compositions and known "cocktail" or multivalent or combination compositions; to provide methods for making and using such; and most preferably to provide compositions which can be efficacious as "cocktail" or multivalent or combination compositions for canines, as well as for other hosts, such as felines, and which also most preferably can provide long-term response or protection, especially in canines, and/or a response or protection in spite of maternal immunity.

It is a further object of this invention to provide a modified vector for expressing a gene product in a host, wherein the vector is modified so that it has attenuated virulence in the host.

It is another object of this invention to provide a method for expressing a gene product in a cell cultured in vitro using a modified recombinant virus or modified vector having an increased level of safety and to provide the use of such product in compositions.

These and other objects and advantages of the present invention will become more readily apparent after consideration of the following.

In one aspect, the present invention relates to a modified recombinant virus having inactivated virus-encoded genetic functions so that the recombinant virus has attenuated virulence and enhanced safety. The functions can be nonessential, or associated with virulence. The virus is advantageously a poxvirus, particularly a vaccinia virus or an avipox virus, such as fowlpox virus and canarypox virus. The modified recombinant virus can include, within a nonessential region of the virus genome, a heterologous DNA sequence which encodes an antigen or epitope derived from rabies virus, either alone or with antigens of other maladies.

In another aspect, the present invention relates to an antigenic, immunological or vaccine composition or a therapeutic composition for inducing an antigenic or immunological or protective response in a host animal inoculated with the composition, said composition including a carrier and a modified recombinant virus having inactivated nonessential virus-encoded genetic functions so that the recombinant virus has attenuated virulence and enhanced safety. The virus used in the composition according to the present invention is advantageously a poxvirus, particularly a vaccinia virus or an avipox virus, such as fowlpox virus and canarypox virus. The modified recombinant virus can include, within a non-essential region of the virus genome, a heterologous DNA sequence which encodes an antigenic protein, e.g., derived from rabies virus and further, the composition can contain additional antigens such as any one of: canine distemper virus antigen, e.g., CDV HA and/or F glycoproteins, canine adenovirus type 2 antigen, canine coronavirus antigen, canine parainfluenza antigen, canine parvovirus antigen, Leptospira Canicola-Icterohaemorrhagiae Bacterin antigen, any combination of these antigens, or feline leukemia virus antigen or feline herpesvirus antigen, or any combination of these antigens; or other recombinants such as other poxvirus recombinants which express any or all of these additional antigens; or, the composition can contain a recombinant poxvirus which contains coding for and expresses rabies antigen and another antigen or antigens.

In yet another aspect, the present invention relates to methods employing the aforementioned composition; for instance, for obtaining an in vivo response to rabies antigen either alone or with any one of: canine distemper virus antigen, e.g., CDV HA and/or F glycoproteins, canine adenovirus type 2 antigen, canine coronavirus antigen, canine parainfluenza antigen, canine parvovirus antigen, Leptospira Canicola-Icterohaemorrhagiae Bacterin antigen, any combination of these antigens, or feline leukemia virus antigen or feline herpesvirus antigen, or any combination of these antigens. The method can comprise administering the composition either to canines or other hosts, such as felines. The method can be administering to canines or other hosts for long term immunity or response, or for response or protection in newborns, e.g., pups, despite maternal immunity.

In a further aspect, the present invention relates to a method for expressing a gene product in a cell in vitro by introducing into the cell a modified recombinant virus having attenuated virulence and enhanced safety. The modified recombinant virus can include, within a nonessential region of the virus genome, a heterologous DNA sequence which encodes an antigenic protein, e.g. derived from rabies virus. The product can then be administered to individuals or animals to stimulate an immune response, and the administration can be alone or with other antigens in a multivalent or "cocktail" composition. The antibodies raised can be useful in individuals for the prevention or treatment of rabies or other maladies and, the antibodies from individuals or animals or the isolated in vitro expression products can be used in diagnostic kits, assays or tests to determine the presence or absence in a sample such as sera of rabies or other maladies or antigens therefrom or antibodies thereto (and therefore the absence or presence of the virus or of the products, or of an immune response to the virus or antigens).

In a still further aspect, the present invention relates to a modified recombinant virus and compositions containing such, either alone or with additional antigens or additional recombinants expressing such antigens in a "cocktail" or combination or multivalent composition and to methods employing such virus or composition to induce a response in a host, e.g., canines, felines, canines having maternal immunity. The virus can have nonessential virus-encoded genetic functions inactivated therein so that the virus has attenuated virulence, and the modified recombinant virus further contains DNA from a heterologous source in a nonessential region of the virus genome. The DNA can code for rabies virus antigen, either alone or in combination with other antigens of other maladies. In particular, the genetic functions are inactivated by deleting an open reading frame encoding a virulence factor or by utilizing naturally host restricted viruses. The virus used according to the present invention is advantageously a poxvirus, particularly a vaccinia virus or an avipox virus, such as fowlpox virus and canarypox virus. Advantageously, the open reading frame is selected from the group consisting of J2R, B13R+B14R, A26L, A56R, C7L–K1L, and I4L (by the terminology reported in Goebel et al., 1990a,b); and, the combination thereof. In this respect, the open reading frame comprises genomic regions which comprise a thymidine kinase gene, a hemorrhagic region, an A type inclusion body region, a hemagglutinin gene, a host range gene region or a large subunit, ribonucleotide reductase; or, the combination thereof. A suitable modified Copenhagen strain of vaccinia virus is identified as NYVAC (Tartaglia et al., 1992), or a vaccinia virus from which has been deleted J2R, B13R+B14R, A26L, A56R, C7L-K11 and I4L or a thymidine kinase gene, a hemorrhagic region, an A type inclusion body region, a hemagglutinin gene, a host range region, and a large subunit, ribonucleotide reductase (See also U.S. Pat. No. 5,364,773). Alternatively, a suitable poxvirus is an ALVAC or, a canarypox virus (Rentschler vaccine strain) which was attenuated, for instance, through more than 200 serial passages on chick embryo fibroblasts, a master seed therefrom was subjected to four successive plaque purifications under agar from which a plaque clone was amplified through five additional passages.

The invention in yet a further aspect relates to the product of expression of the inventive poxvirus-rabies recombinant and uses therefor, such as to form antigenic, immunological or vaccine compositions especially multivalent or "cocktail" or combination compositions for administration to a host, e.g., animals, such as canines or felines, or to a newborn animal or for administration for long-term protection or response or for treatment, prevention, diagnosis or testing, and, to methods employing such compositions.

These and other embodiments are disclosed or are obvious from and encompassed by the follow detailed description. It is, however, at this point noted that a multivalent or "cocktail" or combination composition can comprise any of: (i) a composition containing a poxvirus-rabies recombinant and an additional antigen such as an antigen from any one of: canine distemper virus antigen, e.g., CDV HA and/or F glycoproteins, canine adenovirus type 2 antigen, canine coronavirus antigen, canine parainfluenza antigen, canine parvovirus antigen, Leptospira Canicola-Icterohaemorrhagiae Bacterin antigen, any combination of these antigens, or feline leukemia virus antigen or feline herpesvirus antigen, or any combination of these antigens; or (ii) a composition containing a poxvirus-rabies recombinant and another poxvirus recombinant which contains coding for and expresses another antigen, such as an antigen from any one of: canine distemper virus antigen, e.g., CDV HA and/or F glycoproteins, canine adenovirus type 2 antigen, canine coronavirus antigen, canine parainfluenza antigen, canine parvovirus antigen, Leptospira Canicola-Icterohaemorrhagiae Bacterin antigen, any combination of these antigens, or feline leukemia virus antigen or feline herpesvirus antigen, or any combination of these antigens; or (iii) a composition containing a recombinant poxvirus which contains coding for and expresses rabies antigen and another antigen such as an antigen selected from any one of: canine distemper virus antigen, e.g., CDV HA and/or F glycoproteins, canine adenovirus type 2 antigen, canine coronavirus antigen, canine parainfluenza antigen, canine parvovirus antigen, Leptospira Canicola-Icterohaemorrhagiae Bacterin antigen, any combination of these antigens, or feline leukemia virus antigen or feline herpesvirus antigen, or any combination of these antigens.

Of course, in (i), the poxvirus-rabies recombinant can be substituted with the expression product therefrom; in (ii), the poxvirus-rabies recombinant can contain coding for and express additional antigens; and, in (iii), additional antigens can be present.

The present invention (compositions and methods and uses) finds a basis in the discoveries that NYVAC and ALVAC recombinants, particularly NYVAC- and ALVAC-rabies recombinants, do not exhibit efficacy interference in combinations with other antigens, be those other antigens present as the antigens themselves or as the product of co-or simultaneous expression (by being from expression of the same recombinant or additional recombinant(s)); and, that NYVAC- and ALVAC-rabies recombinants provide long-term protection and protection in the presence of maternal immunity. The present invention does not necessarily require an adjuvant, and can employ recombinant(s).

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 8 shows the DNA sequence (SEQ ID NO:27) of a canarypox PvuII fragment containing the C5 ORF.

DETAILED DESCRIPTION OF THE INVENTION

Figure 1:
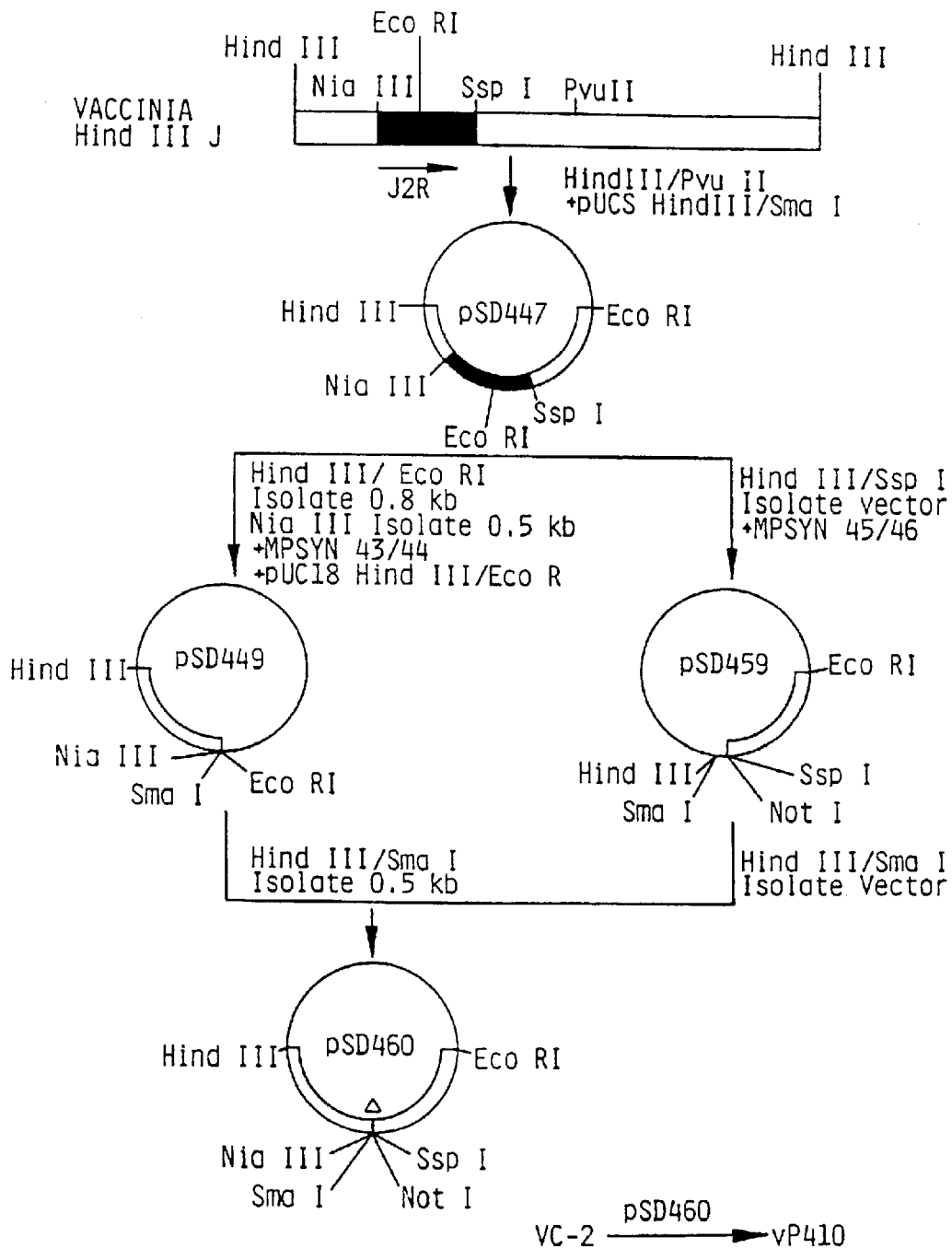
FIG. 1 schematically shows a method for the construction of plasmid pSD460 for deletion of thymidine kinase gene and generation of recombinant vaccinia virus vP410.

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed below (See U.S. Pat. No. 5,364,773). NYVAC was deposited on Mar. 6, 1997 under the terms of the Budapest Treaty with the American Type Culture Collection (ATCC), 12301 Parklawn Drive, Rockville, Md., 20852, USA, ATCC, accession number VR-2559. All designations of vaccinia restriction fragments, open reading frames and nucleotide positions are based on the terminology reported in Goebel et al., 1990a,b.

The deletion loci were also engineered as recipient loci for the insertion of foreign genes.

The regions deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;
(2) hemorrhagic region (u; B13R+B14R) vP553;
(3) A type inclusion body region (ATI; A26L) vP618;
(4) hemagglutinin gene (HA; A56R) vP723;
(5) host range gene region (C7L–K1L) vP804; and
(6) large subunit, ribonucleotide reductase (I4L) vP866 (NYVAC).

NYVAC is a genetically engineered vaccinia virus strain that was generated by the specific deletion of eighteen open reading frames encoding gene products associated with virulence and host range. NYVAC is highly attenuated by a number of criteria including i) decreased virulence after intracerebral inoculation in newborn mice, ii) inocuity in genetically ($nu^+/nu^+$) or chemically (cyclophosphamide) immunocompromised mice, iii) failure to cause disseminated infection in immunocompromised mice, iv) lack of significant induration and ulceration on rabbit skin, v) rapid clearance from the site of inoculation, and vi) greatly reduced replication competency on a number of tissue culture cell lines including those of human origin. Nevertheless, NYVAC based vectors induce excellent responses to extrinsic immunogens and provided protective immunity.

TROVAC refers to an attenuated fowlpox that was a plaque-cloned isolate derived from the FP-1 vaccine strain of fowlpoxvirus which is licensed for vaccination of chicks. ALVAC is an attenuated canarypox virus-based vector that was a plaque-cloned derivative of the licensed canarypox vaccine, Kanapox (Tartaglia et al., 1992). ALVAC has some general properties which are the same as some general properties of Kanapox. ALVAC-based recombinant viruses expressing extrinsic immunogens have also been demonstrated efficacious as vaccine vectors (Tartaglia et al., 1993a, b). This avipox vector is restricted to avian species for productive replication. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen (Taylor et al., 1992; Taylor et al., 1991b). Recent Phase I clinical trials in both Europe and the United States of a canarypox/rabies glycoprotein recombinant (ALVAC-RG) demonstrated that the experimental vaccine was well tolerated and induced protective levels of rabiesvirus neutralizing antibody titers (Cadoz et al., 1992; Fries et al., 1992). Additionally, peripheral blood mononuclear cells (PBMCs) derived from the ALVAC-RG vaccinates demonstrated significant levels of lymphocyte proliferation when stimulated with purified rabies virus (Fries et al., 1992).

NYVAC, ALVAC and TROVAC have also been recognized as unique among all poxviruses in that the National Institutes of Health ("NIH")(U.S. Public Health Service), Recombinant DNA Advisory Committee, which issues guidelines for the physical containment of genetic material such as viruses and vectors, i.e., guidelines for safety procedures for the use of such viruses and vectors which are based upon the pathogenicity of the particular virus or vector, granted a reduction in physical containment level: from BSL2 to BSL1. No other poxvirus has a BSL1 physical containment level. Even the Copenhagen strain of vaccinia virus—the common smallpox vaccine—has a higher physical containment level; namely, BSL2. Accordingly, the art has recognized that NYVAC, ALVAC and TROVAC have a lower pathogenicity than any other poxvirus.

Clearly based on the attenuation profiles of the NYVAC, ALVAC, and TROVAC vectors and their demonstrated ability to elicit both humoral and cellular immunological responses to extrinsic immunogens (Tartaglia et al., 1993a,b; Taylor et al., 1992; Konishi et al., 1992) such recombinant viruses offer a distinct advantage over previously described vaccinia-based recombinant viruses.

The administration procedure for recombinant poxvirus-rabies virus or expression product thereof, compositions of the invention such as immunological, antigenic or vaccine compositions or therapeutic compositions, including multivalent, "cocktail" or combination compositions, can be via a parenteral route (intradermal, intramuscular or subcutaneous). Such an administration enables a systemic immune response.

More generally, the inventive antigenic, immunological or vaccine poxvirus-rabies virus compositions or therapeutic compositions (compositions containing the poxvirus-rabies virus recombinants of the invention) can be prepared in accordance with standard techniques well known to those skilled in the pharmaceutical or veterinary art. Such compositions can be administered in dosages and by techniques well known to those skilled in the medical or veterinary arts taking into consideration such factors as the age, sex, weight, species and condition of the particular patient, and the route of administration. The compositions can be administered alone, or can be co-administered or sequentially administered with compositions of the invention or with "other" immunological, antigenic or vaccine or therapeutic compositions thereby providing multivalent or "cocktail" or combination compositions of the invention and methods employing them.

Such "other" compositions can include purified antigens from any one of: canine distemper virus antigen, e.g., CDV HA and/or F glycoproteins, canine adenovirus type 2 antigen, canine coronavirus antigen, canine parainfluenza antigen, canine parvovirus antigen, Leptospira Canicola-Icterohaemorrhagiae Bacterin antigen, any combination of these antigens, or feline leukemia virus antigen or feline herpesvirus antigen or any combination of these antigens; or, from the expression of such antigens by a recombinant poxvirus or other vector system in vitro; or, such "other" compositions can include a recombinant poxvirus or poxviruses which expresses(es) antigens from any one of: canine distemper virus antigen, e.g., CDV HA and/or F glycoproteins, canine adenovirus type 2 antigen, canine coronavirus antigen, canine parainfluenza antigen, canine parvovirus antigen, Leptospira Canicola-Icterohaemorrhagiae Bacterin antigen, any combination of these antigens, or feline leukemia virus antigen or feline herpes virus or any combination of these antigens. Again, the ingredients and manner (sequential or co-administration) of administration, as well as dosages can be determined taking into consideration such factors as the age, sex, weight, species and condition of the particular patient, and, the route of administration. In this regard, mention is also made of copending applications Ser. Nos. 08/220,151 filed Mar. 30, 1994 and 08/413,118 filed Mar. 29, 1995, directed to nucleotide and amino acid sequences of canine herpesvirus antigens and recombinants therefrom and uses thereof, and to U.S. applications Ser. Nos. 08/224,657, filed Apr. 6, 1994 and 08/416,616 filed Apr. 5, 1995, directed to poxvirus-canine distemper virus (CDV) recombinants and compositions and methods employing those recombinants, each of which is hereby incorporated herein by reference, especially insofar as recombinants, expression products therefrom and nucleic acid coding disclosed in these applications can be employed in "cocktail", multivalent or combination compositions or recombinants thereof of the present invention.

Examples of compositions of the invention include liquid preparations for orifice, e.g., oral, nasal, anal, vaginal, peroral, intragastric, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant poxvirus or antigens may be in admixture with a suitable carrier, diluent, or excipient such as sterile water, physiological saline, glucose or the like. The compositions can also be lyophilized. The compositions can contain auxiliary substances such as wetting or emulsifying agents, pH buffereing agents, adjuvants, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. Suitable dosages can also be based upon the examples below.

Further, the products of expression of the inventive recombinant poxviruses and compositions comprising them can be used directly to stimulate an immune response in individuals or in animals. Thus, the expression products can be used in compositions of the invention instead or in addition to the inventive recombinant poxvirus in the aforementioned compositions.

Additionally, the inventive recombinant poxvirus and the expression products therefrom and compositions of the invention stimulate an immune or antibody response in humans and animals; and therefore, those products are antigens. From those antibodies or antigens, by techniques well-known in the art, monoclonal antibodies can be prepared and, those monoclonal antibodies or the antigens, can be employed in well known antibody binding assays, diagnostic kits or tests to determine the presence or absence of particular rabies or other antigen(s); and therefore, the presence or absence of the virus or the "other" malady or expression of the antigen(s) (in rabies or "other" antigenic systems), or to determine whether an immune response to the virus or "other" malady or antigen(s) has simply been stimulated. Those monoclonal antibodies or the antigens can also be employed in immunoadsorption chromatography to recover or isolate rabies or "other" malady agents or expression products of the inventive recombinant poxvirus or compositions of the invention.

Methods for producing monoclonal antibodies and for uses of monoclonal antibodies, and, of uses and methods for rabies or "other" antigens—the expression products of the inventive poxvirus and compositions—are well known to those of ordinary skill in the art. They can be used in diagnostic methods, kits, tests or assays, as well as to recover materials by immunoadsorption chromatography or by immunoprecipitation.

Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H. U.S. Pat. No. 4,376,110, issued Mar. 8, 1983; incorporated herein by reference. Monoclonal antibodies have also been used to recover materials by immunoadsorption chromatography, e.g., Milstein, C. 1980, Scientific American 243:66, 70, incorporated herein by reference.

Accordingly, the inventive recombinant poxvirus and compositions have several hereinstated utilities. Other utilities also exist for embodiments of the invention.

A better understanding of the present invention and of its many advantages will be had from the following examples, given by way of illustration.

EXAMPLES

DNA Cloning and Synthesis. Plasmids were constructed, screened and grown by standard procedures (Maniatis et al., 1982; Perkus et al., 1985; Piccini et al., 1987). Restriction endonucleases were obtained from Bethesda Research Laboratories, Gaithersburg, MD, New England Biolabs, Beverly, Mass.; and Boehringer Mannheim Biochemicals, Indianapolis, Ind. Klenow fragment of E. coli polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection. The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Piccini et al., 1987).

The origins and conditions of cultivation of the Copenhagen strain of vaccinia virus and NYVAC has been previously described (Guo et al., 1989; Tartaglia et al., 1992). Generation of recombinant virus by recombination, in situ hybridization of nitrocellulose filters and screening for B-galactosidase activity are as previously described (Panicali et al., 1982; Perkus et al., 1989).

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC. ALVAC was deposited on Nov. 14, 1996 under the terms of the Budapest Treaty with the ATCC, accession number VR-2547.

The strain of fowlpox virus (FPV) designated FP-1 has been described previously (Taylor et al., 1988a). It is an attenuated vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established.

NYVAC, ALVAC and TROVAC viral vectors and their derivatives were propagated as described previously (Piccini et al., 1987; Taylor et al., 1988a,b). Vero cells and chick embryo fibroblasts (CEF) were propagated as described previously (Taylor et al., 1988a,b).

As to NYVAC and especially Examples 1 to 6, reference's made to U.S. Pat. No. 5,364,773, incorporated herein by reference.

Example 1

Construction of Plasmid pSD460 for Deletion of Thymidine Kinase Gene (J2R)

Referring now to FIG. 1, plasmid pSD406 contains vaccinia HindIII J (pos. 83359–88377) cloned into pUC8. pSD406 was cut with HindIII and PvuII, and the 1.7 kb fragment from the left side of HindIII J cloned into pUC8 cut with HindIII/SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 1.

To obtain a left flanking arm, a 0.8 kb HindIII/EcoRI fragment was isolated from pSD447, then digested with NlaIII and a 0.5 kb HindIII/NlaIII fragment isolated. Annealed synthetic oligonucleotides MPSYN43/MPSYN44 (SEQ ID NO:1/SEQ ID NO:2)

```
           SmaI
MPSYN43 5'      TAATTAACTAGCTACCCGGG       3'
MPSYN44 3' GTACATTAATTGATCGATGGGCCCTTAA 5'
           NlaIII                  EcoRI
``` were ligated with the 0.5 kb HindIII/NlaIII fragment into pUC18 vector plasmid cut with HindIII/EcoRI, generating plasmid pSD449.

To obtain a restriction fragment containing a vaccinia right flanking arm and pUC vector sequences, pSD447 was cut with SspI (partial) within vaccinia sequences and HindIII at the pUC/vaccinia junction, and a 2.9 kb vector fragment isolated. This vector fragment was ligated with annealed synthetic oligonucleotides MPSYN45/MPSYN46 (SEQ ID NO:3/SEQ ID NO:4)

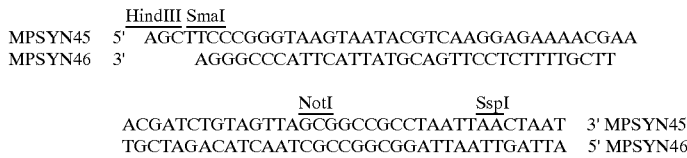

```
           HindIII SmaI
MPSYN45 5' AGCTTCCCGGGTAAGTAATACGTCAAGGAGAAAACGAA
MPSYN46 3'        AGGGCCCATTCATTATGCAGTTCCTCTTTTGCTT NotI              SspI
ACGATCTGTAGTTAGCGGCCGCCTAATTAACTAAT  3' MPSYN45
TGCTAGACATCAATCGCCGGCGGATTAATTGATTA  5' MPSYN46
``` generating pSD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. $^{32}$P labelled probe was synthesized by primer extension using MPSYN45 (SEQ ID NO:3) as template and the complementary 20 mer oligonucleotide MPSYN47 (SEQ ID NO:5) (5' TTAGTTAATTAGGCGGCCGC 3') as primer. Recombinant virus vP410 was identified by plaque hybridization.

Example 2

Construction of Plasmid pSD486 for Deletion of Hemorrhagic Region (B13R+B14R)

Figure 2:
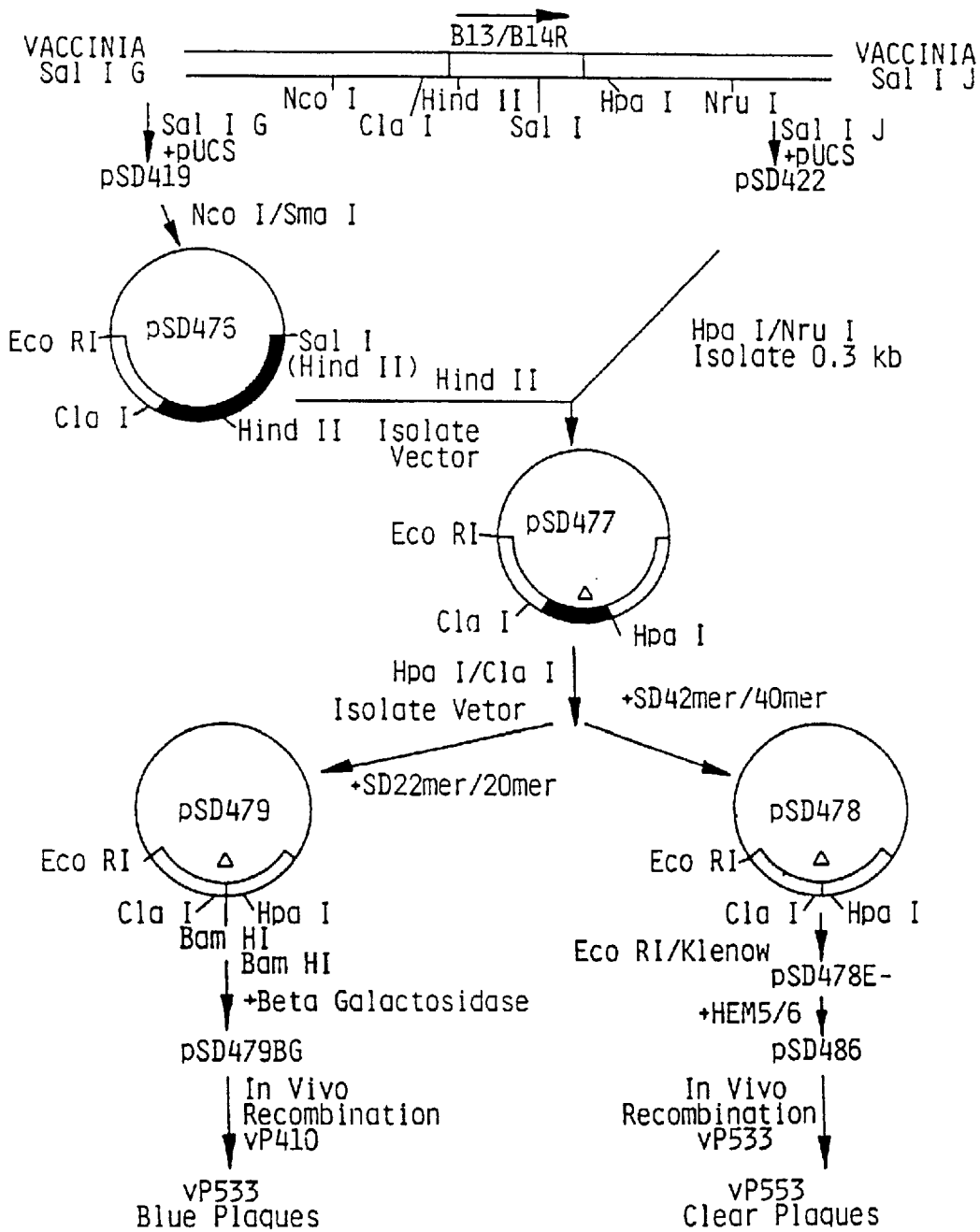
FIG. 2 schematically shows a method for the construction of plasmid pSD486 for deletion of hemorrhagic region and generation of recombinant vaccinia virus vP553.

Referring now to FIG. 2, plasmid pSD419 contains vaccinia SalI G (pos. 160,744–173,351) cloned into pUC8. pSD422 contains the contiguous vaccinia SalI fragment to the right, SalI J (pos. 173,351–182,746) cloned into pUC8. To construct a plasmid deleted for the hemorrhagic region, u, B13R–B14R (pos. 172,549–173,552), pSD419 was used as the source for the left flanking arm and pSD422 was used as the source of the right flanking arm. The direction of transcription for the u region is indicated by an arrow in FIG. 2.

To remove unwanted sequences from pSD419, sequences to the left of the NcoI site (pos. 172,253) were removed by digestion of pSD419 with NcoI/SmaI followed by blunt ending with Klenow fragment of E. coil polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is indicated by a triangle. The remaining B13R coding sequences in pSD477 were removed by digestion with ClaI/HpaI, and the resulting vector fragment was ligated with annealed synthetic oligonucleotides SD22mer/SD20mer (SEQ ID NO:6/SEQ ID NO:7)

```
              ClaI            BamHI HpaI
SD22mer 5' CGATTACTATGAAGGATCCGTT  3'
SD20mer 3'     TAATGATACTTCCTAGGCAA  5'
``` generating pSD479. pSD479 contains an initiation codon (underlined) followed by a BamHI site. To place E. coli Beta-galactosidase in the B13–B14 (u) deletion locus under the control of the u promoter, a 3.2 kb Ba-mHI fragment containing the Beta-galactosidase gene (Shapira et al., 1983) was inserted into the BamHI site of pSD479, generating pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R–B14R region is deleted and is replaced by Beta-galactosidase.

To remove Beta-galactosidase sequences from vP533, plasmid pSD486, a derivative of pSD477 containing a polylinker region but no initiation codon at the u deletion junction, was utilized. First the ClaI/HpaI vector fragment from pSD477 referred to above was ligated with annealed synthetic oligonucleotides SD42mer/SD40mer (SEQ ID NO:8/SEQ ID NO:9)

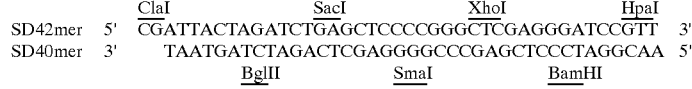

```
           ClaI         SacI         XhoI          HpaI
SD42mer 5' CGATTACTAGATCTGAGCTCCCCGGGCTCGAGGGATCCGTT 3'
SD40mer 3'     TAATGATCTAGACTCGAGGGGCCCGAGCTCCCTAGGCAA 5'
              BglII        SmaI         BamHI
``` generating plasmid pSD478. Next the EcoRI site at the pUC/vaccinia junction was destroyed by digestion of pSD478 with EcoRI followed by blunt ending with Klenow fragment of E. coli polymerase and ligation, generating plasmid pSD478E⁻. pSD478E⁻ was digested with BamHI and HDaI and ligated with annealed synthetic oligonucleotides HEM5/HEM6 (SEQ ID NO:10/SEQ ID NO:11)

```
         BamHI  EcoRI    HpaI
HEM5 5'  GATCCGAATTCTAGCT  3'
HEM6 3'      GCTTAAGATCGA  5'
``` generating plasmid pSD486. pSD486 was used as donor plasmid for recombination with recombinant vaccinia virus vP533, generating vP553, which was isolated as a clear plaque in the presence of X-gal.

Example 3

Construction of Plasmid pMP494Δ for Deletion of ATI Region (A26L)

Figure 3:
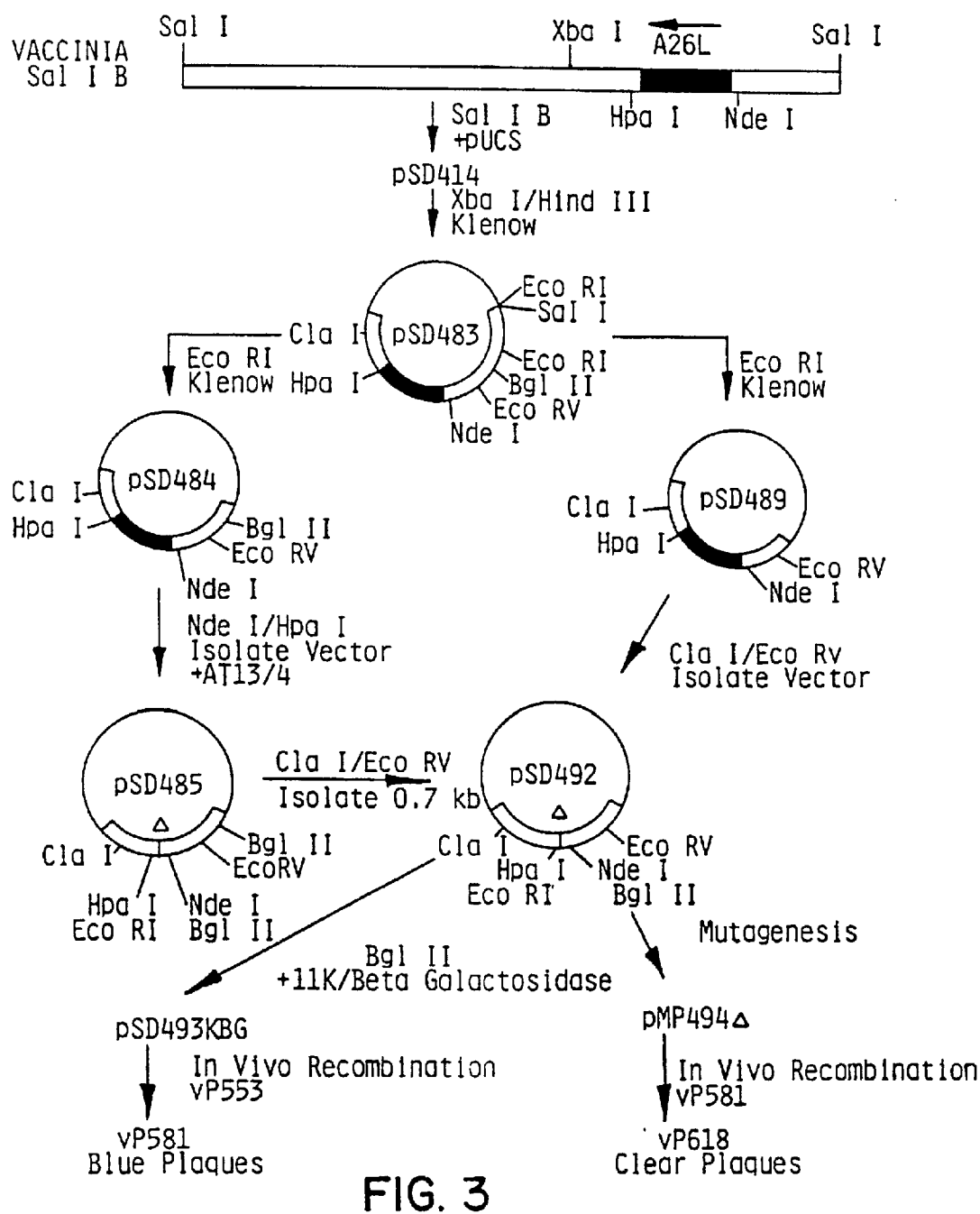
FIG. 3 schematically shows a method for the construction of plasmid pMP494Δ for deletion of ATI region and generation of recombinant vaccinia virus vP618.

Referring now to FIG. 3, pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of E. coli polymerase and ligated, resulting in plasmid pSD483. To remove unwanted vaccinia DNA sequences to the right of the A26L region, pSD483 was cut with EcoRI (pos. 140,665 and at the pUc/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:12/SEQ ID NO:13)

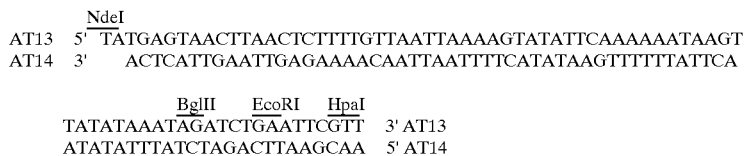

reconstructing the region upstream from A26L and replacing the A26L ORF with a short polylinker region containing the restriction sites BqlII, EcoRI and HDaI, as indicated above. The resulting plasmid was designated pSD485. Since the BqlII and EcoRI sites in the polylinker region of pSD485 are not unique, unwanted BqlII and EcoRI sites were removed from plasmid pSD483 (described above) by digestion with BqlII (pos. 140,136) and with EcoRI at the pUC/vaccinia junction, followed by blunt ending with Klenow fragment of E. coli polymerase and ligation. The resulting plasmid was designated pSD489. The 1.8 kb ClaI (pos. 137,198)/EcoRV (pos. 139,048) fragment from pSD489 containing the A26L ORF was replaced with the corresponding 0.7 kb polylinker-containing ClaI/EcoRV fragment from pSD485, generating pSD492. The BglII and EcoRI sites in the polylinker region of pSD492 are unique.

A 3.3 kb BalII cassette containing the E. coli Beta-galactosidase gene (Shapira et al., 1983) under the control of the vaccinia 11 kDa promoter (Bertholet et al., 1985; Perkus et al., 1990) was inserted into the BqlII site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Beta-galactosidase sequences from vaccinia recombinant virus vP581, the polylinker region of plasmid pSD492 was deleted by mutagenesis (Mandecki, 1986) using synthetic oligonucleotide MPSYN177 (SEQ ID NO:14) (5'AAAATGGGCGTGGATTGTTAACTTTATATAACTT-ATTTTTTGAATATAC 3'). In the resulting plasmid, pMP494Δ, vaccinia DNA encompassing positions [137,889–138,937], including the entire A26L ORF is deleted. Recombination between the pMP494Δ and the Beta-galactosidase containing vaccinia recombinant, vP581, resulted in vaccinia deletion mutant vP618, which was isolated as a clear plaque in the presence of X-gal.

Example 4

Construction of Plasmid pSD467 for Deletion of Hemagglutinin Gene (A56R)

Figure 4:
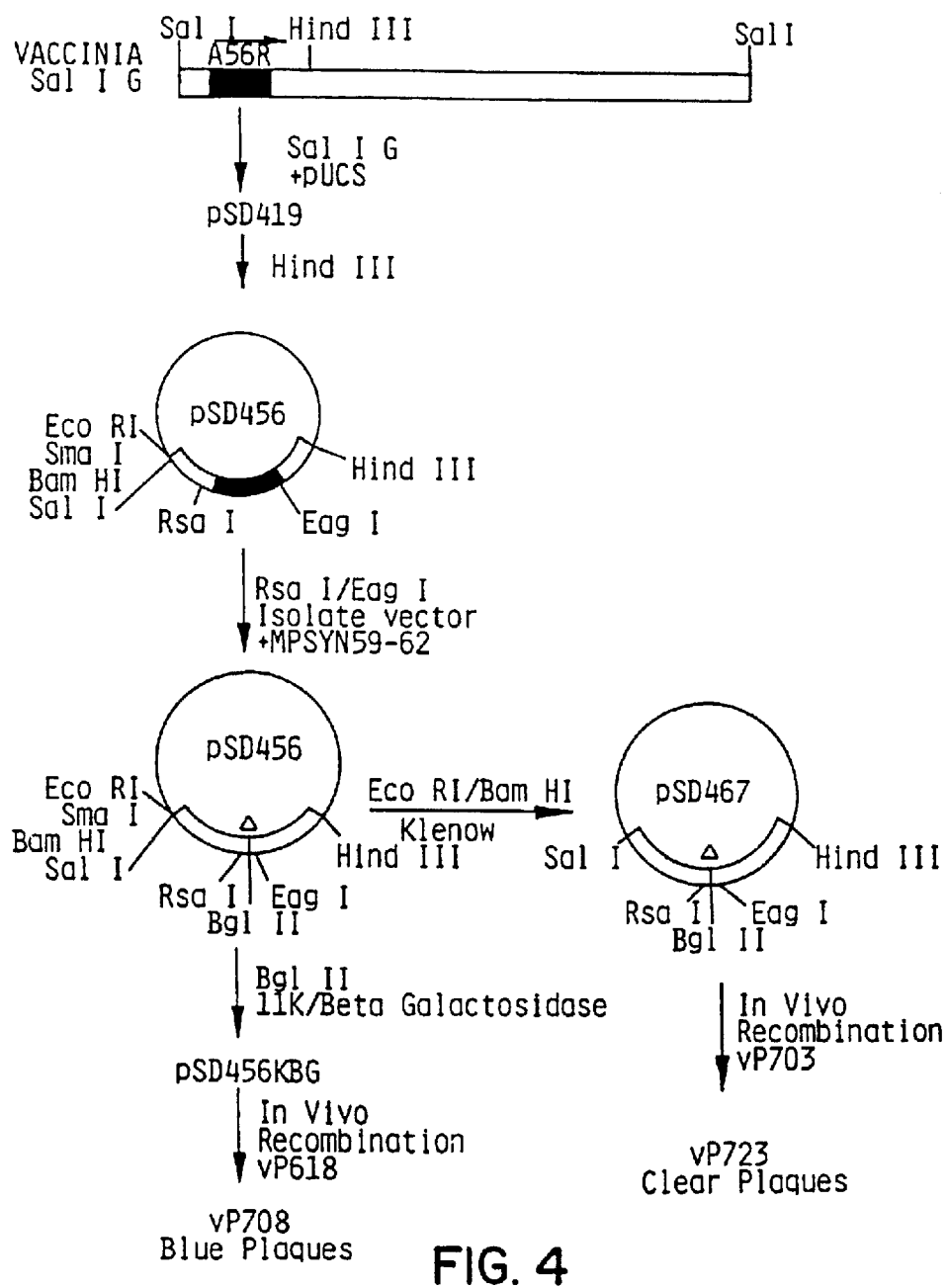
FIG. 4 schematically shows a method for the construction of plasmid pSD467 for deletion of hemagglutinin gene and generation of recombinant vaccinia virus vP723.

Referring now to FIG. 4, vaccinia SalI G restriction fragment (pos. 160,744–173,351) crosses the HindIII A/B junction (pos. 162,539). pSD419 contains vaccinia SalI G cloned into pUC8. The direction of transcription for the hemagglutinin (HA) gene is indicated by an arrow in FIG. 4. Vaccinia sequences derived from HindIII B were removed by digestion of pSD419 with HindIII within vaccinia sequences and at the pUC/vaccinia junction followed by ligation. The resulting plasmid, pSD456, contains the HA gene, A56R, flanked by 0.4 kb of vaccinia sequences to the left and 0.4 kb of vaccinia sequences to the right. A56R coding sequences were removed by cutting pSD456 with RsaI (partial; pos. 161,090) upstream from A56R coding sequences, and with EagI (pos. 162,054) near the end of the gene. The 3.6 kb RsaI/EagI vector fragment from pSD456 was isolated and ligated with annealed synthetic oligonucleotides MPSYN59 (SEQ ID NO:15), MPSYN62 (SEQ ID NO:16), MPSYN60 (SEQ ID NO:17), and MPSYN61 (SEQ ID NO:18)

reconstructing the DNA sequences upstream from the A56R ORF and replacing the A56R ORF with a polylinker region as indicated above. The resulting plasmid is pSD466. The vaccinia deletion in pSD466 encompasses positions [161, 185–162,053]. The site of the deletion in pSD466 is indicated by a triangle in FIG. 4.

A 3.2 kb BglII/BamHI (partial) cassette containing the *E. coli* Beta-galactosidase gene (Shapira et al., 1983) under the control of the vaccinia 11 kDa promoter (Bertholet et al., 1985; Guo et al., 1989) was inserted into the BglII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and Ba-mHI sites were removed from the pUC/vaccinia junction by digestion of pSD466 with EcoRI/BamHI followed by blunt ending with Klenow fragment of *E. coli* polymerase and ligation. Recombination between vP708 and pSD467 resulted in recombinant vaccinia deletion mutant, vP723, which was isolated as a clear plaque in the presence of X-gal.

Example 5

Construction of Plasmid pMPCSK1Δ for Deletion of Open Reading Frames [C7L-K1L]

Figure 5:
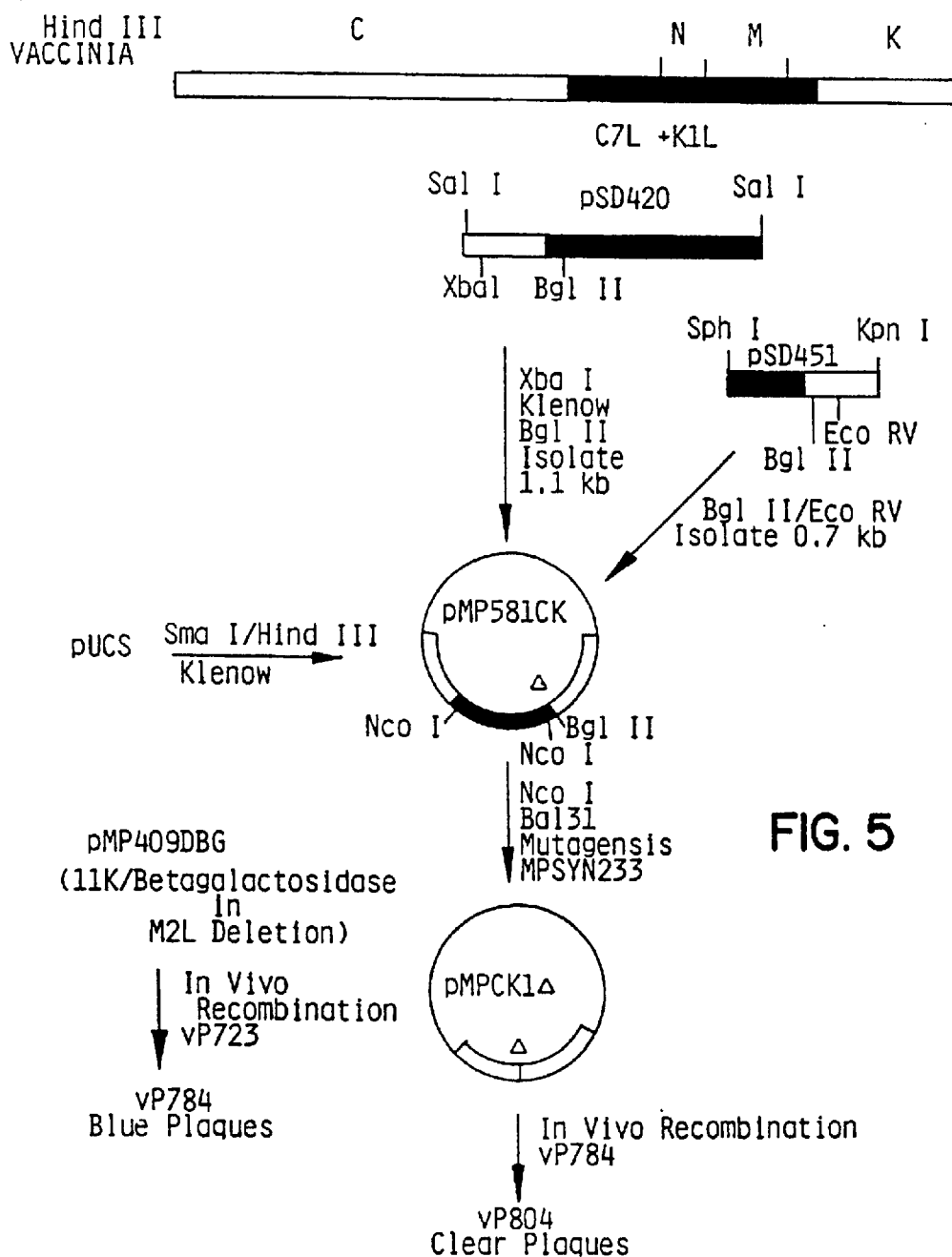
FIG. 5 schematically shows a method for the construction of plasmid PMPCK1Δ for deletion of gene cluster [C7L-K1L] and generation of recombinant vaccinia virus vP804.

Referring now to FIG. 5, the following vaccinia clones were utilized in the construction of pMPCSK1Δ. pSD420 is SalI H cloned into pUC8. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUC8.

To provide a substrate for the deletion of the [C7L-K1L] gene cluster from vaccinia, *E. coli* Beta-galactosidase was first inserted into the vaccinia M2L deletion locus (Guo et al., 1990) as follows. To eliminate the BglII site in pSD409, the plasmid was cut with BcrIII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide BglII MPSYN82 (SEQ ID NO:19) 5'TTTCTGTATATTTGCACCAATTTAGATCTT-ACTCAAAATATGTAACAATA 3'The resulting plasmid, pMP409D, contains a unique BglII site inserted into the M2L deletion locus as indicated above. A 3.2 kb BamHI (partial)/BglII cassette containing the *E. coli* Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L-K1L] was assembled in pUC8 cut with SmaI, HindIII and blunt ended with Klenow fragment of *E. coli* polymerase. The left flanking arm consisting of vaccinia HindIII C sequences was obtained by digestion of pSD420 with XbaI (pos. 18,628) followed by blunt ending with Klenow fragment of *E. coli* polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the BglII site (pos. 29,062) in HindIII K. The site of the deletion of vaccinia sequences in plasmid pMP581CK is indicated by a triangle in FIG. 5.

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide MPSYN233 (SEQ ID NO:20)  5'-TGTCATTTAACA-CTATACTCATATTAATAAAAATAATATTTATT-3'. The resulting plasmid, pMPCSK1Δ, is deleted for vaccinia sequences positions 18,805–29,108, encompassing 12 vaccinia open reading frames [C7L-K1L]. Recombination between pMPCSK1Δ and the Beta-galactosidase containing vaccinia recombinant, vP784, resulted in vaccinia deletion mutant, vP804, which was isolated as a clear plaque in the presence of X-gal.

Example 6

Construction of Plasmid pSD548 for Deletion of Large Subunit, Ribonucleotide Reductase (I4L)

Figure 6:
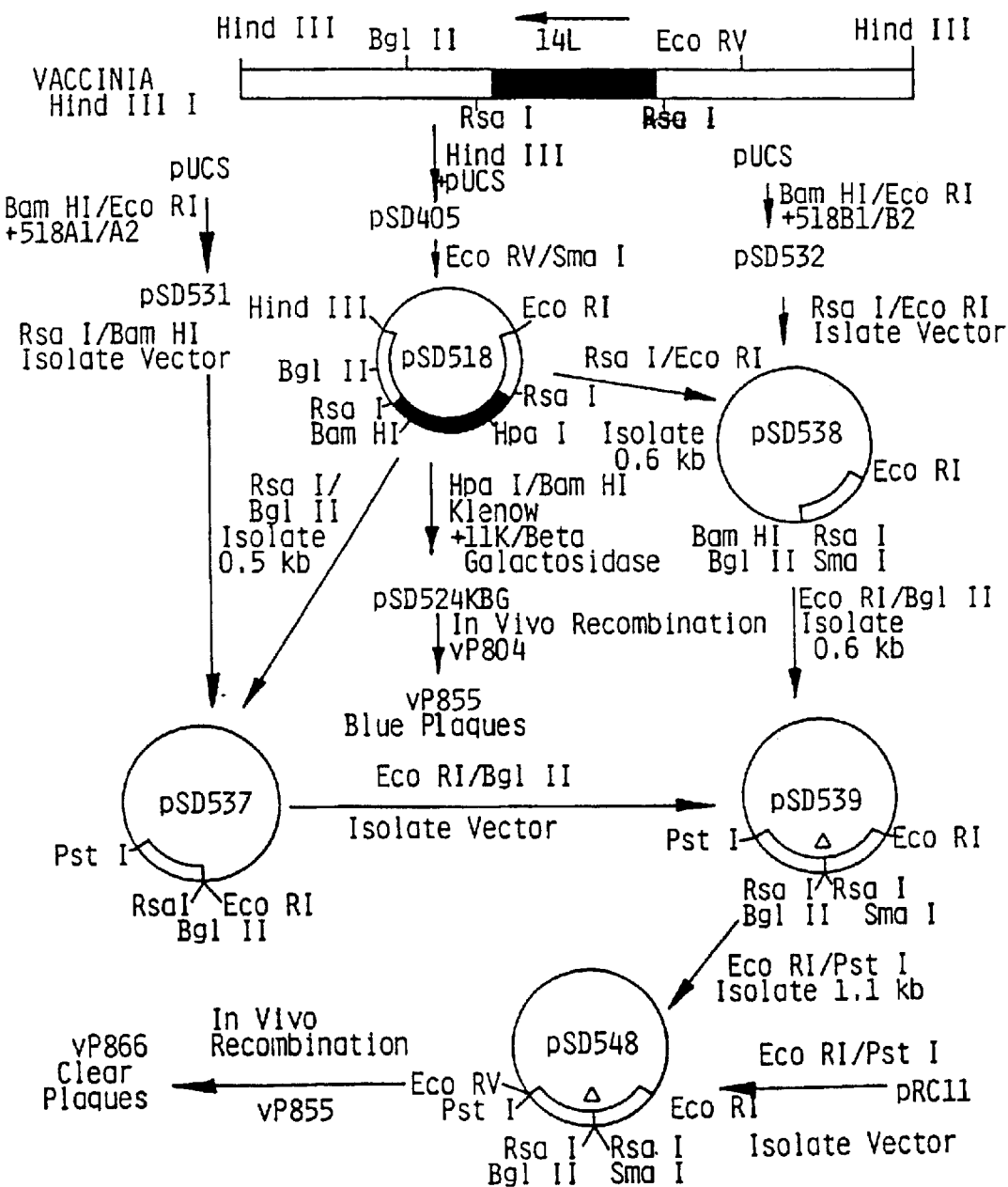
FIG. 6 schematically shows a method for the construction of plasmid pSD548 for deletion of large subunit, ribonucleotide reductase and generation of recombinant vaccinia virus vP866 (NYVAC)

Referring now to FIG. 6, plasmid pSD405 contains vaccinia HindIII I (pos. 63,875–70,367) cloned in pUC8. pSD405 was digested with EcoRV within vaccinia sequences (pos. 67,933) and with SmaI at the pUC/vaccinia junction, and ligated, forming plasmid pSD518. pSD518 was used as the source of all the vaccinia restriction fragments used in the construction of pSD548.

The vaccinia I4L gene extends from position 67,371–65,059. Direction of transcription for I4L is indicated by an arrow in FIG. 6. To obtain a vector plasmid fragment deleted for a portion of the I4L coding sequences, pSD518 was digested with BamHI (pos. 65,381) and HpaI (pos. 67,001) and blunt ended using Klenow fragment of *E. coli* polymerase. This 4.8 kb vector fragment was ligated with a 3.2 kb SmaI cassette containing the *E. coli* Beta-galactosidase gene (Shapira et al., 1983) under the control of the vaccinia 11 kDa promoter (Bertholet et al., 1985; Perkus et al., 1990), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 6.

To construct a vector plasmid to accept the left vaccinia flanking arm, pUC8 was cut with BamHI/EcoRI and ligated with annealed synthetic oligonucleotides 518A1/518A2 (SEQ ID NO:21/SEQ ID NO:22)

```
              BamHI    RsaI
518A1   5'   GATCCTGAGTACTTTGTAATATAATGATATATATTTTCACTTTATCTCAT
518A2   3'           GACTCATGAAACATTATATTACTATATATAAAAGTGAAATAGAGTA

BglII       EcoRI
                TTGAGAATAAAAAGATCTTAGG           3'   518A1
                AACTCTTATTTTTCTAGAATCCTTAA       5'   518A2
``` forming plasmid pSD531. pSD531 was cut with RsaI (partial) and BamHI and a 2.7 kb vector fragment isolated. pSD518 was cut with BclII (pos. 64,459)/RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 (SEQ ID NO:23/SEQ ID NO:24)

Polymerase chain reactions (PCR) (Engelke et al., 1988) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC."

```
              BamHI BglII   SmaI
518B1   5'   GATCCAGATCTCCCGGGAAAAAAATTATTTAACTTTTCATTAATAG—
518B2   3'        GTCTAGAGGGCCCTTTTTTTAATAAATTGAAAAGTAATTATC—

RsaI      EcoRI
       GGATTTGACGTATGTAGCGTACTAGG       3'   518B1
       CCTAAACTGCATACTACGCATGATCCTTAA   5'   518B2
``` forming plasmid pSD532. pSD532 was cut with RsaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of I4L coding sequences.

The right vaccinia flanking arm was isolated as a 0.6 kb EcoRI/BqlII fragment from pSD538 and ligated into pSD537 vector plasmid cut with EcoRI/BqlII. In the resulting plasmid, pSD539, the I4L ORF (pos. 65,047–67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 6. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, a pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected.

Example 7

Insertion of A Rabies Glycoprotein G Gene Into NYVAC

The gene encoding rabies glycoprotein G under the control of the vaccinia H6 promoter (Taylor et al., 1988a,b) was inserted into TK deletion plasmid pSD513. pSD513 is identical to plasmid pSD460 (FIG. 1) except for the presence of a polylinker region.

Figure 7:
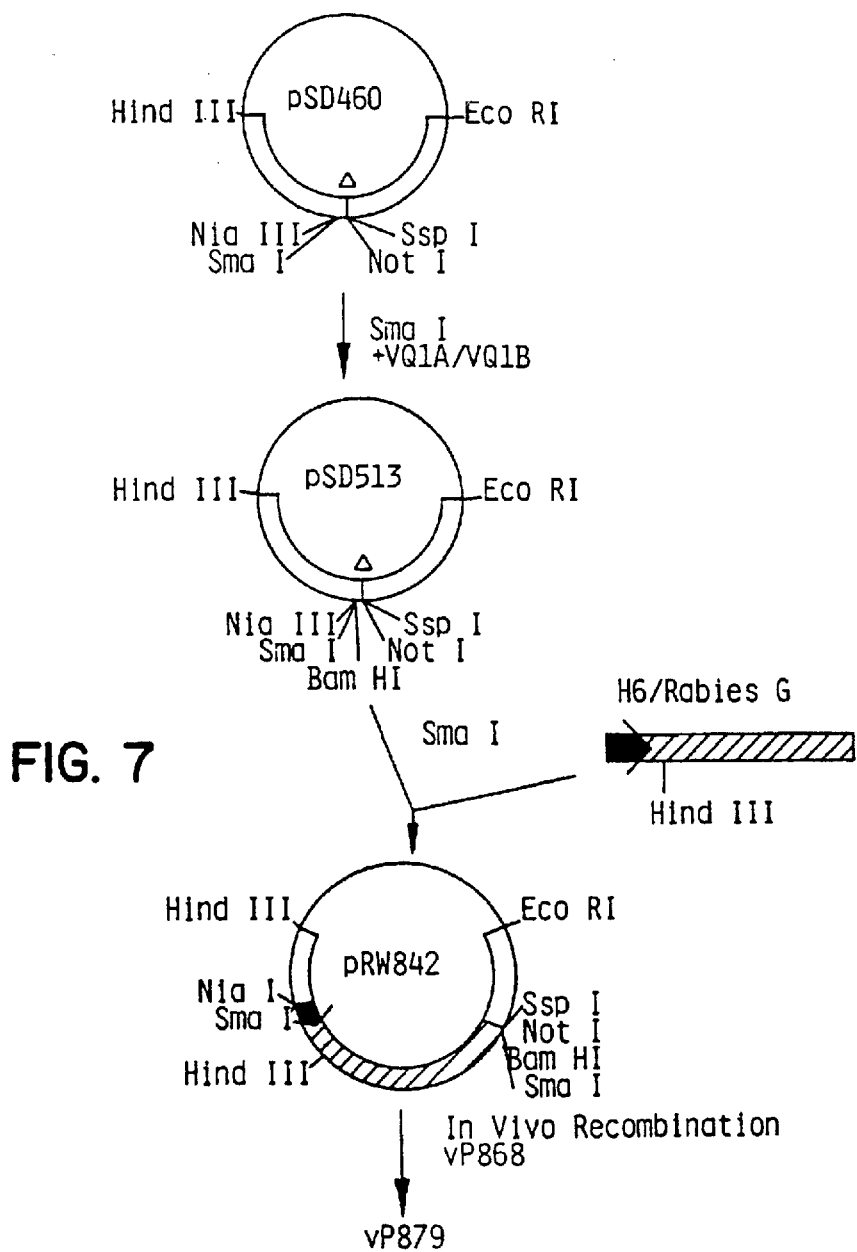
FIG. 7 schematically shows a method for the construction of plasmid pRW842 for insertion of rabies glycoprotein G gene into the TK deletion locus and generation of recombinant vaccinia virus vP879.

Referring now to FIG. 7, the polylinker region was inserted by cutting pSD460 with SmaI and ligating the plasmid vector with annealed synthetic oligonucleotides VQ1A/VQ1B (SEQ ID NO:25/SEQ ID NO:26)

```
              SmaI    BglII   XhoI    PstI      NarI    BamHI
VQ1A   5'   GGGAGATCTCTCGAGCTGCAGGGGCGCCGGATCCTTTTTCT   3'
VQ1B   3'   CCCTCTAGAGAGCTCGACGTCCCGCGGCCTAGGAAAAAGA    5'
``` to form vector plasmid pSD513. pSD513 was cut with SmaI and ligated with a SmaI ended 1.8 kb cassette containing the gene encoding the rabies glycoprotein G gene under the control of the vaccinia H6 promoter (Taylor et al., 1988a,b). The resulting plasmid was designated pRW842. pRW842 was used as donor plasmid for recombination with NYVAC rescuing virus (vP866). Recombinant vaccinia virus vP879 was identified by plaque hybridization using $^{32}$p-labelled DNA probe to rabies glycoprotein G coding sequences.

The modified recombinant viruses of the present invention provide advantages as recombinant vaccine vectors. The attenuated virulence of the vector advantageously reduces the opportunity for the possibility of a runaway infection due to vaccination in the vaccinated individual and also diminishes transmission from vaccinated to unvaccinated individuals or contamination of the environment.

The modified recombinant viruses are also advantageously used in a method for expressing a gene product in a cell cultured in vitro by introducing into the cell the modified recombinant virus having foreign DNA which codes for and expresses gene products in the cell.

Example 8

Construction of ALVAC Recombinants Expressing Rabies Virus Glycoprotein G

This example describes the development of ALVAC, a canarypox virus vector and, of a canarypox-rabies recombinant designated as ALVAC-RG (vCP65) and its safety and efficacy.

Cells and Viruses. The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

Construction of a Canarypox Insertion Vector. An 880 bp canarypox PvuII fragment was cloned between the PvuII sites of pUC9 to form pRW764.5. The sequence of this fragment is shown in FIG. 8 (SEQ ID NO. 27) between positions 1372 and 2251. The limits of an open reading frame designated as C5 were defined. It was determined that the open reading frame was initiated at position 166 within the fragment and terminated at position 487. The C5 deletion was made without interruption of open reading frames. Bases from position 167 through position 455 were replaced with the sequence (SEQ ID NO:28) GCTTCCCGGGAAT-TCTAGCTAGCTAGTTT. This replacement sequence contains HindIII, SmaI and EcoRI insertion sites followed by translation stops and a transcription termination signal recognized by vaccinia virus RNA polymerase (Yuen et al., 1987). Deletion of the C5 ORF was performed as described below. Plasmid pRW764.5 was partially cut with RsaI and the linear product was isolated. The RsaI linear fragment was recut with BglII and the pRW764.5 fragment now with a RsaI to BglII deletion from position 156 to position 462 was isolated and used as a vector for the following synthetic oligonucleotides:

RW145 (SEQ ID NO:29):
  ACTCTCAAAAGCTTCCCGGGAAT-TCTAGCTAGCTAGTTTTTATAAA

RW146 (SEQ ID NO:30):
  GATCTTTATAAAAACTAGCTAGCTA-GAATTCCCGGGAAGCTTTTGAGAGT

Oligonucleotides RW145 and RW146 were annealed and inserted into the pRW 764.5 RsaI and BglII vector described above. The resulting plasmid is designated pRW831.

Construction of Insertion Vector Containing the Rabies G Gene. Construction of pRW838 is illustrated below. Oligonucleotides A through E, which overlap the translation initiation codon of the H6 promoter with the ATG of rabies G, were cloned into pUC9 as pRW737. Oligonucleotides A through E contain the H6 promoter, starting at NruI, through the HindIII site of rabies G followed by BglII. Sequences of oligonucleotides A through E ((SEQ ID NO:31)–(SEQ ID NO:35)) are:

A (SEQ ID NO:31): CTGAAATTATTTCATTATCGC-GATATCCGTTAA GTTTGTATCGTAATGGTTCCT-CAGGCTCTCCTGTTTGT

B (SEQ ID NO:32): CATTACGATACAAACTTAACG-GATATCGCGATAA TGAAATAATTTCAG

C (SEQ ID NO:33): ACCCCTTCTGGTTTTTCCGTTGT-GTTTTGGGAAA TTCCCTATTTACACGATCCCA-GACAAGCTTAGATCTCAG

D (SEQ ID NO:34): CTGAGATCTAAGCTTGTCTGG-GATCGTGTAAATA GGGAATTTCCCAAAACA

E (SEQ ID NO:35): CAACGGAAAAACCA-GAAGGGGTACAAACAGGAGA GCCTGAGGAAC

The diagram of annealed oligonucleotides A through E is as follows:

```
          A                    C
_____|_____
_____|_____|_____
          B           E           D
```

Oligonucleotides A through E were kinased, annealed (95° C. for 5 minutes, then cooled to room temperature), and inserted between the PvuII sites of pUC9. The resulting plasmid, pRW737, was cut with HindIII and BglII and used as a vector for the 1.6 kbp HindIII-BglII fragment of ptg155PRO (Kieny et al., 1984) generating pRW739. The ptg155PRO HindIII site is 86 bp downstream of the rabies G translation initiation codon. BglII is downstream of the rabies G translation stop codon in ptg155PRO. pRW739 was partially cut with NruI, completely cut with BglII, and a 1.7 kbp NruI-BglII fragment, containing the 3' end of the H6 promoter previously described (Taylor et al., 1988a,b; Guo et al., 1989; Perkus et al., 1989) through the entire rabies G gene, was inserted between the NruI and BamHI sites of pRW824. The resulting plasmid is designated pRW832. Insertion into pRW824 added the H6 promoter 5' of NruI. The pRW824 sequence of BamHI followed by SmaI is (SEQ ID NO:36): GGATCCCCGGG. pRW824 is a plasmid that contains a nonpertinent gene linked precisely to the vaccinia virus H6 promoter. Digestion with NruI and BamHI completely excised this nonpertinent gene. The 1.8 kbp pRW832 SmaI fragment, containing H6 promoted rabies G, was inserted into the SmaI of pRW831, to form plasmid pRW838.

Development of ALVAC-RG. Plasmid pRW838 was transfected into ALVAC infected primary CEF cells by using the calcium phosphate precipitation method previously described (Panicali et al., 1982; Piccini et al., 1987). Positive plaques were selected on the basis of hybridization to a specific rabies G probe and subjected to 6 sequential rounds of plaque purification until a pure population was achieved. One representative plaque was then amplified and the resulting ALVAC recombinant was designated ALVAC-RG (vCP65) (see also FIGS. 9A and 9B). The correct insertion of the rabies G gene into the ALVAC genome without subsequent mutation was confirmed by sequence analysis.

Immunofluorescence. During the final stages of assembly of mature rabies virus particles, the glycoprotein component is transported from the golgi apparatus to the plasma membrane where it accumulates with the carboxy terminus extending into the cytoplasm and the bulk of the protein on the external surface of the cell membrane. In order to confirm that the rabies glycoprotein expressed in ALVAC-RG was correctly presented, immunofluorescence was performed on primary CEF cells infected with ALVAC or ALVAC-RG. Immunofluorescence was performed as previously described (Taylor et al., 1990) using a rabies G monoclonal antibody. Strong surface fluorescence was detected on CEF cells infected with ALVAC-RG but not with the parental ALVAC.

Immunoprecipitation. Preformed monolayers of primary CEF, Vero (a line of African Green monkey kidney cells ATCC # CCL81) and MRC-5 cells (a fibroblast-like cell line derived from normal human fetal lung tissue ATCC # CCL171) were inoculated at 10 pfu per cell with parental virus ALVAC and recombinant virus ALVAC-RG in the presence of radiolabelled $^{35}$S-methionine and treated as previously described (Taylor et al., 1990). Immunoprecipitation reactions were performed using a rabies G specific monoclonal antibody. Efficient expression of a rabies specific glycoprotein with a molecular weight of approximately 67 kDa was detected with the recombinant ALVAC-RG. No rabies specific products were detected in uninfected cells or cells infected with the parental ALVAC virus.

Sequential Passaging Experiment. In studies with ALVAC virus in a range of non-avian species no proliferative infection or overt disease was observed (Taylor et al., 1991b). However, in order to establish that neither the parental nor recombinant virus could be adapted to grow in non-avian cells, a sequential passaging experiment was performed.

The two viruses, ALVAC and ALVAC-RG, were inoculated in 10 sequential blind passages in three cell substrates:
  (1) Primary chick embryo fibroblast (CEF) cells produced from 11 day old white leghorn embryos;
  (2) Vero cells—a continuous line of African Green monkey kidney cells (ATCC # CCL81); and
  (3) MRC-5 cells—a diploid cell line derived from human fetal lung tissue (ATCC # CCL171).

The initial inoculation was performed at an m.o.i. of 0.1 pfu per cell using three 60 mm dishes of each cell substrate containing $2 \times 10^6$ cells per dish. One dish was inoculated in the presence of 40 µg/ml of Cytosine arabinoside (Ara C), an inhibitor of DNA replication. After an absorption period of 1 hour at 37° C., the inoculum was removed and the monolayer washed to remove unabsorbed virus. At this time the medium was replaced with 5 ml of EMEM+2% NBCS on two dishes (samples to and t7) and 5 ml of EMEM+2% NBCS containing 40 µg/ml Ara C on the third (sample t7A). Sample t0 was frozen at −70° C. to provide an indication of the residual input virus. Samples t7 and t7A were incubated at 37° C. for 7 days, after which time the contents were harvested and the cells disrupted by indirect sonication.

One ml of sample t7 of each cell substrate was inoculated undiluted onto three dishes of the same cell substrate (to provide samples to, t7 and t7A) and onto one dish of primary CEF cells. Samples t0, t7 and t7A were treated as for passage one. The additional inoculation on CEF cells was included to provide an amplification step for more sensitive detection of virus which might be present in the non-avian cells.

This procedure was repeated for 10 (CEF and MRC-5) or 8 (Vero) sequential blind passages. Samples were then frozen and thawed three times and assayed by titration on primary CEF monolayers.

Virus yield in each sample was then determined by plaque titration on CEF monolayers under agarose. Summarized results of the experiment are shown in Tables 1 and 2.

The results indicate that both the parental ALVAC and the recombinant ALVAC-RG are capable of sustained replication on CEF monolayers with no loss of titer. In Vero cells, levels of virus fell below the level of detection after 2 passages for ALVAC and 1 passage for ALVAC-RG. In MRC-5 cells, a similar result was evident, and no virus was detected after 1 passage. Although the results for only four passages are shown in Tables 1 and 2 the series was continued for 8 (Vero) and 10 (MRC-5) passages with no detectable adaptation of either virus to growth in the non-avian cells.

In passage 1 relatively high levels of virus were present in the t7 sample in MRC-5 and Vero cells. However this level of virus was equivalent to that seen in the to sample and the t7A sample incubated in the presence of Cytosine arabinoside in which no viral replication can occur. This demonstrated that the levels of virus seen at 7 days in non-avian cells represented residual virus and not newly replicated virus.

In order to make the assay more sensitive, a portion of the 7 day harvest from each cell substrate was inoculated onto a permissive CEF monolayer and harvested at cytopathic effect (CPE) or at 7 days if no CPE was evident. The results of this experiment are shown in Table 3. Even after amplification through a permissive cell substrate, virus was only detected in MRC-5 and Vero cells for two additional passages. These results indicated that under the conditions used, there was no adaptation of either virus to growth in Vero or MRC-5 cells.

Inoculation of Macaques. Four HIV seropositive macaques were initially inoculated with ALVAC-RG as described in Table 4. After 100 days these animals were re-inoculated to determine a booster effect, and an additional seven animals were inoculated with a range of doses. Blood was drawn at appropriate intervals and sera analyzed, after heat inactivation at 56° C. for 30 minutes, for the presence of anti-rabies antibody using the Rapid Fluorescent Focus Inhibition Assay (Smith et al., 1973).

Inoculation of Chimpanzees. Two adult male chimpanzees (50 to 65 kg weight range) were inoculated intramuscularly or subcutaneously with $1 \times 10^7$ pfu of vCP65. Animals were monitored for reactions and bled at regular intervals for analysis for the presence of anti-rabies antibody with the RFFI test (Smith et al., 1973). Animals were re-inoculated with an equivalent dose 13 weeks after the initial inoculation.

Inoculation of Mice. Groups of mice were inoculated with 50 to 100 µl of a range of dilutions of different batches of vCP65. Mice were inoculated in the footpad. On day 14, mice were challenged by intracranial inoculation of from 15 to 43 mouse $LD_{50}$ of the virulent CVS strain of rabies virus. Survival of mice was monitored and a protective dose 50% ($PD_{50}$) calculated at 28 days post-inoculation.

Inoculation of Dogs and Cats. Ten beagle dogs, 5 months old, and 10 cats, 4 months old, were inoculated subcutaneously with either 6.7 or 7.7 $\log_{10}$ $TCID_{50}$ of ALVAC-RG. Four dogs and four cats were not inoculated. Animals were bled at 14 and 28 days post-inoculation and anti-rabies antibody assessed in an RFFI test. The animals receiving 6.7 $\log_{10}$ $TCID_{50}$ of ALVAC-RG were challenged at 29 days post-vaccination with 3.7 $\log_{10}$ mouse $LD_{50}$ (dogs) or 4.3 $\log_{10}$ mouse $LD_{50}$ (cats) of the NYGS rabies virus challenge strain.

Inoculation of Squirrel Monkeys. Three groups of four squirrel monkeys (*Saimiri sciureus*) were inoculated with one of three viruses (a) ALVAC, the parental canarypox virus, (b) ALVAC-RG, the recombinant expressing the rabies G glycoprotein or (c) vCP37, a canarypox recombinant expressing the envelope glycoprotein of feline leukemia virus. Inoculations were performed under ketamine anaesthesia. Each animal received at the same time: (1) 20 µl instilled on the surface of the right eye without scarification; (2) 100 µl as several droplets in the mouth; (3) 100 µl in each of two intradermal injection sites in the shaven skin of the external face of the right arm; and (4) 100 µl in the anterior muscle of the right thigh.

Four monkeys were inoculated with each virus, two with a total of 5.0 $\log_{10}$ pfu and two with a total of 7.0 $\log_{10}$ pfu. Animals were bled at regular intervals and sera analyzed for the presence of antirabies antibody using an RFFI test (Smith et al., 1973). Animals were monitored daily for reactions to vaccination. Six months after the initial inoculation the four monkeys receiving ALVAC-RG, two monkeys initially receiving vCP37, and two monkeys initially receiving ALVAC, as well as one naive monkey were inoculated with 6.5 $\log_{10}$ pfu of ALVAC-RG subcutaneously. Sera were monitored for the presence of rabies neutralizing antibody in an RFFI test (Smith et al., 1973).

Inoculation of Human Cell Lines with ALVAC-RG. In order to determine whether efficient expression of a foreign gene could be obtained in non-avian cells in which the virus does not productively replicate, five cell types, one avian and four non-avian, were analyzed for virus yield, expression of the foreign rabies G gene and viral specific DNA accumulation. The cells inoculated were:

(a) Vero, African Green monkey kidney cells, ATCC # CCL81;

(b) MRC-5, human embryonic lung, ATCC # CCL 171;

(c) WISH human amnion, ATCC # CCL 25;

(d) Detroit-532, human foreskin, Downs's syndrome, ATCC # CCL 54; and (e) Primary CEF cells.

Chicken embryo fibroblast cells produced from 11 day old white leghorn embryos were included as a positive control. All inoculations were performed on preformed monolayers of $2 \times 10^6$ cells as discussed below.

A. Methods for DNA analysis. Three dishes of each cell line were inoculated at 5 pfu/cell of the virus under test, allowing one extra dish of each cell line un-inoculated. One dish was incubated in the presence of 40 μg/ml of cytosine arabinoside (Ara C). After an adsorption period of 60 minutes at 37° C., the inoculum was removed and the monolayer washed twice to remove unadsorbed virus. Medium (with or without Ara C) was then replaced. Cells from one dish (without Ara C) were harvested as a time zero sample. The remaining dishes were incubated at 37° C. for 72 hours, at which time the cells were harvested and used to analyze DNA accumulation. Each sample of $2 \times 10^6$ cells was resuspended in 0.5 ml phosphate buffered saline (PBS) containing 40 mM EDTA and incubated for 5 minutes at 37° C. An equal volume of 1.5% agarose prewarmed at 42° C. and containing 120 mM EDTA was added to the cell suspension and gently mixed. The suspension was transferred to an agarose plug mold and allowed to harden for at least 15 min. The agarose plugs were then removed and incubated for 12–16 hours at 50° C. in a volume of lysis buffer (1% sarkosyl, 100 μg/ml proteinase K, 10 mM Tris HCl pH 7.5, 200 mM EDTA) that completely covers the plug. The lysis buffer was then replaced with 5.0 ml sterile 0.5×TBE (44.5 mM Tris-borate, 44.5 mM boric acid, 0.5 mM EDTA) and equilibrated at 4° C. for 6 hours with 3 changes of TBE buffer. The viral DNA within the plug was fractionated from cellular RNA and DNA using a pulse field electrophoresis system. Electrophoresis was performed for 20 hours at 180 V with a ramp of 50–90 sec at 150° C. in 0.5×TBE. The DNA was run with lambda DNA molecular weight standards. After electrophoresis the viral DNA band was visualized by staining with ethidium bromide. The DNA was then transferred to a nitrocellulose membrane and probed with a radiolabelled probe prepared from purified ALVAC genomic DNA.

B. Estimation of virus yield. Dishes were inoculated exactly as described above, with the exception that input multiplicity was 0.1 pfu/cell. At 72 hours post infection, cells were lysed by three successive cycles of freezing and thawing. Virus yield was assessed by plaque titration on CEF monolayers.

C. Analysis of expression of Rabies G gene. Dishes were inoculated with recombinant or parental virus at a multiplicity of 10 pfu/cell, allowing an additional dish as an uninfected virus control. After a one hour absorption period, the medium was removed and replaced with methionine free medium. After a 30 minute period, this medium was replaced with methionine-free medium containing 25 uCi/ml of $^{35}$S-Methionine. Infected cells were labelled overnight (approximately 16 hours), then lysed by the addition of buffer A lysis buffer. Immunoprecipitation was performed as previously described (Taylor et al., 1990) using a rabies G specific monoclonal antibody.

Results: Estimation of Viral Yield. The results of titration for yield at 72 hours after inoculation at 0.1 pfu per cell are shown in Table 5. The results indicate that while a productive infection can be attained in the avian cells, no increase in virus yield can be detected by this method in the four non-avian cell systems.

Analysis of Viral DNA Accumulation. In order to determine whether the block to productive viral replication in the non-avian cells occurred before or after DNA replication, DNA from the cell lysates was fractionated by electrophoresis, transferred to nitrocellulose and probed for the presence of viral specific DNA. DNA from uninfected CEF cells, ALVAC-RG infected CEF cells at time zero, ALVAC-RG infected CEF cells at 72 hours post-infection and ALVAC-RG infected CEF cells at 72 hours post-infection in the presence of 40 μg/ml of cytosine arabinoside all showed some background activity, probably due to contaminating CEF cellular DNA in the radiolabelled ALVAC DNA probe preparation. However, ALVAC-RG infected CEF cells at 72 hours post-infection exhibited a strong band in the region of approximately 350 kbp representing ALVAC-specific viral DNA accumulation. No such band is detectable when the culture is incubated in the presence of the DNA synthesis inhibitor, cytosine arabinoside. Equivalent samples produced in Vero cells showed a very faint band at approximately 350 kbp in the ALVAC-RG infected Vero cells at time zero. This level represented residual virus. The intensity of the band was amplified at 72 hours post-infection indicating that some level of viral specific DNA replication had occurred in Vero cells which had not resulted in an increase in viral progeny. Equivalent samples produced in MRC-5 cells indicated that no viral specific DNA accumulation was detected under these conditions in this cell line. This experiment was then extended to include additional human cell lines, specifically WISH and Detroit-532 cells. ALVAC infected CEF cells served as a positive control. No viral specific DNA accumulation was detected in either WISH or Detroit cells inoculated with ALVAC-RG. It should be noted that the limits of detection of this method have not been fully ascertained and viral DNA accumulation may be occurring, but at a level below the sensitivity of the method. Other experiments in which viral DNA replication was measured by $^3$H-thymidine incorporation support the results obtained with Vero and MRC-5 cells.

Analysis of Rabies Gene Expression. To determine if any viral gene expression, particularly that of the inserted foreign gene, was occurring in the human cell lines even in the absence of viral DNA replication, immunoprecipitation experiments were performed on $^{35}$S-methionine labelled lysates of avian and non-avian cells infected with ALVAC and ALVAC-RG. The results of immunoprecipitation using a rabies G specific monoclonal antibody illustrated specific immunoprecipitation of a 67 kDa glycoprotein in CEF, Vero and MRC-5, WISH and Detroit cells infected with ALVAC-RG. No such specific rabies gene products were detected in any of the uninfected and parentally infected cell lysates.

The results of this experiment indicated that in the human cell lines analyzed, although the ALVAC-RG recombinant was able to initiate an infection and express a foreign gene product under the transcriptional control of the H6 early/late vaccinia virus promoter, the replication did not proceed through DNA replication, nor was there any detectable viral progeny produced. In the Vero cells, although some level of ALVAC-RG specific DNA accumulation was observed, no viral progeny was detected by these methods. These results would indicate that in the human cell lines analyzed the block to viral replication occurs prior to the onset of DNA replication, while in Vero cells, the block occurs following the onset of viral DNA replication.

In order to determine whether the rabies glycoprotein expressed in ALVAC-RG was immunogenic, a number of animal species were tested by inoculation of the recombinant. The efficacy of current rabies vaccines is evaluated in a mouse model system. A similar test was therefore performed using ALVAC-RG. Nine different preparations of virus (including one vaccine batch (J) produced after 10 serial tissue culture passages of the seed virus) with infectious titers ranging from 6.7 to 8.4 $\log_{10}$ $TCID_{50}$ per ml were serially diluted and 50 to 100 μl of dilutions inoculated into the footpad of four to six week old mice. Mice were challenged 14 days later by the intracranial route with 300 μl of the CVS strain of rabies virus containing from 15 to 43 mouse $LD_{50}$ as determined by lethality titration in a control group of mice. Potency, expressed as the $PD_{50}$ (Protective dose 50%), was calculated at 14 days post-challenge. The results of the experiment are shown in Table 6. The results indicated that ALVAC-RG was consistently able to protect mice against rabies virus challenge with a $PD_{50}$ value ranging from 3.33 to 4.56 with a mean value of 3.73 (STD 0.48). As an extension of this study, male mice were inoculated intracranially with 50 μl of virus containing 6.0 $\log_{10}$ $TCID_{50}$ of ALVAC-RG or with an equivalent volume of an uninfected cell suspension. Mice were sacrificed on days 1, 3 and 6 post-inoculation and their brains removed, fixed and sectioned. Histopathological examination showed no evidence for neurovirulence of ALVAC-RG in mice.

In order to evaluate the safety and efficacy of ALVAC-RG for dogs and cats, a group of 14, 5 month old beagles and 14, 4 month old cats were analyzed. Four animals in each species were not vaccinated. Five animals received 6.7 $\log_{10}$ $TCID_{50}$ subcutaneously and five animals received 7.7 $\log_{10}$ $TCID_{50}$ by the same route. Animals were bled for analysis for anti-rabies antibody. Animals receiving no inoculation or 6.7 $\log_{10}$ $TCID_{50}$ of ALVAC-RG were challenged at 29 days post-vaccination with 3.7 $\log_{10}$ mouse $LD_{50}$ (dogs, in the temporal muscle) or 4.3 $\log_{10}$ mouse $LD_{50}$ (cats, in the neck) of the NYGS rabies virus challenge strain. The results of the experiment are shown in Table 7.

No adverse reactions to inoculation were seen in either cats or dogs with either dose of inoculum virus. Four of 5 dogs immunized with 6.7 $\log_{10}$ $TCID_{50}$ had antibody titers on day 14 post-vaccination and all dogs had titers at 29 days. All dogs were protected from a challenge which killed three out of four controls. In cats, three of five cats receiving 6.7 $\log_{10}$ $TCID_{50}$ had specific antibody titers on day 14 and all cats were positive on day 29 although the mean antibody titer was low at 2.9 IU. Three of five cats survived a challenge which killed all controls. All cats immunized with 7.7 $\log_{10}$ $TCID_{50}$ had antibody titers on day 14 and at day 29 the Geometric Mean Titer was calculated as 8.1 International Units.

The immune response of squirrel monkeys (*Saimiri sciureus*) to inoculation with ALVAC, ALVAC-RG and an unrelated canarypox virus recombinant was examined. Groups of monkeys were inoculated as described above and sera analyzed for the presence of rabies specific antibody. Apart from minor typical skin reactions to inoculation by the intradermal route, no adverse reactivity was seen in any of the monkeys. Small amounts of residual virus were isolated from skin lesions after intradermal inoculation on days two and four post-inoculation only. All specimens were negative on day seven and later. There was no local reaction to intra-muscular injection. All four monkeys inoculated with ALVAC-RG developed anti-rabies serum neutralizing antibodies as measured in an RFFI test. Approximately six months after the initial inoculation all monkeys and one additional naive monkey were re-inoculated by the subcutaneous route on the external face of the left thigh with 6.5 $\log_{10}$ $TCID_{50}$ of ALVAC-RG. Sera were analyzed for the presence of anti-rabies antibody. The results are shown in Table 8.

Four of the five monkeys naive to rabies developed a serological response by seven days post-inoculation with ALVAC-RG. All five monkeys had detectable antibody by 11 days post-inoculation. Of the four monkeys with previous exposure to the rabies glycoprotein, all showed a significant increase in serum neutralization titer between days 3 and 7 post-vaccination. The results indicate that vaccination of squirrel monkeys with ALVAC-RG does not produce adverse side-effects and a primary neutralizing antibody response can be induced. An anamnestic response is also induced on re-vaccination. Prior exposure to ALVAC or to a canarypox recombinant expressing an unrelated foreign gene does not interfere with induction of an anti-rabies immune response upon re-vaccination.

The immunological response of HIV-2 seropositive macaques to inoculation with ALVAC-RG was assessed. Animals were inoculated as described above and the presence of anti-rabies serum neutralizing antibody assessed in an RFFI test. The results, shown in Table 9, indicated that HIV-2 positive animals inoculated by the subcutaneous route developed anti-rabies antibody by 11 days after one inoculation. An anamnestic response was detected after a booster inoculation given approximately three months after the first inoculation. No response was detected in animals receiving the recombinant by the oral route. In addition, a series of six animals were inoculated with decreasing doses of ALVAC-RG given by either the intra-muscular or subcutaneous routes. Five of the six animals inoculated responded by 14 days post-vaccination with no significant difference in antibody titer.

Two chimpanzees with prior exposure to HIV were inoculated with 7.0 $\log_{10}$ pfu of ALVAC-RG by the subcutaneous or intra-muscular route. At 3 months post-inoculations both animals were re-vaccinated in an identical fashion. The results are shown in Table 10.

No adverse reactivity to inoculation was noted by either intramuscular or subcutaneous routes. Both chimpanzees responded to primary inoculation by 14 days and a strongly rising response was detected following re-vaccination.

TABLE 1

Sequential Passage of ALVAC in Avian and non-Avian Cells.

| | CEF | Vero | MRC-5 |
|---|---|---|---|
| Pass 1 | | | |
| Sample to[a] | 2.4 | 3.0 | 2.6 |
| t7[b] | 7.0 | 1.4 | 0.4 |
| t7A[c] | 1.2 | 1.2 | 0.4 |
| Pass 2 | | | |
| Sample to | 5.0 | 0.4 | N.D.[d] |
| t7 | 7.3 | 0.4 | N.D. |
| t7A | 3.9 | N.D. | N.D. |
| Pass 3 | | | |
| Sample to | 5.4 | 0.4 | N.D. |
| t7 | 7.4 | N.D. | N.D. |
| t7A | 3.8 | N.D. | N.D. |
| Pass 4 | | | |
| Sample to | 5.2 | N.D. | N.D. |
| t7 | 7.1 | N.D. | N.D. |
| t7A | 3.9 | N.D. | N.D. |

[a]This sample was harvested at zero time and represents the residual input virus. The titer is expressed as $\log_{10}$ pfu per ml.
[b]This sample was harvested at 7 days post-infection.
[c]This sample was inoculated in the presence of 40 μg/ml of Cytosine arabinoside and harvested at 7 days post infection.
[d]Not detectable

TABLE 2

Sequential Passage of ALVAC-RG in Avian and non-Avian Cells

| | CEF | Vero | MRC-5 |
|---|---|---|---|
| Pass 1 | | | |
| Sample to[a] | 3.0 | 2.9 | 2.9 |
| t7[b] | 7.1 | 1.0 | 1.4 |
| t7A[c] | 1.8 | 1.4 | 1.2 |
| Pass 2 | | | |
| Sample t0 | 5.1 | 0.4 | 0.4 |
| t7 | 7.1 | N.D.[d] | N.D. |
| t7A | 3.8 | N.D. | N.D. |
| Pass 3 | | | |
| Sample t0 | 5.1 | 0.4 | N.D. |
| t7 | 7.2 | N.D. | N.D. |
| t7A | 3.6 | N.D. | N.D. |
| Pass 4 | | | |
| Sample t0 | 5.1 | N.D. | N.D. |
| t7 | 7.0 | N.D. | N.D. |
| t7A | 4.0 | N.D. | N.D |

[a]This sample was harvested at zero time and represents the residual input virus. The titer is expressed as $\log_{10}$ pfu per ml.
[b]This sample was harvested at 7 days post-infection.
[c]This sample was inoculated in the presence of 40 μg/ml of Cytosine arabinoside and harvested at 7 days post-infection.
[d]Not detectable.

TABLE 3

Amplification of residual virus by passage in CEF cells

| | CEF | Vero | MRC-5 |
|---|---|---|---|
| a) ALVAC | | | |
| Pass 2[a] | 7.0[b] | 6.0 | 5.2 |
| 3 | 7.5 | 4.1 | 4.9 |
| 4 | 7.5 | N.D.[c] | N.D. |
| 5 | 7.1 | N.D. | N.D. |
| b) ALVAC-RG | | | |
| Pass 2[a] | 7.2 | 5.5 | 5.5 |
| 3 | 7.2 | 5.0 | 5.1 |
| 4 | 7.2 | N.D. | N.D. |
| 5 | 7.2 | N.D. | N.D. |

[a]Pass 2 represents the amplification in CEF cells of the 7 day sample from Pass 1.
[b]Titer expressed as $\log_{10}$ pfu per ml
[c]Not Detectable

TABLE 4

Schedule of inoculation of rhesus macaques with ALVAC-RG (VCP65)

| Animal | | Inoculation |
|---|---|---|
| 176L | Primary: | $1 \times 10^8$ pfu of vCP65 orally in TANG |
| | Secondary: | $1 \times 10^7$ pfu of vCP65 plus $1 \times 10^7$ pfu of vCP82[a] by SC route |
| 185 L | Primary: | $1 \times 10^8$ pfu of vCP65 orally in Tang |
| | Secondary: | $1 \times 10^7$ pfu of vCP65 plus $1 \times 10^7$ pfu of vCP82 by SC route |
| 177 L | Primary: | $5 \times 10^7$ pfu SC of vCP65 by SC route |
| | Secondary: | $1 \times 10^7$ pfu of vCP65 plus $1 \times 10^7$ pfu of vCP82 by SC route |
| 186L | Primary: | $5 \times 10^7$ pfu of vCP65 by SC route |
| | Secondary: | $1 \times 10^7$ pfu of vCP65 plus $1 \times 10^7$ pfu of vCP82 by SC route |
| 178L | Primary: | $1 \times 10^7$ pfu of vCP65 by SC route |
| 182L | Primary: | $1 \times 10^7$ pfu of vCP65 by IM route |
| 179L | Primary: | $1 \times 10^6$ pfu of vCP65 by SC route |
| 183L | Primary: | $1 \times 10^6$ pfu of vCP65 by IM route |
| 180L | Primary: | $1 \times 10^6$ pfu of vCP65 by SC route |
| 184L | Primary: | $1 \times 10^5$ pfu of vCP65 by IM route |
| 187L | Primary | $1 \times 10^7$ pfu of vCP65 orally |

[a]vCP82 is a canarypox virus recombinant expressing the measles virus fusion and hemagglutinin genes.

TABLE 5

Analysis of yield in avian and non-avian cells inoculated with ALVAC-RG

| Sample Time Cell Type | t0 | t72 | t72A[b] |
|---|---|---|---|
| Expt 1 | | | |
| CEF | 3.3[a] | 7.4 | 1.7 |
| Vero | 3.0 | 1.4 | 1.7 |
| MRC-5 | 3.4 | 2.0 | 1.7 |
| Expt 2 | | | |
| CEF | 2.9 | 7.5 | <1.7 |

TABLE 5-continued

Analysis of yield in avian and non-avian cells inoculated with ALVAC-RG

| Sample Time Cell Type | t0 | t72 | t72A[b] |
|---|---|---|---|
| WISH | 3.3 | 2.2 | 2.0 |
| Detroit-532 | 2.8 | 1.7 | <1.7 |

[a]Titer expressed as $\log_{10}$ pfu per ml
[b]Culture incubated in the presence of 40 μg/ml of Cytosine arabinoside

TABLE 6

Potency of ALVAC-RG as tested in mice

| Test | Challenge Dose[a] | PD$_{50}$[b] |
|---|---|---|
| Initial seed | 43 | 4.56 |
| Primary seed | 23 | 3.34 |
| Vaccine Batch H | 23 | 4.52 |
| Vaccine Batch I | 23 | 3.33 |
| Vaccine Batch K | 15 | 3.64 |
| Vaccine Batch L | 15 | 4.03 |
| Vaccine Batch M | 15 | 3.32 |
| Vaccine Batch N | 15 | 3.39 |
| Vaccine Batch J | 23 | 3.42 |

[a]Expressed as mouse LD$_{50}$
[b]Expressed as $\log_{10}$ TCID$_{50}$

TABLE 7

Efficacy of ALVAC-RG in dog and cats

| | Dogs | | Cats | |
|---|---|---|---|---|
| Dose | Antibody[a] | Survival[b] | Antibody | Survival |
| 6.7 | 11.9 | 5/5 | 2.9 | 3/5 |
| 7.7 | 10.1 | N.T. | 8.1 | N.T. |

[a]Antibody at day 29 post inoculation expressed as the geometric mean titer in International Units.
[b]Expressed as a ratio of survivors over animals challanged

TABLE 8

Anti-rabies serological response of Squirrel monkeys inoculated with canarypox recombinants

| Monkey # | Previous Exposure | Rabies serum-neutralizing antibody[a] | | | | | |
|---|---|---|---|---|---|---|---|
| | | -196[b] | 0 | 3 | 7 | 11 | 21 | 28 |
| 22 | ALVACC | NT[g] | <1.2 | <1.2 | <1.2 | 2.1 | 2.3 | 2.2 |
| 51 | ALVACC | NT | <1.2 | <1.2 | 1.7 | 2.2 | 2.2 | 2.2 |
| 39 | vCP37[d] | NT | <1.2 | <1.2 | 1.7 | 2.1 | 2.2 | N.T.[g] |
| 55 | vCP37[d] | NT | <1.2 | <1.2 | 1.7 | 2.2 | 2.1 | N.T. |
| 37 | ALVAC-RG[e] | 2.2 | <1.2 | <1.2 | 3.2 | 3.5 | 3.5 | 3.2 |
| 53 | ALVAC-RG[e] | 2.2 | <1.2 | <1.2 | 3.6 | 3.6 | 3.6 | 3.4 |
| 38 | ALVAC-RG[f] | 2.7 | <1.7 | <1.7 | 3.2 | 3.8 | 3.6 | N.T. |
| 54 | ALVAC-RG[f] | 3.2 | <1.7 | <1.5 | 3.6 | 4.2 | 4.0 | 3.6 |
| 57 | None | NT | <1.2 | <1.2 | 1.7 | 2.7 | 2.7 | 2.3 |

[a]As determined by RFFI test on days indicated and expressed in International Units
[b]Day-196 represents serum from day 28 after priinary vaccination
[c]Animals received 5.0 $\log_{10}$ TCID$_{50}$ of ALVAC
[d]Animals received 5.0 $\log_{10}$ TCID$_{50}$ of vCP37
[e]Animals received 5.0 $\log_{10}$ TCID$_{50}$ of ALVAC-RG
[f]Animals received 7.0 $\log_{10}$ of ALVAC-RG
[g]Not tested.

TABLE 9

Inoculation of rhesus macaques with ALVAC-RG[a]

| | Route of Primary Inoculation | | | | | | | | | |
|---|---|---|---|---|---|---|---|---|---|---|
| Days post-Inoculation | or/Tang 176L[b] | SC 185L | SC 177L | SC 186L | SC 178L | IM 182L | SC 179L | IM 183L | SC 180L | IM 184L | OR 187L[b] |
| -84 | — | — | — | — | | | | | | | |
| -9 | — | — | — | — | — | | — | | | | |
| 3 | — | — | — | — | | | | | | | |
| 6 | — | — | ± | ± | | | | | | | |
| 11 | — | — | 16[d] | 128 | | | | | | | |
| 19 | — | — | 32 | 128 | — | | — | | | | |
| 35 | — | — | 32 | 512 | | | | | | | |
| 59 | — | — | 64 | 256 | | | | | | | |
| 75 | — | — | 64 | 128 | — | | — | | | | |
| 99[c] | — | — | 64 | 256 | — | — | — | — | — | — | |
| 2 | — | — | 32 | 256 | — | — | — | — | — | — | |
| 6 | — | — | 512 | 512 | — | — | — | — | — | — | |
| 15 | 16 | 16 | 512 | 512 | 64 | 32 | 64 | 128 | 32 | — | — |
| 29 | 16 | 32 | 256 | 256 | 64 | 64 | 32 | 128 | 32 | — | — |
| 55 | | 32 | | | | 32 | | 32 | 16 | | — |
| 57 | 16 | | 128 | 128 | 16 | | 16 | | | | — |

[a]See Table 9 for schedule of inoculations.
[b]Animals 176L and 185L received 8.0 $\log_{10}$ pfu by the oral route in 5 ml Tang. Animal 187L received 7.0 $\log_{10}$ pfu by oral route not in Tang.
[c]Day of re-vaccination for animals 176L, 185L, 177L and 186L by S.C. route, and primary vaccination for animals 178L, 182L, 179L, 183L, 180L, 184L and 187L.
[d]Titers expressed as reciprocal of last dilution showing inhibition of fluorescence in an RFFI test.

TABLE 10

Inoculation of chimpanzees with ALVAC-RG

| Weeks post-Inoculation | Animal 431 I.M. | Animal 457 S.C. |
|---|---|---|
| 0 | <8[a] | <8 |
| 1 | <8 | <8 |
| 2 | 8 | 32 |
| 4 | 16 | 32 |
| 8 | 16 | 32 |
| 12[b]/10 | 16 | 8 |
| 13/1 | 128 | 128 |
| 15/3 | 256 | 512 |
| 20/8 | 64 | 128 |
| 26/12 | 32 | 128 |

[a]Titer expressed as reciprocal of last dilution showing inhibition of fluorescence in an RFFI test
[b]Day of re-inoculation Example 9

Immunization of Humans Using Canarypox Expressing Rabies Glycoprotein (ALVAC-RG: vCP65)

Figure 9A:
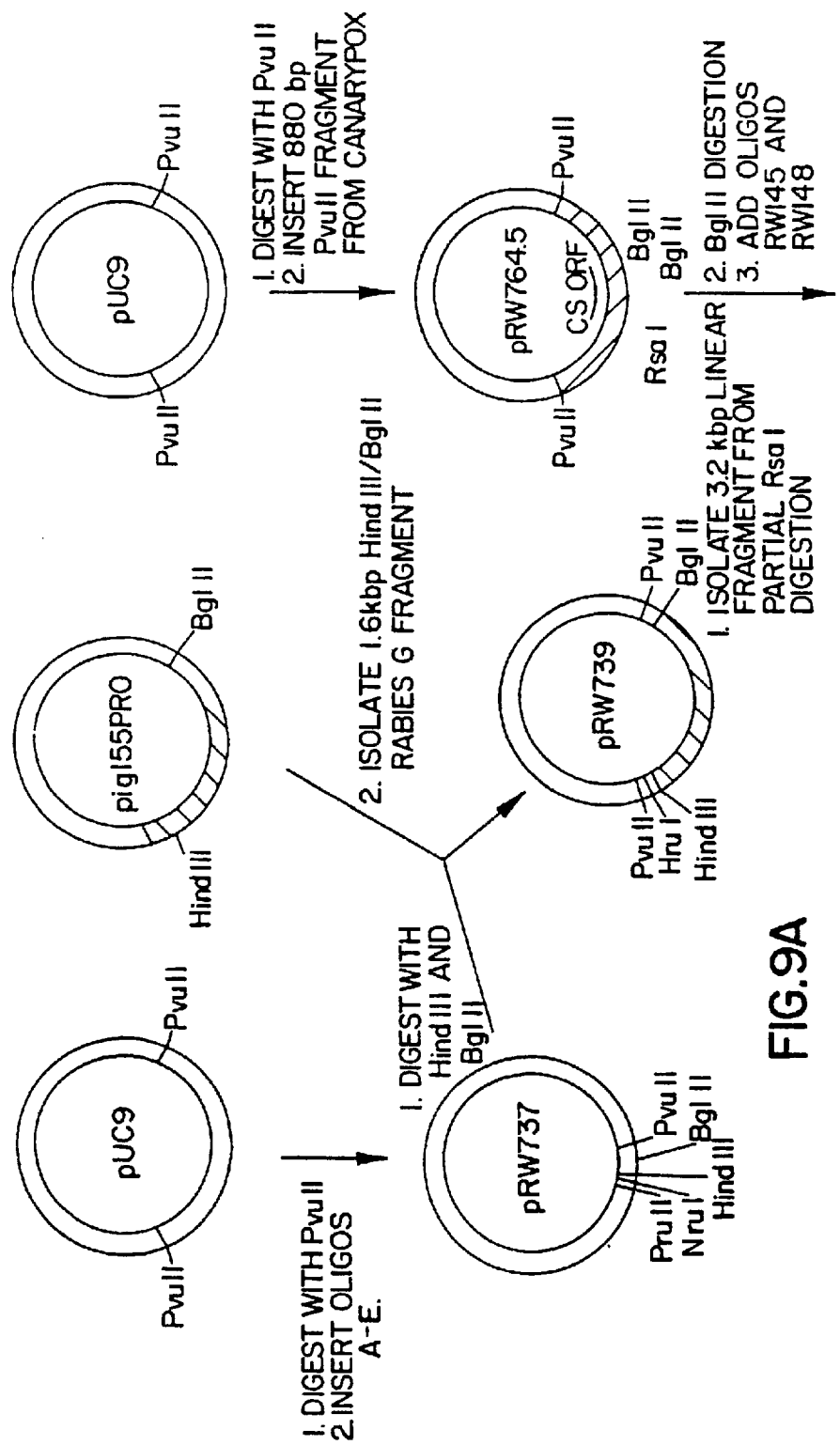
FIGS. 9A and 9B schematically show a method for the construction of recombinant canarypox virus vCP65 (ALVAC-RG)
Figure 9B:
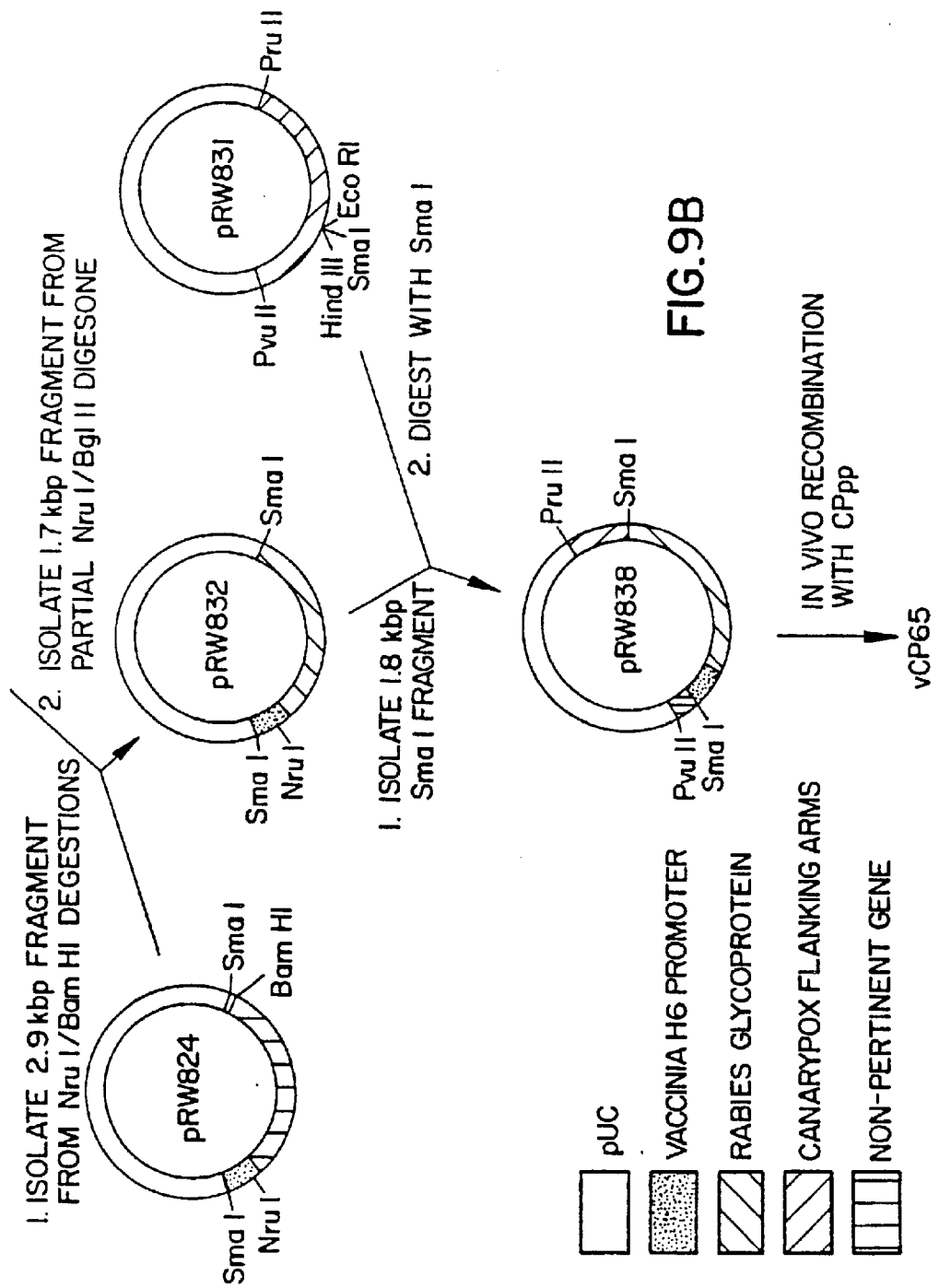

ALVAC-RG (vCP65) was generated as described in Example 9 and FIGS. 9A and 9B. For scaling-up and vaccine manufacturing ALVAC-RG (vCP65) was grown in primary CEF derived from specified pathogen free eggs. Cells were infected at a multiplicity of 0.1 and incubated at 37° C. for three days.

The vaccine virus suspension was obtained by ultrasonic disruption in serum free medium of the infected cells; cell debris were then removed by centrifugation and filtration. The resulting clarified suspension was supplemented with lyophilization stabilizer (mixture of amino-acids), despensed in single dose vials and freeze dried. Three batches of decreasing titer were prepared by ten-fold serial dilutions of the virus suspension in a mixture of serum free medium and lyophilization stabilizer, prior to lyophilization.

Quality control tests were applied to the cell substrates, media and virus seeds and final product with emphasis on the search for adventitious agents and inocuity in laboratory rodents. No undesirable trait was found.

Preclinical data. Studies in vitro indicated that VERO or MRC-5 cells do not support the growth of ALVAC-RG (vCP65); a series of eight (VERO) and 10 (MRC) blind serial passages caused no detectable adaptation of the virus to grow in these non avian lines. Analyses of human cell lines (MRC-5, WISH, Detroit 532, HEL, HNK or EBV-transformed lymphoblastoid cells) infected or inoculated with ALVAC-RG (vCP65) showed no accumulation of virus specific DNA suggesting that in these cells the block in replication occurs prior to DNA synthesis. Significantly, however, the expression of the rabies virus glycoprotein gene in all cell lines tested indicating that the abortive step in the canarypox replication cycle occurs prior to viral DNA replication.

The safety and efficacy of ALVAC-RG (vCP65) were documented in a series of experiments in animals. A number of species including canaries, chickens, ducks, geese, laboratory rodents (suckling and adult mice), hamsters, guinea-pigs, rabbits, cats and dogs, squirrel monkeys, rhesus macaques and chimpanzees, were inoculated with doses ranging from $10^5$ to $10^8$ pfu. Humans have also been inoculated with ALVAC-rabies virus and NYVAC-rabies virus with safety and neutralizing antibodies observed (see also discussion infra). A variety of routes were used, most commonly subcutaneous, intramuscular and intradermal but also oral (monkeys and mice) and intracerebral (mice).

In canaries, ALVAC-RG (vCP65) caused a "take" lesion at the site of scarification with no indication of disease or death. Intradermal inoculation of rabbits resulted in a typical poxvirus inoculation reaction which did not spread and healed in seven to ten days. There was no adverse side effects due to canarypox in any of the animal tests. Immunogenicity was documented by the development of anti-rabies antibodies following inoculation of ALVAC-RG (vCP65) in rodents, dogs, cats, and primates, as measured by Rapid Fluorescent Focus Inhibition Test (RFFIT). Protection was also demonstrated by rabies virus challenge experiments in mice, dogs, and cats immunized with ALVAC-RG (vCP65).

Volunteers. Twenty-five healthy adults aged 20–45 with no previous history of rabies immunization were enrolled. Their health status was assessed by complete medical histories, physical examinations, hematological and blood chemistry analyses. Exclusion criteria included pregnancy, allergies, immune depression of any kind, chronic debilitating disease, cancer, injection of immune globins in the past three months, and seropositivity to human immunodeficiency virus (HIV) or to hepatitis B virus surface antigen.

Study design. Participants were randomly allocated to receive either standard Human Diploid Cell Rabies Vaccine (HDC) batch no E0751 (Pasteur Merieux Serums & Vaccine, Lyon, France) or the study vaccine ALVAC-RG (vCP65).

The trial was designated as a dose escalation study. Three batches of experimental ALVAC-RG (vCP65) vaccine were used sequentially in three groups of volunteers (Groups A, B and C) with two week intervals between each step. The concentration of the three batches was $10^{3.5}$, $10^{4.5}$, $10^{5.5}$ Tissue Culture Infectious Dose ($TCID_{50}$) per dose, respectively.

Each volunteer received two doses of the same vaccine subcutaneously in the deltoid region at an interval of four weeks. The nature of the injected vaccine was not known by the participants at the time of the first injection but was known by the investigator.

In order to minimize the risk of immediate hypersensitivity at the time of the second injection, the volunteers of Group B allocated to the medium dose of experimental vaccine were injected 1 h previously with the lower dose and those allocated to the higher dose (Group C) received successively the lower and the medium dose at hourly intervals.

Six months later, the recipients of the highest dosage of ALVAC-RG (vCP65) (Group C) and HDC vaccine were offered a third dose of vaccine; they were then randomized to receive either the same vaccine as previously or the alternate vaccine. As a result, four groups were formed corresponding to the following immunization scheme: 1. HDC, HDC—HDC; 2. HDC, HDC-ALVAC-RG (vCP65); 3. ALVAC-RG (vCP65), ALVAC-RG (vCP65)-HDC; 4. ALVAC-RG (vCP65), ALVAC-RG (vCP65), ALVAC-RG (vCP65).

Monitoring of Side Effects. All subjects were monitored for 1 h after injection and re-examined every day for the next five days. They were asked to record local and systemic reactions for the next three weeks and were questioned by telephone two times a week.

Laboratory Investigators. Blood specimens were obtained before enrollment and two, four and six days after each injection. Analysis included complete blood cell count, liver enzymes and creatine kinase assays.

Antibody assays. Antibody assays were performed seven days prior to the first injection and at days 7, 28, 35, 56, 173, 187 and 208 of the study.

The levels of neutralizing antibodies to rabies were determined using the Rapid Fluorescent Focus Inhibition test (RFFIT) (Smith et al., 1973). Canarypox antibodies were measured by direct ELISA. The antigen, a suspension of purified canarypox virus disrupted with 0.1% Triton X100, was coated in microplates. Fixed dilutions of the sera were reacted for two hours at room temperature and reacting antibodies were revealed with a peroxidase labelled anti-human IgG goat serum. The results are expressed as the optical density read at 490nm.

Analysis. Twenty-five subjects were enrolled and completed the study. There were 10 males and 15 females and the mean age was 31.9 (21 to 48). All but three subjects had evidence of previous smallpox vaccination; the three remaining subjects had no typical scar and vaccination history. Three subjects received each of the lower doses of experimental vaccine ($10^{3.5}$ and $10^{4.5}$ $TCID_{50}$), nine subjects received $10^{5.5}$ $TCID_{50}$ and ten received the HDC vaccine.

Safety (Table 11). During the primary series of immunization, fever greater than 37.7° C. was noted within 24 hours after injection in one HDC recipient (37.8° C.) and in one vCP65 $10^{5.5}$ $TCID_{50}$ recipient (38° C.). No other systemic reaction attributable to vaccination was observed in any participant.

Local reactions were noted in 9/10 recipients of HDC vaccine injected subcutaneously and in 2/3, 1/3 and 2/9 recipients of vCP65 $10^{3.5}$, $10^{4.5}$, $10^{5.5}$ $TCID_{50}$, respectively.

Tenderness was the most common symptoms and was always mild. Other local symptoms included redness and induration which were also mild and transient. All symptoms usually subsided within 24 hours and never lasted more than 72 hours.

There was no significant change in blood cell counts, liver enzymes or creatine kinase values.

Immune Responses; Neutralizing Antibodies to Rabies (Table 12). Twenty eight days after the first injection all the HDC recipients had protective titers ($\geq 0.5$ IU/ml). By contrast none in groups A and B ($10^{3.5}$ and $10^{4.5}$ $TCID_{50}$) and only 2/9 in group C ($10^{5.5}$ $TCID_{50}$) ALVAC-RG (vCP65) recipients reached this protective titer.

At day 56 (i.e. 28 days after the second injection) protective titers were achieved in 0/3 of Group A, 2/3 of Group B and 9/9 of Group C recipients of ALVAC-RG (vCP65) vaccine and persisted in all 10 HDC recipients.

At day 56 the geometric mean titers were 0.05, 0.47, 4.4 and 11.5 IU/ml in groups A, B, C and HDC respectively.

At day 180, the rabies antibody titers had substantially decreased in all subjects but remained above the minimum protective titer of 0.5 IU/ml in 5/10 HCD recipients and in 5/9 ALVAC-RG (vCP65) recipients; the geometric mean titers were 0.51 and 0.45 IU/ml in groups HCD and C, respectively.

Antibodies to the Canarypox virus (Table 13). The preimmune titers observed varied widely with titers varying from 0.22 to 1.23 O.D. units despite the absence of any previous contact with canary birds in those subjects with the highest titers. When defined as a greater than two-fold increase between preimmunization and post second injection titers, a seroconversion was obtained in 1/3 subjects in group B and in 2/9 subjects in group C whereas no subject seroconverted in groups A or HDC.

Booster Injection. The vaccine was similarly well tolerated six months later, at the time of the booster injection: fever was noted in 2/9 HDC booster recipients and in 1/10 ALVAC-RG (vCP65) booster recipients. Local reactions were present in 5/9 recipients of HDC booster and in 9/10 recipients of the ALVAC-RG (vCP65) booster.

Observations. FIGS. 11A–11D show graphs of rabies neutralizing antibody titers (Rapid Fluorescent Focus Inhibition Test or RFFIT, IU/ml): Booster effect of HDC and vCP65 ($10^{5.5}$ $TCID_{50}$) in volunteers previously immunized with either the same or the alternate vaccine. Vaccines were given at days 0, 28 and 180. Antibody titers were measured at days 0, 7, 28, 35, 56, 173, and 187 and 208.

As shown in FIGS. 11A to 11D, the booster dose given resulted in a further increase in rabies antibody titers in every subject whatever the immunization scheme. However, the ALVAC-RG (vCP65) booster globally elicited lower immune responses than the HDC booster and the ALVAC-RG (vCP65), ALVAC-RG (vCP65)–ALVAC-RG (vCP65) group had significantly lower titers than the three other groups. Similarly, the ALVAC-RG (vCP65) booster injection resulted in an increase in canarypox antibody titers in 3/5 subjects who had previously received the HDC vaccine and in all five subjects previously immunized with ALVAC-RG (vCP65).

In general, none of the local side effects from administration of vCP65 was indicative of a local replication of the virus. In particular, lesions of the skin such as those observed after injection of vaccine were absent. In spite of the apparent absence of replication of the virus, the injection resulted in the volunteers generating significant amounts of antibodies to both the canarypox vector and to the expressed rabies glycoprotein.

Rabies neutralizing antibodies were assayed with the Rapid Fluorescent Focus Inhibition Test (RFFIT) which is known to correlate well with the sero neutralization test in mice. Of 9 recipients of $10^{5.5}$ $TCID_{50}$, five had low level responses after the first dose. Protective titers of rabies antibodies were obtained after the second injection in all recipients of the highest dose tested and even in 2 of the 3 recipients of the medium dose. In this study, both vaccines were given subcutaneously as usually recommended for live vaccines, but not for the inactivated HDC vaccine. This route of injection was selected as it best allowed a careful examination of the injection site, but this could explain the late appearance of antibodies in HDC recipients: indeed, none of the HDC recipients had an antibody increase at day 7, whereas, in most studies where HDC vaccine is give intramuscularly a significant proportion of subjects do (Klietmann et al., Geneva, 1981; Kuwert et al., Geneva, 1981). However, this invention is not necessarily limited to the subcutaneous route of administration.

The GMT (geometric mean titers) of rabies neutralizing antibodies was lower with the investigational vaccine than with the HDC control vaccine, but still well above the minimum titer required for protection. The clear dose effect response obtained with the three dosages used in this study suggest that a higher dosage might induce a stronger response. Certainly from this disclosure the skilled artisan can select an appropriate dosage for a given patient.

The ability to boost the antibody response is another important result of this Example; indeed, an increase in rabies antibody titers was obtained in every subject after the 6 month dose whatever the immunization scheme, showing that preexisting immunity elicited by either the canarypox vector or the rabies glycoprotein had no blocking effect on the booster with the recombinant vaccine candidate or the conventional HDC rabies vaccine. This contrasts findings of others with vaccinia recombinants in humans that immune response may be blocked by pre-existing immunity (Cooney et al., 1991; Etinger et al., 1991).

Thus, this Example clearly demonstrates that a non-replicating poxvirus can serve as an immunizing vector in humans, with all of the advantages that replicating agents confer on the immune response, but without the safety problem created by a fully permissive virus. And, from this disclosure such as this Example and other Examples suitable dosages and modes or routes for administration or immunization of recombinants containing either rabies or other coding, or expression products thereof, are within the ambit of the skilled artisan as well modes for in vitro expression.

TABLE 11

Reactions in the 5 days following vaccination

| vCP65 dosage (TCID50) | $10^{3.5}$ | | $10^{4.5}$ | | $10^{5.5}$ | | HDC control | |
|---|---|---|---|---|---|---|---|---|
| Injection | 1st | 2nd | 1st | 2nd | 1st | 2nd | 1st | 2nd |
| No. vaccinees | 3 | 3 | 3 | 3 | 9 | 9 | 10 | 10 |
| temp >37.7° C. | 0 | 0 | 0 | 0 | 0 | 1 | 1 | 0 |
| soreness | 0 | 0 | 1 | 1 | 6 | 8 | 8 | 6 |
| redness | 0 | 0 | 0 | 0 | 0 | 4 | 5 | 4 |
| induration | 0 | 0 | 0 | 0 | 0 | 4 | 5 | 4 |

TABLE 12

Rabies neutralizing antibodies (REFIT; IU/ml)
Individual titers and geometric mean titers (GMT)

| No. | TCID50/ dose | Days | | | | |
|---|---|---|---|---|---|---|
| | | 0 | 7 | 28 | 35 | 56 |
| 1 | $10^{3.5}$ | <0.1 | <0.1 | <0.1 | <0.1 | 0.2 |
| 3 | $10^{3.5}$ | <0.1 | <0.1 | <0.1 | <0.1 | <0.1 |
| 4 | $10^{3.5}$ | <0.1 | <0.1 | <0.1 | <0.1 | <0.1 |
| G.M.T. | | <0.1 | <0.1 | <0.1 | <0.1 | <0.1 |
| 6 | $10^{4.5}$ | <0.1 | <0.1 | <0.1 | <0.1 | <0.1 |
| 7 | $10^{4.5}$ | <0.1 | <0.1 | <0.1 | 2.4 | 1.9 |
| 10 | $10^{4.5}$ | <0.1 | <0.1 | <0.1 | 1.6 | 1.1 |
| G.M.T. | | <0.1 | <0.1 | 0.1 | 0.58 | 0.47 |
| 11 | $10^{5.5}$ | <0.1 | <0.1 | 1.0 | 3.2 | 4.3 |
| 13 | $10^{5.5}$ | <0.1 | <0.1 | 0.3 | 6.0 | 8.8 |
| 14 | $10^{5.5}$ | <0.1 | <0.1 | 0.2 | 2.1 | 9.4 |
| 17 | $10^{5.5}$ | <0.1 | <0.1 | <0.1 | 1.2 | 2.5 |
| 18 | $10^{5.5}$ | <0.1 | <0.1 | 0.7 | 8.3 | 12.5 |
| 20 | $10^{5.5}$ | <0.1 | <0.1 | <0.1 | 0.3 | 3.7 |
| 21 | $10^{5.5}$ | <0.1 | <0.1 | 0.2 | 2.6 | 3.9 |
| 23 | $10^{5.5}$ | <0.1 | <0.1 | <0.1 | 1.7 | 4.2 |
| 25 | $10^{5.5}$ | <0.1 | <0.1 | <0.1 | 0.6 | 0.9 |
| G.M.T. | | <0.1 | <0.1 | 0.16 | 1.9 | 4.4* |
| 2 | HDC | <0.1 | <0.1 | 0.8 | 7.1 | 7.2 |
| 5 | HDC | <0.1 | <0.1 | 9.9 | 12.8 | 18.7 |
| 8 | HDC | <0.1 | <0.1 | 12.7 | 21.1 | 16.5 |
| 9 | HDC | <0.1 | <0.1 | 6.0 | 9.9 | 14.3 |
| 12 | HDC | <0.1 | <0.1 | 5.0 | 9.2 | 25.3 |
| 15 | HDC | <0.1 | <0.1 | 2.2 | 5.2 | 8.6 |
| 16 | HDC | <0.1 | <0.1 | 2.7 | 7.7 | 20.7 |
| 19 | HDC | <0.1 | <0.1 | 2.6 | 9.9 | 9.1 |
| 22 | HDC | <0.1 | <0.1 | 1.4 | 8.6 | 6.6 |
| 24 | HDC | <0.1 | <0.1 | 0.8 | 5.8 | 4.7 |
| G.M.T. | | <0.1 | <0.1 | 2.96 | 9.0 | 11.5* |

*p = 0.007 student t test

TABLE 13

Canarypox antibodies: ELISA Geometric Mean Titers*

| vCP65 dosage | Days | | | | |
|---|---|---|---|---|---|
| TCID50/dose | 0 | 7 | 28 | 35 | 56 |
| $10^{3.5}$ | 0.69 | ND | 0.76 | ND | 0.68 |
| $10^{4.5}$ | 0.49 | 0.45 | 0.56 | 0.63 | 0.87 |
| $10^{5.5}$ | 0.38 | 0.38 | 0.77 | 1.42 | 1.63 |
| HDC control | 0.45 | 0.39 | 0.40 | 0.35 | 0.39 |

*optical density at 1/25 dilution

Example 10

Comparison of the $LD_{50}$ of ALVAC and NYVAC With Various Vaccinia Virus Strains Mice. Male outbred Swiss Webster mice were purchased from Taconic Farms (Germantown, N.Y.) and maintained on mouse chow and water ad libitum until use at 3 weeks of age ("normal" mice). Newborn outbred Swiss Webster mice were of both sexes and were obtained following timed pregnancies performed by Taconic Farms. All newborn mice used were delivered within a two day period.

Viruses. ALVAC was derived by plaque purification of a canarypox virus population and was prepared in primary chick embryo fibroblast cells (CEF). Following purification by centrifugation over sucrose density gradients, ALVAC was enumerated for plaque forming units in CEF cells. The WR(L) variant of vaccinia virus was derived by selection of large plaque phenotypes of WR (Panicali et al., 1981). The Wyeth New York State Board of Health vaccine strain of vaccinia virus was obtained from Pharmaceuticals Calf Lymph Type vaccine Dryvax, control number 302001B. Copenhagen strain vaccinia virus VC-2 was obtained from Institut Merieux, France. Vaccinia virus strain NYVAC was derived from Copenhagen VC-2. All vaccinia virus strains except the Wyeth strain were cultivated in Vero African green monkey kidney cells, purified by sucrose gradient density centrifugation and enumerated for plaque forming units on Vero cells. The Wyeth strain was grown in CEF cells and enumerated for plaque forming units in CEF cells.

Inoculations. Groups of 10 normal mice were inoculated intracranially (ic) with 0.05 ml of one of several dilutions of virus prepared by 10-fold serially diluting the stock preparations in sterile phosphate-buffered saline. In some instances, undiluted stock virus preparation was used for inoculation.

Groups of 10 newborn mice, 1 to 2 days old, were inoculated ic similarly to the normal mice except that an injection volume of 0.03 ml was used.

All mice were observed daily for mortality for a period of 14 days (newborn mice) or 21 days (normal mice) after inoculation. Mice found dead the morning following inoculation were excluded due to potential death by trauma.

The lethal dose required to produce mortality for 50% of the experimental population ($LD_{50}$) was determined by the proportional method of Reed and Muench (Reed and Muench, 1938).

Comparison of the $LD_{50}$ of ALVAC and NYVAC with Various Vaccinia Virus Strains for Normal, Young Outbred Mice by the ic Route. In young, normal mice, the virulence of NYVAC and ALVAC were several orders of magnitude lower than the other vaccinia virus strains tested (Table 14).

NYVAC and ALVAC were found to be over 3,000 times less virulent in normal mice than the Wyeth strain; over 12,500 times less virulent than the parental VC-2 strain; and over 63,000,000 times less virulent than the WR(L) variant. These results would suggest that NYVAC is highly attenuated compared to other vaccinia strains, and that ALVAC is generally nonvirulent for young mice when administered intracranially, although both may cause mortality in mice at extremely high doses ($3.85 \times 10^8$ PFUs, ALVAC and $3 \times 10^8$ PFUs, NYVAC) by an undetermined mechanism by this route of inoculation.

Comparison of the $LD_{50}$ of ALVAC and NYVAC with Various Vaccinia Virus Strains for Newborn Outbred Mice by the ic Route. The relative virulence of 5 poxvirus strains for normal, newborn mice was tested by titration in an intracranial (ic) challenge model system (Table 15). With mortality as the endpoint, $LD_{50}$ values indicated that ALVAC is over 100,000 times less virulent than the Wyeth vaccine strain of vaccinia virus; over 200,000 times less virulent than the Copenhagen VC-2 strain of vaccinia virus; and over 25,000,000 times less virulent than the WR-L variant of vaccinia virus. Nonetheless, at the highest dose tested, $6.3 \times 10^7$ PFUs, 100% mortality resulted. Mortality rates of 33.3% were observed at $6.3 \times 10^6$ PFUs. The cause of death, while not actually determined, was not likely of toxicological or traumatic nature since the mean survival time (MST) of mice of the highest dosage group (approximately 6.3 $LD_{50}$) was 6.7±1.5 days. When compared to WR(L) at a challenge dose of 5 $LD_{50}$, wherein MST is 4.8±0.6 days, the MST of ALVAC challenged mice was significantly longer (P=0.001).

Relative to NYVAC, Wyeth was found to be over 15,000 times more virulent; VC-2, greater than 35,000 times more virulent; and WR(L), over 3,000,000 times more virulent. Similar to ALVAC, the two highest doses of NYVAC, $6 \times 10^8$ and $6 \times 10^7$ PFUs, caused 100% mortality. However, the MST of mice challenged with the highest dose, corresponding to 380 $LD_{50}$, was only 2 days (9 deaths on day 2 and 1 on day 4). In contrast, all mice challenged with the highest dose of WR-L, equivalent to 500 $LD_{50}$, survived to day 4.

TABLE 14

Calculated 50% Lethal Dose for mice by various vaccinia virus strains and for canarypox virus (ALVAC) by the ic route.

| POXVIRUS STRAIN | CALCULATED $LD_{50}$ (PFUs) |
|---|---|
| WR(L) | 2.5 |
| VC-2 | $1.26 \times 10^4$ |
| WYETH | $5.00 \times 10^4$ |
| NYVAC | $1.58 \times 10^8$ |
| ALVAC | $1.58 \times 10^8$ |

TABLE 15

Calculated 50% Lethal Dose for newborn mice by various vaccinia virus strains and for canarypox virus (ALVAC) by the ic route.

| POXVIRUS STRAIN | CALCULATED $LD_{50}$ (PFUs) |
|---|---|
| WR(L) | 0.4 |
| VC-2 | 0.1 |
| WYETH | 1.6 |
| NYVAC | $1.58 \times 10^6$ |
| ALVAC | $1.00 \times 10^7$ |

Example 11

Evaluation of NYVAC (vP866) and NYVAC-RG (vP879)

Immunoprecipitations. Preformed monolayers of avian or non-avian cells were inoculated with 10 pfu per cell of parental NYVAC (vP866) or NYVAC-RG (vP879) virus. The inoculation was performed in EMEM free of methionine and supplemented with 2% dialyzed fetal bovine serum. After a one hour incubation, the inoculum was removed and the medium replaced with EMEM (methionine free) containing 20 µCi/ml of $^{35}$S-methionine. After an overnight incubation of approximately 16 hours, cells were lysed by the addition of Buffer A (1% Nonidet P-40, 10 mM Tris pH7.4, 150 mM NaCl, 1 mM EDTA, 0.01% sodium azide, 500 units per ml of aprotinin, and 0.02% phenyl methyl sulfonyl fluoride). Immunoprecipitation was performed using a rabies glycoprotein specific monoclonal antibody designated 24-3F10 supplied by Dr. C. Trinarchi, Griffith Laboratories, New York State Department of Health, Albany, N.Y., and a rat anti-mouse conjugate obtained from Boehringer Mannheim Corporation (Cat. #605–500). Protein A Sepharose CL-48 obtained from Pharmacia LKB Biotechnology Inc., Piscataway, N.J., was used as a support matrix. Immunoprecipitates were fractionated on 10% polyacrylamide gels according to the method of Dreyfuss et. al. (1984). Gels were fixed, treated for fluorography with 1M Na-salicylate for one hour, and exposed to Kodak XAR-2 film to visualize the immunoprecipitated protein species.

Sources of Animals. New Zealand White rabbits were obtained from Hare-Marland (Hewitt, N.J.). Three week old male Swiss Webster outbred mice, timed pregnant female Swiss Webster outbred mice, and four week old Swiss Webster nude (nu$^+$nu$^+$) mice were obtained from Taconic Farms, Inc. (Germantown, N.Y.). All animals were maintained according to NIH guidelines. All animal protocols were approved by the institutional IACUC. When deemed necessary, mice which were obviously terminally ill were euthanized.

Evaluation of Lesions in Rabbits. Each of two rabbits was inoculated intradermally at multiple sites with 0.1 ml of PBS containing $10^4$, $10^5$, $10^6$, $10^7$, or $10^8$ pfu of each test virus or with PBS alone. The rabbits were observed daily from day 4 until lesion resolution. Indurations and ulcerations were measured and recorded.

Virus Recovery from Inoculation Sites. A single rabbit was inoculated intradermally at multiple sites of 0.1 ml of PBS containing $10^6$, $10^7$, or $10^8$ pfu of each test virus or with PBS alone. After 11 days, the rabbit was euthanized and skin biopsy specimens taken from each of the inoculation sites were aseptically prepared by mechanical disruption and indirect sonication for virus recovery. Infectious virus was assayed by plaque titration on CEF monolayers.

Virulence in Mice. Groups of ten mice, or five in the nude mice experiment, were inoculated ip with one of several dilutions of virus in 0.5 ml of sterile PBS. Reference is also made to Example 11.

Cyclophosphamide (CY) Treatment. Mice were injected by the ip route with 4 mg (0.02 ml) of CY (SIGMA) on day −2, followed by virus injection on day 0. On the following days post infection, mice were injected ip with CY: 4 mg on day 1; 2 mg on days 4, 7 and 11; 3 mg on days 14, 18, 21, 25 and 28. Immunosuppression was indirectly monitored by enumerating white blood cells with a Coulter Counter on day 11. The average white blood cell count was 13,500 cells per $\mu$l for untreated mice (n=4) and 4,220 cells per $\mu$l for CY-treated control mice (n=5).

Calculation of $LD_{50}$. The lethal dose required to produce 50% mortality ($LD_{50}$) was determined by the proportional method of Reed and Muench (Reed and Muench 1938).

Potency Testing of NYVAC-RG in Mice. Four to six week old mice were inoculated in the footpad with 50 to 100 $\mu$l of a range of dilutions (2.0–8.0 $\log_{10}$ tissue culture infective dose 50% ($TCID_{50}$)) of either VV-RG (Kieny et al., 1984), ALVAC-RG (Taylor et al., 1991b), or the NYVAC-RG. Each group consisted of eight mice. At 14 days post-vaccination, the mice were challenged by intracranial inoculation with 15 $LD_{50}$ of the rabies virus CVS strain (0.03 ml). On day 28, surviving mice were counted and protective does 50% ($PD_{50}$) calculated.

Figure 10:
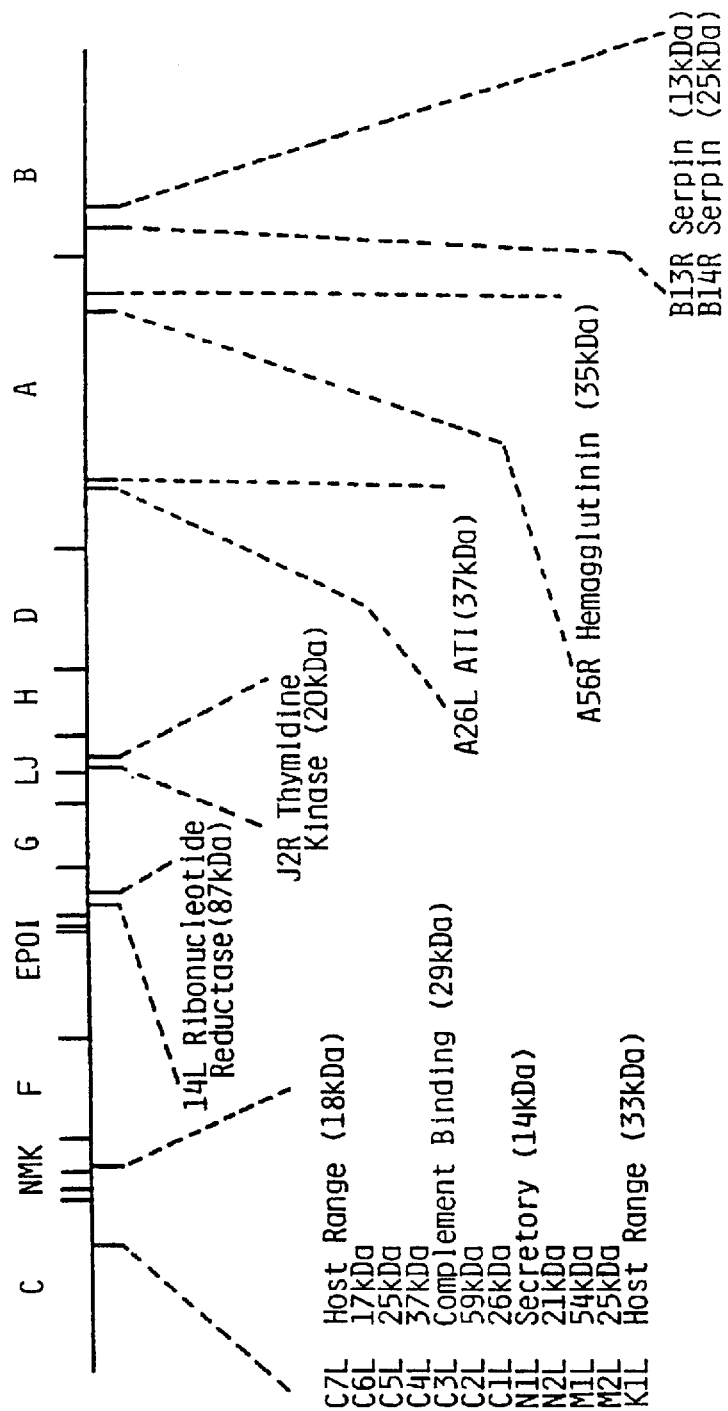
FIG. 10 shows schematically the ORFs deleted to generate NYVAC.
Figure 11A:
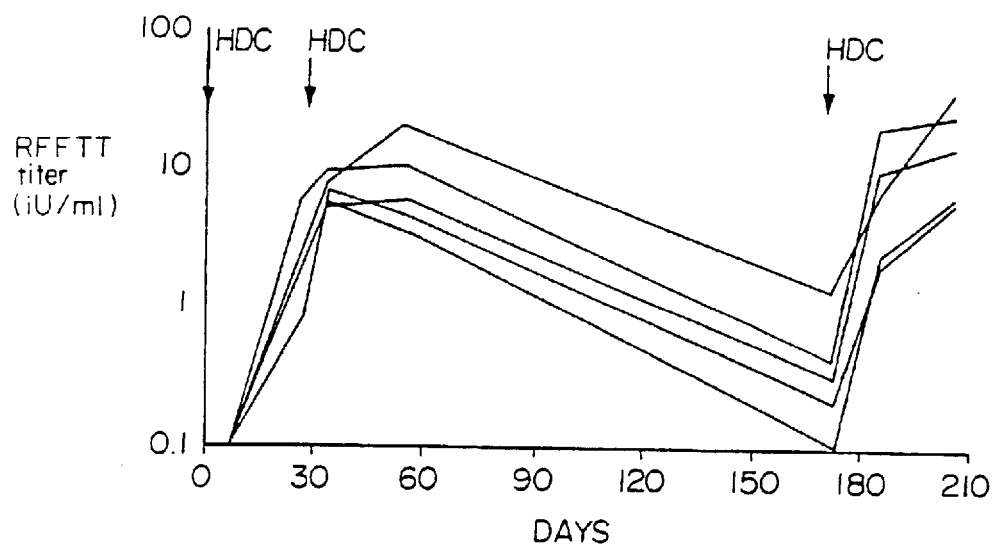
FIGS. 11A to 11D show graphs of rabies neutralizing antibody titers (RFFIT, IU/ml), booster effect of HDC and vCP65 ($10^{5.5}$ $TCID_{50}$) in volunteers previously immunized with either the same or the alternate vaccine (vaccines given at days 0, 28 and 180, antibody titers measured at days 0, 7, 28, 35, 56, 173, 187 and 208).
Figure 11C:
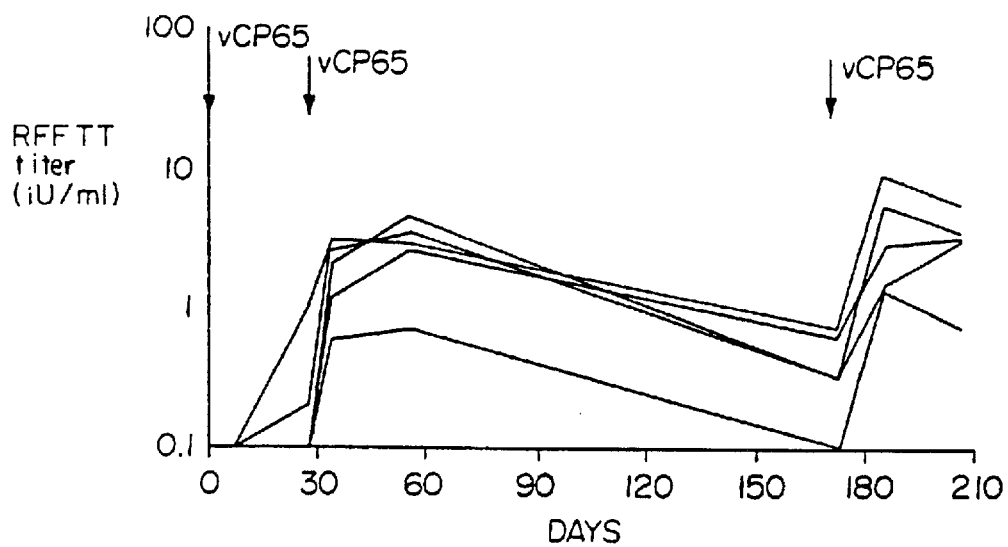
Figure 11B:
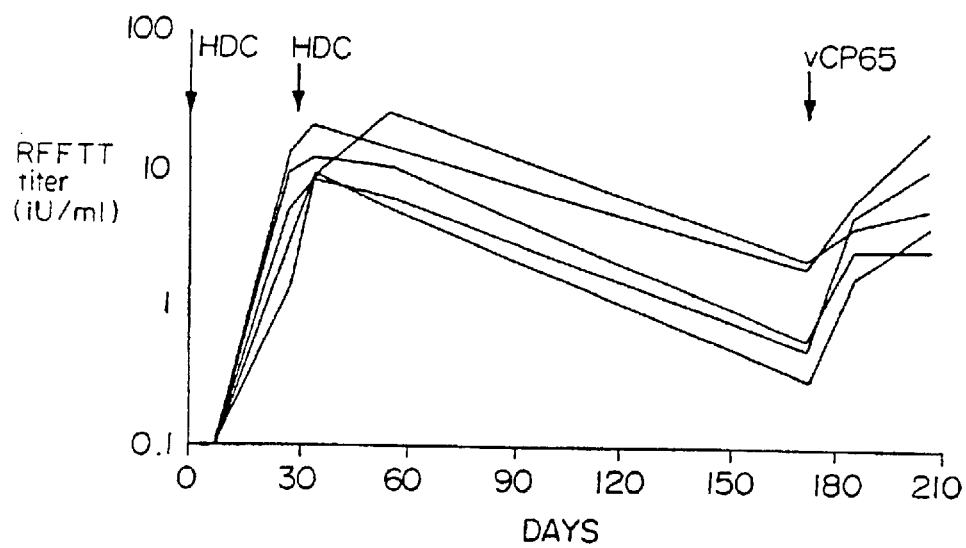
Figure 11D:
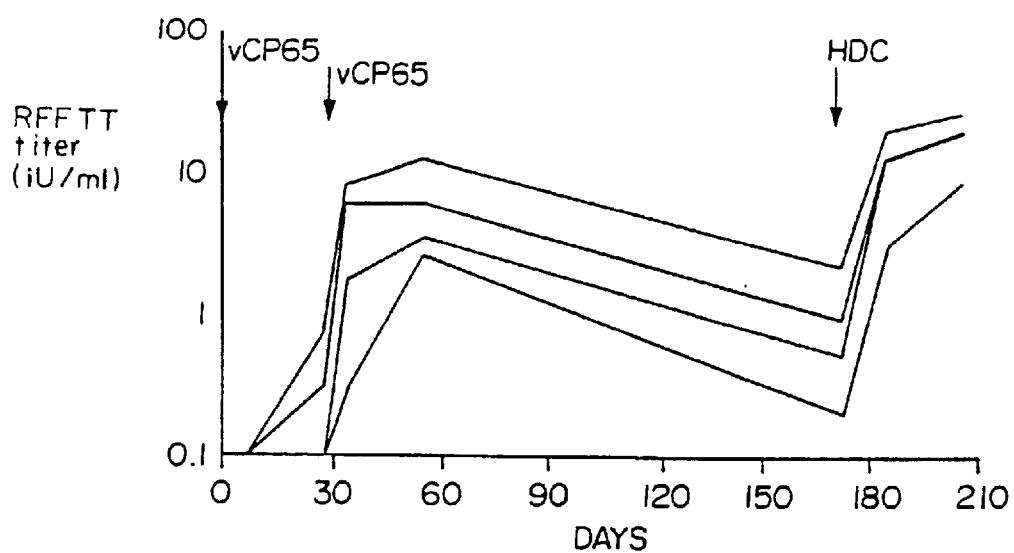

Derivation of NYVAC (vP866). The NYVAC strain of vaccinia virus was generated from VC-2, a plaque cloned isolate of the COPENHAGEN vaccine strain. To generate NYVAC from VC-2, eighteen vaccinia ORFs, including a number of viral functions associated with virulence, were precisely deleted in a series of sequential manipulations as described earlier in this disclosure. These deletions were constructed in a manner designed to prevent the appearance of novel unwanted open reading frames. FIG. 10 schematically depicts the ORFs deleted to generate NYVAC. At the top of FIG. 10 is depicted the HindIII restriction map of the vaccinia virus genome (VC-2 plaque isolate, COPENHAGEN strain). Expanded are the six regions of VC-2 that were sequentially deleted in the generation of NYVAC. The deletions were described earlier in this disclosure (Examples 1 through 6). Below such deletion locus is listed the ORFs which were deleted from that locus, along with the functions or homologies and molecular weight of their gene products.

Replication Studies of NYVAC and ALVAC on Human Tissue Cell Lines. In order to determine the level of replication of NYVAC strain of vaccinia virus (vP866) in cells of human origin, six cell lines were inoculated at an input multiplicity of 0.1 pfu per cell under liquid culture and incubated for 72 hours. The COPENHAGEN parental clone (VC-2) was inoculated in parallel. Primary chick embryo fibroblast (CEF) cells (obtained from 10–11 day old embryonated eggs of SPF origin, Spafas, Inc., Storrs, Conn.) were included to represent a permissive cell substrate for all viruses. Cultures were analyzed on the basis of two criteria: the occurrence of productive viral replication and expression of an extrinsic antigen.

The replication potential of NYVAC in a number of human derived cells are shown in Table 16. Both VC-2 and NYVAC are capable of productive replication in CEF cells, although NYVAC with slightly reduced yields. VC-2 is also capable of productive replication in the six human derived cell lines tested with comparable yields except in the EBV transformed lymphoblastoid cell line JT-1 (human lymphoblastoid cell line transformed with Epstein-Barr virus, see Rickinson et al., 1984). In contrast, NYVAC is highly attenuated in its ability to productively replicate in any of the human derived cell lines tested. Small increases of infectious virus above residual virus levels were obtained from NYVAC-infected MRC-5 (ATCC #CCL171, human embryonic lung origin), DETROIT 532 (ATCC #CCL54, human foreskin, Downs Syndrome), HEL 299 (ATCC #CCL137, human embryonic lung cells) and HNK (human neonatal kidney cells, Whittiker Bioproducts, Inc. Walkersville, Md., Cat #70–151) cells. Replication on these cell lines was significantly reduced when compared to virus yields obtained from NYVAC-infected CEF cells or with parental VC-2 (Table 16). It should be noted that the yields at 24 hours in CEF cells for both NYVAC and VC-2 is equivalent to the 72-hour yield. Allowing the human cell line cultures to incubate an additional 48 hours (another two viral growth cycles) may, therefore, have amplified the relative virus yield obtained.

Consistent with the low levels of virus yields obtained in the human-derived cell lines, MRC-5 and DETROIT 532, detectable but reduced levels of NYVAC-specific DNA accumulation were noted. The level of DNA accumulation in the MRC-5 and DETROIT 532 NYVAC-infected cell lines relative to that observed in NYVAC-infected CEF cells paralleled the relative virus yields. NYVAC-specific viral DNA accumulation was not observed in any of the other human-derived cells.

An equivalent experiment was also performed using the avipox virus, ALVAC. The results of virus replication are also shown in Table 16. No progeny virus was detectable in any of the human cell lines consistent with the host range restriction of canarypox virus to avian species. Also consistent with a lack of productive replication of ALVAC in these human-derived cells is the observation that no ALVAC-specific DNA accumulation was detectable in any of the human-derived cell lines.

Expression of Rabies Glycoprotein by NYVAC-RG (vP879) in Human Cells. In order to determine whether efficient expression of a foreign gene could be obtained in the absence of significant levels of productive viral replication, the same cell lines were inoculated with the NYVAC recombinant expressing the rabies virus glycoprotein (vP879, Example 7) in the presence of $^{35}$S-methionine. Immunoprecipitation of the rabies glycoprotein was performed from the radiolabelled culture lysate using a monoclonal antibody specific for the rabies glycoprotein. Immunoprecipitation of a 67kDa protein was detected consistent with a fully glycosylated form of the rabies glycoprotein. No serologically crossreactive product was detected in uninfected or parental NYVAC infected cell lysates. Equivalent results were obtained with all other human cells analyzed.

Inoculations on the Rabbit Skin. The induction and nature of skin lesions on rabbits following intradermal (id) inoculations has been previously used as a measure of pathogenicity of vaccinia virus strains (Buller et al., 1988; Child et al., 1990; Fenner, 1958, Flexner et al., 1987; Ghendon and Chernos 1964). Therefore, the nature of lesions associated with id inoculations with the vaccinia strains WR (ATCC #VR119 plaque purified on CV-1 cells, ATCC #CCL70, and a plaque isolate designated L variant, ATCC #VR2035 selected, as described in Panicali et al., 1981)), WYETH (ATCC #VR325 marketed as DRYVAX by Wyeth Laboratories, Marietta, Pa.), COPENHAGEN (VC-2), and NYVAC was evaluated by inoculation of two rabbits (A069 and A128). The two rabbits displayed different overall sensitivities to the viruses, with rabbit A128 displaying less severe reactions than rabbit A069. In rabbit A128, lesions were relatively small and resolved by 27 days post-inoculation. On rabbit A069, lesions were intense, especially for the WR inoculation sites, and resolved only after 49 days. Intensity of the lesions was also dependent on the location of the inoculation sites relative to the lymph drainage network. In particular, all sites located above the backspine displayed more intense lesions and required longer times to resolve the lesions located on the flanks. All lesions were measured daily from day 4 to the disappearance of the last lesion, and the means of maximum lesion size and days to resolution were calculated (Table 17). No local reactions were observed from sites injected with the control PBS. Ulcerative lesions were observed at sites injected with WR, VC-2 and WYETH vaccinia virus strains. Significantly, no induration or ulcerative lesions were observed at sites of inoculation with NYVAC.

Persistence of Infectious Virus at the Site of Inoculation. To assess the relative persistence of these viruses at the site of inoculation, a rabbit was inoculated intradermally at multiple sites with 0.1 ml PBS containing $10^6$, $10^7$ or $10^8$ pfu of VC-2, WR, WYETH or NYVAC. For each virus, the $10^7$ pfu dose was located above the backspine, flanked by the $10^6$ and $10^8$ doses. Sites of inoculation were observed daily for 11 days. WR elicited the most intense response, followed by VC-2 and WYETH (Table 18). Ulceration was first observed at day 9 for WR and WYETH and day 10 for VC-2. Sites inoculated with NYVAC or control PBS displayed no induration or ulceration. At day 11 after inoculation, skin samples from the sites of inoculation were excised, mechanically disrupted, and virus was titrated on CEF cells. The results are shown in Table 18. In no case was more virus recovered at this timepoint than was administered. Recovery of vaccinia strain, WR, was approximately $10^6$ pfu of virus at each site irrespective of amount of virus administered. Recovery of vaccinia strains WYETH and VC-2 was $10^3$ to $10^4$ pfu regardless of amount administered. No infectious virus was recovered from sites inoculated with NYVAC.

Inoculation of Genetically or Chemically Immune Deficient Mice. Intraperitoneal inoculation of high doses of NYVAC ($5 \times 10^8$ pfu) or ALVAC ($10^9$ pfu) into nude mice caused no deaths, no lesions, and no apparent disease through the 100 day observation period. In contrast, mice inoculated with WR ($10^3$ to $10^4$ pfu), WYETH ($5 \times 10^7$ or $5 \times 10^8$ pfu) or VC-2 ($10^4$ to $10^9$ pfu) displayed disseminated lesions typical of poxviruses first on the toes, then on the tail, followed by severe orchitis in some animals. In mice infected with WR or WYETH, the appearance of disseminated lesions generally led to eventual death, whereas most mice infected with VC-2 eventually recovered. Calculated $LD_{50}$ values are given in Table 19.

In particular, mice inoculated with VC-2 began to display lesions on their toes (red papules) and 1 to 2 days later on the tail. These lesions occurred between 11 and 13 days post-inoculation (pi) in mice given the highest doses ($10^9$, $10^8$, $10^7$ and $10^6$ pfu), on day 16 pi in mice given $10^5$ pfu and on day 21 pi in mice given $10^4$ pfu. No lesions were observed in mice inoculated with $10^3$ and $10^2$ pfu during the 100 day observation period. Orchitis was noticed on day 23 pi in mice given $10^9$ and $10^8$ pfu, and approximately 7 days later in the other groups ($10^7$ to $10^4$ pfu). Orchitis was especially intense in the $10^9$ and $10^8$ pfu groups and, although receding, was observed until the end of the 100 day observation period. Some pox-like lesions were noticed on the skin of a few mice, occurring around 30–35 days pi. Most pox lesions healed normally between 60–90 days pi. Only one mouse died in the group inoculated with $10^9$ pfu (Day 34 pi) and one mouse died in the group inoculated with $10^8$ pfu (Day 94 pi). No other deaths were observed in the VC-2 inoculated mice.

Mice inoculated with $10^4$ pfu of the WR strain of vaccinia started to display pox lesions on Day 17 pi. These lesions appeared identical to the lesions displayed by the VC-2 injected mice (swollen toes, tail). Mice inoculated with $10^3$ pfu of the WR strain did not develop lesions until 34 days pi. Orchitis was noticed only in the mice inoculated with the highest dose of WR ($10^4$ pfu). During the latter stages of the observation period, lesions appeared around the mouth and the mice stopped eating. All mice inoculated with $10^4$ pfu of WR died or were euthanized when deemed necessary between 21 days and 31 days pi. Four out of the 5 mice injected with $10^3$ pfu of WR died or were euthanized when deemed necessary between 35 days and 57 days pi. No deaths were observed in mice inoculated with lower doses of WR (1 to 100 pfu).

Mice inoculated with the WYETH strain of vaccinia virus at higher doses $5 \times 10^7$ and $5 \times 10^8$ pfu) showed lesions on toes and tails, developed orchitis, and died. Mice injected with $5 \times 10^6$ pfu or less of WYETH showed no signs of disease or lesions.

As shown in Table 19, CY-treated mice provided a more sensitive model for assaying poxvirus virulence than did nude mice. $LD_{50}$ values for the WR, WYETH, and VC-2 vaccinia virus strains were significantly lower in this model system than in the nude mouse model. Additionally, lesions developed in mice injected with WYETH, WR and VC-2 vaccinia viruses, as noted below, with higher doses of each virus resulting in more rapid formation of lesions. As was seen with nude mice, CY-treated mice injected with NYVAC or ALVAC did not develop lesions. However, unlike nude mice, some deaths were observed in CY-treated mice challenged with NYVAC or ALVAC, regardless of the dose. These random incidences are suspect as to the cause of death.

Mice injected with all doses of WYETH ($9.5 \times 10^4$ to $9.5 \times 10^8$ pfu) displayed pox lesions on their tail and/or on their toes between 7 and 15 days pi. In addition, the tails and toes were swollen. Evolution of lesions on the tail was typical of pox lesions with formation of a papule, ulceration and finally formation of a scab. Mice inoculated with all doses of VC-2 ($1.65 \times 10^5$ to $1.65 \times 10^9$) also developed pox lesions on their tails and/or their toes analogous to those of WYETH injected mice. These lesions were observed between 7–12 days post inoculation. No lesions were observed on mice injected with lower doses of WR virus, although deaths occurred in these groups.

Potency Testing of NYVAC-RG. In order to determine that attenuation of the COPENHAGEN strain of vaccinia virus had been effected without significantly altering the ability of the resulting NYVAC strain to be a useful vector, comparative potency tests were performed. In order to monitor the immunogenic potential of the vector during the sequential genetic manipulations performed to attenuate the virus, a rabiesvirus glycoprotein was used as a reporter extrinsic antigen. The protective efficacy of the vectors expressing the rabies glycoprotein gene was evaluated in the standard NIH mouse potency test for rabies (Seligmann, 1973). Table 20 demonstrates that the $PD_{50}$ values obtained with the highly attenuated NYVAC vector are identical to those obtained using a COPENHAGEN-based recombinant containing the rabies glycoprotein gene in the tk locus (Kieny et al., 1984) and similar to $PD_{50}$ values obtained with ALVAC-RG, a canarypox based vector restricted to replication to avian species.

Observations. NYVAC, deleted of known virulence genes and having restricted in vitro growth characteristics, was analyzed in animal model systems to assess its attenuation characteristics. These studies were performed in comparison with the neurovirulent vaccinia virus laboratory strain, WR, two vaccinia virus vaccine strains, WYETH (New York City Board of Health) and COPENHAGEN (VC-2), as well as with a canarypox virus strain, ALVAC (See also Example 11). Together, these viruses provided a spectrum of relative pathogenic potentials in the mouse challenge model and the rabbit skin model, with WR being the most virulent strain, WYETH and COPENHAGEN (VC-2) providing previously utilized attenuated vaccine strains with documented characteristics, and ALVAC providing an example of a poxvirus whose replication is restricted to avian species. Results from these in vivo analyses clearly demonstrate the highly attenuated properties of NYVAC relative to the vaccinia virus strains, WR, WYETH and COPENHAGEN (VC-2) (Tables 14–20). Significantly, the $LD_{50}$ values for NYVAC were comparable to those observed with the avian host restricted avipoxvirus, ALVAC. Deaths due to NYVAC, as well as ALVAC, were observed only when extremely high doses of virus were administered via the intracranial route (Example 11, Tables 14, 15, 19). It has not yet been established whether these deaths were due to nonspecific consequences of inoculation of a high protein mass. Results from analyses in immunocompromised mouse models (nude and CY-treated) also demonstrate the relatively high attenuation characteristics of NYVAC, as compared to WR, WYETH and COPENHAGEN strains (Tables 17 and 18). Significantly, no evidence of disseminated vaccinia infection or vaccinial disease was observed in NYVAC-inoculated animals or ALVAC-inoculated animals over the observation period. The deletion of multiple virulence-associated genes in NYVAC shows a synergistic effect with respect to pathogenicity. Another measure of the inocuity of NYVAC was provided by the intradermal administration on rabbit skin (Tables 17 and 18). Considering the results with ALVAC, a virus unable to replicate in nonavian species, the ability to replicate at the site of inoculation is not the sole correlate with reactivity, since intradermal inoculation of ALVAC caused areas of induration in a dose dependent manner. Therefore, it is likely that factors other than the replicative capacity of the virus contribute to the formation of the lesions. Deletion of specific virulence-associated genes in NYVAC prevents lesion occurrence.

Together, the results in this Example and in foregoing Examples, including Example 10, demonstrate the highly attenuated nature of NYVAC relative to WR, and the previously utilized vaccinia virus vaccine strains, WYETH and COPENHAGEN. In fact, the pathogenic profile of NYVAC, in the animal model systems tested, was similar to that of ALVAC, a poxvirus known to productively replicate only in avian species. The apparently restricted capacity of NYVAC to productively replicate on cells derived from humans (Table 16) and other species, including the mouse, swine, dog and horse, provides a considerable barrier that limits or prevents potential transmission to unvaccinated contacts or to the general environment in addition to providing a vector with reduced probability of dissemination within the vaccinated individual.

Significantly, NYVAC-based vaccine candidates have been shown to be efficacious. NYVAC recombinants expressing foreign gene products from a number of pathogens have elicited immunological responses towards the foreign gene products in several animal species, including primates. In particular, a NYVAC-based recombinant expressing the rabies glycoprotein was able to protect mice against a lethal rabies challenge. The potency of the NYVAC-based rabies glycoprotein recombinant was comparable to the $PD_{50}$ value for a COPENHAGEN-based recombinant containing the rabies glycoprotein in the tk locus (Table 20). NYVAC-based recombinants have also been shown to elicit measles virus neutralizing antibodies in rabbits and protection against pseudorabies virus and Japanese encephalitis virus challenge in swine. The highly attenuated NYVAC strain confers safety advantages with human, animal, medical and veterinary applications (Tartaglia et al., 1992). Furthermore, the use of NYVAC as a general laboratory expression vector system may greatly reduce the biological hazards associated with using vaccinia virus.

By the following criteria, the results of this Example and the Examples herein, including Example 10, show NYVAC to be highly attenuated: a) no detectable induration or ulceration at site of inoculation (rabbit skin); b) rapid clearance of infectious virus from intradermal site of inoculation (rabbit skin); c) absence of testicular inflammation (nude mice); d) greatly reduced virulence (intracranial challenge, both three-week old and newborn mice); e) greatly reduced pathogenicity and failure to disseminate in immunodeficient subjects (nude and cyclophosphamide treated mice); and f) dramatically reduced ability to replicate on a variety of human tissue culture cells. Yet, in spite of being highly attenuated, NYVAC, as a vector, retains the ability to induce strong immune responses to extrinsic antigens.

TABLE 16

Replication of COPENHAGEN (VC-2), NYVAC and ALVAC in avian or human derived cell lines

| Cells | Hours post-infection | Yield[a] VC-2 | NYVAC | ALVAC | % Yield |
|---|---|---|---|---|---|
| CEF | 0 | 3.8[b] | 3.7 | 4.5 | |
| | 24 | 8.3 | 7.8 | 6.6 | |
| | 48 | 8.6 | 7.9 | 7.7 | |
| | 72 | 8.3 | 7.7 | 7.5 | 25 |
| | 72A[c] | <1.4 | 1.8 | 3.1 | |
| MRC-5 | 0 | 3.8 | 3.8 | 4.7 | |
| | 72 | 7.2 | 4.6 | 3.8 | 0.25 |
| | 72A | 2.2 | 2.2 | 3.7 | |
| WISH* | 0 | 3.4 | 3.4 | 4.3 | |
| | 72 | 7.6 | 2.2 | 3.1 | 0.0004 |
| | 72A | —[d] | 1.9 | 2.9 | |
| DETROIT | 0 | 3.8 | 3.7 | 4.4 | |
| | 72 | 7.2 | 5.4 | 3.4 | 1.6 |
| | 72A | 1.7 | 1.7 | 2.9 | |
| HEL | 0 | 3.8 | 3.5 | 4.3 | |
| | 72 | 7.5 | 4.6 | 3.3 | 0.125 |
| | 72A | 2.5 | 2.1 | 3.6 | |
| JT-1 | 0 | 3.1 | 3.1 | 4.1 | |
| | 72 | 6.5 | 3.1 | 4.2 | 0.039 |
| | 72A | 2.4 | 2.1 | 4.4 | |

TABLE 16-continued

Replication of COPENHAGEN (VC-2), NYVAC and ALVAC in avian or human derived cell lines

| Cells | Hours post-infection | Yield[a] VC-2 | NYVAC | ALVAC | % Yield |
|---|---|---|---|---|---|
| HNK | 0 | 3.8 | 3.7 | 4.7 | |
| | 72 | 7.6 | 4.5 | 3.6 | 0.079 |
| | 72A | 3.1 | 2.7 | 3.7 | |

[a]Yield of NYVAC at 72 hours post-infection expressed as a percentage of yield of VAC-2 after 72 hours on the same cell line.
[b]Titer expressed as $LOG_{50}$ pfu per ml.
[c]Sample was incubated in the presence of 40 μg/ml of cytosine arabinoside.
[d]Not determined.
*ATCC #CCL25 Human amnionic cells.

TABLE 17

Induration and ulceration at the site of intradermal inoculation of the rabbit skin

| VIRUS STRAIN | DOSE[a] | INDURATION Size[b] | Days[c] | ULCERATION Size | Days |
|---|---|---|---|---|---|
| WR | $10^4$ | 386 | 30 | 88 | 30 |
| | $10^5$ | 622 | 35 | 149 | 32 |
| | $10^6$ | 1057 | 34 | 271 | 34 |
| | $10^7$ | 877 | 35 | 204 | 35 |
| | $10^8$ | 581 | 25 | 88 | 26 |
| WYETH | $10^4$ | 32 | 5 | —[d] | — |
| | $10^5$ | 116 | 15 | — | — |
| | $10^6$ | 267 | 17 | 3 | 15 |
| | $10^7$ | 202 | 17 | 3 | 24 |
| | $10^8$ | 240 | 29 | 12 | 31 |
| VC-2 | $10^4$ | 64 | 7 | — | — |
| | $10^5$ | 86 | 8 | — | — |
| | $10^6$ | 136 | 17 | — | — |
| | $10^7$ | 167 | 21 | 6 | 10 |
| | $10^8$ | 155 | 32 | 6 | 8 |
| NYVAC | $10^4$ | — | — | — | — |
| | $10^5$ | — | — | — | — |
| | $10^6$ | — | — | — | — |
| | $10^7$ | — | — | — | — |
| | $10^8$ | — | — | — | — |

[a]pfu of indicated vaccinia virus in 0.1 ml PBS inoculated intradermally into one site.
[b]mean maximum size of lesions (mm²)
[c]mean time after inoculation for complete healing of lesion.
[d]no lesions discernable.

TABLE 18

Persistence of poxviruses at the site of intradermal inoculation

| Virus | Inoculum Dose | Total Virus Recovered |
|---|---|---|
| WR | 8.0[a] | 6.14 |
| | 7.0 | 6.26 |
| | 6.0 | 6.21 |
| WYETH | 8.0 | 3.66 |
| | 7.0 | 4.10 |
| | 6.0 | 3.59 |
| VC-2 | 8.0 | 4.47 |
| | 7.0 | 4.74 |
| | 6.0 | 3.97 |
| NYVAC | 8.0 | 0 |
| | 7.0 | 0 |
| | 6.0 | 0 |

[a]expressed as $log_{10}$ pfu.

TABLE 19

Virulence studies in immunocompromised mice

| Poxvirus Strain | $LD_{50}$[a] Nude mice | Cyclophosphamide treated mice |
|---|---|---|
| WR | 422 | 42 |
| VC-2 | $>10^9$ | $<1.65 \times 10^5$ |
| WYETH | $1.58 \times 10^7$ | $1.83 \times 10^6$ |
| NYVAC | $>5.50 \times 10^8$ | $7.23 \times 10^8$ |
| ALVAC | $>10^9$ | $\geq 5.00 \times 10^{8b}$ |

[a]Calculated 50% lethal dose (pfu) for nude or cyclophosphamide treated mice by the indicated vaccinia viruses and for ALVAC by intraperitoneal route.
[b]5 out of 10 mice died at the highest dose of $5 \times 10^8$ pfu.

TABLE 20

Comparative efficacy of NYVAC-RG and ALVAC-RG in mice

| Recombinant | $PD_{50}$[a] |
|---|---|
| VV-RG | 3.74 |
| ALVAC-RG | 3.86 |
| NYVAC-RG | 3.70 |

[a]Four to six week old mice were inoculated in the footpad with 50–100 μl of a range of dilutions (2.0–8.0 $log_{10}$ tissue culture infection dose 50% ($TCID_{50}$) of either the VV-RG (Kieny et al., 1984), ALVAC-RG (vCP65) or NYVAC-RG (vP879). At day 14, mice of each group were challenged by intracranial inoculation of 30 μl of a live CVS strain rabies virus correspondinq to 15 lethal dose 50% ($LD_{50}$) per mouse. At day 28, surviving mice were counted and a protective dose 50% ($PD_{50}$) was calculated.

Example 12

Duration of Immunity in Dog by vCP-65

This Example tests in dogs the duration of immunity induced by the Canarypox-rabies recombinant vCP65, using a single immunization with $10^{6.7}$ $TCID_{50}$.

Materials:

53 dogs, 8 months old, without rabies antibodies (Beagle) and, vCP-65 recombinant produced on CEF at 6th passage, containing $10^{6.7}$ $TCID_{50}$/ml.

Methods:

Immunization

On day 0, 41 dogs were inoculated by subcutaneous route, with 1 ml of the suspension of vCP65. Twelve (12) dogs were not inoculated (control animals). Two vaccinated animals died of nonspecific death.

Serological testing

All the dogs were bled on day 0 and after 1, 2, 3, 6 months following vaccination. Some of the dogs were bled at additional times (12, 24, and 36 months after vaccination).

For a short time follow-up, 10 dogs were bled on days 0, 7, 14 and 21.

Rabies antibodies: RFFITest (SN).

Canarypox antibodies: ELISA: indirect technique against a whole purified virus.

Safety test

From day 0 to day 7: daily observation and temperature recording on each animal.

From day 7 to day 28: weekly observation.

Challenge

A first group of 5 dogs was challenged six months after vaccination, by intramuscular inoculation of $10^{3.4}$ lethal doses (LD) 50 %/mouse, in temporal muscle (2×0.5 ml). Three (3) unvaccinated control animals received the same challenge at the same time.

A second group of 11 vaccinated dogs was challenged under the same conditions, 12 months following vaccination, and, at the same time, three (3) control animals were also challenged.

A third group of 11 vaccinates was challenged, under the same conditions, 24 months following vaccination. At the same time, three (3) control animals were also challenged.

A fourth group of twelve (12) vaccinated dogs was challenged, under the same conditions, 36 months following vaccination. At the same time, three (3) control animals were also challenged.

Results:

Safety of vCP65

None of the dogs exhibited local or general reaction (see temperature Tables 26 and 27).

Serology

Rabies antibodies: Rabies SN Ab were elicited by immunization in all of the 41 vaccinated dogs. The maximum level is observed between 14 and 28 days and followed by a rapid decrease (see Tables 21, 22, and 29).

CP antibodies: All dogs were positive on day 28. Only one dog elicited very low Ab level and this is correlated with a low rabies antibody level (see Tables 23 and 24).

Challenge

All vaccinated dogs survived after challenge carried out 6 or 12 months later (see Table 25). Ten out of eleven (10/11) survived challenge at 24 months and 11/12 survived challenge 36 months after vaccination (see Table 28).

Rabies Ab titration was done 2 months following challenge on surviving dogs (challenge at 6 months). The five (5) dogs had a high Ab level.

Discussion:

Antibody kinetics observed on immunized dogs was very fast and at the time of challenge, at 12 months, most of them were near "negative". In spite of this fact, 100% were protected. Several dogs elicited particularly low levels of rabies Ab.: less than 1 I.U. one month following vaccination. One of them was resistant to challenge at 12 months. The 3 others were challenged later.

TABLE 21

CANARY-POX/RABIES RECOMBINANT vCP65
RABIES ANTIBODIES KINETICS (RFFIT)
1: Long time follow-up

| GROUP | N°DOGS | ANTIBODIES IN I.U. (time in months) | | | | | | |
|---|---|---|---|---|---|---|---|---|
| | | 0 | 1 | 2 | 3 | 6 | (°)8 | 12 |
| | N1V9 | 0.74 | 7.45 | 0.93 | 0.07 | 0.18 | | 0.09 |
| | N3V9 | 0.29 | 7.45 | 0.29 | 0.23 | 0.74 | | 0.15 |
| | N2V9 | 1.17 | 3.73 | 0.29 | 0.23 | 0.23 | | 0.07 |
| | N3W22 | 0.23 | 9.38 | 0.93 | 0.23 | 0.12 | | 0.05 |
| | N5W22 | 0.23 | 4.70 | 0.93 | 0.23 | 0.59 | 7.40 | |
| | N4V9 | 0.59 | 11.80 | 0.74 | 0.18 | 0.23 | | 0.15 |
| | N1W38 | 0.47 | 18.71 | 1.17 | 0.74 | 0.47 | | 0.15 |
| | N8W22 | 0.74 | 2.35 | 0.59 | 0.23 | 1.85 | | 0.15 |
| | N7W22 | 0.74 | 7.45 | 1.17 | 0.23 | 0.18 | 7.40 | |
| | N8V14 | 0.23 | 7.45 | 0.74 | 0.23 | 0.23 | | 0.38 |
| | N7V14 | 0.47 | 3.73 | 0.29 | 0.15 | 0.15 | | 0.15 |
| | N1R54 | 0.23 | 7.45 | 2.94 | 0.47 | 0.59 | | 0.12 |
| | N9V14 | 0.23 | 0.94 | 0.29 | 0.07 | 0.18 | | 0.15 |
| | N2S44 | 0.47 | 0.74 | 0.09 | 0.07 | 0.07 | | 0.05 |
| | N3T2 | 0.47 | 2.35 | 0.29 | 0.07 | 0.07 | | 0.05 |

TABLE 21-continued

CANARY-POX/RABIES RECOMBINANT vCP65
RABIES ANTIBODIES KINETICS (RFFIT)
1: Long time follow-up

| GROUP | N°DOGS | ANTIBODIES IN I.U. (time in months) | | | | | | |
|---|---|---|---|---|---|---|---|---|
| | | 0 | 1 | 2 | 3 | 6 | (°)8 | 12 |
| VCP 65 10.67/ ml | N5V49 | 0.23 | 18.71 | 1.48 | 0.47 | 0.59 | | 0.38 |
| | N4V49 | 0.23 | 7.45 | 0.93 | 0.23 | 0.29 | 2.30 | |
| | N2V49 | 0.29 | 2.35 | 0.19 | 0.15 | 0.18 | | 0.05 |
| | N1V49 | 0.23 | 7.45 | 0.93 | 0.23 | 0.12 | | 0.09 |
| | N1V83 | 0.07 | 1.87 | 0.59 | 0.12 | 0.18 | | 0.05 |
| | N2T90 | 0.23 | 7.45 | 1.17 | 0.59 | 0.23 | 1.80 | |
| | N3V57 | 0.47 | 14.86 | 1.17 | 0.47 | 0.74 | 7.40 | |
| | N2V57 | 0.23 | 7.45 | 1.17 | 0.23 | 0.23 | | 0.15 |
| | N10W22 | 0.07 | 7.45 | 0.37 | 0.23 | 0.15 | | 0.15 |
| | N5W38 | 0.23 | 4.70 | 0.93 | 0.23 | 0.23 | | 0.15 |
| | N9W22 | 0.18 | 2.96 | 0.59 | 0.23 | 0.29 | | 0.15 |
| | N13V14 | 0.74 | 7.45 | 0.37 | 0.18 | 0.07 | | 0.15 |
| | N12V14 | 0.59 | 2.35 | 0.15 | 0.07 | 0.12 | | 0.05 |
| | N3S44 | 0.07 | 0.93 | 0.18 | | | | |
| VCP 65 10.6.7/ ml | N4R54 | 0.29 | 7.45 | 2.34 | 0.29 | 0.74 | 0.47 | |
| | N5V9 | 0.07 | 7.45 | 0.93 | 0.18 | 0.47 | | 0.09 |
| | N6V9 | 0.47 | 2.35 | 0.93 | 0.23 | 0.74 | | 0.15 |
| | N8V9 | 0.29 | 7.45 | 0.93 | 0.23 | 0.15 | | 0.05 |
| | N4R18 | 0.23 | 7.45 | 0.93 | 0.23 | 0.93 | | 0.12 |
| | N3W38 | 0.12 | 37.33 | 2.34 | 0.23 | 0.93 | | 0.15 |
| | N4W38 | 0.23 | 18.71 | 4.67 | 0.47 | 0.74 | | 0.47 |
| | N4V57 | 0.23 | 7.45 | 2.94 | 0.47 | 1.17 | | 0.29 |
| | N5T90 | 0.23 | 2.35 | 0.74 | 0.12 | 0.74 | | 0.07 |
| | N6V49 | 0.18 | 2.35 | 0.29 | 0.23 | 0.23 | | 0.15 |
| | N3S110 | 0.59 | 7.45 | 0.93 | 0.47 | 0.74 | | 0.29 |
| | N9R27 | 0.07 | 0.94 | 0.93 | 0.23 | 0.59 | | 0.09 |
| | geom. mean | 0.28 | 6.11 | 0.71 | 0.22 | 0.31 | | 0.13 |
| | N1S44 | 0.74 | 0.74 | 0.07 | 0.02 | 0.07 | | 0.05 |
| | N1V57 | 0.07 | 0.07 | 0.07 | 0.07 | 0.07 | | 0.05 |
| | N3T90 | 0.23 | 0.94 | 0.09 | 0.07 | 0.07 | | 0.05 |
| | N1S10 | 0.74 | 0.47 | 0.09 | 0.07 | 0.07 | | 0.05 |
| Controls | N10V14 | 0.23 | 0.74 | 0.09 | 0.07 | 0.07 | | 0.05 |
| | N14V14 | 0.23 | 0.59 | 0.07 | 0.07 | 0.07 | | 0.05 |
| | N5R54 | 0.23 | 0.59 | 0.07 | 0.07 | 0.07 | | 0.05 |
| | N7V9 | 0.59 | 0.49 | 0.09 | 0.07 | 0.07 | | 0.05 |
| | N2W38 | 0.74 | 1.17 | 0.15 | 0.07 | 0.07 | | 0.05 |
| | 195 | 0.07 | 0.07 | 0.07 | 0.07 | 0.07 | | |
| | 194 | 0.59 | 0.47 | 0.09 | 0.07 | 0.07 | | |
| | 198 | 0.29 | 0.05 | 0.18 | 0.07 | 0.07 | | |
| | X | 0.30 | 0.37 | 0.09 | 0.06 | 0.07 | | |

TABLE 22

**CANARY-POX/RABIES RECOMBINANT VCP-65
RABIES ANTIBODIES KINETICS (RFFIT)**
II: Short time follow-up ANTIBODIES IN I.U.
(time in months)

| GROUP | N°DOGS | 0 | 7 | 14 | 21 | 28 | 60 | 90 | 180 | 360 |
|---|---|---|---|---|---|---|---|---|---|---|
| | N10W22 | 0.07 | 0.74 | 4.70 | 9.38 | 7.45 | 0.37 | 0.23 | 0.15 | 0.15 |
| | N9W22 | 0.18 | 0.74 | 11.80 | 4.70 | 2.95 | 0.59 | 0.23 | 0.29 | 0.15 |
| | N3S44 | 0.07 | 0.29 | 3.73 | 2.96 | 0.93 | 0.18 | | | |
| | NSV9 | 0.07 | 0.74 | 7.45 | 7.45 | 7.45 | 6.93 | 0.18 | 0.47 | 0.09 |
| | N3W38 | 0.12 | 0.74 | 59.16 | 59.16 | 37.33 | 2.34 | 0.23 | 0.93 | 0.15 |
| | N4V57 | 0.23 | 0.74 | 9.38 | 18.71 | 7.45 | 2.94 | 0.47 | 1.17 | 0.29 |
| | N5T90 | 0.23 | 1.17 | 4.70 | 7.45 | 2.35 | 0.74 | 0.12 | 0.74 | 0.07 |
| | N6V49 | 0.18 | 0.74 | 11.80 | 7.45 | 2.35 | 0.29 | 0.23 | 0.23 | 0.15 |
| | N3S110 | 0.59 | 3.73 | 4.86 | 4.70 | 7.45 | 0.93 | 0.47 | 0.74 | 0.29 |
| | N9R27 | 0.07 | 0.23 | 2.35 | 4.45 | 0.94 | 0.93 | 0.23 | 0.59 | 0.09 |
| | geom. mean | 0.14 | 0.74 | 7.47 | 8.12 | 4.18 | 0.74 | 0.24 | 0.49 | 0.14 |

TABLE 23

**CANARY-POX/RABIES RECOMBINANT VCP-65
CANARY-POX ANTIBODIES KINETICS (ELISA)**
I: Long time follow-up O.D. at 450 nm (sera at 1/100)
(time in months)

| GROUP | N°DOGS | 0 | 1 | 2 | 3 | 6 | (°)8 | 12 |
|---|---|---|---|---|---|---|---|---|
| | N1V9 | 0.10 | 0.40 | 0.33 | 0.17 | 0.04 | | 0.01 |
| | N3V9 | 0.14 | 0.30 | 0.20 | 0.11 | 0.02 | | 0 |
| | N2V9 | 0.10 | 0.27 | 0.24 | 0.11 | 0.09 | | 0 |
| | N3W22 | 0.11 | 0.26 | 0.27 | 0.15 | 0.03 | | 0 |
| | N5W22 | 0.12 | 0.26 | 0.22 | 0.15 | 0.00 | 0.03 | |
| | N4V9 | 0.14 | 0.32 | 0.17 | 0.07 | 0.00 | | 0 |
| | N1W38 | 0.10 | 0.42 | 0.30 | 0.14 | 0.03 | | 0 |
| | N8W22 | 0.13 | 0.28 | 0.22 | 0.10 | 0.03 | | 0 |
| | N7W22 | 0.08 | 0.37 | 0.29 | 0.21 | 0.03 | 0.02 | |
| | N8V14 | 0.10 | 0.44 | 0.29 | 0.09 | 0.04 | | 0 |
| | N7V14 | 0.08 | 0.28 | 0.19 | 0.05 | 0.00 | | 0.02 |
| | N1RS4 | 0.03 | 0.23 | 0.18 | 0.09 | 0.00 | | 0 |
| | N9V14 | 0.08 | 0.34 | 0.26 | 0.05 | 0.04 | | 0 |
| | N2S44 | 0.15 | 0.31 | 0.25 | 0.09 | 0.03 | | 0.01 |
| | N3T2 | 0.06 | 0.20 | 0.13 | 0.00 | 0.00 | | 0 |
| VCP 65 10.6.7/ml | N5V49 | 0.05 | 0.38 | 0.24 | | | | |
| | N4V49 | 0.09 | 0.34 | 0.20 | 0.01 | 0.00 | | 0 |
| | N2V49 | 0.02 | 0.32 | 0.22 | 0.00 | 0.06 | | 0 |
| | N1V49 | 0.09 | 0.33 | 0.25 | 0.14 | 0.00 | | 0 |
| | N1V83 | 0.13 | 0.25 | 0.28 | 0.10 | 0.00 | | 0.02 |
| | N2T90 | 0.05 | 0.42 | 0.37 | 0.09 | 0.14 | | 0.01 |
| | N3V57 | 0.04 | 0.53 | 0.51 | 0.28 | 0.17 | | 0.01 |
| | N2V57 | 0.05 | 0.38 | 0.39 | 0.11 | 0.07 | | 0.01 |
| | N10W22 | 0.05 | 0.28 | 0.26 | 0.01 | 0.05 | | 0 |
| | N5W38 | 0.04 | 0.44 | 0.37 | 0.24 | 0.05 | | 0 |
| | N9W22 | 0.10 | 0.31 | 0.25 | 0.18 | 0.05 | 0.00 | 0.01 |
| | N13V14 | 0.15 | 0.30 | 0.13 | 0.15 | 0.00 | | 0.01 |
| | N12V14 | 0.18 | 0.33 | 0.20 | 0.18 | 0.01 | | 0.03 |
| | N3S44 | 0.10 | 0.37 | 0.33 | | | | |
| | N4R54 | 0.10 | 0.28 | 0.26 | 0.16 | 0.06 | | 0 |
| | N5V9 | 0.11 | 0.33 | 0.24 | 0.14 | 0.05 | | 0.02 |
| | N6V9 | 0.00 | 0.31 | 0.40 | 0.08 | 0.05 | | 0.02 |
| | N8V9 | 0.09 | 0.35 | 0.29 | 0.08 | 0.06 | | 0.01 |
| | N4R18 | 0.13 | 0.30 | 0.23 | 0.09 | 0.02 | | 0.01 |
| | N3W38 | 0.10 | 0.38 | 0.26 | 0.05 | 0.06 | | |
| | N4W38 | 0.07 | 0.58 | 0.41 | 0.16 | 0.08 | | 0 |
| | N4V57 | 0.07 | 0.29 | 0.24 | 0.08 | 0.04 | | 0.01 |
| | N5T90 | 0.06 | 0.23 | 0.22 | 0.06 | 0.00 | | 0 |
| | N6V49 | 0.08 | 0.28 | 0.30 | 0.14 | 0.07 | | 0.01 |
| | N3S110 | 0.10 | 0.23 | 0.28 | 0.18 | 0.10 | | 0.01 |
| | N9R27 | 0.06 | 0.11 | 0.17 | 0.07 | 0.01 | | 0.01 |
| | geom. mean | 0.09 | 0.33 | 0.26 | 0.11 | 0.04 | | 0.01 |
| | N1S44 | 0.06 | 0.18 | 0.16 | 0.02 | 0.00 | | 0.01 |
| | N1VS7 | 0.04 | 0.17 | 0.13 | 0.00 | 0.00 | | 0.01 |
| | N3T90 | 0.00 | 0.16 | 0.07 | 0.00 | 0.00 | | 0.00 |
| | N1S10 | 0.09 | 0.16 | 0.16 | 0.00 | 0.00 | | 0.01 |
| CON-TROLS | N10V14 | 0.09 | 0.18 | 0.08 | 0.00 | 0.00 | | 0.00 |
| | N14V14 | 0.04 | 0.19 | 0.06 | 0.00 | 0.00 | | 0.00 |
| | N5R54 | 0.09 | 0.17 | 0.09 | 0.00 | 0.00 | | 0.00 |
| | N7V9 | 0.13 | 0.15 | 0.15 | 0.00 | 0.00 | | 0.00 |
| | N2W38 | 0.10 | 0.18 | 0.10 | 0.00 | 0.00 | | |
| | 195 | 0.06 | 0.12 | 0.17 | 0.00 | 0.00 | | |
| | 194 | 0.90 | 0.13 | 0.23 | 0.00 | 0.00 | | |
| | 198 | 0.13 | 0.05 | 0.13 | 0.00 | 0.00 | | |
| | geom. mean | 0.08 | 0.15 | 0.13 | 0.00 | 0.00 | | 0.00 |

(*): 8 months antibodies titration 2 months following challenge

TABLE 24

CANARYPOX/RABIES RECOMBINANT vCP65
CANARYPOX ANTIBODIES KINETICS (ELISA)
II: short time follow-up

| GROUP | N°DOGS | O.D. at 450 nm (sera at 1/100) on days | | | | | | | | |
|---|---|---|---|---|---|---|---|---|---|---|
| | | 0 | 7 | 14 | 21 | 28 | 60 | 90 | 180 | 360 |
| VCP 65 10.6,7/ml | N10W22 | 0.05 | 0.19 | 0.24 | 0.22 | 0.28 | 0.26 | 0.01 | 0.05 | 0 |
| | N9W22 | 0.10 | 0.14 | 0.29 | 0.32 | 0.31 | 0.25 | 0.18 | 0.05 | 0 |
| | N3544 | 0.10 | 0.15 | 0.23 | 0.33 | 0.37 | 0.33 | | | |
| | N5V9 | 0.11 | 0.15 | 0.30 | 0.30 | 0.33 | 0.24 | 0.14 | 0.05 | 0.02 |
| | N3W38 | 0.10 | 0.11 | 0.40 | 0.37 | 0.38 | 0.26 | 0.05 | 0.06 | |
| | N4V57 | 0.07 | 0.13 | 0.31 | 0.29 | 0.39 | 0.24 | 0.08 | 0.04 | 0.01 |
| | N5T90 | 0.06 | 0.07 | 0.27 | 0.29 | 0.23 | 0.22 | 0.06 | 0 | 0 |
| | N6V49 | 0.08 | 0.11 | 0.36 | 0.34 | 0.28 | 0.30 | 0.14 | 0.07 | 0.01 |
| | N3S110 | 0.10 | 0.14 | 0.28 | 0.37 | 0.23 | 0.28 | 0.18 | 0.1 | 0.01 |
| | N9R27 | 0.06 | 0.08 | 0.15 | 0.11 | 0.11 | 0.17 | 0.07 | 0.01 | 0.01 |
| | X | 0.08 | 0.13 | 0.28 | 0.29 | 0.29 | 0.26 | 0.10 | 0.05 | 0.01 |

TABLE 25

CP/RABIES RECOMBINANT ON DOGS
LONG-LASTING IMMUNITY

| | |
|---|---|
| 1: ANIMALS: | Dogs (Beagle) 8 months old, without rabies antibodies |
| 2: RECOMBINANT: | VCP-65, 6th passage on CEF cells. |
| 3: IMMUNIZATION: | 1 ml ($10^{6.7}$ tcid$_{50}$), by subcutaneous route, on day zero |
| 4: SEROLOGICAL TESTING: | SN rabies antibodies, "Rapid Fluorescent Focus Inhibition Test." |
| 5: CHALLENGE: | 0.5 ml virulent strain in each temporal muscle (NYGS strain). |

I: 6 months challenge (10 3.4 LD$_{50}$-mouse/dog)
RABIES SN ANTIBODIES (RFFIT)

| | | maximum observed | | day of challenge | | RESULT | SURVIVING |
|---|---|---|---|---|---|---|---|
| GROUP | N.DOG | LOG | I.U. | LOG | I.U | (*) | RATE |
| vaccinated | N2T90 | 2.2(D28) | 7.45 | 0.7 | 0.23 | S | 100% |
| | N3V57 | 2.5(D28) | 14.8 | 0.7 | 0.23 | S | |
| | N4V49 | 2.2(D28)2 (D28) | 7.45 | 0.8 | 0.29 | S | |
| | N5W22 | 2.2(D28) | 8.7 | 1.1 | 0.59 | S | |
| | N7W22 | | 7.45 | 0.6 | 0.18 | S | |
| controls | 194 | 1(D28) | 0.47 | 0.2 | 0.07 | D(16) | 0% |
| | 195 | 0.2(D28) | 0.07 | 0.2 | 0.07 | D(24) | |
| | 198 | 1(D28) | 0.47 | 0.2 | 0.07 | D(17) | |

II: 12 months challenge (10 3.5 LD$_{50}$-mouse/dog)
RABIES ON ANTIBODIES (RFFIT)

| | | maximum observed | | day of challenge | | RESULT | SURVIVING |
|---|---|---|---|---|---|---|---|
| GROUP | N.DOG | LOG | I.U. | LOG | I.U | (*) | RATE |
| vaccinated | N1V9 | 2.2(D28) | 7.45 | 0.5 | 0.09 | S | 100% |
| | N3V9 | 2.2(D28) | 7.45 | 0.7 | 0.15 | S | |
| | N2V9 | 1.9(D28)2.3(D28) | 3.73 | 0.4 | 0.07 | S | |
| | N7W22 | 2.2(D28) | 9.78 | 0.2 | 0.05 | S | |
| | N4V9 | 2.6(D28) | 7.45 | 0.7 | 0.15 | S | |
| | N1W38 | 1.7(D28) | 18.7 | 0.7 | 0.15 | S | |
| | N8W22 | 2.2(D28) | 2.35 | 0.7 | 0.15 | S | |
| | N8V14 | 1.9(D28) | 7.45 | 1.1 | 0.38 | S | |
| | N7V14 | 2.2(D28) | 3.73 | 0.7 | 0.15 | S | |
| | N1R45 | 1.3(D28) | 7.45 | 0.6 | 0.12 | S | |
| | N9V14 | | 0.94 | 0.7 | 0.15 | S | |
| controls | N10V14 | 1.2(D28) | 0.74 | 0.2 | 0.05 | D(14) | 0% |
| | N14V14 | 1.1(D28) | 0.59 | 0.2 | 0.05 | D(13) | |
| | N5R54 | 1.2(D28) | 0.74 | 0.2 | 0.05 | D(14) | |

(*): S = SURVIVING, D(16) = DEAD, 16 days following challenge

TABLE 26

RECOMBINANT CANARY-POX RABIES VCP 65 STUDY OF THE DURATION OF IMMUNITY ON DOGS: TEMPERATURES

| DOG | DAY 0 | 1 | 2 | 3 | 4 | 7 |
|---|---|---|---|---|---|---|
| N8 W22 | 39.5 | 38.6 | 38.4 | 39.3 | 39.4 | 39 |
| N5 W22 | 40.2 | 39.5 | 38.8 | 39.7 | 39.9 | 39.6 |
| N7 W22 | 39.7 | 38.3 | 38.5 | 39.6 | 39.4 | 39.3 |
| N7 V14 | 39.9 | 39.6 | 39.1 | 39.5 | 39.4 | 39.6 |
| N1 W38 | 39.2 | 39.5 | 38.1 | 38.9 | 38.8 | 38.9 |
| N9 V14 | 39.4 | 38.7 | 38.9 | 39.3 | 39.8 | 39.2 |
| N2 V9 | 39.4 | 38.4 | 39.3 | 39 | 38.5 | 39.2 |
| N4 V9 | 39.7 | 39 | 39.4 | 39.1 | 39.2 | 39.3 |
| N5 V49 | 39.6 | 39.5 | 39.5 | 39.2 | 39 | 39.1 |
| N1 V9 | 40 | 38.7 | 39.2 | 39.3 | 38.9 | 39.3 |
| N2 V49 | 39.4 | 39.2 | 39.2 | 39.2 | 39.1 | 38.8 |
| N1 V83 | 40 | 39.2 | 39.3 | 39.3 | 39.1 | 39.2 |
| N3 S110 | 39.1 | 38.4 | 38.7 | 38.7 | 38.8 | 38.3 |
| N3 S44 | 39.4 | 38.5 | 39 | 38.9 | 39 | 38.7 |
| N5 T90 | 38.9 | 38.5 | 38.9 | 38.9 | 36.8 | 38.7 |
| N9 R27 | 38.9 | 38.7 | 39.2 | 38.8 | 38.8 | 38.7 |
| N6 V49 | 39.2 | 39 | 38.7 | 38.7 | 38.7 | 38.4 |
| N3 W38 | 39.1 | 38.4 | 38.9 | 38.9 | 38.6 | 38.3 |
| N5 V9 | 39.9 | 39.3 | 39.8 | 39.2 | 39.3 | 39.2 |
| N4 V57 | 39.7 | 39.8 | 39.8 | 39.8 | 39 | 39.2 |
| N10 W22 | 39.4 | 39.7 | 39.3 | 39 | 38.8 | 38.8 |
| N4 W38 | 38.6 | 38.4 | 38.5 | 38.3 | 38.4 | 38.2 |
| N8 V9 | 39.8 | 39.6 | 39.9 | 39.5 | 39.3 | 39.3 |
| N5 W38 | 39.4 | 38.3 | 38.8 | 38.2 | 38.3 | 38.6 |
| N12 V14 | 38.7 | 38.2 | 39 | 38.9 | 38.6 | 38.8 |
| N9 W22 | 39.2 | 39 | 39.3 | 39.5 | 39.1 | 38.8 |
| N12 V14 | 38.7 | 38.2 | 39 | 38.9 | 38.6 | 38.8 |
| N4 R18 | 39.2 | 38.7 | 39.3 | 39.3 | 39.2 | 39.2 |
| N4 R54 | 39.2 | 39.2 | 39.1 | 39.3 | 39.1 | 38.8 |
| N6 V9 | 39.2 | 39.6 | 39.7 | 39.4 | 39.2 | 39.3 |
| N13 V14 | 39.2 | 39.2 | 39 | 39.2 | 39 | 38.9 |
| N2 V44 | 39.1 | 39.8 | 39.2 | 39.1 | 38.6 | 38.6 |
| N8 V14 | 39.9 | 38.9 | 39.3 | 38.8 | 39.1 | 39.2 |
| N1 V49 | 39.3 | 39 | 39.1 | 39.2 | 38.7 | 39 |
| N4 V49 | 39.1 | 38.7 | 39.5 | 39 | 38.6 | 39.1 |
| N1 R54 | 39.6 | 38.5 | 39.6 | 39.1 | 38.6 | 39.1 |
| N3 V57 | 39.2 | 38.6 | 39.2 | 38.8 | 38.9 | 39 |
| N3 V9 | 39.6 | 39.4 | 39.5 | 39.3 | 38.7 | 39.4 |
| N3 W22 | 39.4 | 39.5 | 39.2 | 39.4 | 39.1 | 39 |
| N3 T2 | 39.3 | 39.3 | 39.4 | 39.1 | 39.2 | 39.3 |
| N2 T90 | 39.5 | 39 | 39.3 | 38.9 | 38.9 | 38.9 |
| N2 V57 | 39.4 | 39 | 39.5 | 39.2 | 38.7 | 38.9 |
| MEAN | 39.4 | 39.0 | 39.2 | 39.1 | 38.9 | 39.0 |

TABLE 27

TEMPERATURES

| DOG | DAY 0 | 1 | 2 | 3 | 4 | 7 |
|---|---|---|---|---|---|---|
| N1 V57 | 39.5 | 39.2 | 39.6 | 39.5 | 39.4 | 39.1 |
| N1 S10 | 39.3 | 38.4 | 39.3 | 39.4 | 38.9 | 39.1 |
| N1 S44 | 39.2 | 39.6 | 39.6 | 39.7 | 39.1 | 39.3 |
| N3 T90 | 39.4 | 39.4 | 39.8 | 39.9 | 38.9 | 39 |
| N2 W38 | 38.5 | 38.4 | 38.8 | 38.6 | 38.5 | 38.5 |
| N5 R54 | 39.2 | 39.2 | 39.1 | 39.2 | 39 | 39.2 |
| N7 V9 | 39.1 | 39.5 | 39.6 | 39.4 | 39.1 | 39.5 |
| N10 V14 | 38.5 | 39.9 | 39.3 | 39 | 39.5 | 38.8 |
| N14 V14 | 38.9 | 39.7 | 39.3 | 39.4 | 39.2 | 39.3 |
| 195 | 38 | 37.2 | 37.6 | 37.6 | 38.6 | 38 |
| 194 | 38.4 | 38.2 | 38.3 | 38.3 | 37.6 | 38.4 |
| 198 | 39 | 38.2 | 38.1 | 38 | 38.4 | 37.8 |
| MEAN | 38.9 | 38.9 | 39.0 | 39.0 | 38.9 | 38.8 |

TABLE 28

| | |
|---|---|
| 1. Animals: | Dogs (Beagle) 8 months old without rabies antibodies |
| 2. Recombinant: | vCP-65 8th passage on CEF cells |
| 3. Immunization: | 1 ml ($10^{6.7}$ tcid$_{50}$), by sub-cutaneous route on day zero |
| 4. Serological Testing: | SN rabies antibodies * Rapid Fluorescent Focus Inhibition Test.* |
| 5. Challenge: | 0.5 ml virulent strain in each temporal muscle (NYGS strain) 24 months challenge ($10^{6.7}$ LD$_{50}$-mouse/dog) |

| | | RABIES SN ANTIBODIES (RFFIT) | | | | | | SN antibodies 40 days following challenge | |
|---|---|---|---|---|---|---|---|---|---|
| | | maximum observed | | day of challenge | | RESULT | SURVIVING | | |
| GROUP | N.DOG | LOG | I.U. | LOG | I.U. | (*) | RATE | LOG | I.U. |
| vaccinated | N2944 | 1 2 (D25) | 0.74 | 0.2 | 0.02 | D (14) | | | |
| | N3 T2 | 1 7 (D25) | 2.35 | 0.5 | 0.04 | S | | 2.6 | 9.3 |
| | N5 V49 | 2.6 (D25) | 18.7 | 1.6 | 0.47 | S | | 2.6 | 9.3 |
| | N2 V49 | 1.7 (D25) | 2.35 | 10.4 | 0.03 | S | 10/11 | 2.5 | 14.7 |
| | N1 V49 | 2.2 (D25) | 7.35 | 1.2 | 0.12 | S | | 2.5 | 7.4 |
| | N1 V83 | 1 (D28) | 1.87 | 1.1 | 0.15 | S | 91% | — | — |
| | N2 V57 | 2.2 (D28) | 7.35 | 1.2 | 0.19 | S | | 2.6 | 9.3 |
| | N10 W22 | 2.3 (D21) | 9.38 | 1 | 0.12 | S | | 2.6 | 9.3 |
| | N5 W38 | 2 (D25) | 4.70 | 1.1 | 0.15 | S | | 2.6 | 9.3 |
| | N9 W22 | 2.4 (D14) | 11.8 | 0.5 | 0.07 | S | | 2.5 | 7.4 |

TABLE 28-continued

|  |  |  |  |  |  |  |  |  |  |
|---|---|---|---|---|---|---|---|---|---|
|  | N13 | 2.2 (D25) | 7.35 | 1.3 | 0.23 | S |  | 2.6 | 9.3 |
|  | V14 |  |  |  |  |  |  |  |  |
| controls | N1 V57 | 0.2 (D28) | 0.07 | 0.2 | 0.02 | D (14) |  | — | — |
|  | N2 W38 | 1.4 (D28) | 1.17 | 0.2 | 0.02 | D (15) | 0% | — | — |
|  | N7 V8 | 1.1 (D14) | 0.49 | 0.2 | 0.02 | D (14) |  | — | — |

IV 36 months challenge ($10^{6.7}$ $LD_{50}$ mouse/dog)

RABIES SN ANTIBODIES (REFIT)

| GROUP | N.DOG | maximum observed | | day of challenge | | RESULT | SURVIVING |
|---|---|---|---|---|---|---|---|
|  |  | LOG | I.U. | LOG | I.U. | (*) | RATE |
| vaccinated | N V14 | 1.7 (D28) | 2.35 | 0.6 | 0.05 | D (13) |  |
|  | N4 R54 | 2.2 (D25) | 7.45 | 1.6 | 0.59 | S |  |
|  | N5 V9 | 2.2 (D14) | 7.45 | 1 | 0.29 | S |  |
|  | N6 V9 | 1.7 (D25) | 2.35 | 1.2 | 0.23 | S | 10/11 |
|  | N6 V9 | 2.2 (D26) | 7.45 | 1.3 | 0.15 | S | 11/12 |
|  | N3 W35 | >3.1 (D14) | >59 | 1 | 0.15 | S |  |
|  | N4 W36 | 2.6 (D28) | 18.71 | 1.6 | 0.59 | S | 92% |
|  | N4 V57 | 2.6 (D21) | 18.71 | 1 | 0.15 | S |  |
|  | N5 T90 | 2.2 (D21) | 7.45 | 1.1 | 0.19 |  |  |
|  | N6 V49 | 2.4 (D14) | 11.8 | 1 | 0.15 | S |  |
|  | N3 S110 | 2.2 (D25) | 7.45 | 1.4 | 0.37 | S |  |
|  | N9R27 | 2.2 (D21) | 7.45 | 0.5 | 0.09 | S |  |
| controls | N1844 | 1.7 (3 years) |  | 1.7 | 0.74 | D (15) |  |
|  | N3T90 | 0.2 (D25) | 0.94 | 0.2 | 0.02 | D (17) | 0/3 0% |
|  | N1510 | 1.3 (D0) | 0.74 | 1.3 | 0.29 | D (16) |  |

TABLE 29

CANARYPOX/RABIES RECOMBINANT vCP65
RABIES ANTIBODIES KINETICS (RFFIT)

| | | ANTIBODIES IN I.U. (time in months) | | | | | | | | | |
|---|---|---|---|---|---|---|---|---|---|---|---|
| GROUP | N.DOGS | 0 | 1 | 2 | 3 | 6 | (*) 8 | 12 | 24 | (**) 25 | 36 |
| VCP 65 | N1V9 | 0.74 | 7.45 | 0.93 | 0.07 | 0.18 |  | 0.09 |  |  |  |
| 106.7/ml | N3V9 | 0.29 | 7.45 | 0.29 | 0.23 | 0.74 |  | 0.15 |  |  |  |
|  | N2V9 | 1.17 | 3.73 | 0.29 | 0.23 | 0.23 |  | 0.07 |  |  |  |
|  | N3W22 | 0.23 | 9.38 | 0.93 | 0.23 | 0.12 |  | 0.05 |  |  |  |
|  | N5W22 | 0.23 | 4.70 | 0.93 | 0.23 | 0.59 | 7.40 |  |  |  |  |
|  | N4V9 | 0.59 | 11.80 | 0.74 | 0.18 | 0.23 |  | 0.15 |  |  |  |
|  | N1W38 | 0.47 | 18.71 | 1.17 | 0.74 | 0.47 |  | 0.15 |  |  |  |
|  | N8W22 | 0.74 | 2.35 | 0.59 | 0.23 | 1.85 |  | 0.15 |  |  |  |
|  | N7W22 | 0.74 | 7.45 | 1.17 | 0.23 | 0.18 | 7.40 |  |  |  |  |
|  | N8V14 | 0.23 | 7.45 | 0.74 | 0.23 | 0.23 |  | 0.38 |  |  |  |
|  | N7V14 | 0.47 | 3.73 | 0.29 | 0.15 | 0.15 |  | 0.15 |  |  |  |
|  | N1R54 | 0.23 | 7.45 | 2.94 | 0.47 | 0.59 |  | 0.12 |  |  |  |
|  | N9V14 | 0.23 | 0.94 | 0.29 | 0.07 | 0.18 |  | 0.15 |  |  |  |
|  | N2S44 | 0.47 | 0.74 | 0.09 | 0.07 | 0.07 |  | 0.05 | 0.02 |  |  |
|  | N3T2 | 0.47 | 2.35 | 0.29 | 0.07 | 0.07 |  | 0.05 | 0.04 | 9.3 |  |
|  | N5V49 | 0.23 | 18.71 | 1.48 | 0.47 | 0.59 |  | 0.38 | 0.47 | 9.3 |  |
|  | N4V49 | 0.23 | 7.45 | 0.93 | 0.23 | 0.29 | 2.30 |  |  |  |  |
|  | N2V49 | 0.29 | 2.35 | 0.19 | 0.15 | 0.18 |  | 0.05 | 0.03 | 14.7 |  |
|  | N1V49 | 0.23 | 7.45 | 0.93 | 0.23 | 0.12 |  | 0.09 | 0.12 | 7.4 |  |
|  | N1V83 | 0.07 | 1.87 | 0.59 | 0.12 | 0.18 |  | 0.05 | 0.15 |  |  |
|  | N2T90 | 0.23 | 7.45 | 1.17 | 0.59 | 0.23 | 1.80 |  |  |  |  |
|  | N3V57 | 0.47 | 14.86 | 1.17 | 0.47 | 0.74 | 7.40 |  |  |  |  |
|  | N2V57 | 0.23 | 7.45 | 1.17 | 0.23 | 0.23 |  | 0.15 | 0.19 | 9.3 |  |
|  | N10W22 | 0.07 | 7.45 | 0.37 | 0.23 | 0.15 |  | 0.15 | 0.12 | 9.3 |  |
|  | N5W38 | 0.23 | 4.70 | 0.93 | 0.23 | 0.23 |  | 0.15 | 0.15 | 9.3 |  |
|  | N9W22 | 0.18 | 2.96 | 0.59 | 0.23 | 0.29 |  | 0.15 | 0.07 | 7.4 |  |
|  | N13V14 | 0.74 | 7.45 | 0.37 | 0.18 | 0.07 |  | 0.15 | 0.23 | 9.3 |  |
|  | N12V14 | 0.59 | 2.35 | 0.15 | 0.07 | 0.12 |  | 0.05 |  |  | 0.05 |
|  | N3S44 | 0.07 | 0.93 | 0.18 |  |  |  |  |  |  |  |
|  | N4R54 | 0.29 | 7.45 | 2.34 | 0.29 | 0.74 |  | 0.47 | 0.74 |  | 0.59 |
|  | N5V9 | 0.07 | 7.45 | 0.93 | 0.18 | 0.47 |  | 0.09 | 0.07 |  | 0.29 |
|  | N6V9 | 0.47 | 2.35 | 0.93 | 0.23 | 0.74 |  | 0.15 | 0.12 |  | 0.23 |

TABLE 29-continued

CANARYPOX/RABIES RECOMBINANT vCP65
RABIES ANTIBODIES KINETICS (RFFIT)

| | | ANTIBODIES IN I.U. (time in months) | | | | | | | | |
|---|---|---|---|---|---|---|---|---|---|---|
| GROUP | N.DOGS | 0 | 1 | 2 | 3 | 6 | (*) 8 | 12 | (**) 24 25 | 36 |
| | N8V9 | 0.29 | 7.45 | 0.93 | 0.23 | 0.15 | | 0.05 | 0.05 | 0.15 |
| | N4R18 | 0.23 | 7.45 | 0.93 | 0.23 | 0.93 | | 0.12 | 0.15 dead | before chall. |
| | N3W38 | 0.12 | 37.33 | 2.34 | 0.23 | 0.93 | | 0.15 | 0.15 | 0.15 |
| | N4W38 | 0.23 | 18.71 | 4.67 | 0.47 | 0.74 | | 0.47 | 1.5 | 0.59 |
| | N4V57 | 0.23 | 7.45 | 2.94 | 0.47 | 1.17 | | 0.29 | 0.15 | 0.15 |
| | N5T90 | 0.23 | 2.35 | 0.74 | 0.12 | 0.74 | | 0.07 | 0.05 | 0.19 |
| | N6V49 | 0.18 | 2.35 | 0.29 | 0.23 | 0.23 | | 0.15 | 0.05 | 0.15 |
| | N3S110 | 0.59 | 7.45 | 0.93 | 0.47 | 0.74 | | 0.29 | 0.6 | 0.37 |
| | N9R27 | 0.07 | 0.94 | 0.93 | 0.23 | 0.59 | | 0.09 | 0.15 | 0.09 |
| | geom. mean | 0.28 | 5.11 | 0.71 | 0.22 | 0.31 | | 0.13 | 0.13 | 0.20 |
| controls | N1S44 | 0.74 | 0.74 | 0.07 | 0.02 | 0.07 | | 0.05 | | 0.74 |
| | N1V57 | 0.07 | 0.07 | 0.07 | 0.07 | 0.07 | | 0.05 | 0.02 | |
| | N3T90 | 0.23 | 0.94 | 0.09 | 0.07 | 0.07 | | 0.05 | | 0.02 |
| | NIS10 | 0.74 | 0.47 | 0.09 | 0.07 | 0.07 | | 0.05 | | 0.29 |
| | N10V14 | 0.23 | 0.74 | 0.09 | 0.07 | 0.07 | | 0.05 | | |
| | N14V14 | 0.23 | 0.59 | 0.07 | 0.07 | 0.07 | | 0.05 | | |
| | N5R54 | 0.23 | 0.74 | 0.09 | 0.07 | 0.07 | | 0.05 | | |
| | N7V9 | 0.59 | 0.49 | 0.09 | 0.07 | 0.07 | | 0.05 | 0.02 | |
| | N2W38 | 0.74 | 1.17 | 0.15 | 0.07 | 0.07 | | 0.05 | 0.02 | |
| | 195 | 0.07 | 0.07 | 0.07 | 0.07 | 0.07 | | | | |
| | 194 | 0.59 | 0.47 | 0.09 | 0.07 | 0.07 | | | | |
| | 198 | 0.29 | 0.05 | 0.18 | 0.07 | 0.07 | | | | |
| | X | 0.30 | 0.37 | 0.09 | 0.06 | 0.07 | | 0.05 | 0.02 | 0.45 |

(*): 8 months = antibodies titration 2 months following challenge
(**): 25 months = antibodies titration 40 days following challenge

TABLE 30

ALVAC/RABIES RECOMBINANT
VCP-65
DURATION OF IMMUNITY ON DOGS
SUMMARY OF THE RESULTS
OF EXAMPLE 12

| VACCINATED DOGS: | 41 |
|---|---|
| NON SPECIFIC DEADS: | 2 |
| VACCINATED AND CHALLENGED DOGS: | 39 |
| CONTROLS AND CHALLENGED DOGS: | 12 |

| | VACCINATED | | CONTROLS | |
|---|---|---|---|---|
| | Nb. | Survivals | Nb. | Survivals |
| Challenge 6 months | 5 | 5/5 | 3 | 0/3 |
| Challenge 12 months | 11 | 11/11 | 3 | 0/3 |
| Challenge 24 months | 11 | 10/11 | 3 | 0/3 |
| Challenge 36 months | 12 | 11/12 | 3 | 0/3 |
| TOTAL | 39 | 37/39 | 12 | 0/12 |
| % | | 94.9% | | 0% |

Example 13

ALVAC/Rabies Recombinant vCP65 Immunization of Pups With Maternal Antibodies

Materials:

Animals: 16 Beagle pups born from immune bitches, boostered with Rabisin two weeks before whelping.

Vaccines: Alvac/Rabies (vCP65): freeze-dried batch, containing $10^8$ $TCID_{50}$ 1 ml and Rabisin: batch 1 RBN of 581, 7 I.U./dose.

Methods:

Immunization: Pups remained with their mother until weaning. then they were two weeks old, they were randomized and distributed into 4 groups:

A: 4 pups receiving 1 ml SC vCP65 at $10^8$ $TCID_{50}$/ml

B: 4 pups receiving 1 ml SC vCP65 at $10^{6.7}$ $TCID_{50}$/ml

C: 4 pups receiving 1 ml SC/Rabisin

D: 4 pups remaining unvaccinated="Controls"

Serology: All pups were bled on days 0, 14, 28, 49, 82, 105 and 119. The animals surviving after challenge were also bled on day 160. Rabies Ab titration: RFFIT. CP Ab titration: ELISA.

Challenge: On day 119 following immunization, all the pups were Challenged by IM inoculation of $10^{4.1}MLD_{50}$ in temporal muscle.

Results:

CP (canarypox) antibodies (See table 31): In spite of high and heterologous background observed, vaccination was shown by mean CP Ab canarypox antibodies) increasing.

Rabies antibody (Ab) and protection rate (See Tables 31 and 32): In comparison with passive Ab decreasing on controls, a stabilization, or even a limited increase in SN titer on the vaccinated groups was observed until day 28. It is not possible to differentiate the 3 vaccinated groups. All pups immunized with Rabisin or vCP65 at $10^8$ $TCID_{50}$ survived following challenge whereas 50% (2/4) $10^{6.7}$ TCID vaccinated pups are protected.

Immunization of pups 2 weeks old, having high SN Ab-rate, was possible with Rabisin or vCP65 at $10^8$ $TCID_{50}$ Vaccination under the same conditions, using vCP-65 at $10^{6.7}TCID_{50}$, induced 50% of protection.

This Example illustrates that recombinant poxvirus-rabies compositions (e.g., vCP65 compositions) can elicit protection in spite of maternal immunity in pups.

TABLE 31

IMMUNIZATION OF PUPS WITH MATERNAL ANTIBODIES

| GROUP | N° PUPS | CP ANTIBODIES OD at 450 nm, SERA 1/100, ON DAYS | | | | |
|---|---|---|---|---|---|---|
| | | 0 | 28 | 49 | 82 | 119 |
| A | 465D19 | 0.223 | 0.234 | 0.175 | 0.367 | 0.237 |
| | 464A6C | 0.131 | 0.332 | 0.232 | 0.361 | 0.311 |
| vCP65 | 464C62 | 0.108 | 0.297 | 0.203 | 0.266 | 0.283 |
| | 463B7E | 0.026 | 0.269 | 0.261 | 0.203 | 0.053 |
| $10^8$ | X | 0.122 | 0.283 | 0.218 | 0.299 | 0.221 |
| | STD | 0.070 | 0.036 | 0.032 | 0.069 | 0.101 |
| B | 26356A | 0.06 | 0.198 | 0.307 | 0.505 | 0.313 |
| | 260545 | 0.065 | 0.404 | 0.308 | 0.374 | 0.24 |
| VCP65 | 263906 | 0.121 | 0.322 | 0.255 | 0.363 | 0.298 |
| | 26033F | 0.107 | 0.234 | 0.229 | 0.328 | 0.295 |
| $10^{6.7}$ | X | 0.088 | 0.290 | 0.275 | 0.393 | 0.287 |
| | STD | 0.026 | 0.080 | 0.034 | 0.067 | 0.028 |
| | 222C01 | 0.039 | 0.221 | 0.105 | 0.282 | 0.211 |
| | 221465 | 0.227 | 0.184 | 0.11 | 0.254 | 0.286 |
| D | 221D62 | 0.15 | 0.141 | 0.227 | 0.144 | 0.234 |
| | 221B11 | 0.1 | 0.142 | 0.167 | 0.208 | 0.232 |
| CONTROLS | X | 0.129 | 0.172 | 0.152 | 0.222 | 0.241 |
| | STD | 0.069 | 0.033 | 0.050 | 0.052 | 0.028 |

TABLE 32

ALVAC/RABIES RECOMBINANT vCP65
IMMUNIZATION OF PUPS WITH MATERNAL ANTIBODIES

| GROUP | N° PUPS | RABIES ANTIBODIES IN $LOG_{10}$, ON DAYS: | | | | | | | | survival following challenge | |
|---|---|---|---|---|---|---|---|---|---|---|---|
| | | 0 | 14 | 28 | 49 | 82 | 105 | 119 | 160 | | |
| A | 465D19 | 1.9 | 2.5 | 1.8 | 1.1 | 0.8 | 1.1 | 0.8 | 1.2 | S | |
| | 464A6C | 2.6 | 2.3 | 2.6 | 0.7 | 0.6 | 0.8 | 0.4 | 1.1 | S | |
| vCP65 | 464C62 | 2.4 | 1.8 | 2.5 | 1.2 | 0.7 | 1.2 | 0.7 | 1.2 | S | 100% |
| | 463B7E | 1.8 | 2.5 | 2.3 | 1.i | 0.6 | 1.2 | 0.7 | 1 | S | |
| $10^8$ | X | 2.18 | 2.28 | 2.30 | 1.03 | 0.68 | 1.08 | 0.65 | 1.13 | | |
| | STD | 0.33 | 0.29 | 0.31 | 0.19 | 0.08 | 0.16 | 0.15 | 0.08 | | |
| B | 26358A | 2.2 | 2.3 | 2.2 | 1.3 | 1.4 | 1.7 | 1.4 | 2.2 | S | |
| | 260545 | 2.3 | 2.6 | 2.2 | 1.8 | 1.2 | 0.8 | 0.2 | | D(13) | |
| vCP65 | 263906 | 1.47 | 1.9 | 1.7 | 0.8 | 0.5 | 0.6 | 0.7 | | D(17) | 50% |
| | 26033F | 2 | 2.2 | 1.9 | 1.3 | 1.2 | 1.1 | 0.7 | 1 | S | |
| $10^{6.7}$ | X | 1.99 | 2.25 | 2.00 | 1.30 | 1.08 | 1.05 | 0.75 | 1.60 | | |
| | STD | 0.32 | 0.25 | 0.21 | 0.35 | 0.34 | 0.42 | 0.43 | | | |
| | 254363 | 2.8 | 2.5 | 2.2 | 1.7 | 1.7 | 1.7 | 1.4 | 1.7 | S | |
| | 253054 | 2 | 2.2 | 2.4 | 1.7 | 1.1 | 0.8 | 0.4 | 1.2 | S | |
| C | 254809 | 2 | 2.6 | 2.6 | 1.7 | 1.2 | 1.6 | 1.7 | 1.2 | S | 100% |
| | 251F30 | 2.4 | 2.4 | 2.5 | 1.4 | 1.4 | 1.4 | 1.2 | 1.1 | S | |
| RABISIN | X | 2.30 | 2.43 | 2.43 | 1.68 | 1.35 | 1.38 | 1.18 | 1.30 | | |
| | STD | 0.33 | 0.15 | 0.15 | 0.18 | 0.23 | 0.35 | 0.48 | 0.23 | | |
| | 222C01 | 2.2 | 2 | 1.7 | 0.6 | 0.5 | 0.6 | 0.4 | | D(14) | |
| | 221465 | 2 | 2.4 | 1.7 | 0.8 | 1 | 1 | 0.6 | | D(14) | |
| D | 221D62 | 2.2 | 2 | 1.7 | 0.6 | 0.7 | 0.5 | 0.2 | | D(14) | 0% |
| | 221B11 | 2.4 | 1.7 | 1.4 | 0.2 | 0.2 | 0.5 | 0.2 | | D(17) | |
| CONTROLS | X | 2.20 | 2.03 | 1.63 | 0.55 | 0.60 | 0.65 | 0.35 | | | |
| | STD | 0.14 | 0.25 | 0.13 | 0.22 | 0.29 | 0.21 | 0.17 | | | |

*: challenge on day 121, with $10^{4.1}$ $MLD_{50/dog}$

TABLE 33

ALVAC/RABIES RECOMBINANT vCP65
IMMUNIZATION OF PUPS WITH MATERNAL ANTIBODIES

| GROUP | N° PUPS | \multicolumn{8}{c}{RABIES ANTIBODIES IN INTERNATIONAL UNITS (I.U.), ON DAYS:} | survival following challenge |
|---|---|---|---|---|---|---|---|---|---|---|
|  |  | 0 | 14 | 28 | 49 | 82 | 105 | 119 | 160 |  |
| A | 465D19 | 1.17 | 4.7 | 0.93 | 0.15 | 0.07 | 0.09 | 0.09 | 0.47 | S |
|  | 464A6C | 5.88 | 2.95 | 5.88 | 0.06 | 0.05 | 0.05 | 0.04 | 0.37 | S |
| vCP65 | 565C62 | 3.71 | 0.93 | 4.7 | 0.19 | 0.06 | 0.12 | 0.07 | 0.47 | S  100% |
|  | 463B7E | 0.93 | 4.7 | 2.95 | 0.15 | 0.05 | 0.12 | 0.07 | 0.29 | S |
| $10^8$ | X (geom.) | 2.21 | 2.79 | 2.95 | 0.13 | 0.06 | 0.09 | 0.06 | 0.39 |  |
| B | 26356A | 2.34 | 2.95 | 2.34 | 0.23 | 0.3 | 0.37 | 0.37 | 4.67 | S |
|  | 260545 | 2.95 | 5.88 | 2.34 | 0.74 | 0.19 | 0.05 | 0.02 |  | D(13) |
| vCP65 | 263906 | 0.37 | 1.17 | 0.74 | 0.07 | 0.04 | 0.03 | 0.07 |  | D(17) 50% |
|  | 26033F | 1.48 | 2.34 | 1.17 | 0.23 | 0.19 | 0.09 | 0.07 | 0.29 | S |
| $10^{6.7}$ | X (geom.) | 1.39 | 2.63 | 1.48 | 0.23 | 0.14 | 0.08 | 0.08 | 1.35 |  |
|  | 254362 | 9.32 | 4.7 | 2.34 | 0.59 | 0.59 | 0.37 | 0.37 | 1.48 | S |
|  | 253054 | 1.48 | 2.34 | 3.71 | 0.59 | 0.15 | 0.05 | 0.04 | 0.47 | S |
| C | 254809 | 1.48 | 5.88 | 5.88 | 0.59 | 0.19 | 0.29 | 0.74 | 0.47 | S  100% |
|  | 251F30 | 3.71 | 3.71 | 4.7 | 0.3 | 0.3 | 0.18 | 0.23 | 0.37 | S |
| RABISIN | X (geom.) | 2.95 | 3.94 | 3.94 | 0.50 | 0.27 | 0.18 | 0.22 | 0.59 |  |
|  | 222C01 | 2.34 | 2 | 1.7 | 0.05 | 0.04 | 0.03 | 0.04 |  | D(14) |
|  | 221465 | 1.48 | 2.4 | 1.7 | 0.07 | 0.12 | 0.09 | 0.06 |  | D(14) |
| D | 221D62 | 2.34 | 2 | 1.7 | 0.05 | 0.06 | 0.02 | 0.02 |  | D(14) 0% |
|  | 221B11 | 3.71 | 1.7 | 1.4 | 0.02 | 0.02 | 0.02 | 0.02 |  | D(17) |
| CONTROLS | X (geom.) | 2.34 | 2.01 | 1.62 | 0.04 | 0.05 | 0.03 | 0.03 |  |  |

*: challenge on day 212, with $10^{4.1}$ $MLD_{50/dog}$

Example 14

One Year Rabies Immunogenicity and Safety Test in Dogs of a Vaccine Using a Recombinant Rabies Fraction (vCP65) In Combination with Conventional Fractions: Canine Distemper, Adenovirus Type 2, Coronavirus, Parainfluenza, Parvovirus, Rabies Vaccine, Modified Live Virus, Canarypox Vector, Leptospira Canicola-Icterohaemorrhagiae Bacterin This example demonstrates protection against rabies challenge for at least one year after vaccination and evaluates efficacy, safety and lack of interference of this recombinant vaccine in 9 to 12 week old puppies.

More specifically, this Example demonstrates protection against rabies for a least one year by a recombinant rabies antigen (vCP65) included in the canine combination vaccine DACPiP-CP65 and DACIP+LCI, and evaluates the safety of this combination vaccine when administered by the subcutaneous (SQ) route in young puppies and the lack of interference of the different fractions on each other (See also Example 15, infra).

A live canarypox vector was used to prepare a vectored recombinant rabies vaccinal virus. The Canarypox vector has been manipulated by genetic engineering techniques to contain the gene coding for the rabies virus surface glycoprotein (G). The rabies recombinant vaccinal antigen was prepared with the fifth passage (vCP65×+5) from the master seep. This antigen producer can be used in a monovalent vaccine. It can also be lyophilized in combination with five other modified live canine antigens. For clarification purposes, the following abbreviations for these antigens will be used in this Example and Tables included in this Example:

MLV Component

Abbreviation

Canine Distemper Virus (CDV) D
Canine Adenovirus (CAV-2) A
Canine Coronavirus (CCV) C
Canine Parainfluenza (CPi) Pi
Canine Parvovirus (CPV) P
Canarypox Vector/Rabies (recombinant) CP65

The *Leptospira canicola* and *Leptospira icterohaemorrhagiae* bivalent bacterin used to rehydrate the vaccine DACPiP-CP65 and DACPiP is abbreviated as LCI.

Procedure:

Thirty (30) rabies seronegative dogs were vaccinated twice subcutaneously with a 1 ml dose of a lyophilized combination (DACPiP-CP65+LCI) vaccine containing DACPiP and a recombinant rabies fraction (vCP65), diluted in a two-way leptospira combination bacterin (LCI). Thirty (30) rabies seronegative dogs were vaccinated with the same combination vaccine without the recombinant rabies fraction (DACPiP+LCI) and served as rabies controls. Serum samples were collected at Days 0, 28 60, 90, 180, 270, and 390 days postvaccination and RFFIT was used to obtain their rabies antibody titer. All dogs were challenged 365 days after the second vaccination. Symptoms and deaths were recorded daily for 90 days after challenge. More specifically, Animals: Sixty (60) rabies seronegative dogs between 9 and 12 weeks of age were obtained from Harlan Sprague Dawley.

Vaccinates: Thirty (30) of the dogs received their first vaccination with the recombinant rabies combination (DACPiP-CP65+LCI) at the following ages (Table 34):

TABLE 34

| Number of Dogs | Age at 1st Vaccination |
|---|---|
| 1 | 9 weeks |
| 6 | 10 weeks |
| 9 | 11 weeks |
| 14 | 12 weeks |

Controls: Thirty (30) control dogs that received the same combination vaccine less the recombinant rabies (DACPiP+ LCI) were categorized on age basis as follows:

TABLE 35

| Number of Dogs | Age at 1st Vaccination |
|---|---|
| 1 | 9 weeks |
| 7 | 10 weeks |
| 9 | 11 weeks |
| 13 | 12 weeks |

Vaccines: DACPiP-CP65 AND DACPiP: These vaccines were prepared by the following formulation:

TABLE 36

| Antigen | Volume in DACPiP-CP65 (ml) | Volume in DACPiP (ml) |
|---|---|---|
| D | 157.00 | 157.00 |
| A | 1.57 | 1.57 |
| C | 35.00 | 40.00 |
| Pi | 70.00 | 70.00 |
| P | 52.00 | 56.00 |
| CP65 | 10.00 | 0.00 |
| Stabilizer | 174.00 | 174.00 |
| TOTAL | 499.57 | 498.57 |

These vaccinal suspensions DACPiP-CP65 and DACPiP were distributed in vials containing 1.3 ml of suspension and lyophilized on day -8 and -61, respectively. Their titers after lyophilization are set forth below.

Leptospira Bacterin (LCI): The LCI was a USDA released-commercial Ser. No. 32010.

Challenge Virus: The challenge virus culture was a NYC strain of rabies street virus obtained from NVSL. Upon receipt, the challenge culture was diluted 1:100 in CVS, aliquoted in 1 ml vials and kept frozen at $-70°$ C. until use.

The following schedule was used during this study (Table 37):

TABLE 37

| Days Post-First Vaccination | Activity |
|---|---|
| 0 | Bleed and Vaccinate ($V_1$) |
| 28 | Bleed and Vaccinate ($V_2$) |
| 60 | Bleed |
| 90 | Bleed |
| 180 | Bleed |
| 270 | Bleed |
| 390 | Bleed |
| 395 | Challenge |
| 485 | End of Study |

Vaccination:

Vaccination Group: Thirty (30) dogs received a 1 ml dose, SQ, of the lyophilized vaccine (DACPiP-CP65) rehydrated with the liquid (LCI) bacterin.

Control Group: Thirty (30) dogs received a 1 ml dose, SQ, of DACPIP rehydrated with LCI.

Booster Vaccination: Four weeks post-first vaccination, vaccinate group received a 1 ml dose, SQ, of DACPIP-CP65 and the control group receive a second 1 ml dose, SQ, of DACPiP. Both vaccines were rehydrated with LCI.

Preliminary Challenge: Nine dogs were divided into three group of three dogs each. Group 1 dogs were challenged with the challenge culture diluted to $10^{-4}$, Group 2 dogs were challenged with the challenge culture diluted to $10^{-5}$ and Group 3 dogs were challenged with the challenge culture diluted to $10^{-6}$. Dilution of challenge culture was done in CVS diluent. One-half of 1 ml of the challenge culture was injected intramuscularly (IM) in each masseter muscle of each dog. The dogs were observed daily for mortality and/or clinical signs associated with rabies.

Challenge: Based on the results of the preliminary challenge, the challenge culture was diluted to $10^{-4.3}$ in CVS solution. Two vials previously diluted to $10^{-2}$ and kept frozen at $-70°$ C. were thawed and pooled. One and one-half milliliter (1.5 ml) of the pool was added to 28.5 ml of CVS diluent to obtain $10^{-3.3}$ dilution. A second dilution from the $10^{-3.3}$ was made by transferring 15 ml into 135 ml of CVS to obtain a final challenge culture dilution of $10^{-4.3}$.

The final dilution of the challenge culture was dispensed into 15, 10 ml vials, immediately placed in two ice boxes and transported to where the dogs were housed. The diluted challenge culture was maintained in ice throughout the challenge administration. All the dogs (vaccinates and controls) were challenged by IM inoculation of 0.5 ml of the challenge culture injected into each masseter muscle.

Results:

The titer of the rabies recombinant fraction was $10^{5.6}$ $TCID_{50}$/dose.

None of the puppies showed any local or generalized reactions after vaccination.

No interference was observed for any fraction (See Example 15, infra).

The vaccine protected 28 out of 30 (93.3%) of the vaccinated dogs against a challenge which killed 26 out of 30 (86.7%) of the control dogs.

More specifically,

Post Challenge: The dogs were observed every day for 90 days post-challenge and the results recorded. Observations such as nervous signs, paralysis and death were recorded daily. Brain tissues from the cerebellum, the pons and the hippocampus were removed from each dog that died post-challenge. The tissues were kept frozen until the end of the observation period. At the end of the observation period, all surviving dogs were euthanized.

Brain impression smears from each animal that died from rabies infection were prepared, acetone fixed and stained with fluorescein labelled anti-rabies globulin. An FA positive slide was considered as confirmation of rabies virus infection.

Blood samples were collected at or about Days 0, 30, 60, 90, 180, 270, 365 and 395 days post-first vaccination and tested by Rapid Focus Fluorescent Inhibition Test (RFFIT). This was performed in accordance with 9 CFR 113.209.

Also for safety, dogs were observed daily for any clinical local or systemic adverse reactions related to vaccine administrations.

Vaccine Titers: Each fraction of the lyophilized component of the vaccine samples retained after vaccination was titrated and gave the following titers (Table 38):

TABLE 38

| Fraction | Titer $Log_{10}$ $TCID_{50}$/ml | |
|---|---|---|
| | DACPiP-CP65 | DACPiP |
| Distemper | 4.3 | 4.8 |
| Adenovirus Type 2 | 4.3 | 4.9 |
| Coronavirus | 6.0 | 5.7 |
| Parainfluenza | 4.2 | 3.8 |
| Parvovirus | 6.0 | 6.2 |
| Rabies (CP65) | 5.6* | N/A |

*Mean of five replicate titrations.

Preliminary Challenge: The results of the preliminary challenge are displayed in Table 39 below:

TABLE 39

| Challenge Culture Dilution | Dog # | Mortality Days Post-Challenge |
|---|---|---|
| $10^{-4}$ | 2015 | 15 |
| | 2014 | 12 |
| | 2004 | 13 |
| $10^{-5}$ | 2025* | N/A |
| | 3017 | 14 |
| | 2003 | 16 |
| $10^{-6}$ | 3022* | N/A |
| | 3019 | 17 |
| | 3020 | 31 |

*Dogs # 2025 and 3022 were euthanized by lethal injection 45 days post challenge.

Challenge Culture Titration: The back titration in mice of the challenge culture results for both the pre-challenge and final challenge are reported in Table 40. The real challenge titer was $10^{7.2}$ $MLD_{50}$/ml.

Dog challenge: The results of the final challenge are summarized in table 41 (vaccinates) and Table 42 (Controls). Each dog received a challenge dose of $10^{7.15}$ $MLD_{50}$/ml based on replicate titrations.

Mortality:

Controls: Twenty-six (26) of the 30 control dogs died between 11 and 23 days post-challenge. This represents a death rate of 86.7%.

Vaccinates: Twenty-eight of the 30 vaccinated dogs survived the challenge. This a protection rate of 93.3%.

FA Test of Brain Smears (Tables 41 and 42):

Vaccinates: Direct FA on brain impression slides of the two dogs that died showed that both were positive for rabies virus.

Controls: Direct FA brain impression slides showed that death of 26 control dogs was caused by rabies virus.

Serology: RFFIT titers of sera samples collected at Days 0, 30, 60, 90, 180, 270, and 390 post-first vaccination are shown in Tables 43 and 44. The results show that dogs were seronegative for rabies when the study began and that the controls remained negative through the day of challenge. The test was done in accordance with 9 CFR 113.209.

Seroconversion with respect to the age at which the puppies were vaccinated was analyzed and the mean titer at Day 30 post-second vaccination calculated (Table 45). The table showed that post-vaccinal antibody titer response increased irrespective of age of vaccination.

Safety: None of the vaccinated puppies showed any adverse local or systemic reaction after any of the two vaccinations.

Conclusion:

Two doses given subcutaneously of a DACPiP-CP65+ LCI vaccine containing $10^{5.6}$ $TCID_{50}$/dose of vCP65 rabies:

Are safe in 9 to 12 week old dogs.

Induce low and temporary seroconversion.

Very efficiently protect dogs against a severe rabies challenge for at least one year.

More specifically, dogs vaccinated at age 9 to 12 weeks are protected by the recombinant rabies vaccine (vCP65) in combination with other canine vaccines (DACPiP) and rehydrated with Leptospira Bacteria. Mortality by the challenge culture is not dependent on the age of dog when first vaccinated.

Dogs seroconverted significantly even though they were vaccinated at 9 weeks to 12 weeks of age, at which time maternal antibody was present. However, at the time of challenge vaccinated dogs had virtually no detectable antibody and were protected.

Challenge culture diluted in convenient buffer and conserved at −70° C. can be used to challenge dogs. Prechallenge titration is necessary before conducting a major immunogenicity study. The challenge dose administered was 50 times higher than the dose that caused 100% mortality in experiments conducted by NVSL.

The recombinant rabies vaccine VCP65 with a titer of $10^{5.6}TCID_{50}$/ml in combination with DACPiP with or without LCI confers protection for a period of at least one year.

The fractions of this combination vaccine do not interfere with the immunogenicity of the recombinant rabies fraction: The recombinant rabies vaccine protected 93.3% of the vaccinates against a severe, virulent challenge which killed 86.7% of the controls. The canine combination recombinant rabies vaccine is safe when administered to puppies by the subcutaneous route.

TABLE 40

| Mouse Titration of Rabies Challenge Virus, Lot 92-5, Diiuted $10^{-4.3}$ for Dog Challenge. | | | |
|---|---|---|---|
| Dilution | Titration #1 | Dilution | Titration #2 |
| $10^{-2}$ | 6/6 Dead | $10^{-4.3}$ | 6/6 Dead |
| $10^{-2.6}$ | 6/6 Dead | $10^{-4.9}$ | 4/6 Dead |
| $10^{-3.2}$ | 6/6 Dead | $10^{-5.5}$ | 2/6 Dead |
| $10^{-3.8}$ | 6/6 Dead | $10^{-6.1}$ | 1/6 Dead |
| $10^{-4.4}$ | 6/6 Dead | $10^{-6.7}$ | 1/6 Dead |
| $10^{-5.0}$ | 5/6 Dead | $10^{-7.3}$ | 0/6 Dead |
| $10^{-5.6}$ | 3/6 Dead | $10^{-7.9}$ | 0/6 Dead |
| $10^{-6.2}$ | 3/6 Dead | $10^{-8.5}$ | 0/6 Dead |
| $10^{-6.8}$ | 1/6 Dead | | |

[1]Challenge/0.3 ml = $10^{5.9}$ $MLD_{50}$/Challenge/0.03 ml − $10^{5.4}MLD_{50}$

[2]Challenge/1 ml dog dose = $10^{7.4}$ $MLD_{50}$/Challenge/1 ml dog dose = $10^{6.9}$ $MLD_{50}$ Dog Dose Mean = $10^{7.15}$ Mouse Lethal $Dose_{50}$

[1]0.03 ml mouse dose administered intracranially

[2]Equivalent titer of rabies administered to dogs 51 days post-challenge.

TABLE 41

| One Year Canine Duration of Immunity Rabies Study Challenge Results of Vaccinates. | | | |
|---|---|---|---|
| Dog # | Age (weeks) | Mortality DPC | Brain FA |
| 192 | 12 | | N/A |
| 196 | 12 | | N/A |
| 410 | 12 | | N/A |
| 211 | 12 | | N/A |
| 221 | 12 | | N/A |
| 228 | 12 | | N/A |
| 234 | 12 | | N/A |
| 414 | 11 | | N/A |
| 239 | 11 | | N/A |

TABLE 41-continued

One Year Canine Duration of Immunity Rabies Study Challenge Results of Vaccinates.

| Dog # | Age (weeks) | Mortality DPC | Brain FA |
|---|---|---|---|
| 249 | 11 |  | N/A |
| 260 | 11 |  | N/A |
| 267 | 11 |  | N/A |
| 270 | 10 |  | N/A |
| 420 | 10 |  | N/A |
| 430 | 10 | 21 | + |
| 200 | 12 |  | N/A |
| 417 | 12 |  | N/A |
| 205 | 12 |  | N/A |
| 208 | 12 |  | N/A |
| 216 | 12 |  | N/A |
| 226 | 12 |  | N/A |
| 232 | 12 |  | N/A |
| 245 | 11 |  | N/A |
| 254 | 11 |  | N/A |
| 256 | 11 |  | N/A |
| 264 | 11 |  | N/A |
| 275 | 10 |  | N/A |
| 423 | 10 |  | N/A |
| 427 | 10 | 16 | + |
| J401 | 9 |  | N/A |

DPC = Days post-challenge.
Result: 2/30 Dead = 6.7% Dead or 93.3% Protected.

TABLE 42

One Year Canine Duration of Immunity Rabies Study Challenge Results of Controls.

| Dog # | Age (weeks) | Mortality DPC | Brain FA |
|---|---|---|---|
| 409 | 12 | 12 | + |
| 415 | 12 | 13 | + |
| 419 | 11 | 12 | + |
| 426 | 10 | 14 | + |
| 434 | 10 | 12 | + |
| 440 | 10 | 13 | + |
| 403 | 9 | 12 | + |
| 194 | 12 | Survived | N/A |
| 199 | 12 | Survived | N/A |
| 203 | 12 | 14 | + |
| 207 | 12 | 16 | + |
| 210 | 12 | 23 | + |
| 215 | 12 | 15 | + |
| 219 | 12 | 12 | + |
| 223 | 12 | 19 | + |
| 225 | 12 | 15 | + |
| 230 | 12 | 15 | + |
| 235 | 12 | 12 | + |
| 238 | 11 | 11 | + |
| 243 | 11 | 14 | + |
| 247 | 11 | 14 | + |
| 250 | 11 | 14 | + |
| 253 | 11 | Survived | N/A |
| 258 | 11 | Survived | N/A |
| 262 | 11 | 18 | + |
| 265 | 11 | 21 | + |
| 271 | 10 | 12 | + |
| 272 | 10 | 14 | + |
| 276 | 10 | 14 | + |
| 280 | 10 | 14 | + |

DPC = Days post-challenge

TABLE 43

Vaccinate Group Rabies Titer ($Log_{10}$) by RFFIT.

| Dog # | Day 0 | Day 28 | Day 60 | Day 90 | Day 180 | Day 270 | Day 390 |
|---|---|---|---|---|---|---|---|
| 410 | 0.48 | 0.46 | 1.41 | 1.19 | 1.32 | 1.41 | 1.23 |
| 417 | 0.41 | 0.57 | 1.32 | 0.85 | 0.57 | 0.80 | 0.60 |
| 414 | 0.57 | 0.80 | 0.97 | 0.80 | 0.58 | 0.46 | 0.48 |
| 420 | 0.58 | 0.57 | 1.67 | 1.06 | 0.59 | 1.02 | 0.90 |
| 423 | 0.58 | 0.38 | 1.06 | 0.84 | 0.43 | 0.61 | 0.60 |
| 427 | 0.85 | 0.58 | 0.61 | 0.93 | 1.06 | 0.38 | 0.48 |
| 430 | 1.02 | 0.97 | 1.19 | 0.94 | 0.38 | 0.62 | 0.60 |
| 401 | 0.57 | 0.56 | 1.76 | 1.06 | 0.57 | 1.11 | 0.60 |
| 192 | 0.85 | 0.89 | 1.32 | 0.97 | 0.57 | 0.7 | 0.70 |
| 196 | 0.97 | 0.61 | 0.97 | 1.06 | 0.46 | 0.61 | 0.48 |
| 200 | 0.97 | 0.53 | 1.06 | 0.62 | 0.34 | 0.43 | 1.00 |
| 205 | 1.19 | 0.37 | 1.72 | 1.11 | 0.59 | 1.19 | 0.60 |
| 208 | 1.32 | 0.65 | 1.28 | 0.93 | 0.38 | 0.38 | 0.30 |
| 211 | 0.57 | 1.06 | 1.32 | 0.85 | 0.63 | 0.89 | 0.48 |
| 216 | 1.11 | 0.46 | 1.50 | 1.32 | 1.19 | 0.74 | 0.70 |
| 221 | 1.06 | 1.02 | 1.24 | 1.02 | 0.51 | 0.97 | 0.70 |
| 226 | 0.89 | 1.19 | 1.59 | 1.15 | 1.11 | 0.93 | 0.48 |
| 228 | 1.02 | 1.02 | 1.15 | 0.65 | 0.46 | 0.38 | 0.70 |
| 232 | 0.89 | 0.57 | 1.85 | 1.24 | 1.41 | 1.32 | 1.28 |
| 234 | 0.97 | 1.41 | 1.32 | 1.15 | 0.36 | 0.65 | 0.48 |
| 239 | 0.57 | 1.02 | 1.15 | 0.89 | 0.48 | 0.48 | 0.30 |
| 245 | 0.97 | 1.41 | 2.02 | 1.37 | 1.24 | 1.28 | 1.23 |
| 249 | 1.19 | 1.02 | 1.24 | 0.93 | 1.02 | 1.28 | 1.00 |
| 254 | 0.89 | 0.59 | 1.24 | 1.06 | 1.24 | 1.59 | 1.32 |
| 256 | 0.97 | 1.54 | 2.02 | 1.54 | 1.98 | 1.15 | 1.51 |
| 260 | 0.93 | 1.54 | 1.81 | 1.19 | 1.15 | 1.06 | 1.20 |
| 264 | 1.06 | 1.24 | 1.63 | 1.06 | 1.02 | 0.80 | 0.60 |
| 267 | 1.06 | 0.79 | 1.24 | 0.65 | 1.02 | 0.52 | 0.48 |
| 270 | 1.15 | 0.61 | 1.63 | 1.06 | 1.19 | 1.11 | 0.60 |
| 275 | 0.66 | 0.46 | 1.19 | 1.32 | 1.28 | 1.02 | 0.60 |
| Average | 0.88 | 0.86 | 1.38 | 1.03 | 1.84 | 0.87 | 0.72 |
| STD | 0.24 | 0.36 | 0.33 | 0.22 | 0.41 | 0.34 | 0.32 |

STD = Standard deviation

TABLE 44

Vaccinate Group Rabies Titer ($Log_{10}$) by RFFIT.

| Dog # | Day 0 | Day 28 | Day 60 | Day 90 | Day 180 | Day 270 | Day 390 |
|---|---|---|---|---|---|---|---|
| 409 | 0.46 | 0.97 | 0.36 | 0.34 | 0.58 | 0.36 | 0.30 |
| 415 | 0.59 | 0.53 | 0.36 | 0.41 | 0.38 | 0.46 | 0.30 |
| 419 | 0.54 | 0.80 | 0.34 | 0.38 | 0.36 | 0.58 | 0.30 |
| 426 | 0.97 | 0.85 | 0.46 | 0.58 | 0.62 | 0.38 | 0.60 |
| 434 | 1.19 | 0.57 | 0.38 | 0.62 | 0.53 | 0.36 | 0.30 |
| 440 | 1.19 | 0.80 | 0.34 | 0.49 | 0.46 | 0.38 | 0.30 |
| 403 | 1.11 | 0.57 | 0.48 | 0.58 | 0.43 | 0.38 | 0.70 |
| 194 | 0.85 | 0.80 | 0.97 | 0.49 | 0.93 | 0.52 | 0.48 |
| 199 | 0.57 | 0.48 | 0.38 | 0.46 | 0.63 | 0.59 | 0.95 |
| 203 | 0.78 | 0.46 | 0.41 | 0.45 | 0.54 | 0.61 | 0.60 |
| 207 | 0.61 | 0.46 | 0.38 | 0.58 | 0.53 | 0.45 | 0.30 |
| 210 | 0.61 | 0.80 | 0.65 | 0.45 | 0.58 | 0.46 | 0.48 |
| 215 | 1.19 | 0.80 | 0.36 | 0.58 | 0.54 | 0.58 | 0.70 |
| 219 | 0.65 | 0.43 | 0.36 | 0.38 | 0.52 | 0.36 | 0.60 |
| 223 | 1.15 | 0.48 | 0.34 | 0.34 | 0.46 | 0.46 | 0.48 |
| 225 | 1.37 | 0.59 | 0.58 | 0.38 | 0.51 | 0.56 | 0.48 |
| 230 | 1.28 | 0.46 | 0.38 | 0.51 | 0.49 | 0.97 | 0.48 |
| 235 | 0.97 | 1.06 | 0.53 | 0.58 | 0.36 | 0.58 | 0.30 |
| 238 | 1.11 | 0.97 | 0.41 | 0.89 | 0.52 | 0.93 | 0.48 |
| 243 | 0.53 | 0.73 | 0.36 | 0.62 | 0.58 | 0.48 | 0.48 |
| 247 | 0.57 | 0.38 | 0.58 | 0.43 | 0.51 | 0.58 | 0.90 |
| 250 | 1.41 | 0.97 | 1.19 | 0.65 | 0.54 | 1.24 | 0.70 |
| 253 | 0.93 | 0.58 | 0.36 | 0.49 | 0.53 | 0.43 | 0.30 |
| 258 | 0.97 | 0.89 | 0.71 | 0.53 | 0.43 | 0.72 | 0.60 |
| 262 | 1.19 | 1.11 | 0.38 | 0.53 | 0.56 | 0.38 | 0.60 |
| 265 | 1.19 | 0.70 | 0.63 | 0.36 | 0.49 | 0.89 | 0.48 |
| 271 | 0.85 | 0.48 | 0.85 | 0.51 | 0.45 | 0.58 | 0.48 |
| 272 | 0.65 | 0.58 | 0.34 | 0.38 | 0.36 | 0.34 | 0.60 |
| 276 | 1.41 | 1.02 | 0.70 | 0.43 | 0.58 | 0.58 | 0.60 |

TABLE 44-continued

Vaccinate Group Rabies Titer (Log$_{10}$) by RFFIT.

| Dog # | Day 0 | Day 28 | Day 60 | Day 90 | Day 180 | Day 270 | Day 390 |
|---|---|---|---|---|---|---|---|
| 280 | 1.24 | 1.15 | 0.54 | 0.46 | 0.46 | 1.06 | 0.48 |
| Average | 0.94 | 0.71 | 0.51 | 0.50 | 0.52 | 0.58 | 0.52 |
| STD | 0.30 | 0.23 | 0.21 | 0.12 | 0.11 | 0.23 | 0.17 |

STD = Standard deviation

TABLE 45

Rabies Antibody Titer (Log$_{10}$) by RFFIT.

| Vaccination Statue | No. of Dogs | Age at First Vaccination | Mean Antibody Titer Day 0 | Day 60 * | Increase in Titer Post-Vaccination |
|---|---|---|---|---|---|
| Vaccinates (DACPiP-CP65) | 1 | 9 | 0.57 | 1.76 | 1.19 |
| | 6 | 10 | 0.81 | 1.23 | 0.42 |
| | 9 | 11 | 0.86 | 1.48 | 0.62 |
| | 14 | 12 | 0.91 | 1.36 | 0.45 |
| Controls (DACPiP) | 1 | 9 | 1.11 | 0.48 | ≦0.0 |
| | 7 | 10 | 1.07 | 0.52 | |
| | 9 | 11 | 0.94 | 0.55 | |
| | 13 | 12 | 0.85 | 0.47 | |

* 60 days post first vaccination or 30 days post second vaccination

Example 15

Interference Study in Dogs of a Vaccine Using a Recombinant Rabies Fraction (vCP65) in Combination With Conventional Fractions: Canine Distemper, Adenovirus Type 2, Coronavirus, Parainfluenza, Parvovirus, Rabies Vaccine, Modified Live Virus, Live Canarypox Vector, Leptospira Bacterin This example demonstrates the absence of interference in dogs of the recombinant rabies vCP65 fraction incorporated in combination with other lyophilized fractions of CDV, CAV-2, CCV, CPi, CPV, and diluted in Leptospira bacterin (LCI) for immunization of dogs.

Procedure:

Thirty (30) rabies seronegative dogs were vaccinated twice subcutaneously with 1 ml dose of a lyophilized combination (DACPiP-CP65+LCI) vaccine containing DACPIP and a recombinant rabies fraction (vCP65), diluted in a two-way leptospira combination bacterin (LCI). Thirty (30) rabies seronegative dogs were vaccinated with the same combination vaccine without the recombinant rabies fraction (DACPiP+LCI) and served as rabies controls for the efficacy study described in Example 14.

Serum samples were collected at Day 0, Day 30 and Day 60 post-vaccination from the dogs of each group and were tested by virus seroneutralization methods, and RFFIT was employed for the rabies antibody assay. Seroneutralization test results of each virus were compared using the average titer ± standard deviation between the vaccinates and controls. More specifically: The rabies recombinant vaccinal antigen was prepared with the fifth passage (vCP65x+5) from the master seed as in Example 14. This antigen can be used as a monovalent vaccine. It can also, as described in this Example and in Example 14, be lyophilized in combination with five other modified live canine antigens. The abbreviations in this Example are as in Example 14.

Material:

Vaccines: DACPiP-CP65 AND DACPiP were prepared, distributed, lyophilized as in Example 14. The titer of each vaccine component rehydrated in sterile water after lyophilization was, as in Example 14.

A liquid fraction of Leptospira canicola and Leptospira icterohaemorrhagiae is a normal production vaccine which was released for sale by the USDA-NVSL on 22 Sep. 1992.

Animals, Housing and Vaccination Administration: Sixty (60) dogs 9 to 12 weeks old at first vaccination divided into two groups of 30 each received the following vaccines at 4 weeks interval days interval:

TABLE 46

| Group | V$_1$ (Vaccine) | V$_2$ (Vaccine) |
|---|---|---|
| A Vaccinates | DACPiP-CP65 + LCI | DACPiP-CP65 + LCI |
| B Controls | DACPiP + LCI | DACPiP + LCI |

Serum from each dog was collected at Day 0 (day of vaccination), and Days 28 and 60 post-first vaccination. Serum from each dog was titrated for neutralizing antibodies (SN) for CDV, CAV-2, CPi, CPV, and by RFFIT for the rabies virus. Lack of interference with each component is confirmed whenever seroconversion of comparable magnitude is observed in sera from both the vaccinates and controls.

Results:

Table 47 below summarizes the SN titer for each viral fraction in the vaccine:

TABLE 47

| Virus Component | SN Activity Vaccinates | | | Antibody Titer (Log$_{10}$)** Controls | | |
|---|---|---|---|---|---|---|
| | Day 0 | Day 28 | Day 60 | Day 0 | Day 28 | Day 60 |
| CDV ± | 0.37 | 0.82 | 0.89 | 0.47 | 0.95 | 1.07 |
| STD* | 0.20 | 0.40 | 0.35 | 0.27 | 0.39 | 0.35 |
| CAV-2 ± | 1.65 | 2.62 | 2.72 | 1.54 | 2.57 | 2.70 |
| STD | 0.80 | 0.39 | 0.32 | 0.60 | 0.27 | 0.32 |
| CPi ± | 0.65 | 1.49 | 1.78 | 0.65 | 1.24 | 1.30 |
| STD | 0.44 | 0.41 | 0.32 | 0.46 | 0.24 | 0.11 |
| CPV ± | 2.86 | 3.85 | 4.03 | 3.06 | 3.19 | 3.87 |
| STD | 0.89 | 0.59 | 0.65 | 1.13 | 0.65 | 0.69 |
| CCV ± | 1.61 | 2.15 | 2.10 | 1.61 | 2.13 | 2.04 |
| STD | 0.24 | 0.24 | .022 | 0.21 | 0.25 | 0.25 |
| CP65 ± | 0.88 | 0.86 | 1.38 | 0.94 | 0.71 | 0.51 |
| STD | 0.24 | 0.36 | 0.33 | 0.30 | 0.23 | 0.21 |

*Standard Deviation
**RFFIT

Canine Distemper Virus Neutralizing Antibodies: Individual results are displayed in Table 48, below. Even though most of the dogs were seropositive at Day 0 (pre-vaccination), the vaccination with the combination vaccine increased CDV-specific SN activity seroconversion in both groups with no statistical difference.

Canine Adenovirus Type 2 Virus Neutralizing Antibodies: Individual results are displayed in Table 49, below. The data indicates not only an excellent seroconversion in both groups with no statistical difference, but also a remarkable decrease in the standard deviation in individual titer between animals.

Canine Parainfluenza Virus Neutralizing Antibodies: Individual results are displayed in Table 50, below. The data indicated a seroconversion in both groups with no statistical difference.

Canine Parvovirus Neutralizing Antibodies: Individual results are displayed in Table 51, below. The data indicated excellent seroconversion at Day 30 and Day 60 post-first vaccination with standard deviation of the same magnitude in both groups.

Canine Coronavirus Neutralizing Antibodies: Individual results are displayed in Table 52, below. The data indicated a clear seroconversion induced by the combination vaccine DACPiP-CP65+LC1, after only one injection, with very homogenous titer, and no difference with the control group.

Recombinant Rabies Virus (vCP65) Canarypox Vector: Serum neutralizing Antibodies (See Table 53, below). Neutralizing antibodies for the rabies virus were detected by the Rapid Focus Fluorescein Inhibition Test (RFFIT). There is a clear increase in titer average antibody titer ($\log_{10}$) from $0.88 \pm 0.24$ to $1.38 \pm 0.33$ by Day 60 postvaccination. Out of 20 dogs that had titers <1.0 ($\log_{10}$) at Day 0, 17 had seroconverted to have >1.0 to 2.0 ($\log_{10}$) titers by Day 30 post-vaccination.

Conclusion:

The recombinant rabies fraction (vCP65) does not cause any interference on the immune response of the other lyophilized fractions. In spite of the presence of antibody on the day of first vaccination, a clear seroconversion was seen by vaccination with all of the components with equivalent magnitude in both groups.

Inoculation with the DACPiP-CP65 combination induces significant seroconversion even in the presence of antibodies prior to vaccination. There is an average increase in titer of 0.5 ($\log_{10}$) was found to be sufficient to induce protection against virulent challenge with street rabies virus (See Example 14).

Previous experiences have shown that vaccination with conventional rabies vaccines does not always induce large quantities of detectable circulating antibodies. The same phenomenon was observed with the recombinant rabies combination vaccine; but, even though the seroconversion was of low magnitude the antibody titer had at least doubled in two-thirds of the vaccinates by day 30 post-second vaccination. In this experiment, 93% of vaccinates were protected against rabies challenge. Of the animals surviving virulent rabies challenge, some dogs had seroconverted while others had not. Moreover, at the time of challenge, virtually all of the vaccinated dogs had no rabies-specific SN activity.

TABLE 48

CDV Seroneutralization

| | (DACPiP-CP65 + LCI - Vaccinates) Log (10) of SN Antibody titer | | | | (DACPiP + LCI - Controls) Log (10) of SN Antibody titer | | |
|---|---|---|---|---|---|---|---|
| | pre- | 28 | 60 | | pre-bled | 28 d.p.v. | 60 d.p.v. |
| DOG # | bled Titer | d.p.v. Titer | d.p.v. Titer | DOG # | Titer | Titer | Titer |
| 410 | 1.35 | 1.50 | 0.90 | 409 | 1.35 | 1.95 | 1.80 |
| 417 | 0.45 | 0.45 | 0.45 | 415 | 0.45 | 1.20 | 1.05 |
| 414 | 0.45 | 0.75 | 0.45 | 419 | 0.45 | 0.45 | 1.20 |
| 420 | 0.30 | 0.45 | 0.45 | 426 | 0.45 | 1.20 | 1.50 |
| 423 | 0.30 | 0.75 | 0.75 | 434 | 0.30 | 0.60 | 0.60 |
| 427 | 0.30 | 0.45 | 0.45 | 440 | 0.30 | 0.75 | 0.60 |
| 430 | 0.30 | 0.45 | 0.75 | 403 | 0.45 | 0.90 | 1.05 |
| 401 | 0.30 | 0.75 | 1.20 | 194 | 0.45 | 0.90 | 1.05 |
| 192 | 0.30 | 1.65 | 1.35 | 199 | 0.45 | 0.75 | 0.90 |
| 196 | 0.30 | 0.90 | 1.05 | 203 | 0.45 | 1.05 | 1.05 |
| 200 | 0.45 | 1.35 | 1.20 | 207 | 1.50 | 1.20 | 1.35 |
| 205 | 0.30 | 0.75 | 0.75 | 210 | 0.45 | 0.45 | 1.05 |
| 208 | 0.30 | 1.95 | 1.95 | 215 | 0.45 | 1.05 | 1.50 |
| 211 | 0.30 | 0.90 | 0.75 | 219 | 0.30 | 0.75 | 1.20 |

TABLE 48-continued

CDV Seroneutralization

| | (DACPiP-CP65 + LCI - Vaccinates) Log (10) of SN Antibody titer | | | | (DACPiP + LCI - Controls) Log (10) of SN Antibody titer | | |
|---|---|---|---|---|---|---|---|
| | pre- | 28 | 60 | | pre-bled | 28 d.p.v. | 60 d.p.v. |
| DOG # | bled Titer | d.p.v. Titer | d.p.v. Titer | DOG # | Titer | Titer | Titer |
| 216 | 0.45 | 0.60 | 0.75 | 223 | 0.45 | 0.90 | 1.05 |
| 221 | 0.30 | 0.45 | 0.60 | 225 | 0.45 | 0.90 | 1.05 |
| 226 | 0.30 | 1.20 | 1.20 | 230 | 0.30 | 1.95 | 1.35 |
| 228 | 0.45 | 0.45 | 0.45 | 235 | 0.45 | 1.35 | 1.35 |
| 232 | 0.30 | 0.45 | 0.90 | 238 | 0.45 | 0.75 | 0.45 |
| 234 | 0.30 | 1.05 | 1.05 | 243 | 0.45 | 0.45 | 0.43 |
| 239 | 0.45 | 0.90 | 1.05 | 247 | 0.45 | 1.20 | 1.35 |
| 245 | 0.30 | 0.75 | 0.75 | 250 | 0.30 | 1.05 | 0.90 |
| 249 | 0.30 | 1.35 | 1.35 | 253 | 0.30 | 1.05 | 1.05 |
| 254 | 0.30 | 0.45 | 0.75 | 258 | 0.30 | 0.45 | 0.60 |
| 256 | 0.30 | 0.90 | 0.90 | 262 | 0.30 | 1.20 | 1.35 |
| 260 | 0.30 | 0.60 | 0.60 | 265 | 0.30 | 1.20 | 1.20 |
| 264 | 0.30 | 0.90 | 1.35 | 271 | 0.45 | 1.05 | 1.50 |
| 267 | 0.45 | 0.75 | 0.75 | 272 | 0.45 | 0.90 | 1.35 |
| 270 | 0.30 | 0.45 | 0.75 | 276 | 0.60 | 0.45 | 0.75 |
| 275 | 0.30 | 0.45 | 1.05 | 280 | 0.45 | 0.45 | 0.45 |
| Average | 0.37 | 0.82 | 0.89 | Average | 0.47 | 0.95 | 1.07 |
| Std Dev. | 0.20 | 0.40 | 0.35 | Std Dev. | 0.27 | 0.39 | 0.35 |

TABLE 49

CAV2 Seroneutralization

| | (DACPiP-CP65 + LCI - Vaccinates) Log (10) of SN Antibody titer | | | | (DACPiP + LCI - Controls) Log (10) of SN Antibody titer | | |
|---|---|---|---|---|---|---|---|
| | pre- | 28 | 60 | | pre-bled | 28 d.p.v. | d.p.v. |
| DOG # | bled Titer | d.p.v. Titer | d.p.v. Titer | DOG # | Titer | Titer | Titer |
| 410 | 1.20 | 1.95 | 2.26 | 409 | 1.35 | 2.70 | 2.41 |
| 417 | 0.75 | 2.10 | 2.56 | 415 | 0.45 | 2.25 | 2.41 |
| 414 | 0.60 | 1.95 | 2.86 | 419 | 1.05 | 2.55 | 2.41 |
| 420 | 0.75 | 2.25 | 2.56 | 426 | 0.75 | 2.55 | 2.56 |
| 423 | 0.30 | 2.70 | 2.41 | 434 | 0.45 | 2.85 | 2.71 |
| 427 | 0.30 | 2.85 | 3.16 | 440 | 0.60 | 2.70 | 2.56 |
| 430 | 0.30 | 2.40 | 2.56 | 403 | 0.75 | 2.70 | 2.86 |
| 401 | 0.45 | 2.10 | 2.56 | 194 | 1.65 | 2.85 | 3.01 |
| 192 | 1.95 | 2.85 | 3.01 | 199 | 1.35 | 2.70 | 2.26 |
| 196 | 2.55 | 2.85 | 3.01 | 203 | 1.35 | 2.25 | 2.11 |
| 200 | 1.35 | 2.55 | 2.41 | 207 | 1.65 | 2.40 | 2.26 |
| 205 | 1.95 | 3.00 | 2.86 | 210 | 1.35 | 2.55 | 2.86 |
| 208 | 2.55 | 2.55 | 2.41 | 215 | 1.95 | 2.85 | 3.01 |
| 211 | 2.55 | 3.30 | 3.46 | 219 | 1.35 | 2.55 | 2.56 |
| 216 | 2.55 | 3.15 | 3.31 | 223 | 2.25 | 2.55 | 2.86 |
| 221 | 2.40 | 3.00 | 3.16 | 225 | 1.65 | 2.55 | 2.86 |
| 226 | 2.40 | 2.70 | 2.41 | 230 | 1.80 | 2.55 | 2.56 |
| 228 | 2.25 | 2.70 | 2.71 | 235 | 1.65 | 2.25 | 2.26 |
| 232 | 1.95 | 3.00 | 2.56 | 238 | 1.50 | 2.55 | 3.01 |
| 234 | 2.55 | 2.85 | 2.86 | 243 | 1.35 | 2.25 | 2.41 |
| 239 | 1.05 | 2.25 | 2.41 | 247 | 2.55 | 3.00 | 3.16 |
| 245 | 2.55 | 2.85 | 3.16 | 250 | 2.55 | 3.00 | 3.01 |
| 249 | 1.20 | 1.65 | 2.11 | 253 | 1.35 | 2.25 | 2.56 |
| 254 | 2.55 | 2.85 | 2.86 | 258 | 2.25 | 2.25 | 2.71 |
| 256 | 1.95 | 2.55 | 2.71 | 262 | 2.10 | 2.85 | 3.01 |
| 260 | 1.20 | 2.70 | 2.56 | 265 | 2.10 | 2.70 | 3.01 |
| 264 | 1.95 | 2.70 | 2.71 | 271 | 1.35 | 1.95 | 2.41 |
| 267 | 1.80 | 3.00 | 2.86 | 272 | 1.20 | 2.25 | 2.71 |
| 270 | 1.50 | 2.55 | 2.71 | 276 | 1.95 | 2.85 | 3.01 |
| 275 | 1.95 | 2.55 | 2.56 | 280 | 2.55 | 2.85 | 3.46 |
| Average | 1.65 | 2.62 | 2.72 | Average | 1.54 | 2.57 | 2.70 |

TABLE 49-continued

CAV2 Seroneutralization

| (DACPiP-CP65 + LCI - Vaccinates) Log (10) of SN Antibody titer | | | | (DACPiP + LCI - Controls) Log (10) of SN Antibody titer | | |
|---|---|---|---|---|---|---|
| DOG # | pre-bled Titer | 28 d.p.v. Titer | 60 d.p.v. Titer | DOG # | pre-bled Titer | 28 d.p.v. Titer | 60 d.p.v. Titer |
| Std Dev. | 0.80 | 0.39 | 0.32 | Std Dev. | 0.60 | 0.27 | 0.32 |

TABLE 50

CPi Seroneutralization

| (DACPiP-CP65 + LCI - Vaccinates) Log (10) of SN Antibody titer | | | | (DACPiP + LCI - Controls) Log (10) of SN Antibody titer | | | |
|---|---|---|---|---|---|---|---|
| DOG # | 10/23/92 pre-bled Titer | 11/20/92 28 d.p.v. Titer | 12/22/92 60 d.p.v. Titer | DOG # | 10/23/92 pre-bled Titer | 11/20/92 28 d.p.v. Titer | 12/22/92 60 d.p.v. Titer |
| 410 | 1.35 | 1.05 | 1.50 | 409 | 1.35 | 0.75 | 1.35 |
| 417 | 1.35 | 1.65 | 1.80 | 415 | 1.35 | 0.60 | 1.05 |
| 414 | 1.35 | 1.95 | 2.25 | 419 | 1.05 | 1.35 | 1.35 |
| 420 | 1.35 | 1.95 | 1.65 | 426 | 1.35 | 1.35 | 1.35 |
| 423 | 1.20 | 2.80 | 1.05 | 434 | 1.05 | 1.35 | 1.05 |
| 427 | 0.90 | 1.05 | 1.20 | 440 | 1.35 | 1.35 | 1.05 |
| 430 | 1.35 | 1.20 | 1.35 | 403 | 1.35 | 1.35 | 1.35 |
| 401 | 1.35 | 2.25 | 1.95 | 194 | 0.30 | 1.35 | 1.35 |
| 192 | 0.30 | 1.50 | 1.80 | 199 | 0.30 | 1.35 | 1.35 |
| 196 | 0.75 | 1.35 | 1.35 | 203 | 0.30 | 1.35 | 1.35 |
| 200 | 0.30 | 1.65 | 2.25 | 207 | 0.30 | 1.05 | 1.35 |
| 205 | 0.30 | 1.65 | 1.65 | 210 | 0.30 | 1.35 | 1.35 |
| 208 | 0.30 | 1.20 | 1.65 | 215 | 0.45 | 1.35 | 1.35 |
| 211 | 0.30 | 1.80 | 2.10 | 219 | 1.35 | 1.35 | 1.35 |
| 216 | 0.30 | 1.80 | 2.10 | 223 | 1.35 | 1.35 | 1.35 |
| 221 | 0.90 | 1.20 | 1.50 | 225 | 1.20 | 1.35 | 1.35 |
| 226 | 0.90 | 1.35 | 1.65 | 230 | 0.45 | 1.35 | 1.35 |
| 228 | 0.45 | 1.95 | 1.95 | 235 | 0.30 | 0.90 | 1.35 |
| 232 | 0.30 | 1.05 | 1.80 | 238 | 0.30 | 1.35 | 1.20 |
| 234 | 0.30 | 1.05 | 1.95 | 243 | 0.30 | 1.35 | 1.35 |
| 239 | 0.45 | 1.20 | 1.65 | 247 | 0.45 | 1.35 | 1.35 |
| 245 | 1.05 | 1.50 | 1.65 | 250 | 0.30 | 1.20 | 1.05 |
| 249 | 0.30 | 1.20 | 1.95 | 253 | 0.30 | 0.45 | 1.20 |
| 254 | 0.30 | 1.50 | 1.65 | 258 | 0.30 | 1.35 | 1.35 |
| 256 | 0.30 | 1.35 | 2.10 | 262 | 0.45 | 1.35 | 1.35 |
| 260 | 0.30 | 1.05 | 1.95 | 265 | 0.30 | 1.35 | 1.35 |
| 264 | 0.30 | 1.05 | 2.40 | 271 | 0.30 | 1.35 | 1.35 |
| 267 | 0.45 | 1.35 | 1.80 | 272 | 0.30 | 1.35 | 1.35 |
| 270 | 0.30 | 1.50 | 1.65 | 276 | 0.30 | 1.35 | 1.35 |
| 275 | 0.30 | 1.65 | 2.10 | 280 | 0.30 | 1.20 | 1.35 |
| Average | 0.65 | 1.49 | 1.78 | Average | 0.65 | 1.24 | 1.30 |
| Std Dev. | 0.44 | 0.41 | 0.32 | Std Dev. | 0.46 | 0.24 | 0.11 |

TABLE 51

CPV Seroneutralization

| (DACPiP-CP65 + LCI - Vaccinates) Log (10) of SN Antibody titer | | | | (DACPiP + LCI - Controls) Log (10) of SN Antibody titer | | | |
|---|---|---|---|---|---|---|---|
| DOG # | pre-bled Titer | 28 d.p.v. Titer | 60 d.p.v. Titer | DOG # | pre-bled Titer | 28 d.p.v. Titer | 60 d.p.v. Titer |
| 410 | 1.81 | 4.20 | 3.61 | 409 | 0.30 | 3.90 | 3.31 |
| 417 | 1.20 | 3.60 | 3.61 | 415 | 1.20 | 3.00 | 3.01 |
| 414 | 1.81 | 3.60 | 3.31 | 419 | 0.95 | 2.10 | 3.01 |
| 420 | 1.51 | 3.00 | 3.31 | 426 | 0.60 | 2.10 | 4.52 |
| 423 | 1.51 | 3.30 | 3.31 | 434 | 2.11 | 3.30 | 3.91 |

TABLE 51-continued

CPV Seroneutralization (DACPiP-CP65 + LCI - Vaccinates)
Log (10) of SN Antibody titer (DACPiP + LCI - Controls)
Log (10) of SN Antibody titer

| DOG # | pre-bled Titer | 28 d.p.v. Titer | 60 d.p.v. Titer | DOG # | pre-bled Titer | 28 d.p.v. Titer | 60 d.p.v. Titer |
|---|---|---|---|---|---|---|---|
| 427 | 2.41 | 3.30 | 2.41 | 440 | 2.11 | 3.30 | 3.61 |
| 430 | 1.51 | 3.90 | 5.12 | 403 | 1.81 | 2.40 | 2.71 |
| 401 | 1.81 | 4.20 | 3.61 | 194 | 3.31 | 3.30 | 3.61 |
| 192 | 3.31 | 3.60 | 3.95 | 199 | 3.01 | 3.60 | 3.61 |
| 196 | 3.61 | 3.00 | 3.61 | 203 | 3.61 | 3.60 | 3.61 |
| 200 | 3.01 | 3.90 | 4.52 | 207 | 3.31 | 4.50 | 5.12 |
| 205 | 3.61 | 3.30 | 3.61 | 210 | 3.31 | 4.20 | 5.42 |
| 208 | 3.31 | 3.60 | 4.52 | 215 | 4.21 | 3.90 | 3.61 |
| 211 | 2.11 | 3.60 | 3.95 | 219 | 3.31 | 1.35 | 3.30 |
| 216 | 3.01 | 3.90 | 4.52 | 223 | 3.61 | 3.30 | 4.21 |
| 221 | 2.41 | 3.90 | 4.82 | 225 | 4.82 | 3.90 | 3.61 |
| 226 | 2.71 | 4.80 | 4.52 | 230 | 3.31 | 3.60 | 4.82 |
| 228 | 3.31 | 3.60 | 3.95 | 235 | 4.21 | 3.30 | 4.21 |
| 232 | 4.52 | 4.20 | 4.21 | 238 | 3.01 | 3.00 | 4.21 |
| 234 | 4.21 | 3.60 | 5.12 | 243 | 3.31 | 3.60 | 4.21 |
| 239 | 2.41 | 3.90 | 4.52 | 247 | 4.21 | 3.30 | 3.91 |
| 245 | 4.02 | 3.60 | 4.21 | 250 | 3.31 | 3.00 | 3.61 |
| 249 | 3.61 | 5.10 | 4.21 | 253 | 3.61 | 3.00 | 4.52 |
| 254 | 3.01 | 5.40 | 5.42 | 258 | 3.91 | 3.30 | 5.42 |
| 256 | 3.61 | 4.50 | 3.91 | 262 | 3.91 | 3.30 | 3.31 |
| 260 | 3.31 | 3.60 | 3.91 | 265 | 3.61 | 3.00 | 3.61 |
| 264 | 3.61 | 3.60 | 3.31 | 271 | 4.21 | 2.40 | 3.61 |
| 267 | 3.01 | 4.80 | 4.21 | 272 | 3.01 | 3.00 | 3.01 |
| 270 | 3.61 | 3.19 | 3.31 | 276 | 3.91 | 3.00 | 3.61 |
| 275 | 3.01 | 3.60 | 4.21 | 280 | 2.71 | 3.00 | 3.91 |
| Average | 2.86 | 3.85 | 4.03 | Average | 3.06 | 3.19 | 3.87 |
| Std Dev. | 0.89 | 0.59 | 0.65 | Std Dev. | 1.13 | 0.65 | 0.69 |

TABLE 52

CCV Seroneutralization (CACPiP-CP65 + LCI - Vaccinates)
Log (10) of SN Antibody titer (DACPiP + LCI - Controls)
Log (10) of SN Antibody titer

| DOG # | pre-bled Titer | 28 d.p.v. Titer | 60 d.p.v. Titer | DOG # | pre-bled Titer | 28 d.p.v. Titer | 60 d.p.v. Titer |
|---|---|---|---|---|---|---|---|
| 410 | 1.58 | 2.41 | 2.08 | 409 | 1.38 | 2.08 | 1.58 |
| 417 | 1.38 | 1.78 | 1.88 | 415 | 1.38 | 1.98 | 1.58 |
| 414 | 1.68 | 1.88 | 1.88 | 419 | 1.28 | 1.98 | 1.68 |
| 420 | 1.38 | 2.28 | 2.18 | 426 | 1.08 | 2.13 | 1.83 |
| 423 | 1.38 | 1.68 | 1.68 | 434 | 1.38 | 1.78 | 1.58 |
| 427 | 1.18 | 1.78 | 1.68 | 440 | 1.28 | 1.78 | 1.68 |
| 430 | 1.48 | 1.68 | 1.88 | 403 | 1.38 | 2.18 | 1.68 |
| 401 | 1.38 | 1.98 | 2.28 | 194 | 1.98 | 2.41 | 2.13 |
| 192 | 1.88 | 2.32 | 2.27 | 199 | 1.88 | 2.41 | 2.18 |
| 196 | 1.48 | 2.32 | 2.08 | 203 | 1.78 | 2.38 | 2.08 |
| 200 | 1.88 | 2.41 | 1.88 | 207 | 1.58 | 2.18 | 2.28 |
| 205 | 1.53 | 2.41 | 2.28 | 210 | 1.68 | 2.41 | 2.41 |
| 208 | 1.68 | 2.41 | 2.32 | 215 | 1.68 | 1.98 | 1.98 |
| 211 | 1.98 | 2.32 | 2.41 | 219 | 1.68 | 1.98 | 2.08 |
| 216 | 1.68 | 2.32 | 1.83 | 223 | 1.58 | 2.41 | 2.18 |
| 221 | 1.83 | 1.98 | 2.18 | 225 | 1.68 | 1.83 | 2.28 |
| 226 | 1.68 | 2.08 | 2.08 | 230 | 1.78 | 2.25 | 2.28 |
| 228 | 1.68 | 2.08 | 2.08 | 235 | 1.78 | 2.18 | 2.32 |
| 232 | 1.68 | 2.18 | 2.41 | 238 | 1.58 | 2.18 | 2.08 |
| 234 | 1.68 | 2.18 | 2.34 | 243 | 1.83 | 2.41 | 2.28 |
| 239 | 1.48 | 1.88 | 2.08 | 247 | 1.58 | 2.32 | 1.98 |
| 245 | 1.98 | 1.98 | 2.41 | 250 | 1.68 | 2.41 | 2.18 |
| 249 | 1.98 | 1.98 | 2.32 | 253 | 1.38 | 2.41 | 2.13 |

TABLE 52-continued

CCV Seroneutralization (CACPiP-CP65 + LCI - Vaccinates)
Log (10) of SN Antibody titer (DACPiP + LCI - Controls)
Log (10) of SN Antibody titer

| DOG # | pre-bled Titer | 28 d.p.v. Titer | 60 d.p.v. Titer | DOG # | pre-bled Titer | 28 d.p.v. Titer | 60 d.p.v. Titer |
|---|---|---|---|---|---|---|---|
| 254 | 1.98 | 1.98 | 2.28 | 258 | 1.83 | 2.28 | 1.98 |
| 256 | 1.68 | 2.41 | 1.98 | 262 | 1.68 | 1.78 | 2.32 |
| 260 | 1.58 | 2.18 | 1.68 | 265 | 1.58 | 1.68 | 1.98 |
| 264 | 1.68 | 2.41 | 2.18 | 271 | 1.68 | 1.98 | 2.28 |
| 267 | 1.53 | 2.28 | 1.98 | 272 | 1.83 | 1.53 | 1.83 |
| 270 | 1.08 | 2.18 | 2.08 | 276 | 1.68 | 2.28 | 2.08 |
| 275 | 1.28 | 2.41 | 2.18 | 280 | 1.68 | 2.28 | 2.28 |
| Average | 1.61 | 2.15 | 2.10 | Average | 1.61 | 2.13 | 2.04 |
| Std Dev. | 0.24 | 0.24 | 0.22 | Std Dev. | 0.21 | 0.25 | 0.25 |

TABLE 53

RFFIT Rabies Seroneutralization (DACPiP-CP65 + LCI - Vaccinates)
Log (10) of SN Antibody titer (DACPiP + LCI - Controls)
Log (10) of SN Antibody titer

| DOG # | pre-bled Titer | 28 d.p.v. Titer | 60 d.p.v. Titer | DOG # | pre-bled Titer | 28 d.p.v. Titer | 60 d.p.v. Titer |
|---|---|---|---|---|---|---|---|
| 410 | 0.48 | 0.46 | 1.41 | 409 | 0.46 | 0.97 | 0.36 |
| 417 | 0.41 | 0.57 | 1.32 | 415 | 0.59 | 0.53 | 0.36 |
| 414 | 0.57 | 0.80 | 0.97 | 419 | 0.54 | 0.80 | 0.34 |
| 420 | 0.58 | 0.57 | 1.67 | 426 | 0.97 | 0.85 | 0.46 |
| 423 | 0.58 | 0.38 | 1.06 | 434 | 1.19 | 0.57 | 0.38 |
| 427* | 0.85 | 0.58 | 0.61 | 440 | 1.19 | 0.80 | 0.34 |
| 430* | 1.02 | 0.97 | 1.19 | 403 | 1.11 | 0.57 | 0.48 |
| 401 | 0.57 | 0.56 | 1.76 | 194* | 0.85 | 0.80 | 0.97 |
| 192 | 0.85 | 0.89 | 1.32 | 199* | 0.57 | 0.48 | 0.38 |
| 196 | 0.97 | 0.61 | 0.97 | 203 | 0.78 | 0.46 | 0.41 |
| 200 | 0.97 | 0.53 | 1.06 | 207 | 0.61 | 0.43 | 0.38 |
| 205 | 1.19 | 1.37 | 1.72 | 210 | 0.61 | 0.80 | 0.65 |
| 208 | 1.32 | 0.65 | 1.28 | 215 | 1.19 | 0.80 | 0.36 |
| 211 | 0.57 | 1.06 | 1.32 | 219 | 0.65 | 0.43 | 0.36 |
| 216 | 1.11 | 0.46 | 1.50 | 223 | 1.15 | 0.48 | 0.34 |
| 221 | 1.06 | 1.02 | 1.24 | 225 | 1.37 | 0.59 | 0.58 |
| 226 | 0.89 | 1.19 | 1.59 | 230 | 1.28 | 0.46 | 0.38 |
| 228 | 1.02 | 1.02 | 1.15 | 235 | 0.97 | 1.06 | 0.53 |
| 232 | 0.89 | 0.57 | 1.85 | 238 | 1.11 | 0.97 | 0.41 |
| 234 | 0.97 | 1.41 | 1.32 | 243 | 0.53 | 0.73 | 0.36 |
| 239 | 0.57 | 1.02 | 1.15 | 247 | 0.57 | 0.38 | 0.58 |
| 245 | 0.97 | 1.41 | 2.02 | 250 | 1.41 | 0.97 | 1.19 |
| 249 | 1.19 | 1.02 | 1.24 | 253* | 0.93 | 0.58 | 0.36 |
| 254 | 0.89 | 0.59 | 1.24 | 258* | 0.97 | 0.89 | 0.71 |
| 256 | 0.97 | 1.54 | 2.02 | 262 | 1.19 | 1.11 | 0.38 |
| 260 | 0.93 | 1.54 | 1.81 | 265 | 1.19 | 0.70 | 0.63 |
| 264 | 1.06 | 1.24 | 1.63 | 271 | 0.85 | 0.48 | 0.85 |
| 267 | 1.06 | 0.79 | 1.24 | 272 | 0.65 | 0.58 | 0.34 |
| 270 | 1.15 | 0.61 | 1.63 | 276 | 1.41 | 1.02 | 0.70 |
| 275 | 0.66 | 0.46 | 1.19 | 280 | 1.24 | 1.15 | 0.54 |
| Average | 0.88 | 0.86 | 1.38 | Average | 0.94 | 0.71 | 0.51 |
| Std Dev. | 0.24 | 0.36 | 0.33 | Std Dev. | 0.30 | 0.23 | 0.21 |

Example 16

In Vitro Viricidal Testing of Leptospira Canicola-Icterohaemorrhagiae Bacterian as a Diluent for a Desiccated Vaccine Containing a Recombinant Rabies Fraction (vCP65) in Combination with Conventional Canine Fraction: Canine Distemper-Adenovirus Type 2-Coronavirus-Parainfluenza-Parvovirus-Rabies Vaccine, Modified Live Virus, Canarypox Vector-Leptospira Bacterin The vaccine, DACPiP-CP65, was rehydrated with LCI and water. Each fraction component was titrated in order to assess viricidal effect of LCI by comparing the titers of the same components when diluted in LCI or water. The rabies recombinant vaccinal antigen was prepared with the fifth passage (vCP65x+5) from the master seed as in Example 14. The rabies antigen was lyophilized in combination with five other modified live canine antigen and was used for efficacy and interference studies in dogs as described in Examples 14 and 15. The *Leptospira canicola* and *Leptospira icterohaemorrhagiae* bivalent bacterin was used to rehydrate the vaccine. The abbreviations in Examples 14 and 15 are used herein.

Table 54 below summarizes the titers obtained for each fraction when diluted in LCI or sterile water.

TABLE 54

| | Titer ($Log_{10}$ $TCID_{50}$/dose) | | | | | |
|---|---|---|---|---|---|---|
| Component | CDV | CAV-2 | CPi | CPV | CCV | vCP65 |
| DACPiP-CP65 + $H_2O$ | 3.4 | 5.4 | 5.7 | 6.2 | 6.2 | 6.5 |
| DACPiP-CP65 + LCI | 2.8 | 5.4 | 5.1 | 6.2 | 5.6 | 6.3 |
| Difference | −0.6 | 0.0 | −0.6 | 0.0 | 0.6 | −0.2 |

The formulation below was used to obtain the combination vaccines that were prepared as in Example 14.

The liquid fraction of *L. canicola* and *L. icterohaemorrhagiae* was a normal production serial (No. 32010), expiration date 17 Jul. 1995. This serial was released by NVSL on 22 September 1992.

Cell Lines: Madin Darby Canine Kidney (MDCK) cell line was used for titration of CAV-2, CPi and CCV components. Crandell Feline Kidney (CRFK) cell line was used for titration of CPV. Chicken Embryo Fibroblast (CEF) cells were used for titration of the recombination rabies virus. Growth Medium was F15 with fetal bovine serum.

Viricidal activity of the liquid LCI bacterin used to rehydrate CACPiP-CP65 was performed in accordance with 9 CFR 113.35.

The freeze-dried vaccine DACPiP-CP65 was rehydrated with sterile water diluent and tested in parallel with the above component in accordance with CFR 113.35. Titration methods were standard. Virus titer ($Log_{10}$ $TCID_{50}$ for CDV, CAV-2, CCV, CPi, CPV and CP65) were calculated according to the Spearman-Karber method.

Results of virus titration are summarized in Table 55, below. Rehydration of the lyophilized DACPiP-CP65 with the liquid LCI did not reduce the CDV, CAV-2, CPi, CPV, CCV and CP65 titers when compared to rehydration with sterile water diluent.

TABLE 55

Virus Titers after Rehydration of DACPiP-CP65 with LCI (Serial No. 32010) or with Sterile Water Diluent.

| | Titer ($Log_{10}$ $TCID_{50}$/dose) | | | | | |
|---|---|---|---|---|---|---|
| Component | CDV | CAV-2 | CPi | CPV | CCV | CP65 |
| DACPiP-CP65 + $H_2O$ | 3.4 | 5.4 | 5.7 | 6.2 | 6.2 | 6.5 |
| DACPiP-CP65 + LCI | 2.8 | 5.4 | 5.1 | 6.2 | 5.6 | 6.3 |
| Difference | −0.6 | 0.0 | −0.6 | 0.0 | −0.6 | −0.2 |

Example 17

Recombinant Canine Rabies-Parvovirus Vaccine, Modified Live Virus: Safety and Efficacy After Two Subcutaneous Inoculation of Dogs With vCP136 Vaccine This Example demonstrates the safety, antigenicity, and efficacy of a recombinant rabies/canine parvovirus vCP136 vaccine in dogs (rabies glycoprotein and VP2 canine parvovirus (CPV) genes inserted in the same canarypox vector). Canarypox virus-based recombinant vCP136 contains the rabies glycoprotein and canine parvovirus VP2 genes (VP136 and its construction are disclosed in USSN 08/105,483, incorporated herein by reference); and this Example demonstrates the reaction of dogs following SQ vaccination with two doses of vCP136 vaccine, 22 days apart, the humoral antibody response of dogs inoculated twice with recombinant vCP136 at $10^7$ PFU/dose, and, the protective immune response of vaccinated dogs following oronasal challenge with virulent CPV.

Results

None of the vaccinated dogs showed local adverse local or systemic reaction after vaccination.

Vaccinated dogs developed parvovirus neutralizing antibody titer that ranged from 1:380 to 1:1,530 with a geometric mean antibody titer (GMT) of 1:740.

After oronasal challenge with virulent CPV obtained from NVSL, five or six non-vaccinated dogs developed clinical signs of CPV infection (anorexia and diarrhea). None of the vaccinated dogs showed any clinical signs of CPV infection.

CPV was isolated from all six control dogs at an average of 3.0 isolation days per dog. CPV was isolated from two of four vaccinated dogs at an average of 0.5 isolation day per dog.

The rectal temperature pattern remained normal in vaccinated and non-vaccinated dogs.

A statistically significant difference in leukopenia on Day 6 post-challenge was observed between vaccinates and controls.

Rabies antibody (RFFIT) titers were very high in all vaccinated dogs, even after only one injection with vCP136.

More specifically: Health Status of Beagle Dogs: All dog sera tested negative for VNA to CPV on Day-4 (day of arrival) and again on Day zero (0) (day of first vaccination).

Vaccine Safety: The four dogs vaccinated twice SQ in the upper dorsal region of the neck (on Day 0 and Day 22) with vCP136 showed no adverse local or systemic reactions.

Serological Status for CPV (Table 56): Level of VNA activities to CPV in sera obtained from dogs at two SQ inoculations of vCP136 vaccine and subsequently challenge with virulent CPV are shown in Table 56. All ten dogs had no detectable VNA titer at 1:2 final serum dilution on Day 0. Six non-vaccinated dogs remained susceptible to CPA on Day 37. Twenty-two days post-first vaccination with vCP136, dogs 2002, 2021, and 2025 had detectable level of VNA at 1:8 to 1:12. Dog 2007 had no detectable VNA at 1:4 final serum dilution.

Fifteen days post-booster vaccination with vCP136, a marked increase in VNA titer was recorded. Level of VNA ranged from 1:380 to 1:1,530 (2.6 to 3.2 $\log_{10}$) and GMT of 1:740 (2.8 $\log_{10}$). Thirteen days post-challenge, non-vaccinated control dogs had VNA titer ranging from 1:1,530 to 1:16,380 (GMT=1:5,260). On the other hand, vaccinated dogs had VNA titer ranging from 1:1,530 to 1:3,070 (GMT= 1:2,090).

Serological Status for Rabies Component (Table 57): All four vaccinated dogs seroconverted with excellent antibody titer after the first SQ injection. A highly significant elevation in antibody titer was recorded after the second injection. None of the control dogs seroconverted.

Challenge of Immunity: White Blood Cell Count (Table 58): Four of six non-vaccinated dogs showed leucopenia beginning of Day 6 post-challenge. The white blood cell count returned to normal range of values shortly thereafter. Two of four vaccinated dogs showed a downward trend in white blood cell count until Day 8 post-challenge. Dog 2002 had leucopenia on Day 5 and Dog 2021 on Day 7 post-challenge.

Rectal Temperature (Table 59): No apparent difference in daily rectal temperature values was noted between vaccinated and non-vaccinated dogs; no abnormality was detected.

Clinical Signs (Table 60): Five of six non-vaccinated dogs developed visible evidence of virus infection. Varying degrees of anorexia and occurrence of mucoid to bloody diarrhea were observed. None of the four vaccinated dogs showed clinical evidence of CPV infection.

Virus Isolation (Table 61): Virus was isolated from all six control dogs. In some of these dogs, virus was detected as early as Day 1 post-challenge and as late at Day 8 post-challenge. In some cases, virus was detected only after a second subpassage in CRFK cells. Virus was isolated from two of four vaccinates, only for one day for each dog, and only after the second subpassage in CRFK cell culture.

The test is valid because all six control dogs remained susceptible to CPV on the day of challenge. No difference in daily rectal temperature was recorded between vaccinated and non-vaccinated dogs. Statistical analysis of white blood cell count revealed a significant difference between vaccinated and control dogs only on Day 6 post-challenge. Clinical evidence of CPV infection (anorexia and diarrhea) was observed only among non-vaccinated dogs. Challenge virus was shed for a total of 18 isolation days at an average of 3 isolation day per non-vaccinated dog as compared to a total of 2 isolation days at an average of 0.5 isolation days per vaccinated dog. Moreover, among the vaccinated dogs virus could only be detected after the second subculture in cell culture, suggesting low amount of virus excreted in the fecal specimen.

Dogs were not challenged with virulent rabies virus. However, the level of rabies SN activity displayed after two injections was consistent with levels associated with protection against rabies challenge exposure. Data presented here shows a marked protective response of vaccinated dogs to CPV challenge when compared to that of nonvaccinated dogs.

Conclusion

Two subcutaneous inoculations of susceptible dogs with canarypox-based recombinant rabies-canine parvovirus vaccine (vCP136 composition) with $10^7$ PFU per dose resulted in: Production of excellent levels of rabies virus-neutralizing antibodies even after one injection; production of satisfactory levels of CPV-neutralizing antibodies; and significant difference in clinical and subclinical manifestations of CPV infection between vaccinated and non-vaccinated dogs. Accordingly, vCP136 or, composition containing a recombinant containing coding for rabies and another antigen, is useful and did not exhibit efficacy interference.

TABLE 56

Level of neutralizing antibodies of CPV and rabies virus in sera obtained from VCP136-vaccinated and nonvaccinated dogs.

| GROUP NUMBER | DOG NUMBER | VACCINE TYPE | DAY 0 | DAY 22 | DAY 36 | DAY 50 |
|---|---|---|---|---|---|---|
| I CONTROL 1 | 830 | NO PARVO VACCINE | <2 | <2 | <2 | 2,048 |
| CONTROL 2 | 832 | | <2 | <2 | <2 | 1,536 |
| CONTROL 3 | 843 | | <2 | <2 | <2 | 2,048 |
| CONTROL 4 | 2019 | | <2 | <2 | <2 | 16,384 |
| CONTROL 5 | 2020 | | <2 | <2 | <2 | 8,192 |
| CONTROL 6 | 3015 | | <2 | <2 | <2 | 25,156 |
| II VAX 1 | 2002 | vCP136 | <2 | 8 | 512 | 3,072 |
| VAX 2 | 2007 | | <2 | <4 | 1,024 | 2,048 |
| VAX 3 | 2021 | | <2 | 12 | 384 | 2,048 |
| VAX 4 | 2025 | | <2 | 8 | 1,536 | 1,536 |

TABLE 57

Rabies Antibody Titer of Dogs SQ Vaccinated Twice With VCP136

| Dog Number | | 2002 | 2007 | 2021 | 2025 |
|---|---|---|---|---|---|
| Titer | Day 0 | 21.1 | 3.8 | 4 | 3.8 |
| | Day 22 | 434 | 129.6 | 262.3 | 129.6 |
| | Day 36 | >1778. | >1778.3 | >1778. | 718.3 |
| IU | Day 0 | 0.51 | 0.09 | 0.1 | 0.09 |
| | Day 22 | 10.43 | 3.11 | 6.3 | 3.11 |
| | Day 36 | >42.75 | >42.75 | >42.75 | 17.27 |

Legend: IU - International Units

TABLE 58

Daily White Blood Cell Count of Vaccinated and Control Dogs After Oronasal Challenge With Virulent CPV Lot 90-05.

| Dog Number | Ear Tag Number | White Blood Cell Count on Days Before and After CPV Challenge | | | | | | | | | | | |
|---|---|---|---|---|---|---|---|---|---|---|---|---|---|
| | | Day-2 | Day-1 | Day 0 | Day 1 | Day 2 | Day 3 | Day 4 | Day 5 | Day 6 | Day 7 | Day 8 | Day 9 | Day 10 |
| Control 1 | 830 | 9800 | ND | ND | 11400 | 9100 | 10100 | 10600 | 14200 | 6300 | 9700 | 11300 | 12100 | 14400 |
| Control 2 | 832 | 9300 | ND | ND | 10600 | 10300 | 12600 | 10300 | 9900 | 8600 | 11000 | 8200 | 12100 | 11300 |
| Control 3 | 843 | 10100 | ND | ND | 9000 | 9700 | 9900 | 8400 | 8200 | 6700 | 9000 | 6500 | 5000 | 7400 |
| Control 4 | 2019 | 9200 | ND | ND | 7800 | 8200 | 8400 | 8600 | 8900 | 7500 | 6900 | 7800 | 8700 | 7900 |
| Control 5 | 2020 | 10800 | ND | ND | 9700 | 10000 | 9900 | 7800 | 9000 | 7700 | 10000 | 9900 | 10500 | 10900 |
| Control 6 | 3015 | 8500 | ND | ND | 8000 | 7600 | 8700 | 9700 | 13200 | 6900 | 9900 | 7700 | 8400 | 5800 |
| | Mean | 9616.7 | | | 9416.7 | 9150.0 | 9933.3 | 9140.0 | 10566.7 | 7283.3 | 9416.7 | 8566.7 | 9466.7 | 9616.7 |
| | SD | 729.0 | | | 1304.4 | 970.8 | 1354.8 | 1030.6 | 2288.1 | 753.7 | 1269.4 | 1580.8 | 2470.3 | 2880.6 |
| Vax 1 | 2002 | 9800 | ND | ND | 11600 | 10800 | 11400 | 11600 | 3400 | 10900 | 8500 | 9400 | 11000 | 11600 |
| Vax 2 | 2007 | 9300 | ND | ND | 9000 | 10200 | 10500 | 10200 | 13000 | 8000 | 5900 | 10100 | 9400 | 10500 |
| Vax 3 | 2021 | 11000 | ND | ND | 13100 | 10500 | 9800 | 8500 | 8200 | 8100 | 7900 | 7300 | 8000 | 9600 |
| Vax 4 | 2025 | 10500 | ND | ND | 11000 | 10200 | 10500 | 9600 | 14700 | 10200 | 12100 | 10700 | 10200 | 12300 |
| | Mean | 10150.0 | | | 11175.0 | 10425.0 | 10550.0 | 9975.0 | 9825.0 | 9300.0 | 8600.0 | 9375.0 | 9650.0 | 11000.0 |
| | SD | 650.0 | | | 1470.3 | 248.7 | 567.9 | 1118.9 | 4409.3 | 1274.8 | 2238.3 | 1283.3 | 1107.9 | 1032.0 |

LEGEND: ND = Not Done; SD = Standard Deviation

REMARKS: Three of six nonvaccinated dogs and two of four nonvaccinated dogs displayed a reduced white blood cell count between day 5 and day 7 postchallenge.

TABLE 59

Daily rectal temperature of vaccinated and control dogs after oronasal challenge with virulent CPV.

| Dog Number | Ear Tag Number | Rectal Temperature Before and After Oronasal Challenge With Virulent CPV. | | | | | | | | | | | |
|---|---|---|---|---|---|---|---|---|---|---|---|---|---|
| | | Day-2 | Day-1 | Day 0 | Day 1 | Day 2 | Day 3 | Day 4 | Day 5 | Day 6 | Day 7 | Day 8 | Day 9 | Day 10 |
| Control 1 | 830 | 101.9 | ND | 103.0 | 102.7 | 101.9 | 102.8 | 102.7 | 103.0 | 103.4 | 102.2 | 101.9 | 102.0 | 101.8 |
| Control 2 | 832 | 102.4 | ND | 103.5 | 102.1 | 103.3 | 102.1 | 102.1 | 100.9 | 101.6 | 101.7 | 101.8 | 101.9 | 102.4 |
| Control 3 | 843 | 101.9 | ND | 102.7 | 102.0 | 102.2 | 101.0 | 102.9 | 102.2 | 101.5 | 103.5 | 101.8 | 102.4 | 102.8 |
| Control 4 | 2019 | 102.9 | ND | 102.0 | 102.7 | 101.0 | 101.0 | 102.7 | 101.1 | 101.4 | 101.6 | 101.6 | 101.4 | 104.5 |
| Control 5 | 2020 | 101.4 | ND | 102.9 | 101.8 | 102.2 | 101.2 | 102.3 | 102.8 | 102.1 | 102.7 | 101.9 | 100.9 | 101.7 |
| Control 6 | 3015 | 102.1 | ND | 101.7 | 102.8 | 102.9 | 101.7 | 102.0 | 102.6 | 102.4 | 101.9 | 102.1 | 103.0 | 102.0 |
| | Mean | 102.1 | | 102.6 | 102.4 | 102.3 | 101.6 | 102.5 | 102.1 | 102.1 | 102.3 | 101.9 | 101.9 | 102.5 |
| | SD | 0.5 | | 0.6 | 0.4 | 0.7 | 0.7 | 0.3 | 0.8 | 0.7 | 0.7 | 0.1 | 0.7 | 1.0 |
| Vax 1 | 2002 | 102.1 | ND | 102.0 | 101.5 | 101.8 | 102.4 | 102.7 | 101.8 | 102.0 | 103.4 | 102.3 | 102.3 | 101.9 |
| Vax 2 | 2007 | 104.0 | ND | 100.4 | 102.1 | 102.8 | 102.6 | 103.0 | 103.5 | 102.5 | 102.3 | 102.5 | 102.4 | 102.2 |
| Vax 3 | 2021 | 103.1 | ND | 103.1 | 101.7 | 102.3 | 102.3 | 101.5 | 100.7 | 101.2 | 101.9 | 101.8 | 101.9 | 102.5 |
| Vax 4 | 2025 | 102.5 | ND | 102.5 | 104.1 | 102.0 | 102.4 | 102.7 | 102.2 | 102.1 | 102.4 | 102.8 | 102.9 | 102.4 |
| | Mean | 102.9 | | 102.0 | 102.4 | 102.2 | 102.4 | 102.5 | 102.1 | 102.0 | 102.5 | 102.4 | 102.4 | 102.3 |
| | SD | 0.7 | | 1.0 | 1.0 | 0.4 | 0.1 | 0.6 | 1.0 | 0.5 | 0.6 | 0.4 | 0.4 | 0.2 |

REMARKS: No significant and sustained elevated rectal temperature is apparent between nonvaccinated and vaccinated dogs.

TABLE 60

Daily Clinical Observation of Vaccinated and Control Dogs After Oronasal Challenge With Virulent CPV.

| Dog Number | Ear Tag Number | Clinical Signs on Days Before and After CPV Challenge | | | | | | | | | | | |
|---|---|---|---|---|---|---|---|---|---|---|---|---|---|
| | | Day−2 | Day 0 | Day 1 | Day 2 | Day 3 | Day 4 | Day 5 | Day 6 | Day 7 | Day 8 | Day 9 | Day 10 |
| Control 1 | 830 | N | N | N | N | N | N | A(1);D(1) | A(1); D(3+b) | A(5);a£ | A(1); D(3+b) | N | N |
| Control 2 | 832 | N | N | N | N | N | A(1);D(1) | A(3) | A(1) | A(1);D(1) | D(1) | N | N |
| Control 3 | 843 | N | N | N | A(1) | N | A(1) | A(1) | A(3) | A(5); D(3+b) | A(5); D(3+b) | N | N |
| Control 4 | 2019 | N | N | N | N | N | N | A(1);D(1) | A(1);D(1) | N | N | N | N |
| Control 5 | 2020 | N | N | N | N | N | N | A(1);D(1) | A(3);D(1) | N | N | N | N |
| Control 6 | 3015 | N | N | N | N | N | N | N | N | N | N | N | N |
| | | | | | | | | | | | | | |
| Vax 1 | 2002 | N | N | N | N | N | N | N | N | N | N | N | N |
| Vax 2 | 2007 | N | N | N | N | N | N | N | N | N | N | N | N |
| Vax 3 | 2021 | N | N | N | N | N | N | N | N | N | N | N | N |
| Vax 4 | 2025 | N | N | N | N | N | N | N | N | N | N | N | N |

LEGEND: N = normal A = anorexia (1 = slight; 3 = medium; 5 = severe)
D = diarrhea (1 = slight; 3 = medium; 5 = severe; b = blood in stool)
n/F = no feces collected

TABLE 61

Isolation of Virus From Fecal Specimens Collected From Nonvaccinated and Vaccinated Dogs Following Challenge With Virulent CPV.

| Dog Number | Ear Tag Number | Virus Isolation Before and After Challenge With CPV | | | | | | | | | | |
|---|---|---|---|---|---|---|---|---|---|---|---|---|
| | | Day 0 | Day 1 | Day 2 | Day 3 | Day 4 | Day 5 | Day 6 | Day 7 | Day 8 | Day 9 | Day 10 |
| Control 1 | 830 | | | | | + | + | + | | + | | |
| Control 2 | 832 | | | | | + | + | + | | | | |
| Control 3 | 843 | | + | | | + | + | + | + | | | |
| Control 4 | 2019 | | + | | | + | | | | | | |
| Control 5 | 2020 | | | | | | + | | | | | |
| Control 6 | 3015 | | + | | | + | + | | | | | |
| | | | | | | | | | | | | |
| Vax 1 | 2002 | | | | | | | | | | | |
| Vax 2 | 2007 | | | + | | | | | | | | |
| Vax 3 | 2021 | | | | + | | | | | | | |
| Vax 4 | 2025 | | | | | | | | | | | |

TABLE 61-continued

Isolation of Virus From Fecal Specimens Collected From Nonvaccinated
and Vaccinated Dogs Following Challenge With Virulent CPV.

LEGEND:

 = No CPV was isolated from fecal specimens.

 = CPV was isolated from fecal specimens only after 1st isolation attempt.

 = CPV was isolated from fecal specimens only after second subpassage in cell culture.

Example 18
Rabies Vaccine, Live Canarypox Vector Serological Response and Safety in Feline Leukemia Virus Infected and Non-Infected Cats This Example demonstrates safety and rabies antibody response of a Canarypox rabies recombinant virus (vCP65) in feline leukemia virus infected (FeLV⊕ cats) and non-infected cats (FeLV− cats). Within these groups, 30 cats had previous exposure to a recombinant canarypox feline leukemia virus. The remaining 28 cats were naive to the canarypox vector (See Table 65). Two doses of vCP65 virus were administered subcutaneously (Day 0 and Day 20–22). Rabies antibody responses were determined by rapid fluorescent focus inhibition testing (RFFIT). More specifically: (vCP97 is described in U.S. Ser. No. 08/105,483; vCP212 was generated by using vCP177 (U.S. Ser. No. 08/105,483, Example 50) as the rescuing virus and pC3DOFGAGVQ (U.S. Ser. No. 08/105,483, Example 53) as the donor DNA (U.S. Ser. No. 08/105,483 incorporated herein by reference)).

Animals: Group 1 (FeLV−):

Ten rabies antibody negative cats previously vaccinated with two doses of a recombinant canarypox feline leukemia virus (vCP97) and challenged with feline leukemia virus (FeLV) were used. They had received (vCP97) on Day 0 and Day 21. They were challenged two weeks later following one immunosuppressive dose of corticosteroids. They were bled bi-weekly post-challenge and their sera evaluated for presence of FELV p27 antigen by ELISA. Only one cat (#1953) was transiently antigenemic post-challenge. Nine weeks post-challenge all cats were negative for FeLV antigenemia prior to vaccination with canarypox rabies virus (vCP65).

Group 1 (See Table 64): Cats (n=10) were divided into two dosage groups. One group (N=5) received two doses of $10^{6.0}$ TCID$_{50}$/dose and the other group (n=5) received $10^{7.0}$ TCID$_{50}$/dose. Both groups were vaccinated and then boostered approximately three weeks later. Blood samples were collected according to the following schedule (Table 62):

TABLE 62

| DAY | ACTIVITY |
|---|---|
| 0 | Vaccination |
| 7 | Bleed |
| 22 | Booster/Bleed |
| 36 | Bleed |
| 49 | Bleed |

Group 2 (FeLV+):

Eighteen rabies antibody negative cats were used. The cats were not vaccinated with a recombinant virus prior to challenge. They were challenged with FeLV following one immunosuppression. Eleven weeks post-challenge there were 7 FeLV negative (FeLV⊖) and 11 FeLV positive (FeLV⊕) cats prior to vaccination with canarypox rabies virus (vCP65).

Group 2 (See Table 65): Cats (n=18) were divided into two dosage groups and were to receive either two doses of vCP65 at $10^{5.0}$ or $10^{6.0}$ TCID$_{50}$/dose. They were vaccinated once and then boostered twenty two days later. Blood sample were collected according to the following schedule (Table 63):

TABLE 63

| DAY | ACTIVITY |
|---|---|
| 0 | Vaccination |
| 22 | Booster/Bleed |
| 36 | Bleed |

Group 3: (FeLV−):

Thirty rabies antibody negative cats were used. The cats received one dose of (vCP97) alone or in combination with another canarypox FeLV recombinant (vCP212) and a second dose three weeks later and were challenged two week after the second dose following one immunosuppressive dose or corticosteroids. They were bled bi-weekly post-challenge and their sera evaluated for presence of FeLV p27 antigen by ELISA. Only one cat (K2) was FeLV1 antigenemic post-challenge. Nine weeks post-challenged twenty nine cats were FeLV⊖ and one cat remained FeLV⊕ prior to vaccination with canarypox rabies virus (vCP65) and feline herpes (FHV) recombinants (vCP243 and vP1164).

Generation of an ALVAC-Based Recombinant Expressing the FHV-1 qB. gC, and gD Glycoproteins (vCP243). The genes encoding the FHV-1 homologs of gB, gC and gD, under the control of the I3L, H6 and 42K promoters, respectively, were inserted into a single ALVAC vector at the C6 site to generate vCP243. The donor plasmid required for this insertion, pJCA109, was generated as follows.

Construction of donor plasmid pJCA109. An I3L promoter/FHV-1 gB gene expression cassette was obtained as two fragments from plasmid pJCA079: an 840 bp SmaI/BamHI fragment containing the I3L promoter linked to the 5' portion of the gB gene (fragment A) and a 2155 bp BamHI/HindIII fragment containing the remaining 3' portion of the gB gene (fragment B).

A 1650 bp NruI/EcoRI fragment containing the 3' end of the H6 promoter linked to the FHV-1 gC gene was obtained from plasmid pJCA100 and ligated with an NruI/EcoRI-digested pBS-SK⁺H6 vector fragment (This vector contained the H6 promoter cloned into the pBS-SK⁺ polylinker region). The resulting plasmid was designated pJCA108.

The H6/gC expression cassette was isolated from pJCA10[8] as an 1830 bp HindIII/EcoRI fragment (fragment C).

A 42K promoter/FHV-1 gD gene expression cassette was obtained from plasmid pJCA080 as an EcoRI/XhoI fragment (fragment D).

Fragments A, B, C and D were subsequently ligated with a SmaI/XhoI-digested pC6L vector fragment to generate plasmid pJCA109. The pJCA109 ALVAC C6 site donor plasmid contains the I3L promoter/gB gene, the H6 promoter/gC gene and 42K promoter gD gene expression cassettes oriented from left to right, respectively, between the ALVAC C6 flanking arms.

The derivation of plasmid intermediates used in the generation of pJCA109 is as follows.

pJCA079: Plasmid pJCA001 (U.S. Ser. No. 07/502,834, Example 15) was digested with BamHI and EcoRI to obtain a 900 bp fragment containing the central portion of gB (fragment A). Plasmid pJCA076 was digested with XbaHI and BamHI to obtain an 840 bp fragment containing the I3L promoter linked to the gB mutated 5' portion (fragment B). Plasmid pJCA077 was digested with EcoRI and XhoI to obtain a 1255 bp fragment containing the 3' portion of gB (fragment C). Fragments A, B and C were ligated together into XbaI-XhoI digested pBS-SK$^+$ vector to produce pJCA079.

pJCA076: Primers JCA158 (SEQ ID NO: 37) (5' TTTTTCTAGACTGCAGCCCGGGACATCATGC AGTG-GTTAAAC 3') and JCA211 (SEQ ID NO: 56) (5'GTGGACACATATAGAAAGTCG 3') were used to synthesize by PCR an XbaI-Blunt 510 bp fragment (fragment A) containing a mutated TTTTTNT signal using plasmid pJCA075 as a template. Primers JCA212 (SEQ ID NO: 38) (5' CACCTT CAGGATCTACTGTCG 3') and JCA213 (SEQ ID NO: 39) (5'GGGTTTCAGAGGCAGTTC 3') were used to synthesize by PCR a Blunt-BanHI 330 bp fragment (fragment B) using plasmid pJCA001 as a template. Fragment A was digested with XbaI and kinased. Fragment B was digested with BamHI and kinased. Fragments A and B were then ligated together into XbaI-BamHI-digested pBS-SK$^+$ vector to produce pJCA076.

pJCA075: Primers MP287 (SEQ ID NO: 40) (5'GATTAAACCTAAATAATTGT 3') and JCA158 (SEQ ID NO: 41) (5'TTTTTCTAGACTGCAGCCCGGGA- CAT-CATGCAGTGGTTAAAC 3) were used to synthesize by PCR an XbaI-Blunt 120 bp I3L promoter fragment (fragment A) using plasmid pMP691 as a template (pMP691 contains the I3L promoter linked to an irrelevant gene—the rabies glycoprotein gene—in the pCOPCS plasmid). Primers JCA213 (SEQ ID NO: 42) (5'GGGTTTCAGAGG CAGTTC 3') and JCA238 (SEQ ID NO: 43) (5'ATGTCCACTCGTGGCGATCTT 3') were used to synthesize by PCR a 720 bp fragment that extends from the FHV gB 5'ATG (fragment B) using plasmid pJCA001 as a template. Fragment A was digested with XbaI and kinased. Fragment B was digested with BamHI and kinased. Fragments A and B were then ligated together into XbaI-BamHI digested PBS-SK$^+$ vector to produce plasmid pJCA075.

pJCA077: Primers JCA239 (SEQ ID NO: 44) (5'ACGCATGATGACAAGATTATTATC 3') and JCA249 (SEQ ID NO: 45) (5'CTGTGGA ATTCGCAATGC ) were used to synthesize by PCR a 695 bp EcoRI-blunt FHV gB fragment (fragment A) using plasmid pJCAOOl as a template. Primers JCA221 (SEQ ID NO: 46) (5'AAAACTGCAGCCCGGGAAGCTTACAAAAATTA-GACAAGATTTGTTTC AGTATC 3') and JCA247 (SEQ ID NO: 47) (5'GGTATGGCAAATTTCTTTCAGGGACTC- GGGGATGTG 3') were used to synthesize by PCR a 560 bp FHV gB 3' end blunt-PstI fragment (fragment B) using plasmid pJCA001 as a template. Fragment A was digested with EcoRI and kinased. Fragment B was digested with PstI and kinased. Fragments A and B were then ligated together into EcoRI-PstI digested pIBI24 vector to produce plasmid pJCA077.

pJCA100: Primers JCA274 (SEQ ID NO: 48) (5'CATTATCGCGATATCCGTTAAGTTTGTATCGTAAT-GA GACGATATAGGATGGGAC 3') and JCA275 (SEQ ID NO: 49) (5'ACTATTTTCAATACTGAC 3') were used to synthesize by PCR a 107 bp NruI-SalI fragment containing the 3' end of the H6 promoter linked to the 5' portion of gC (fragment A) using plasmid pFHVEcoRIF as a template. Primers JCA276 (SEQ ID NO: 50) (5'AAATGTGTACCACGGGAC 3') and JCA 277 (SEQ ID NO: 51) (5'AAGAA GCTTCTGCAGAATTCGTTAA-CAAAAATCATTATAATCGCCGGGGATGAG 3) were used to synthesize by PCR a 370 bp EcoRV-HindIII fragment containing the gC 3' portion (fragment B) using plasmid pJCA095 as a template. Fragment A was digested with NruI and SalI. Fragment B was digested with EcoRV and HindIII. A 100 bp HindIII-NruI fragment containing the 5'end of the H6 promoter was obtained (fragment C). Plasmid pJCA095 was digested with BamHI and EcoRV to obtain a 580 bp fragment containing the central portion of gC (fragment D). Fragments A and C were ligated together into HindIII-SalI digested pBS-SK$^+$ vector to produce plasmid pJCA097. Fragments B and D were ligated together into BamHI-HindIII digested pBS-SK$^+$ vector to produce pJCA099. Plasmid pJCA097 was digested with PstI and SalI to obtain a 200 bp fragment containing the H6 promoter linked to the 5' portion of gC (fragment E). Plasmid pFH-VEcoRIF was digested with BamHI and SalI to obtain a 600 bp gC fragment (fragment F). Fragments E and F were ligated together into BamHI-PstI digested pBS-SK$^+$ vector to produce pJCA098. Plasmid pJCA098 was digested with EcoRI and BamHI to obtain the 820 bp fragment containing the H6 promoter linked to the 5' portion of gC (fragment G). Plasmid pJCA099 was digested with BamHI and HindIII to obtain the 960 bp fragment containing the 3' portion of gC (fragment H). Fragments G and H were then ligated together with EcoRI-HindIII digested PBS-SK$^+$ vector to produce pJCA100, which contains the H6/gC (532 aa) gene expression cassette in pBS-SK$^+$.

pFHVEcoRIF: The 7500 bp EcoRI "F" fragment from FHV-1 strain C0 was cloned into EcoRI-digested PBS-SK$^+$ to generate plasmid pFHVEcoRIF. The FHV-1 gC gene was identified within this fragment by nucleotide sequence comparisons with the HSV-1 gC gene.

pJCA080: Plasmid pJCA073 (U.S. Ser. No. 08/105,483, Example 57) was digested with BamHI and XhoI to obtain the 960 bp fragment containing the 3' portion of FHV gD (fragment D). Primers RG286 (SEQ ID NO: 52) (5'TTTATATTGTAATTATA 3') and M13F (SEQ ID NO: 53) (5'GTAAAACGACGGCCAGT 3') were used to synthesize by PCR a 130 bp EcoRI-blunt fragment containing the 42K promoter (fragment E) using plasmid pJCA038 as template. Primers JCA234 (SEQ ID NO: 54) (5'ATGATGACACGTCTACATTTT 3') and JCA235 (SEQ ID NO: 55) (5'TGTTACATAA CGTACTTCAGC 3') were used to synthesize a 185 bp Blunt-BamHI fragment containing the 5' portion of FHV gD (fragment F). Fragments E and F were digested respectively with EcoRI and BamHI, kinased, and ligated together into BamHI-EcoRI-digested pBS-SK$^+$ vector to produce plasmid pJCA078. Plasmid pJCA078 was digested with HpaI and BamHI to obtain a 310 bp fragment containing the 42K promoter linked to the 5' portion of the gD gene (fragment G). Fragments D and G were ligated together into vector PBS-SK+ digested with EcoRV and XhoI to produce pJCA080.

Generation and characterization of vCP243. The FHV-1 gB, gC and gD genes were inserted into the ALVAC genome at the C6 site by in vitro recombination between NotI-linearized pJCA109 donor plasmid and ALVAC genomic DNA. A recombinant containing the gB, gC and gD genes was identified by plaque hybridization, plaque purified and amplified. This recombinant was designated vCP243.

Expression of these glycoproteins in vCP243-infected CRFK, CEF and/or Vero cells was evaluated with sheep monospecific polyclonal antisera to gB, gC and gD by western blot and/or immunoprecipitation analyses. By these assays, the following FHV-1 proteins are expressed in vCP243-infected cells: gB polypeptides of 100, 60 and 55 kDa; a gC polypeptide of 110 kDa; a gD polypeptide of 60 kDa.

Generation of a NYVAC-Based Recombinant Expressing the FHV-1 gB. qC, and gD GLYCOPROTEINS (vP1164). The genes encoding the FHV-1 homologs of gB, gC and gD, under the control of the I3L, H6 and 42K promoters, respectively, were inserted into a single NYVAC vector at the ATI site to generate vP1164. The donor plasmid required for this insertion, pJCA107, was generated as follows.

Construction of donor plasmid pJCA107. An I3L promoter/FHV-1 gB gene expression cassette was obtained as two fragments from plasmid pJCA079: a 1740 bp SmaI/EcoRI fragment containing the I3L promoter linked to the 5' portion of the gB gene (fragment A) and a 1255 bp EcoRI/HindIII fragment containing the remaining 3' portion of the gB gene (fragment B).

An H6 promoter/FHV-1 gC gene expression cassette was obtained from plasmid pJCA100 as a 1755 bp HindIII/PstI fragment (fragment C).

A 42K promoter/FHV-1 gD gene expression cassette was obtained from plasmid pJCA080 as a PstI/XhoI fragment (fragment D).

Fragments A, B, C and D were subsequently ligated with a SmaI/Xho-digested pSD541VC vector fragment to generate plasmid pJCA107. The pJCA107 NYVAC ATI site donor plasmid contains the I3L promoter/gB gene, the H6 promoter/gC gene and 42K promoter gD gene expression cassettes oriented from left to right, respectively, between the NYVAC ATI flanking arms.

Generation and characterization of vP1164. The FHV-1 gB, gC and gD genes were inserted into the NYVAC genome at the ATI site by in vitro recombination between NotI-linearized pJCA107 donor plasmid and NYVAC genomic DNA. A recombinant containing the gB, gC and gD genes was identified by plaque hybridization, plaque purified and amplified. This recombinant was designated vP1164.

Expression of these glycoproteins in vP1164-infected CRFK, CEF and/or Vero cells was evaluated with sheep monospecific polyclonal antisera to gB, gC and gD by western blot and/or immunoprecipitation analyses. By these assays, the following FHV-1 proteins are expressed in vCP243-infected cells: gB polypeptides of 100, 60 and 55 kDa; a gC polypeptide of 110 kDa; a gD polypeptide of 60 kDa.

Group 3 (See Table 65): Cats (n=30) were divided into five dosage groups (n=6/group). Three groups received two doses of vCP65 at $10^{4.0}$, $10^{5.0}$, $10^{6.0}$ $TCID_{50}$/dose. One group (n=6) received only one injection of CP65 at $10^{6.0}$ $TCID_{50}$/dose and one group (n=6) was not vaccinated as contact controls. Cats were vaccinated on and then boostered three weeks later. Blood samples were collected according to the following schedule (Table 64):

TABLE 64

| DAY | ACTIVITY |
|---|---|
| 0 | Vaccination |
| 20 | Booster/Bleed |
| 37 | Bleed |
| 50 | Bleed |

TABLE 65

SUMMARY OF VACCINATION GROUPS

| GROUP | # CATS | FeLV⊖ | FeLV⊕ | Previous Canarypox Vector Exposure # Yes | # No |
|---|---|---|---|---|---|
| 1 | 10 | 10 | 0 | 10 | 0 |
| 2 | 18 | 7 | 11 | 0 | 18 |
| 3 | 30 | 29 | 1 | 20 | 10 |
| TOTAL | 58 | 46 | 12 | 30 | 28 |

Cats were lightly sedated for collection of blood using ketamine hydrochloride (100 mg/ml) or ketamine in combination with xylazine (5–10 mg/ml) administered at 5–10 mg/kg intramuscularly. Atropine (0.54 mg/ml) was administered at 0.1–0.2 ml per cat subcutaneously to decrease salivation during anesthesia. Cats were observed for pain or discomfort following injection, observed daily and monitored bi-weekly for adverse clinical signs.

Serum samples were collected and evaluated for rabies virus neutralizing antibodies by rapid fluorescent focus inhibition test (RFFIT). From samples titers were determined and adjusted to a standard reference virus. Titers were reported as $\log_{10}$, antilog$_{10}$ and international units (iu). Tables 67–71 report data as $\log_{10}$ and antilog$_{10}$.

Cats from Group 3 were also vaccinated with recombinants containing feline herpes virus (FHV) genes vCP243 (n=10) (See Tables 69 and 70). Virus was subcutaneously administered twice, using approximately $10^{7.0}$ $TCID_{50}$/dose, at the same time but at a different site as the CP65 injections.

Virus: Canarypox rabies recombinant virus (vCP65), was an X+5 passage of virus titered to contain $10^{8.0}$ $TCID_{50}$/ml. Prior to use it was diluted in F10–199 tissue culture medium.

Primary Chick Embryo Fibroblasts (CEF): Suspensions of CEF cells received from Select Laboratories were used to titer the virus post-administration.

Virus dilutions were titered post-administration for all three groups of cats. Twelve cats in Group 2 received $10^{6.2}$ $TCID_{50}$/dose and six cats received $10^{5.8}$ $TCID_{50}$/dose instead of the desired $10^{6.0}$ and $10^{5.0}$ $TCID_{50}$/dose, for primary vaccination. Therefore, for booster vaccination, all cats in Group 2 (n=18) received $10^{5.8}$ $TCID_{50}$/dose. The titers of five replicates/vaccine are as follows (Table 66).

TABLE 66

| | Vax 1 | Vax 2 |
|---|---|---|
| Group 1 (n = 5) | $10^{7.2}$ | $10^{7.1}$ |
| Group 1 (n = 5) | $10^{6.1}$ | $10^{6.1}$ |

TABLE 66-continued

|  | Vax 1 | Vax 2 |
| --- | --- | --- |
| Group 2 (n = 12) | $10^{6.2}$ | $10^{5.8}$ |
| Group 2 (n = 6) | $10^{5.8}$ | $10^{5.8}$ |
| Group 3 (n = 6) | $10^{4.0}$ | $10^{4.0}$ |
| Group 3 (n = 6) | $10^{4.7}$ | $10^{4.7}$ |
| Group 3 (n = 6) | $10^{5.8}$ | $10^{5.8}$ |
| Group 3 (n = 6) | $10^{5.8}$ | None |
| Group 3 (n = 6) | Control | Control |

Rabies virus neutralizing antibody titers of individual cats (Group 1, 2, and 3) are shown in Tables 67, 68 and 71 respectively.

Group 1: (See Table 67): FeLVe cats with previous exposure to the canarypox vector (n=10) demonstrated a strong serological response to vCP65. Following booster, five of five cats receiving $10^{7.1}$ $TCID_{50}$/dose had rabies antibody titers greater than 3.0 $\log_{10}$ (GMT=$\log_{10}$3.68±0.4; Antilog=4786). Following booster, five of five cats receiving $10^{6.1}$ $TCID_{50}$/dose responded with three of five cats having rabies antibody titers greater than 3.0 $\log_{10}$ (GMT=$\log_{10}$2.96±0.8, Antilog=912).

Group 2: (See Tables 68, 69 and 70): FeLV⊖ and FeLV⊕ cats not having previous exposure to the canarypox vector (n=18) demonstrated a strong serological response to vCP65 (GMT)=$\log_{10}$ 2.10±0.5, Antilog=631).

As shown in Table 69: FeLV⊖ cats of this group (n=7) responded to primary vaccination with good rabies antibody titers (GMT=190±0.6, Antilog=79). Following booster, these cats demonstrated a good increase in rabies antibodies (GMT=$\log_{10}$ 2.96±0.4, Antilog=912).

As shown in Table 70: FeLV⊕cats of this group (n=11) also demonstrated a good serological response to vCP65 after one injection (GMT=2.24±0.4, Average=174). Following booster, the majority of FeLV⊕ cats demonstrated an increase in rabies antibodies (GMT=$\log_{10}$ 2.80±0.6, Antilog=630). FeLV⊕ cats #82 and #84 did not respond to booster vaccination therefore suppressing the GMT of FeLV⊕ cats post-booster. Analysis of post-booster FeLV⊕ cats without these two non-responders is similar, if not slightly better, than Group 2 FeLVe cats (GMT=$\log_{10}$2.99±0.4, Antilog=977).

There was no significant difference in antibody response of Group 2 cats receiving $10^{6.2}$ $TCID_{50}$ versus $10^{5.8}$ $TCID_{50}$ for primary vaccination. Therefore, these data are averaged together (See $GMT^a$/Table 68; see also Table 69 and 70).

Group 3: (See Table 71): Cats in this group (n=30) demonstrated a variable serological response to vCP65 depending on the titer of virus administered. Cats receiving $10^{4.0}$ $TCID_{50}$/dose did not respond well to primary or booster vaccination (GMT=0.83 $\log_{10}$±0.5, Antilog=7) whether they had or had not been previously vaccinated with the canarypox vector. One exception, C5, responded well to primary vaccination.

Cats receiving $10^{4.7}$ $TCID_{50}$/dose also responded unequally to primary vaccination (GMT=1.65 $\log_{10}$±0.5; Antilog=45) but the cats responded strongly to booster (GMT=2.48 $Log_{10}$±0.5; Antilog=302).

Cats receiving two doses of $10^{5.8}$ $TCID_{50}$/dose demonstrated a slightly higher response to primary vaccination as did the $10^{4.7}TCID_{50}$/dose group (GMT=1.86 $\log_{10}$±0.6; Antilog=72) and booster (GMT=2.74 $\log_{10}$±0.4; Antilog=549).

Cats receiving one dose of CP65 ($10^{5.8}$ $TCID_{50}$/dose) responded with titers equivalent to the two dose group after primary vaccination (GMT=1.92 $\log_{10}$±0.4; Antilog=83).

Group 3: Control cats (n=6) that were not vaccinated but were housed in contact with vaccinates remained serologically negative for rabies antibodies post-vaccination.

Safety: Fifty seven of fifty eight cats remained clinically health throughout the duration of the experiment. The vCP65 virus was administered painlessly. There was no swelling or inflammation observed post-vaccination or signs of systemic illness.

Cat K2 (Group 3) was FeLV⊕ prior to vaccination. This cat was euthanized 37 days post-primary vaccination due to weight loss, anorexia and secondary bacterial infections. A necropsy was performed and lesion were found on both hind limbs and dorsal lip surfaces. No internal abnormalities were noted. Samples of lip tissue were frozen and retained. It is theorized that this cat exhibited signs related to FeLV infection; however, it was the only FeLV⊕cat thus far using the NVSL challenge model to exhibit clinical illness post-challenge. Contact control cats in Group 3 remained clinically healthy throughout duration of the trial.

The virus (vCP65) demonstrated excellent safety in FeLV infected cats. Interestingly, nine of eleven FeLV⊕ cats responded as well as booster vaccination as did the FeLV⊖ cats. This finding is surprising in that suppressed immune function is a often sequelae to FeLV infection. However, as described in the literature, SPF cats housed under "clean" conditions are not subject to environmental infections and therefore may not be as immunocompromised as house cats.

From this disclosure, without undue experimentation one skilled in the art can determine the minimum protective dose of this virus (vCP65) in cats, especially by following the canine combination regime above. Single dose vCP65 product or monovalent vCP65 product, if desired, can be prepared from this disclosure, without undue experimentation.

The Example also demonstrates a lack of immune response suppression to previous administration of the canarypox vector. Previous administration of a FeLV canarypox virus did not negatively affect the immune response of cats to the canarypox rabies virus. Previous exposure may actually enhance subsequent vaccination with the same vector (i.e., Group 1 cats receiving $10^{6.0}$ $TCID_{50}$ responded with a higher GMT (than Group 2 cats receiving the same dose of virus). Thus, multiple vaccinations of recombinant viruses, such as vCP65, over time, are also possible, thereby demonstrating the applicability of poxvirus vectors, e.g., poxvirus-rabies recombinants, and especially this vector (ALVAC), and particularly of vCP65, to yearly vaccination programs. This animal model (i.e., FeLV infected cats) is often used as a parallel to HIV infected humans. FeLV⊕ cats are considered immunocompromised and more susceptible to pathogenic effects of infectious agents.

TABLE 67

SERUM NEUTRALIZING TITERS (RFFIT TITERS) OF GROUP 1 CATS

| Cat # | FeLV (+/−) | FeLV Vax (y/n) | Vaccine vCP65 Titer Vax 1 | Vax 2 | RFFIT Titers ($Log_{10}$) Day 22–26* | Day 36** | Day 49*** |
|---|---|---|---|---|---|---|---|
| 1963 | — | y | $10^{7.2}$ | $10^{7.1}$ | 2.90 | 3.70 | 3.25 |
| 1965 | — | y | | | 3.34 | 4.16 | 4.88 |
| 1993 | — | y | | | 0.65 | 3.11 | 3.16 |
| 1997 | — | y | | | 2.46 | 3.34 | 3.29 |
| 1953 | — | y | | | 2.42 | 4.07 | 3.90 |
| GMT | | | | | 2.35 ± .9 | 3.68 ± .4 | 3.70 ± .6 |
| 2050 | — | y | $10^{6.1}$ | $10^{6.1}$ | 2.76 | 3.16 | 3.25 |
| 2078 | — | y | | | 2.99 | 4.03 | 3.56 |
| 2048 | — | y | | | X | 3.03 | 3.16 |
| 1971 | — | Y | | | 2.50 | 3.12 | 2.94 |
| 1999 | — | Y | | | X | 1.49 | 2.11 |
| GMT | | | | | 2.75 ± .2 | 2.96 ± .8 | 3.00 ± .5 |

* Three weeks post-first vaccination
** Two weeks post-second vaccination
*** Four weeks post-second vaccination
a This titer is a mean titer of two readings (3.56 and 3.81)
X No sample

TABLE 68

SERUM NEUTRALIZING TITERS (RFFIT TITERS) OF GROUP 2 CATS

| Cat # | FeLV (+/−) | FeLV Vax (y/n) | Vaccine vCP65 Titer Vax 1 | Vax 2 | RFFIT Titers ($Log_{10}$) Day 22–26* | Day 36** | Day 49*** |
|---|---|---|---|---|---|---|---|
| B1 | − | n | $10^{6.2}$ | $10^{5.8}$ | 2.68 | 3.69 | |
| T2 | − | n | | | 1.25 | 3.38 | |
| T1 | + | n | | | 2.42 | 1.63 | |
| A2 | + | n | | | 1.63 | 3.34 | |
| X2 | + | n | | | 2.64 | 3.03 | |
| U3 | + | n | | | 1.85 | 2.94 | |
| 37 | − | n | | | 2.29 | 2.64 | |
| 39 | − | n | | | 1.23 | 2.64 | |
| 35 | + | n | | | 2.02 | 2.20 | |
| 23 | + | n | | | 2.72 | 3.47 | |
| 13 | + | n | | | 2.72 | 3.07 | |
| 15 | + | n | | | 2.07 | 2.9 | |
| GMT | | | | | 2.12 ± 0.5 | 2.88 ± 0.4 | |
| 88 | − | n | $10^{5.8}$ | $10^{5.8}$ | 1.67 | 2.64 | |
| 67 | − | n | | | 1.94 | 2.99 | |
| 86 | − | n | | | 2.37 | 2.72 | |
| 84 | + | n | | | 2.55 | 2.37 | |
| 85 | + | n | | | 2.20 | 3.29 | |
| 82 | + | n | | | 1.63 | 1.63 | |
| GMT | | | | | 2.06 ± 0.3 | 2.61 ± 0.5 | |
| GMT[a] | | | | | 2.10 ± 0.5 | 2.80 ± 0.5 | |

*Three weeks post-first vaccination
**Two weeks post-second vaccination
***Four weeks post-second vaccination-no sample taken
[a]Geometric mean titer for all cats of Group 2 (n = 18)

TABLE 69

FeLV⊖ Cats Group 2.

| Cat # | RFFIT Day 22 | Day 36 |
|---|---|---|
| B1 | 2.68 | 3.69 |
| T2 | 1.15 | 3.38 |
| 37 | 2.29 | 2.64 |
| 39 | 1.23 | 2.64 |
| 88 | 1.67 | 2.64 |
| 67 | 1.94 | 2.99 |
| 86 | 2.37 | 2.72 |
| GMT | 1.90 ± 0.5 | 2.96 ± 0.4 |

TABLE 70

FeLV⊕ Cats Group 2

| | RFFIT | |
|---|---|---|
| Cat # | Day 22 | Day 36 |
| T1 | 2.42 | 3.38 |
| A1 | 1.63 | 3.34 |
| X2 | 2.64 | 3.03 |
| U3 | 1.85 | 2.94 |
| 35 | 2.02 | 2.20 |
| 23 | 2.72 | 3.47 |
| 13 | 2.72 | 3.07 |
| 15 | 2.07 | 2.59 |
| 84 | 2.55 | 2.37 |
| 85 | 2.20 | 3.29 |
| 82 | 1.63 | 1.63 |
| K2 | 1.83 | X |
| TOTAL | 2.24 ± 0.4 | 2.80 ± 0.6 |

TABLE 71

Serum Neutralizing Titers (RFFIT Titers) of Group 3 Cats

| Cat # | FeLV (+/−) | FeLV Vax (y/n) | Vaccine vCP65 Titer Vax 1 | Vaccine vCP65 Titer Vax 2 | RFFIT Titers ($Log_{10}$) Day 22–26* | RFFIT Titers ($Log_{10}$) Day 36** | RFFIT Titers ($Log_{10}$) Day 49*** |
|---|---|---|---|---|---|---|---|
| Y1[a] | − | n | $10^{4.0}$ | $10^{4.0}$ | 0.58 | 0.63 | 0.37 |
| U1[c] | − | n | | | 0.41 | 0.48 | 0.48 |
| M1[b] | − | y | | | 0.39 | 1.06 | 0.53 |
| X1[b] | − | y | | | 0.37 | 0.56 | 0.67 |
| R5[1] | − | y | | | 0.35 | 0.37 | 0.35 |
| C5[a] | − | y | | | 1.85 | 1.89 | 2.20 |
| GMT | | | | | 0.65 ± 0.5 | 0.83 ± 0.5 | 0.77 ± 0.6 |
| R4[c] | − | n | $10^{4.7}$ | $10^{4.7}$ | 1.46 | 3.12 | 3.08 |
| E3[c] | − | n | | | 1.11 | 2.20 | 2.59 |
| F2[b] | − | y | | | 1.98 | 2.72 | 2.86 |
| I1[b] | − | y | | | 1.76 | 2.37 | 2.59 |
| K3[a] | − | y | | | 2.72 | 2.81 | 2.77 |
| R2[a] | − | y | | | 0.89 | 1.67 | 1.81 |
| GMT | | | | | 1.65 ± 0.6 | 2.48 ± 0.5 | 2.62 ± 0.4 |
| C6[c] | − | n | $10^{5.6}$ | $10^{5.6}$ | 2.33 | >3.25 | >3.12 |
| B1[a] | − | n | | | 1.37 | >3.25 | >3.25 |
| J1[b] | − | y | | | 2.11 | 2.51 | 2.55 |
| A1[c] | − | y | | | 1.32 | 2.11 | 2.03 |
| C4[a] | − | y | | | 2.77 | 2.90 | 2.94 |
| Q1[b] | − | y | | | 1.28 | 2.42 | 2.59 |
| GMT | | | | | 1.86 ± 0.6 | 2.74 ± 0.4 | 2.75 ± 0.4 |
| K2[a] | + | n | $10^{5.6}$ | none | 1.85 | X | X |
| U2[a] | − | n | | | 1.37 | 1.37 | 1.54 |
| Y3[c] | − | y | | | 2.51 | 2.16 | 2.64 |
| Q2[c] | − | y | | | 2.29 | 2.29 | 2.38 |
| D4[b] | | y | | | 1.67 | 2.33 | 2.59 |
| M2[b] | − | y | | | 1.85 | 1.85 | 2.20 |
| GMT | | | | | 1.92 ± 0.4 | 2.00 ± 0.4 | 2.27 ± 0.4 |
| Q5[a] | − | n | Control | Control | 0.35 | 0.52 | 0.35 |
| E4[a] | − | n | | | 0.58 | 0.60 | 0.35 |
| I3[c] | − | y | | | 0.35 | 0.35 | 0.35 |
| Q3[c] | − | y | | | 0.35 | 0.39 | 0.35 |
| Q4[b] | − | y | | | 0.37 | 0.35 | 0.35 |
| R1[b] | − | y | | | 0.35 | 0.35 | 0.35 |
| GMT | | | | | 0.39 ± 0.1 | 0.43 ± 0.1 | 0.35 ± 0.0 |

*Three weeks post-first vaccination
**Two weeks post-second vaccination
***Four weeks post-second vaccination
[a]Vaccinated with CP243-Feline Herpes Recombinant/ALVAC Vector
[b]Vaccinated with VP164-Feline Herpes Recombinant/NYVAC Vector
[c]Control

Example 19

Protection of Dogs Against CDV Challenge by ALVAC-CDVHF (vCP258)

vCP258 is discussed in U.S. Ser. No. 08/416,616, filed Apr. 5, 1995, incorporated herein by reference. The protective efficacy of the:ALVAC-based CDV HA and F recombinant virus was assessed by exposure of dogs to a live CDV challenge following vaccination. In this experiment, 13 CDV seronegative beagles were divided into two vaccinated groups (3 dogs for $10^7$ pfu vCP258 vaccine dose and 4 dogs for $10^{5.5}$ pfu vaccine dose) and a non-vaccinated control group (6 dogs). Vaccination consisted of two subcutaneous inoculations with either $10^7$ TCID$_{50}$/dose (group 1) or $10^{5.5}$ TCID$_{50}$ dose (group 2) of vCP258 three weeks apart. On day 42, all dogs were challenged by a intracranial administration of a 1:10 NVSL CDV challenge stock. Dogs were observed daily for 28 days following challenge to monitor morbidity/mortality.

No local or systemic adverse reactions were noted in dogs vaccinated with vCP258. All non-vaccinated control dogs developed clinical signs of CDV infection including anorexia, conjunctivitis, depression, weight loss, and dehydration from 6 to 17 days post-challenge. Four febrile peaks (>103.5° F.) were observed on days 1, 3, 8, and 13 days post-challenge. Four of the 6 control animals had more severe clinical manifestations. In fact, one of these dogs died 12 days post-challenge while the other three were euthanized between 13 and 17 days post-challenge. The two surviving control animals, which had milder disease symptomology, started to recover and, in fact, began gaining weight 19 days post-challenge.

Significantly, no dogs in either vaccine dose group developed clinical signs of CDV infection. They all gained weight and displayed normal behavior during the observation period. Further, no febrile episodes were observed.

Table 72 lists the CDV-specific serological responses in each group at various times prior to challenge. The antibody titers are expressed as the 50% neutralization endpoint and represent the mean titer for each group. Interestingly, despite the $10^{5.5}$ TCID$_{50}$ vaccine dose not eliciting equivalent levels of CDV serum neutralizing activity, all dogs vaccinated with this lower dose were completely protected against the virulent CDV challenge.

TABLE 72

CDV-SPECIFIC SEROLOGICAL RESPONSES

| Vaccine Group | Day 0 | Day 14 | Day 21 | Day 42 |
|---|---|---|---|---|
| $10^{5.5}$ | <1:3 | 1:16 | 1:21 | 1:50 |
| $10^{7.0}$ | <1:3 | 1:19 | 1:19 | 1:151 |
| Control | <1:3 | ND | ND | <1:3 |

ND = not determined

Example 20

Efficacy in dogs of ALVAC-CDV (vCP258) and ALVAC-Rabies (vCP65) When Used In a Combination Form With Other Canine Pathogens In order to determine whether ALVAC-CDV (vCP258) would provide protective efficacy when used in a vaccine combination with other canine pathogens the following study was performed. ALVAC-CDV (vCP258) was diluted to doses of $10^{4.6}$, $10^{4.8}$ and $10^{5.5}$ TCID$_{50}$ per ml and mixed with vaccine doses of Canine Adenovirus type 2 (CAV$_2$), Canine Corona Virus (CCV), Canine Parainfluenza (CPi), Canine Parvovirus CPV$_{x1}$), Leptospira Canicola-Icterohaemorrhagiae Bacterin (LCI) and ALVAC-Rabies (vCP65). Twenty four seronegative dogs and two seropositive dogs were inoculated as shown in Table 73 with ALVAC-CDV alone or in the canine combination. Dogs received two inoculations at 0 and 21 days by the subcutaneous route. Blood was collected for determination of CDV serum neutralizing titers at days 0, 21 and prior to challenge. Dogs were challenged in two groups at either 24 or 50 days after the second inoculation by the intracranial route with the CDV challenge virus supplied by the USDA. After challenge dogs were observed for up to 5 months to monitor signs of CDV infection. The results of serology and challenge are shown in Table 74.

The results indicate that dogs inoculated with 4.8 log$_{10}$ TCID$_{50}$ of ALVAC-CDV (vCP258) alone induced a CDV-specific mean neutralizing antibody titer of 1.2 while doses of 5.5 log$_{10}$ and 4.8 log$_{10}$ in the canine vaccine combination induced mean titers of 1.0 and 0.7 respectively. All dogs in each of these vaccine groups survived challenge. One dog in the group receiving the combination plus 5.5 log$_{10}$TCID$_{50}$ had non-specific symptoms following challenge while one dog in the group receiving the combination plus 4.8 log$_{10}$ TCID$_{50}$ developed symptoms specific of CDV infection. Virus titrations, CDV antibody titers, rabies antibody titers, morbidity/morality, and weight loss/gain are shown in Tables 75 to 80.

In this study, the serological response to vaccination with the canine coronavirus vaccine, and the ALVAC-rabies vaccine was also monitored. Significantly, inclusion of the ALVAC-CDV in the combination vaccine did not interfere with the serological response to the other component(s), especially canine coronavirus and rabies virus components. And, the rabies virus component, vCP65 did not interfere with other antigens.

TABLE 73

SCHEDULE OF VACCINATION OF DOGS INOCULATED WITH ALVAC-CDV (VCP258) ALONE OR IN COMBINATION WITH OTHER CANINE VACCINES

| Vaccine Group | # Dogs | 44 day Challenge | 70 day Challenge |
|---|---|---|---|
| vCP258/$10^{4.8}$ dose | 6 | 5 | 1 |
| Combination + vCP258/$10^{5.5}$ dose | 5 | 5 | — |
| Combination only | 5 | 3 | 2 |
| Combination + vCP258/$10^{4.8}$ dose | 4 | 1 | 3 |
| Combination + vCP258/$10^{4.6}$ dose | 4 | — | 4 |
| CDV-seropositive dogs | 2 | — | 2 |
| Total | 26 | 14 | 12 |

TABLE 74

RESULTS OF SEROLOGY AND CHALLENGE OF DOGS INOCULATED WITH ALVAC-CDV (VCP258) ALONE OR IN COMBINATION WITH OTHER CANINE VACCINES

| Vaccine Group | # Dogs | CDV Neutralizing Titer (Titer expressed as mean) | | | | Morbidity | Mortality |
|---|---|---|---|---|---|---|---|
| | | Day 0 | Day 21 | Day 44[a] | Day 70[b] | | |
| Combination vCP258 $10^{5.5}$ dose | 5 | ≦0.3 | 1.0 | 1.0 | — | 1/5[c] | 0/5 |
| Combination vCP258 $10^{4.8}$ dose | 4 | ≦0.3 | 0.8 | 0.7 | — | 1/4[d] | 0/4 |
| Combination vCP258 $10^{4.6}$ dose | 4 | ≦0.3 | ≦0.3 | 0.6 | 0.5 | 4/4 | 4/4 |
| vCP258 $10^{4.8}$ dose | 6 | ≦0.3 | 0.9 | 1.2 | 1.3 | 1/6 | 0/6 |
| Combination only | 5 | ≦0.3 | ≦0.3 | ≦0.3 | — | 5/5 | 3/5 |
| CDV-sero positive dogs | 2 | Not done | Not done | Not done | 2.1 | 0/2 | 0/2 |

[a]: Challenge on day 44, 24 days after the second inoculation
[b]: Challenge on day 70, 50 days after the second vaccination
[c]: One dog had non-specific symptoms of anorexia and depression
[d]: One dog displayed specific CDV signs (enter-ic/respiratory/nervous symptoms)

TABLE 75

VIRUS TITRATIONS OF VACCINES (GEOMETRIC MEAN TITER OF FIVE REPLICATE TESTS)

| Component | ACPiP$_{XL}$CP65/LCI (TCID$_{50}$) | "$10^{4.5}$" (TCID$_{50}$) | "$10^{5.0}$" (TCID$_{50}$) | "$10^{5.5}$" (TCID$_{50}$) |
|---|---|---|---|---|
| CP258-CDV | | $10^{4.6}$ | $10^{4.8}$ | $10^{5.5}$ |
| CAV$_2$ | $10^{6.0}$ | | | |
| CCV | $10^{4.6}$ | | | |
| CPi | $10^{5.5}$ | | | |
| CPV$_{XL}$ | $10^{4.6}$ | | | |
| CP65-Rabies | $10^{5.8}$ | | | |

NOTE:
For clarification purposes, the following abbreviations are used:
Antigen
Canine distemper, Live Canary pox Vector (cCP258)
Canine Adenovirus Type 2 (CAV$_2$)
Canine Coronavirus (CCV)
Canine Parainfluenza (CPi)
Canine Parvovirus (CPV$_{XL}$)
Canine Rabies, Live Canarypox Vector (vCP65)
Leptospira Canicola-Icterohaemorrhagiae Bacterin (LCI)

TABLE 76

SERONEUTRALIZING ANTIBODY TITERS (LOG$_{10}$) TO CANINE DITEMPER VIRUS.

| Group | Dog # | Day 0 1st Vaccination | Day 21 2nd Vaccination | Day 44 Challenge | Challenge Results |
|---|---|---|---|---|---|
| Combo + $10^{5.5}$ | 00 | ≦0.3 | 0.9 | 0.8 | P |
| | 31 | ≦0.3 | 0.9 | 0.8 | P |
| | 37 | ≦0.3 | 0.8 | 1.0 | S(U) |
| | 38 | ≦0.3 | 1.2 | 1.1 | P |
| | 39 | ≦0.3 | 1.1 | 1.1 | P |
| GMT | | ≦0.3 | 1.0 | 1.0 | |
| STD | | 0.0 | 0.2 | 0.2 | |
| Combo + $10^{4.8}$ | 40 | ≦0.3 | 0.7 | 0.5 | P |
| | 42 | ≦0.3 | 0.6 | 0.9 | P |
| | 49 | ≦0.3 | 0.8 | 0.5 | Signs |
| | 70 | ≦0.3 | 1.0 | 1.0 | P |
| GMT | | ≦0.3 | 0.8 | 0.7 | |
| STD | | 0.0 | 0.2 | 0.3 | |

| Group | Dog # | Day 0 1st Vaccination | Day 21 2nd Vaccination | Day 44 (Day 24 Post 2nd Vaccination) | Day 70 Challenge | Challenge Results |
|---|---|---|---|---|---|---|
| Combo + $10^{4.6}$ | 29 | ≦0.3 | ≦0.3 | 0.6 | 0.6 | D |
| | 43 | ≦0.3 | ≦0.3 | 0.3 | 0.3 | D |
| | 8 | ≦0.3 | ≦0.3 | 0.6 | 0.6 | D |
| | 57 | ≦0.3 | ≦0.3 | 0.8 | 0.8 | D |
| GMT | | ≦0.3 | ≦0.3 | 0.6 | 0.5 | |
| STD | | 0.0 | 0.0 | 0.2 | 0.3 | |
| $10^{4.8}$ Only | 34 | ≦0.3 | 0.9 | 1.6 | 1.6 | S(U) |
| | 69 | ≦0.3 | 0.6 | 0.9 | 0.8 | P |

TABLE 76-continued

SERONEUTRALIZING ANTIBODY TITERS (LOG$_{10}$) TO CANINE DITEMPER VIRUS.

|  | 71 | ≦0.3 | 0.5 | 0.5 | 1.3 | P |
|---|---|---|---|---|---|---|
|  | 96 | ≦0.3 | 1.7 | 2.4 | 1.9 | P |
|  | 97 | ≦0.3 | 0.9 | 1.5 | 1.5 | P |
|  | 98 | ≦0.3 | 0.5 | 0.6 | 0.8 | P |
| GMT |  | ≦0.3 | 0.9 | 1.2 | 1.3 |  |
| STD |  | 0.0 | 0.5 | 0.7 | 0.4 |  |

| Group | Dog # | Day 0 | Day 21 | Day 44 | Day 70 | Challenge Results |
|---|---|---|---|---|---|---|
| ⊖CDV | 64$^A$ | ≦0.3 | ≦0.3 | ≦0.3 | D | D |
| Controls | 94$^A$ | ≦0.3 | ≦0.3 | ≦0.3 | D | D |
| (Combo | 95$^A$ | ≦0.3 | ≦0.3 | ≦0.3 | D | D |
| Only) | 66$^B$ | ≦0.3 | ≦0.3 | ≦0.3 | ≦0.3 | Signs |
|  | 74$^B$ | ≦0.3 | ≦0.3 | 0.5 | 0.8 | Sings |
| GMT |  | ≦0.3 | ≦0.3 | ≦0.3 | N/A |  |
| STD |  | 0.0 | 0.0 | 0.1 | N/A |  |
| ⊕CDV | 2010 | N/A | N/A | N/A | ≧2.1 | P |
| Controls | 1976 | N/A | N/A | N/A | ≧2.1 | P |
| GMT |  | N/A | N/A | N/A | ≧2.1 |  |
| STD |  | N/A | N/A | N/A | 0.0 |  |

$^A$= Challenged on Day 44 (24 days after second vaccination)
$^B$= Challenged on Day 70 (50 days after second vaccination)
D= Dead
P= Protected (no morbidity/mortality)
S(U)= Unspecific signs (anorexia, depression)
Signs= CDV signs; enteric and/or respiratory and/or nervous

TABLE 77

SERONEUTRALIZING ANTIBODY TITERS (LOG$_{10}$) TO CANINE CORONAVIRUS

| Group | Dog # | Day 0 1$^{st}$ Vaccination | Day 21 2$^{nd}$ Vaccination | Day 44 Challenge |
|---|---|---|---|---|
| Combo + | 00 | ≦0.3 | 0.9 | 2.1 |
| 10$^{5.5}$ | 31 | ≦0.3 | 0.8 | 1.6 |
|  | 37 | ≦0.3 | 0.9 | 1.9 |
|  | 38 | ≦0.3 | 0.6 | 2.1 |
|  | 39 | ≦0.3 | 0.6 | 2.1 |
| GMT |  | ≦0.3 | 0.8 | 2.0 |
| STD |  | 0.0 | 0.2 | 0.2 |
| Combo + | 40 | ≦0.3 | 1.1 | 1.9 |
| 10$^{4.8}$ | 42 | ≦0.3 | 0.6 | 2.1 |
|  | 49 | ≦0.3 | 1.0 | 2.1 |
|  | 70 | ≦0.3 | 1.5 | 1.2 |
| GMT |  | ≦0.3 | 1.0 | 1.9 |
| STD |  | 0.0 | 0.4 | 0.4 |
| Combo + | 29 | ≦0.3 | 1.2 | 1.9 |
| 10$^{4.6}$ | 43 | ≦0.3 | 0.8 | 1.8 |
|  | 8 | ≦0.3 | 0.6 | 2.1 |
|  | 57 | ≦0.3 | 0.6 | 2.1 |
| GMT |  | ≦0.3 | 0.8 | 2.0 |
| STD |  | 0.0 | 0.2 | 0.2 |

| Group | Dog # | Day 0 | Day 21 | Day 70 |
|---|---|---|---|---|
| 10$^{4.8}$ | 35 | ≦0.3 | 0.6 | 0.6 |
| Only | 69 | ≦0.3 | 0.6 | ≦0.3 |
|  | 71 | ≦0.3 | 0.3 | ≦0.3 |
|  | 96 | ≦0.3 | ≦0.3 | ≦0.3 |
|  | 97 | ≦0.3 | ≦0.3 | ≦0.3 |
|  | 98 | ≦0.3 | ≦0.3 | ≦0.3 |
| GMT |  | ≦0.3 | 0.5 | 0.4 |
| STD |  | 0.0 | 0.2 | 0.1 |

| Group | Dog # | Day 0 | Day 21 | Day 44 | Day 70 |
|---|---|---|---|---|---|
| ⊖CDV | 64 | ≦0.3 | 1.4 | 2.0 | 2.0 |
| Controls | 94 | ≦0.3 | 0.4 | 2.1 | 2.1 |
| (Combo | 95 | ≦0.3 | 0.8 | 2.1 | 2.1 |
| Only) | 66 | ≦0.3 | 0.9 | 1.5 | 2.1 |
|  | 74 | ≦0.3 | 1.2 | 1.7 | 2.1 |
| GMT |  | ≦0.3 | 0.9 | 1.8 | 2.1 |
| STD |  | 0.0 | 0.3 | 0.3 | 0.1 |

TABLE 78

RABIES RFFIT ANTIBODY TITERS (LOG$_{10}$).

| Group | Dog # | Day 0 1$^{st}$ Vaccination | Day 21 2$^{nd}$ Vaccination | Day 44 Challenge |
|---|---|---|---|---|
| Combo + | 00 | ≦1.0 | 2.2 | 2.8 |
| 10$^{5.5}$ | 31 | ≦1.0 | 2.1 | 3.1 |
|  | 37 | ≦1.0 | 1.8 | 2.8 |
|  | 38 | ≦1.0 | 1.9 | 3.0 |
|  | 39 | ≦1.0 | 2.0 | 3.0 |
| GMT |  | ≦1.0 | 2.0 | 2.9 |
| STD |  | 0.0 | 0.3 | 0.1 |
| Combo + | 40 | ≦1.0 | 2.3 | 2.6 |
| 10$^{4.8}$ | 42 | ≦1.0 | 2.3 | 2.4 |
|  | 49 | ≦1.0 | 2.1 | 2.7 |
|  | 70 | ≦1.0 | 2.2 | 2.8 |
| GMT |  | ≦1.0 | 2.3 | 2.6 |
| STD |  | 0.0 | 0.1 | 0.2 |
| Combo + | 27 | ≦1.0 | 2.2 | 2.9 |
| 10$^{4.6}$ | 43 | ≦1.0 | 2.5 | 2.8 |
|  | 8 | ≦1.0 | 2.6 | 2.8 |
|  | 57 | ≦1.0 | 1.5 | 2.4 |
| GMT |  | ≦1.0 | 2.2 | 2.7 |
| STD |  | 0.0 | 0.4 | 0.2 |

TABLE 78-continued

RABIES RFFIT ANTIBODY TITERS (LOG$_{10}$).

| Group | Dog # | Day 0 1$^{st}$ Vaccination | Day 21 2$^{nd}$ Vaccination | Day 44 | Day 70 Challenge |
|---|---|---|---|---|---|
| 10$^{4.8}$ | 35 | ≤1.0 | ≤1.0 | ≤1.0 | ≤1.0 |
| Only | 69 | ≤1.0 | ≤1.0 | ≤1.0 | ≤1.0 |
|  | 71 | ≤1.0 | ≤1.0 | ≤1.0 | ≤1.0 |
|  | 96 | ≤1.0 | ≤1.0 | ≤1.0 | ≤1.0 |
|  | 97 | ≤1.0 | ≤1.0 | ≤1.0 | ≤1.0 |
|  | 98 | ≤1.0 | ≤1.0 | ≤1.0 | ≤1.0 |
| GMT |  | ≤1.0 | ≤1.0 | ≤1.0 | ≤1.0 |
| STD |  | 0.0 | 0.0 | 0.0 | 0.0 |
| ⊖CDV | 64$^A$ | ≤1.0 | 1.3 | 1.5 | D |
| Controls | 94$^A$ | ≤1.0 | 3.1 | 2.1 | D |
| (Combo | 95$^A$ | ≤1.0 | 3.2 | 2.4 | D |
| Only) | 66$^B$ | ≤1.0 | ND | 1.9 | 2.3 |
|  | 74$^B$ | ≤1.0 | ND | 2.1 | 2.6 |
| GMT |  | ≤1.0 | 2.2 | 2.0 | 2.5 |
| STD |  | 0.0 | 0.9 | 0.3 | 0.2 |

$^A$= CDV challenge on Day 44 (24 days after second vaccination).
$^B$= CDV challenge on Day 70 (50 days after second vaccination).
ND= Not done
D= Dead

TABLE 79

MORBIDITY/MORTALITY DAY 28 POSTCHALLENGE WITH CANINE DISTEMPER VIRUS.

| Group | # Dogs Challenged | Morbidity | Mortality | # Dogs Survived | CDV GMT Antibody at Challenge |
|---|---|---|---|---|---|
| CP258 10$^{4.8}$ | 6 | 1/6$^I$ | 0/6 | 6/6 | 1.30 |
| Combo + CP258 10$^{5.5}$ | 5 | 1/5$^I$ | 0/5 | 5/5 | 0.98 |
| Combo + CP258 10$^{4.8}$ | 4 | 1/4$^{II}$ | 0/4 | 4/4 | 0.74 |
| Combo + CP258 10$^{4.6}$ | 4 | 4/4$^{II,III}$ | 4/4 | 0/4 | 0.47 |
| ⊕Controls | 2 | 0/2 | 0/2 | 2/2 | >2.7 |
| Controls (Combo only) | 5 | 3/3$^{II,III}$ 2/2$^{II}$ | 3/5 | 2/5* | <0.4 |

$^I$= Anorexia/depression/fever three to four days postchallenge = "unspecific signs"
$^{II}$= Anorexia/weight loss/bloody diarrhea/fever = enteric CDV signs
$^{III}$=Weight loss/fever/spasm/myoclonia/epileptic attacks/paresis/tenesmus = nervous CDV signs
*= Survivors showed enteric signs

TABLE 80

WEIGHT LOSS/GAIN AFTER CHALLENGE B. EXPRESSED IN LBS/BODY WEIGHT.

| Group | Dog No. | Individual Body Weight/Lbs (Days Postchallenge) | | | | Average Gain/Loss at End of Observation |
|---|---|---|---|---|---|---|
|  |  | 0 | 7 | 14 | 21 |  |
| ⊕Control | 2010 | 25 | 26 | 29 | 29 | +6.5 lbs |
|  | 1976* | 24 | 33 | 33 | 33 |  |
| ⊖Control | 66 | 35 | 32 | 30 | 30 | −4.5 lbs |
|  | 74* | 25 | 20 | 20 | 21 |  |
| Combo + CP258 10$^{4.6}$ | 29 | 12 | D | D | D | −2.5 lbs |
|  | 43* | 15 | 12 | D | D |  |
|  | 48 | 22 | 20 | D | D |  |
|  | 57 | 20 | 18 | D | D |  |
| Combo + CP258 | 40 | 22 | 20 | 26 | 26 | +4.5 lbs |
|  | 42 | 17 | 22 | 20 | 22 |  |

TABLE 80-continued

WEIGHT LOSS/GAIN AFTER CHALLENGE B. EXPRESSED IN LBS/BODY WEIGHT.

| Group | Dog No. | Individual Body Weight/Lbs (Days Postchallenge) | | | | Average Gain/Loss at End of Observation |
|---|---|---|---|---|---|---|
|  |  | 0 | 7 | 14 | 21 |  |
| 10$^{4.8}$ | 71 | 20 | 23 | 21 | 20 |  |
|  | 49** | 25 | 23 | 17 | 20 |  |

D= Dogs did not survive challenge.
*= Dogs challenged by oronasal route.
**= From this group, Dog #49 was the only dog to show enteric CDV signs and had a weight loss of 5 lbs.

Example 21

Canine Rabies Combination Vaccine with vCP65 Recombinant: Lack of Interference of vCP65, CDV Rockborn, and CPV$_{XL}$, In Vaccine DACPiPCP65+ LCI This example demonstrates that CPV (P$_{XL}$) and CDV (Rockborn) can be used interchangeably with the CPV and CDV (Onderstepoort) strains respectively without causing any interference to the other components of the combination vaccine: DACPiPCP65+LCI, that addition of CP65 to the canine combo vaccine (DACPiP) does not interfere with the immunogenicity of the other components, and that the combination vaccine (DACPiPCP65) is safe to dogs to obtain a license for the combination vaccine+LCI and its fallout products.

General Procedure: Seven lots of vaccines with varying antigen components were prepared. Thirty eight (38) dogs were divided into different groups based on the vaccine they received and their immune response measured by serology. Canine coronavirus efficacy was measured by vaccination/ challenge. Seroneutralizing (SN) antibody titers were used to demonstrate whether or not interference was caused by addition of different vaccine antigens. All the vaccines were reconstituted with USDA licensed and satisfactorily tested serial (32010) of LCI and injected into dogs.

ABBREVIATIONS

| Component | Abbreviation |
| --- | --- |
| Canine Distemper Virus, Rockborn ($CDV_R$) | $D_R$ |
| Canine Distemper Virus, Onderstepoort ($CDV_O$) | $D_O$ |
| Canine Adenovirus Type 2 ($CAV_2$) | A |
| Canine Coronavirus, MLV ($CCV_L$) | C |
| *Canine parainfluenza* Type 2 (CPi) | Pi |
| Canine Parvovirus, (CPV) | P |
| Canine Parvovirus, ($CPV_{XL}$) | $P_{XL}$ |
| Canarypox Rabies Recombinant (CP65) | CP65 |
| Leptospira Bacterin (*L. canicola, L. icterohaemorrhagiae*) | LCI |

Materials:

Animals. Source, Age: Seventeen (17) dogs of various ages were purchased from Harlan Sprague Dawley (HSD). Five dogs, 12–16 weeks old, purchased from James A. Baker Institute of Animal Health, Cornell University. Sixteen dogs, 8–10 weeks old, purchased from Liberty. They were seronegative for all vaccine components involved in their respective studies.

Vaccines:

All vaccines were prepared with different harvests of antigen issued from the same Master Seed virus.

Four vaccine lots were prepared:

$D_R$APiP (lot A)

$D_R$ACPiP$_{XL}$ (lot B)

$D_O$ACPiPCP65 (lot C)

$D_R$ACPiP$_{XL}$CP65 (lot D)

The above vaccines were formulated with the following components:

| Component | Titer/ml ($Log_{10}$) |
| --- | --- |
| $D_R$ | 5.2 |
| $D_O$ | 5.4 |
| A | 7.4 |
| C | 6.6 |
| Pi | 7.5 |
| P | 7.0 |
| $P_{XL}$ | 5.3 |
| CP65 | 7.9 |

Two additional vaccines were produced:

$D_R$ACPiP$_{XL}$CP65

$D_O$ACPiPCP65

Vaccine $D_R$ACPiP$_{XL}$CP65

| Component | Titer/ml |
| --- | --- |
| $D_R$ | 5.2 |
| A | 7.4 |
| C | 6.6 |
| Pi | 6.9 |
| $P_{XL}$ | 5.3 |
| CP65 | 8.0 |

Vaccine: $D_O$ACPiPCP65

| Component | Titer/ml |
| --- | --- |
| $D_O$ | 5.4 |
| A | 7.4 |
| C | 3.1 |
| Pi | 6.9 |
| P | 7.0 |
| CP65 | 8.0 |

A vaccine which did not include the CDV fraction was also prepared:

Vaccine: ACPiP$_{XL}$CP65

| Component | Titer/ml |
| --- | --- |
| A | 7.4 |
| C | 6.2 |
| Pi | 6.8 |
| $P_{XL}$ | 5.4 |
| CP65 | 8.0 |

Titration: Each fraction of the different vaccine lots was titrated on the day of either first vaccination or both days of vaccination. Titration was performed on three to five replicates.

Methods: Vaccination: All the vaccines (1 dose=1 ml) were administered twice by the subcutaneous route at 21-day intervals. A released serial (No. 32010) of LCI was used as diluent for each vaccine.

Bleeding: Dogs were bled at 0, 21, and 35–42 days postvaccination.

Evaluation of Results: Seroneutralization Titers: Serum samples derived from each dog and each bleed date were tested for presence of virus neutralizing antibody titers. Seroconversion interpreted by antibody titer was used as a parameter to measure interference. Different groups of dogs were used per component of vaccine studied because some groups were already exposed to certain viruses and had high antibody titers even before vaccination: for example, the HSD dogs that received the first four (A–D) vaccine lots were confirmed to have experienced a canine Parvovirus break in their colony before purchase.

Vaccination/Challenge (CCV): Twelve (12) dogs vaccinated with CP65 combination containing $CCV_L$ vaccine and six (6) control dogs vaccinated with a combination vaccine without CP65 and $CCV_L$ were challenged with virulent CCV at Day 35 postvaccination and necropsied at Day 41. The results of virus reisolation in the feces were used to demonstrate noninterference of vCP65 on protection conferred by CCV vaccine.

Safety Evaluation: After each administration of the vaccine, each dog was palpated at the site of inoculation and observed for at least two hours postvaccination for any adverse clinical local or systemic reaction. Observation was continued throughout the study period.

Results: The antibody titers (SN) induced by CP65 prepared in combination with CDV (Rockborn or Onderstepoort) and CPV (Old MSV or $P_{XL}$) MSV are equivalent. CP65 added to the other components (D, A, C, Pi, P) did not interfere with the immune response of any of them. The CCV (MLV) in the combination vaccine protected dogs from challenge in the presence of all other components, including CP65, irrespective of the MSVs of CDV or CPV used. No clinical sign, systemic or local, was observed in the dogs throughout the experiment.

Titer of Antigen Components in Vaccines: The titer of each antigen in each lot of vaccine tested at first vaccination and/or second vaccination is in Tables 81a, b and c below:

TABLE 81a

Titer ($Log_{10}$) of Virus Components: Titrations Performed at Days of Vaccination ($V_1$ and $V_2$*).

Titer/ml ($Log_{10}$)

| Lot | Vaccine | $D_O$ | $D_R$ | A | C | Pi | P | $P_{XL}$ | CP65 |
|---|---|---|---|---|---|---|---|---|---|
| A | $D_R$APiP | — | 3.3–3.6* | 5 | — | 5.8 | 6.0 | — | — |
| B | $D_R$ACPiP$_{XL}$ | — | 3.5–3.6* | 5.1 | 4.5 | 5.6 | — | 5.0 | — |
| C | $D_O$ACPiPCP65 | 4.6–4.1* | — | 5.1 | 4.5 | 5.5 | 6.0 | — | 6.0 |
| D | $D_R$ACPiP$_{XL}$CP65 | — | 3.3–3.6* | 5.3 | 4.4 | 5.4 | — | 3.8 | 5.8 |

TABLE 81b

Titer ($Log_{10}$) of Virus Components Tested at Day of Vaccination.

Titer/ml ($Log_{10}$)

| Vaccines | $D_O$ | $D_R$ | A | C | Pi | P | $P_{XL}$ | CP65 |
|---|---|---|---|---|---|---|---|---|
| $D_R$ACPiP$_{XL}$CP65 | — | 4.5 | 5.9 | 3.1 | 3.7 | — | 4.7 | 6.4 |
| $D_O$ACPiPCP65 | 4.5 | — | 5.2 | 3.1 | 4.3 | 7.0 | — | 6.4 |

TABLE 81c

Titer of Virus Components.

Titer/ml ($Log_{10}$)

| Vaccine | $D_O$ | $D_R$ | A | C | Pi | P | $P_{XL}$ | CP65 |
|---|---|---|---|---|---|---|---|---|
| ACPiP$_{XL}$CP65 | — | — | 6.0 | 4.6 | 5.5 | — | 4.6 | 6.1 |

Results show that:

CP65 titers are mostly between MPD (5.6) and expected titer at dating (6.3)

$D_R$ titers are always above release titer, 3.2 ($log_{10}$/ml).

$P_{XL}$ titers are always above expected release titer, 3.3 ($log_{10}$ ml)

Recombination Rabies (CP65) Seroneutralizing Antibody Titers (RFFIT): Two of the vaccines in which the only differences were a change of CDV and CPV strains gave the following rabies neutralizing antibody titers (Table 82):

TABLE 82

Rabies Virus Neutralizing Antibody Titer ($log_{10}$):

| Vaccine | Dog # | Titers/ml ($log_{10}$) (Days postvaccination) (D 0) $V_1$ | (D 21) $V_2$ | (D 42) |
|---|---|---|---|---|
| $D_R$ACPi$P_{XL}$CP65/LCI | 4804 | 1.1 | 1.3 | 1.4 |
| | 4502 | 0.6 | 0.7 | 1.6 |
| | 4503 | 1.2 | 1.1 | 2.1 |
| | 4507 | 1.1 | 1.2 | 2.7 |
| | 4801 | 1.0 | 1.3 | 2.4 |
| | 4501 | 1.0 | 1.2 | 2.2 |
| GMT | | 1.0 | 1.1 | 2.1 |
| SD | | ±0.2 | ±0.2 | ±0.5 |
| $D_O$ACPiPCP65/LCI | 4401 | 0.7 | 1.0 | 2.4 |
| | 4803 | 1.2 | 1.2 | 2.0 |
| | 4806 | 1.1 | 1.1 | 2.0 |

TABLE 82-continued

Rabies Virus Neutralizing Antibody Titer ($log_{10}$):

| Vaccine | Dog # | Titers/ml ($log_{10}$) (Days postvaccination) (D 0) $V_1$ | (D 21) $V_2$ | (D 42) |
|---|---|---|---|---|
| | 4901 | 1.2 | ND | 3.4 |
| | 4902 | 1.0 | 1.3 | 3.1 |
| | 4404 | 0.6 | 1.1 | 2.0 |
| GMT | | 0.9 | 1.1 | 2.5 |
| SD | | ±0.3 | ±0.2 | ±0.6 |

The rabies SN antibodies demonstrate good seroconversion titer comparable to those obtained in the above Example.

Statistical analysis (t test) showed that the rabies neutralizing antibody titers in the above vaccines (Table 82) are not significantly different: both changes in Distemper Master Seed and Parvovirus Master Seed have no in vivo interference on the efficacy of vCP65 in dogs.

Respective influence of CDV and CPV on Rabies (CP65) SN Titers: Influence of CDV (Rockborn Strain) on Rabies (CP65) SN Titers.

TABLE 83

Individual rabies antibody titers (RFFIT) in two vaccines produced with and without $CDV_R$ are displayed in Table 83 (below):

| Vaccine | Dog # | Titers/ml ($log_{10}$) (Days postvaccination) (D 0) $V_1$ | (D 21) $V_2$ * | (D 42) |
|---|---|---|---|---|
| ACPi$P_{XL}$CP65 | 64 | ≦1.0 | ND | 1.5 |
| | 94 | ≦1.0 | ND | 2.1 |
| | 95 | ≦1.0 | ND | 2.4 |
| | 66 | ≦1.0 | ND | 1.9 |
| | 74 | ≦1.0 | ND | 2.1 |
| GMT | | ≦1.0 | ND | 2.0 |
| SD | | ±0.0 | ND | ±0.3 |
| $D_R$ACPi$P_{XL}$CP65 | 4804 | 1.1 | ND | 1.4 |
| | 4502 | 0.6 | ND | 1.6 |
| | 4503 | 1.2 | ND | 2.1 |
| | 4507 | 1.1 | ND | 2.7 |
| | 4801 | 1.0 | ND | 2.4 |
| | 4501 | 1.0 | ND | 2.2 |
| GMT | | 1.0 | ND | 2.1 |
| SD | | ±0.2 | ND | ±0.5 |

NS = not done

* = Antibody titration not performed at $V_2$ because available serum was exhausted.

When CDV (Rockborn) is added to a canine Combo Vaccine (ACPi$P_{XL}$CP65) no interference is caused to the rabies seroneutralizing antibody titer induced by vCP65.

Influence of CPV ($P_{XL}$) on Rabies (CP65) SN Titers: Recombinant rabies CP65 in combination vaccine ($D_O$ACPiPCP65) has been shown to be efficacious against rabies challenge (as shown by the Examples above). Table 82 shows that changing the Distemper MSV from Onderstepoort to Rockborn does not affect the rabies SN antibody titer elicited by vCP65. It needs to be stressed that CP65 dose was very low (under titer at dating, and close to MPD). The obvious lack of interference of CPV ($P_{XL}$) on recombinant rabies (vCP65) vaccine is presented in Table 84 and confirms results displayed in Table 82.

TABLE 84

INDIVIDUAL RABIES ANTIBODY TITERS.

| Vaccine | Dog # | Titer/ml ($Log_{10}$) (Dams Postvaccination) | | |
|---|---|---|---|---|
| | | (D 0) $V_1$ | (D 21) $V_2$ | (D 35) |
| $C_0$ACPiPCP65 | H4B810 | 0.5 | 1.0 | 2.9 |
| Lot C | H3B808 | 1.1 | 1.1 | 2.1 |
| | H3L807 | 0.6 | 0.6 | 1.1 |
| | H4B822 | 1.0 | 1.3 | 2.9 |
| | (8513)* | (2.4) | (2.6) | (2.7) |
| GMT | | 0.8 | 1.0 | 2.25 |
| SD | | ±0.3 | ±0.3 | ±0.9 |
| $D_R$ACPiP$_{XL}$CP65 | H4B815 | 1.0 | 1.2 | 1.7 |
| Lot D | H3L811 | 0.5 | 1.1 | 1.5 |
| | H4B820 | 1.1 | 1.2 | 2.3 |
| | 8616032 | 1.2 | 1.2 | 1.3 |
| GMT | | 1.0 | 1.2 | 1.7 |
| SD | | ±0.3 | ±0.1 | ±0.4 |

*Dog #8513 excluded from study due to high antibody titer at Day 0.

The change from the CPV to a new CPV masterseed ($P_{XL}$) did not result in any significant difference in the rabies SN antibody titer. Good seroconversion was observed in all the dogs even though CP65 dose was close to the Minimum Protective Dose in the group vaccinated with lot D receiving $D_R$ and $P_{XL}$.

Influence of adding Recombinant Rabies (vCP65) on the other fraction of canine Vaccine.

Influence of CP65 on CDV (Rockborn strain) SN Titer.

TABLE 85

Distemper SN Titers ($Log_{10}$/ml):

| Vaccine | Dog # | CDV Titer/ml ($Log_{10}$) (Days Postvaccination) | | |
|---|---|---|---|---|
| | | (D 0) $V_1$ | (D 21) $V_2$ | (D 35) |
| $D_R$APiP/LCI (Lot A) | H3B801 | <.3 | 2.3 | 2.7 |
| | H3K837 | <.3 | >2.9 | >2.9 |
| | H4B803 | 0.5 | >2.9 | >2.9 |
| | 8435 | 0.9 | >2.9 | >2.9 |
| $D_R$ACPiP$_{XL}$/LCI (Lot B) | H3B806 | <0.3 | >2.9 | >2.9 |
| | H4B813 | <0.3 | >2.9 | 2.7 |
| | H4B818 | <0.3 | 2.7 | 2.6 |
| | 1G1A | 0.5 | >2.9 | >2.9 |
| GMT (without CP65) | | 0.4 | 2.8 | 2.8 |
| SD | | ±0.2 | ±0.2 | ±0.1 |
| $D_R$ACPiP$_{XL}$CP65/LCI (Lot D) | H4B815 | 0.5 | ≥2.9 | >2.9 |
| | H3L811 | 0.3 | >2.9 | >2.9 |
| | H4B820 | <0.3 | >2.9 | >2.9 |
| | 8616032 | 0.9 | 2.7 | 2.9 |
| $D_R$ACPiP$_{XL}$CP65/LCI | 4804 | <0.3 | >2.1 | 3.0 |
| | 4502 | <0.3 | >2.1 | 2.6 |
| | 4503 | <0.3 | >2.1 | 2.4 |
| | 4507 | <0.3 | >2.1 | 2.7 |
| | 4801 | <0.3 | >2.1 | 2.7 |
| | 4501 | <0.3 | >2.1 | 2.7 |
| $D_R$APiP$_{XL}$CP65/LCI | 4302 | <0.3 | >2.1 | 2.8 |
| | 4601 | <0.3 | >2.1 | 2.6 |
| | 5003 | <0.3 | <2.1 | 2.9 |
| | 3901 | 0.5 | >2.1 | 2.9 |
| | 3905 | 1.1 | >2.1 | 2.7 |
| | 4103 | 1.2 | >2.1 | 3.0 |
| GMT (with CP65) | | 0.5 | 2.3 | 2.8 |
| SD | | ±0.3 | ±0.3 | ±0.2 |

Recombinant rabies (vCP65) vaccine when incorporated in different canine combo vaccines, does not interfere with the production of neutralizing antibodies against CDV. Even at low titers, combined $D_R$ induces excellent seroconversions in all animals.

Influence of adding rabies recombinant (CP65) on the SN Titer of CPV ($P_{XL}$).

TABLE 86

Individual CPV ($P_{XL}$) titers ($log_{10}$/ml).

| Vaccine | Dog # | CPV ($P_{XL}$) Titer/ml ($log_{10}$) (Days Postvaccination) | | |
|---|---|---|---|---|
| | | ($D_0$) V1 | ($D_{21}$) V2 | ($D_{35}$) |
| $D_R$APiP/LCI | 4302 | 1.5 | 2.4 | 3.3 |
| | 4601 | 1.5 | 4.2 | 4.5 |
| | 5003 | ND | 3.6 | 4.5 |
| GMT (without CP65) | | 1.5 | 3.4 | 4.1 |
| SD | | ±0.0 | ±0.9 | ±0.7 |
| $D_R$ACPiP$_{XL}$CP65/LCI | 4502 | 1.5 | 2.7 | 3.6 |
| | 4503 | 1.8 | 2.4 | 4.5 |
| | 4804 | 1.8 | 2.4 | 3.9 |
| | 4501 | 1.8 | 4.5 | 4.5 |
| | 4507 | 1.5 | 3.0 | 4.2 |
| | 4801 | 1.8 | 2.4 | 3.6 |
| ACPiP$_{XL}$CP65/LCI | 64 | 1.8 | 3.6 | 4.2 |
| | 66 | 1.5 | 4.2 | 4.2 |
| | 74 | 1.8 | 3.6 | 3.6 |
| | 94 | 1.5 | 3.9 | 4.5 |
| | 95 | 1.5 | 3.9 | 4.2 |
| GMT (with CP65) | | 1.7 | 3.3 | 4.1 |
| SD | | ±0.2 | ±0.8 | ±0.4 |

V1 = Day of first vaccination
V2 = Day of second vaccination

Recombinant rabies (vCP65) when added to canine combo vaccine containing DACPiP (P or $P_{XL}$) has no interference on seroneutralizing (SN) antibody production against CPV in naive animals.

Influence of adding rabies recombinant (CP65) on the SN Titer of CAV-2.

TABLE 87

Individual CAV-2 antibody titers ($log_{10}$/ml)

| Vaccine | Dog # | CAV-2 Titer/ml ($Log_{10}$) (Days Postvaccination) | | |
|---|---|---|---|---|
| | | (D 0) $V_1$ | (D 21) $V_2$ | (D 35) |
| $D_R$APiP/LCI (Lot A) | H3B801 | 0.6 | 1.8 | 2.3 |
| | H3K837 | <0.6 | 2.7 | 2.7 |
| | H4B803 | <0.6 | >2.9 | 2.9 |
| | 8435* | (2.1) | (2.4) | (2.4) |
| $D_R$ACPiP$_{XL}$/LCI (Lot B) | H3B806 | <0.6 | 2.3 | 2.4 |
| | H4B813 | <0.6 | 2.7 | >2.9 |
| | H4B818 | <0.6 | 2.1 | 2.6 |
| | 1G1A | <0.6 | 0.8 | 1.0 |
| GMT (without CP65) | | 0.6 | 2.2 | 2.4 |
| SD | | ±0.5 | ±0.7 | ±0.7 |
| $D_R$ACPiP$_{XL}$CP65/LCI (Lot D) | H4B815 | <0.6 | 1.7 | >2.9 |
| | H3L811 | <0.6 | 2.0 | >2.9 |
| | H4B820 | ≤0.6 | 1.7 | ≥2.9 |
| | 8616032 | 0.6 | <0.6 | 0.9 |
| GMT (with CP65) | | 0.6 | 1.5 | 2.4 |
| SD | | ±0.0 | ±0.6 | ±1.0 |

*Dog 8435 was excluded from calculation due to pre-existing high CAV-2 SN titer prior to vaccination.

Addition of CP65 (recombinant rabies vaccine) to canine combination vaccines that contain CAV-2 does not interfere with the immune response to CAV-2 measured by serologic methods.

Influence of adding Rabies Recombinant (CP65) on the SN Titer of CPi.

TABLE 88

Individual CPi Antibody titers (log$_{10}$/ml):

| Vaccine | Dog # | (D 0) V$_1$ | (D 21) V$_2$ | (D 35) |
|---|---|---|---|---|
| D$_R$APiP/LCI | H3B801 | <0.3 | <0.3 | 1.2 |
| (Log A) | H3K837 | <0.3 | <0.3 | 1.7 |
|  | H4B803 | <0.3 | 1.2 | 2.4 |
|  | 8435 | 0.8 | 1.4 | 1.9 |
| D$_R$ACPiP$_{XL}$/LCI | H3B806 | <0.3 | <0.3 | 0.9 |
| (Lot B) | H4B813 | <0.3 | <0.3 | 2.0 |
|  | H4B818 | <0.3 | <0.3 | 1.2 |
|  | 1G1A | <0.3 | <0.5 | <0.3 |
| GMT (without CP65) |  | 0.4 | 0.6 | 1.5 |
| SD |  | ±0.2 | ±0.5 | ±0.7 |
| D$_R$ACPiP$_{XL}$CP65/LCI | H4B815 | <0.3 | ≧2.9 | ≧2.9 |
| (Lot D) | H3L811 | <0.3 | ≧2.9 | ≧2.9 |
|  | H4B820 | <0.3 | ≧2.9 | ≧2.9 |
|  | 8616032 | <0.5 | 2.7 | 2.9 |
| D$_O$ACPiPCP65/LCI | H4B810 | <0.3 | 1.0 | 2.0 |
| (Lot C) | H3B808 | <0.3 | <0.3 | 1.2 |
|  | H3L807 | <0.3 | <0.3 | 1.0 |
|  | H4B822 | <0.3 | <0.3 | 2.3 |
|  | 8513* | (1.5) | (2.4) | (2.1) |
| GMT (with CP65) |  | 0.3 | 1.7 | 2.3 |
| SD |  | ±0.1 | ±1.3 | ±0.8 |

*8513 was excluded from SN calculation due to high titer at Day 0.

Addition of vCP65 to the existing vaccine with D$_R$P$_{XL}$ causes no interference on CPI seroneutralizing antibody titers.

Influence of Adding Rabies Recombinant (CP65) on CCV immunogenicity (By Serology):

TABLE 89

Individual CCV antibody titers in log$_{10}$/ml:

| Vaccine | Dog # | (D 0) V$_1$ | (D 21) V$_2$ | (D 35) |
|---|---|---|---|---|
| D$_R$ACPiP$_{XL}$/LCI | H3B806 | <0.03 | 1.7 | >2.1 |
| (Lot B) | H4B813 | 0.5 | >2.1 | >2.1 |
|  | H4B818 | <0.3 | >2.1 | >2.1 |
|  | 1G1A | <0.3 | 0.5 | 2.0 |
| GMT (without CP65) |  | 0.4 | 1.6 | 2.1 |
| SD |  | ±0.1 | ±0.8 | ±0.05 |
| D$_R$ACPiP$_{XL}$ | H4B815 | <0.3 | >2.1 | >2.1 |
| CP65 | H3L811 | <0.3 | 1.6 | >2.1 |
| Lot D | H4B820 | <0.3 | <2.1 | >2.1 |
|  | 8616032 | <0.3 | 1.1 | >2.1 |
| GMT (with CP65) |  | <0.3 | 1.7 | 2.1 |
| SD |  | ±0.0 | ±0.5 | ±0.0 |

Table 89 demonstrates that the recombinant rabies vaccine (CP65) when added to the components (DACPiP) of the licensed DrACPiP does not interfere with the immunogenicity as measured by SN titers.

BY Challenge: The non-interference of CDV (D$_R$) and CPV$_{XL}$ on CCV efficacy in the D$_R$ACPiP$_{XL}$ vaccine had been demonstrated by vaccination/challenge in the Examples above.

Three groups of dogs were vaccinated with vaccines containing vCP65 or not containing CP65 as shown in Table 89 and discussed above. All the dogs were challenged with CCV following the procedure described in Examples above. Efficacy of the vaccines was evaluated by virus reisolation in the feces of the dogs six days after challenge.

TABLE 90

Protection After Challenge

| Vaccine | Dog # | CCV Isolation (+) | % protection after challenge |
|---|---|---|---|
| D$_R$APiP | 3901 | + | 0% |
| (Control) | 3905 | + | (no CCV, no |
|  | 4103 | + | CP65) |
|  | 4302 | + |  |
|  | 4601 | + |  |
|  | 5003 | + |  |
| D$_R$ACPiP$_{XL}$CP65 | 4501 | − | 75% |
|  | 4502 | + | (CCV + CP65) |
|  | 4503 | − |  |
|  | 4507 | + |  |
|  | 4801 | − |  |
|  | 4804 | − |  |
| D$_O$ACPiPCP65 | 4401 | − |  |
|  | 4404 | + |  |
|  | 4803 | − |  |
|  | 4806 | − |  |
|  | 4901 | − |  |
|  | 4902 | − |  |

Table 90 confirms that CP65 does not interfere in the vaccination by CCV as judged by protection after challenge. All canine coronavirus vaccines containing CP65 protect very efficiently dogs against a very severe challenge which affected all control dogs.

All the vaccines in this Example were found to be safe to dogs following close observation after vaccination. No local or systemic clinical reaction was observed throughout the test period.

These experiments demonstrated by serologic methods that the addition of rabies recombinant fraction, vCP65, does not cause any interference with any of the other components including D$_R$ and P$_{XL}$.

Comparison of the two lyophilized complete combination vaccines D$_O$ACPiPCP65/LCI and D$_R$ACPiP$_{XL}$CP65/LCI, where D$_O$ is changed to D$_R$ has shown that there is no interference in the rabies antibody response. The rabies antibody level with D$_R$ACPiP$_{XL}$CP65 is even greater or equal to the level of those dogs vaccinated with D$_O$ACPiPCP65 and that survived challenge.

To further demonstrate that D$_R$ does not interfere with the immune response of vCP65, SN antibodies comparison of two vaccines with and without D$_R$ was made. The results in either case were equivalent indicating that D$_R$ strain can be added to the rest of the ACPiP$_{XL}$CP65 fraction.

When Canine Parvovirus (P$_{XL}$) was added to a complete combination vaccine (D$_R$ACPiP$_{XL}$CP65) and compared to another combination vaccine (D$_O$ACPiPCP65), no interference vis-a-vis CP65 serology was observed.

Humoral immune response of canine parvovirus in the combination vaccines (DACPiPCP65) where P and P$_{XL}$ were used interchangeably is equivalent in either case. Moreover, results confirmed that changing from one MSV of canine parvovirus to another one does not interfere with the immunologic responses of dogs to the other fractions.

Evaluation of the non-interference of D$_R$, P$_{XL}$ and CP65 on the protection conferred by CCV MLV vaccine was performed by vaccination/challenge. The fecal reisolation of CCV shows that the CDV (Rockborn) and CPV (P$_{XL}$) MSV can be used in the combination vaccine D$_R$ACPiP$_{XL}$ CP65. Both canine corona vaccines containing CP65 protect very efficiently dogs against coronavirus challenge which affected 100% of unvaccinated control dogs (Table 89).

The recombinant rabies (vCP65) canarypox vector vaccine combined with D, A, C, Pi, P virus antigens is safe and efficacious in dogs irrespective of the MSV of Canine Parvovirus or Canine Distempervirus used.

As evaluated by serologic methods, addition of the recombinant rabies vCP65 to DACPIP does not cause any interference on any the other canine virus fractions.

As evaluated by challenge, presence of the recombinant rabies (vCP65), $D_R$, $P_{XL}$. in the combination vaccine does not cause any interference on the efficacy of the CCV component.

The canine rabies combination rehydrated induces excellent protective immune responses with respect to all components.

Example 22

Canarypox/Rabies (CP65): Preliminary Safety and Immunogenicity Study in Combination With Other Vaccine Antigens In Cats This Example demonstrates the safety and immunogenicity of rabies combination vaccines and to show that conventional antigens do not interfere with the immunogenicity of vCP65; and to show safety in cats.

General Procedure: Twenty-five cats (five cats per group) were vaccinated with experimental lots of vaccine containing $10^{4.8}$–$10^{5.3}$ TCID$_{50}$/dose of vCP65 in combination with conventional antigens (FVR-C-P-FPn+FeLV). Cats received one or two doses of vaccine, subcutaneously, and were bled Day 0, Day 18, Day 32 post-primary vaccination.

Materials: Animals: Twenty five cats, concurrently on test, were used. Cats were approximately 14–16 weeks of age at the time of primary vaccination. They had recently recovered from a feline Herpes virus infection originating from the supplier prior to receipt.

Vaccine: Experimental feline five-way vaccines (Lots B and C; see Table 92) containing feline rhinotracheitis (FVR); feline calicivirus (C); feline panleukopenia virus (P); Chlamydia psittici (FPn) and recombinant canarypox rabies virus (CP65), were prepared.

The lyophilized vaccines were rehydrated prior to injection using a conventional Feline Leukemia Vaccine (Product Code 1555.20; Ser. No. 65026) or sterile water. This serial of FeLV vaccine had relative potency test results of 2.6, 2.8, 2.6.

The cats were vaccinated as shown in Table 92.

TABLE 92

| GROUP | VACCINE | LOT # | # of Doses | Number of Cats |
|---|---|---|---|---|
| 1 | FVR-C-P-FPn + CP65/FeLV | B | 1 | 5 |
| 2 | FVR-C-P-FPn + CP65/FeLV | B | 2 | 5 |
| 3 | FVR-C-P-FPn + CP65/Water | B | 1 | 4* |
| 4 | FVR-C-P-FPn + CP65/Water | B | 2 | 5 |
| 5 | FVR-C-P-FPn + CP65/FeLV | C | 2 | 5 |

The cats were vaccinated, subcutaneously in the scapular area, once or twice eighteen days apart. A shortened interval between injections was necessary to allow adequate time to analyze the rabies antibody titers. The cats were bled prior to vaccination and at 18 and 32 days post-primary vaccination. Sera was analyzed for rabies antibody evaluation by the rapid fluorescent focus inhibition test (RFFIT). The cats were observed for approximately 15 minutes post-injection for adverse reactions to the vaccine (i.e., pain or scratching). The site of vaccination was also palpated 18 and 32 days post-injection. The modified live viruses FVR-C-P-FPn were titered. The recombinant vCP65 virus was titered. During primary vaccination, cat FXI received two injections of $10^{4.8}$ TCID$_{50}$/dose; thus reducing the number of cats in Group 3 to four animals.

Results: Are shown generally in Table 93.

TABLE 93

| GROUP | # OF DOSES | TITER OF CP65 (TCID$_{50}$/dose) | (Day 32) RABIES ANTIBODY TITER* |
|---|---|---|---|
| FVRCP FPn + CP65/FeLV | 1 | $10^{4.8}$ | 0.84 ± 0.51 |
| FVRCP FPn + CP65/FeLV | 2 | $10^{4.8}$ | 0.77 ± 0.43 |
| FVRCP FPn + CP65/H$_2$O | 1 | $10^{4.8}$ | 0.80 ± 0.49 |
| FVRCP FPn + CP65/H$_2$O | 2 | $10^{4.8}$ | 1.56 ± 0.43 |
| FVRCP FPn + CP65/FeLV | 2 | $10^{5.3}$ | 2.12 ± 1.03 |

*GMT = Geometric mean titer per group (log$_{10}$) two weeks post booster.

Vaccines were titered to contain the following amounts of viruses (Table 94). Titration values of vCP65 are reported as geometric mean titers of three replicates.

TABLE 94

| Antigen | Product Minimum Release per dose | Experimental Vaccine Titer per dose |
|---|---|---|
| FVR | $10^{5.4}$ TCID$_{50}$ | $10^{5.5}$ TCID$_{50}$ |
| FCV | $10^{5.2}$ TCID$_{50}$ | $10^{5.6}$ TCID$_{50}$ |
| FPL | $10^{4.0}$ TCID$_{50}$ | $10^{5.5}$ TCID$_{50}$ |
| FPn | $10^{3.0}$ ELD$_{50}$ | $10^{4.4}$ ELD$_{50}$ |
| CP65 | probably between $10^{4.5}$ and $10^{5.3}$ TCID$_{50}$ | Lot B = $10^{4.8}$ TCID$_{50}$ Lot C = $10^{5.3}$ TCID$_{50}$ |

Individual and group antibody titers are summarized in Table 95. The geometric mean titer (GMT) was calculated for each group for each date. Cat HB1's rabies antibody titer on Day 0 was erroneously reported to be 1.58.

No adverse reactions to the vaccines were observed. Sites of inoculation were palpated on Day 18 and Day 32. No lumps or abnormalities were observed. The majority of vaccinated cats appeared healthy for the duration of the trial. However, chronic respiratory signs due to the Herpes infection were evident in a few cats.

Rabies antibody titers $\geq 1.0$ log$_{10}$ indicated a response to the vaccines. Cats in Groups 1, 2, and 3 had a few cats (2–3 per group) that weakly responded post-vaccination. These cats received one or two doses of vaccine ($10^{4.8}$ TCID$_{50}$/dose) rehydrated with the conventional FeLV vaccine; or one dose rehydrated with water.

Group 4 had two cats (FZ1 & HH3) that weakly responded to vaccination using two doses of vaccine ($10^{4.8}$ TCID$_{50}$/dose) rehydrated with water. The remaining cats in this group (FU2, GR3 and HG1) responded well with individual rabies antibody titers $\geq 1.8$ post-second vaccination.

Group 5 received two doses of vaccine ($10^{5.3}$ TCID$_{50}$/dose) rehydrated with FeLV. This group had the best overall response to vaccination (GMT=2.2±1.03). However, one cat GQ3 did not respond to vaccination.

This Example demonstrates the immunogenicity and safety of poxvirus rabies recombinant combination vaccines in cats. It also shows the serological response of canarypox vector naive cats to one or two doses of vCP65.

This Example also demonstrated that there is no actual interference between vCP65 and conventional vaccine components. In comparing Groups 2 and 4, it appears that at low doses of vCP65 (i.e., $10^{4.8}$ TCID$_{50}$/dose) the FeLV vaccine used in this experiment (Product Code 1555.20) appeared to mildly suppress rabies antibody titers at two weeks post-secondary vaccination. Since no additional samples were collected beyond Day 32, the rabies antibody response in these cats may have been merely delayed. However, vaccines containing vCP65 at $10^{5.3}$ TCID$_{50}$/dose, rehydrated with conventional FeLV vaccine, were immunogenic in cats; thus, demonstrating lack of interference.

This Example indicates that vCP65 ($10^{5.3}$ TCID$_{50}$/dose), in combination with conventional antigens, is safe and will induce good rabies antibody titers after two doses in cats (i.e., Group 5 GMT=2.12±1.03). Thus, one can conclude that:

Poxvirus-rabies recombinants (vCP65), in combination with conventional antigens are safe in cats;

Conventional antigens do not interfere with the immunogenicity of poxvirus-rabies recombinants (e.g., vCP65), especially at $10^{5.3}$ TCID$_{50}$/dose;

And, two doses of poxvirus-rabies recombinant (e.g. vCP65) ($10^{5.3}$ TCID$_{50}$/dose), combined with conventional antigens and rehydrated with FeLV vaccine, resulted in the highest rabies antibody response.

TABLE 95

Individual and Group Rabies Antibody Titers of Cats Vaccinated with Experimental Rabies Combination Vaccines (log$_{10}$).

| Cat ID# | Vaccine Group | Day 0 (VAX 1) | Day 18 (VAX 2) | Day 32 (2 weeks post-VAX 2) |
|---|---|---|---|---|
| GQ4 | GROUP 1 | .40 | 1.23 | 1.04 |
| GR2 | Lot B | .30 | .6 | 1.40 |
| HI4 | $10^{4.8}$ + FeLV | .60 | 1.31 | .30 |
| HI5 | One Dose | .30 | .48 | .30 |
| ED3 | | .30 | 1.15 | 1.17 |
| GMT | | 0.38 ± 0.13 | 0.95 ± 0.38 | 0.84 ±0.51 |
| GZ4 | GROUP 2 | .48 | .70 | .30 |
| FY5 | LOT B | .48 | .48 | .60 |
| GH1 | $10^{4.8}$ + FeLV | .30 | 1.04 | .48 |
| HJ1 | Two Doses | .30 | .93 | 1.15 |
| FX1* | | .54 | 1.06 | 1.30 |
| GMT | | 0.42 ± 0.11 | 0.84 ± 0.25 | 0.77 ± 0.43 |
| FZ3 | GROUP 3 | .30 | 1.04 | .48 |
| HB1 | LOT B | to be repeated | 1.15 | 1.36 |
| HH2 | $10^{4.8}$ + Water | .60 | .30 | 1.04 |
| HI3 | One Dose | .30 | .30 | .30 |
| GMT | | | .70 ± 0.46 | .80 ± 0.49 |
| FU2 | GROUP 4 | .30 | 1.38 | 1.83 |
| FZ1 | LOT B | .48 | .95 | 1.0 |
| GR3 | $10^{4.8}$ + Water | .48 | .60 | 1.94 |
| HG1 | Two Doses | .70 | 1.15 | 1.84 |
| HH3 | | .74 | 1.20 | 1.18 |
| GMT | | 0.54 ± 0.18 | 1.04 ± 0.27 | 1.56 ± 0.43 |
| GJ3 | GROUP 5 | .30 | .78 | 2.86 |
| GQ3 | LOT C | .30 | .70 | .78 |
| GZ1 | $10^{5.3}$ + FeLV | .30 | .95 | 1.28 |
| GZ5 | Two Doses | .30 | 1.94 | 3.12 |
| HH1 | | .60 | 1.89 | 2.55 |
| GMT | | 0.36 ± 0.13 | 1.25 ± 0.61 | 2.12 ± 1.03 |

*Received two doses of vaccine (VAX$_1$) in error.

Having thus described in detail preferred embodiments of the present invention, it is to be understood that the invention defined by the appended claims is not to be limited by particular details set forth in the above description as many apparent variations thereof are possible without departing from the spirit or scope thereof.

References

1. Abimiku, A., Franchini, G., Tartaglia, J., Aldrich, K., Myagkikh, M., Markham, P D., Chong, P., Klein, M., Kieny, M., Paoletti, E., Gallo, R. C., and Robert-Guroff, M., "Highly attenuated HIV-1 recombinant poxviruses induce cross-protection against HIV-2 challenge in rhesus macaques", Submitted.
2. Altenburger, W., C-P. Suter and J. Altenburger, Archives Virol. 105:15–27 (1989).
3. Arp, J., Ford, C. M., Falker, T. J., King, E. E., Dekaban, G. A., J. Gen. Virol. 74:211–220 (1993).
4. Avery, R. J., and J. Niven., Infect. and Immun. 26:795–801 (1979).
5. Barre-Siunoussi, F., Cherman, J. C., Rey, F., Nugeyre, M. T., Chamaret, S., Greust, J., Dauguet, C., Alexer-Blin, C., Veinet-Brun, F., Rouzioux, C., Rosenbaum, W., and Montagnier, L., Science 220:868–870 (1983).
6. Behbehani, A. M., Microbiological Reviews 47:455–509 (1983).
7. Benson, J., Tschachler, E., Gessain, A., Yanagihara, R., Gallo, R. C., and Franchini, G., AIDS Res. Hum. Retroviruses 10:91–96 (1994).
8. Bergoin, M., and Dales, S., In Comparative Virology, eds. K. Maramorosch and E. Kurstak, (Academic Press, NY) pp. 169–205 (1971).
9. Berman, P., Gregory, T., Riddle, L., Nakamura, G., Champe, M., Porter, J., Wurm, F., Hershberg, R., Cobb, E. and Eichberg, J., Nature 345:622–625 (1990).
10. Bertholet, C., Drillien, R., and Wittek, R., Proc. Natl. Acad. Sci. USA 82:2096–2100 (1985).
11. Boursnell, M. E. G., P. F. Green, J. I. A. Campbell, A. Deuter, R. W. Peters., F. M. Tomley, A. C. R. Samson, P. Chambers, P. T. Emmerson, and M. M. Binns, J. Gen. Virol. 71:621–628 (1990a).
12. Boursnell, M. E. G., P. F. Green, J. I. A. Campbell, A. Deuter, R. W. Peters, F. M. Tomley, A. C. R. Samson, P. T. Emmerson, and M. M. Binns, Veterinary Microbiology 23:305–316 (1990b).
13. Boursnell, M. E. G., P. F. Green, A. C. R. Samson, J. I. A. Campbell, A. Deuter, R. W. Peters, N. S. Millar, P. T. Emmerson, and M. M. Binns, Virology 178:297–300. (1990c).
14. Buller, R. M. L., G. L. Smith, Cremer, K., Notkins, A. L., and Moss, B., Nature 317:813–815 (1985).
15. Buller, R. M. L., Chakrabarti, S., Cooper, J. A., Twardzik, D. R., and Moss, B., J.Virol. 62:866–874 (1988).
16. Cadoz, M., A. Strady, B. Meignier, J. Taylor, J. Tartaglia, E. Paoletti and S. Plotkin, The Lancet, 339:1429 (1992).
17. Cardoso, E. A., Robert-Guroff, M., Franchini, G., Gartner, S., Moura-Nunes, J. F., Gallo, R. C., and Terrinha, A. M., Int. J. Cancer 43:195–200 (1989).
18. Chambers, P., N. S. Millar, and P. T. Emmerson, J. Gen. Virol. 67:2685–2694 (1986).
19. Child, S. J., Palumbo, G. J., Buller, R. M. L., and Hruby, D. E. Virology 174:625–629 (1990).
20. Clark, N., Kushner, N., Barrett, C. B., Kensil, C. R., Salsbury, D., and Cotter, J., Am. Vet. Med. Assoc. 199:1433–1443 (1991).
21. Clewell, D. B. and D. R. Helinski, Proc. Natl. Acad. Sci. USA 62:1159–1166 (1969).
22. Clewell, D. B., J. Bacteriol 110:667–676 (1972).

23. Colinas, R. J., R. C. Condit and E. Paoletti, Virus Research 18:49–70 (1990).
24. Cooney, E. L., Corrier, A. C., Greenberg, P. D., et al., Lancet 337:567–572 (1991).
25. Cox, W. I., Tartaglia, J., and E. Paoletti. Virology 195:845–850 (1993).
26. Daglesh, A., Champagne, E., Chamaret, S., Gruest, J., Guetard, D., Hercent, T., Gluckman, J. C., Montagnier, L., Nature 312:767–770 (1984).
27. De Rossi, A., Aldovini, A., Franchini, G., Mann, D., Gallo, R. C., Wong-Staal, F., Virology 163:640–645 (1985).
28. Dreyfuss, G., Adam, S. A., and Choi, Y. D., Mol. Cell. Biol. 4:415–423 (1984).
29. Drillien, R., Kochren, F., and Kirn, A., Virology 111:488–499 (1981).
30. Earl, P. L., Moss, B., Morrison, R. P., Wehrly, K., Nishlo, J., and Chesebro, B., Science 234:728–731 (1986).
31. Edbauer, C., R. Weinberg, J. Taylor, A. Rey-Senelonge, J. F. Bouquet, P. Desmettre, E. Paoletti, Virology 179:901–904 (1990).
32. Emini, E., Schleif, W., Nunberg, J., Conley, A., Eda, Y., Tokiyoshi, S., Putney, S., Matsushita, S., Cobb, K., Jett, C., Eichberg, J., and K. Murthy, Nature 355:728–730 (1992).
33. Engelke, D. R., Hoener, P. A., Collins, F. S., Proc. Natl. Acad. Sci. USA 85:544–548 (1988).
34. Espion, D., S. de Henau, C. Letellier, C.-D. Wemers, R. Brasseur, J. F. Young, M. Gross, M. Rosenberg, G. Meulemans and A. Burny, Arch. Virol. 95:79–95 (1987).
35. Fenner, F., Virology 5:502–529 (1958).
36. Flexner, C., Hugen, A., and Moss, B., Nature 330:259–262 (1987).
37. Franchini, G., Robert-Guroff, M., Tartaglia, J., Aggarwal, A., Abimiku, A., Benson, J., Markham, P., Limbach, K., Hurteau, G., Fullen, J., Aldrich, K., Miller, N., Sasoff, J., Paoletti, E., and Gallo, R. C., Highly attenuated HIV-2 recominant poxviruses, but not HIV-2 recombinant salmonella vaccines, induce long lasting protection in rhesus macaques. Submitted.
38. Fries et al., 32nd Interscience Conference on Antimicrobial Agents and Chemotherapy, Anaheim, Calif. (October 1992).
39. Fultz, P., Nara, P., Barre-Sinoussi, F., Chaput, A., Greenberg, M., Muchmore, E., Kieny, M.-P. and Girard, M. Science 256:1687–1689 (1992).
40. Funahashi, S., T. Sato and H. Shida, J. Gen. Virol. 69:35–47 (1988).
41. Gallo, R. C., Sci. Am. 256:47–56 (1987).
42. Gallo, R. C., Sci. Am. 255:88–98 (1986).
43. Garten, W., Kohama, T., and H-D. Klenk. J. Gen. Virol. 51:207–211 (1980).
44. Gessain, A., Gallo, R. C., and Franchini, G., J. Virol. 66:2288–2295 (1992).
45. Gessain, A., Boeri, E., Yanagihara, R., Gallo, R. C., and Franchini, G., J. Virol. 67:1015–1023 (1933).
46. Ghendon, Y. Z., and Chernos, V. I., Acta Virol. 8:359–368 (1964).
47. Gillard, S., Spehner, D., Drillien, R., and Kirn, A., Proc. Natl. Acad. Sci. USA 83:5573–5577 (1986).
48. Girard, M., Kieny, M.-P., Pinter, A., Barre-Sinoussi, F., Nara, P., Kolbe, H., Kusui, K., Chaput, A., Reinhart,-T., Muchmore, E., Ronco, J., Kaczorek, M., Gomard, E., Gluckman, J.-C. and Fultz, P., Proc. Natl. Acad. Sci. USA 88:542–546 (1991).
49. Goebel, S. J., Johnson, G. P., Perkus, M. E., Davis, S. W., Winslow, J. P., Paoletti, E., Virology 179:247–266 (1990a).
50. Goebel, S. J., G. P. Johnson, M. E. Perkus, S. W. Davis, J. P. Winslow and E. Paoletti, Virology 179:517–563 (1990b).
51. Golding, H., Robey, F., Gates, F., Linder, W., Beining, P., Hoffman, T. and Golding, B., J. Exp, Med. 167:914–923 (1988).
52. Golding, H., Shearer, G., Hillman, K., Lucas, P., Manischewitz, J., Zajac, R., Clerici, M., Gress, R., Boswell, R. and Golding, B., J. Clin. Invest. 83:1430–1435 (1989).
53. Goldstein, D. J. and S. K. Weller, Virology 166:41–51 (1988).
54. Guo, P., Goebel, S., Davis, S., Perkus, M. E., Languet, B., Desmettre, P., Allen, G., and Paoletti, E., J. Virol. 63:4189–4198 (1989).
55. Guo et al., J. Virol. 64:2399–2406 (1990).
56. Hammond, S., Bollinger, R., Stanhope, P., Quinn, T., Schwartz, D., Clements, M. and Siliciano, R., J. Exp. Med. 176:1531–1542 (1992).
57. Haseltine, W., Terwilliger, E. F., Rosen, C. A., and Sodrowski, J. G., In Retrovirus Biology Human Disease, eds. Gallo R. C. and Wong-Staal F., (Marcel Dekker, N.Y.) pp. 241–270 (1989).
58. Hinuma, Y., Nagata, K., Hanaoka, M., Nakai, M., Matsumoto, T., Kinoshita, K., Shirakawa, S., and Miyoshi, I., Proc. Natl. Acad. Sci. USA 79:6476–6480 (1981).
59. Homma, M., and M. Ohuchi, J. Virol. 12:1457–1465 (1973).
60. Hruby, D. E., R. A. Maki, D. B. Miller and L. A. Ball, Proc. Natl. Acad. Sci. USA 80:3411–3415 (1983).
61. Hruby, D. E. and L. A. Ball, J. Virol. 43:403–409 (1982).
62. Hu, S.-L., Abrams, K., Barber, G., Morn, P., Zarling, J., Langlois, A., Kuller, L., Morton, W. and Benveniste, R., Science 255:456–459 (1992).
63. Ichihashi, Y. and Dales, S., Virology 46:533–543 (1971).
64. Issel, C. J., Horohov, D. W., Lea, D. F., Adams, Jr., W. V., Haglus, S. D., McManus, J. M., Allison, A. C., and Montelaro, R. C., J. Virol. 66:3398–3408 (1992).
65. Itamura, S., H. Iinuma, H. Shida, Y. Morikawa, K. Nerome and A. Oya, J. Gen. Virol. 71:2859–2865 (1990).
66. Jacobson, J. G., D. A. Leib, D. J. Goldstein, C. L. Bogard, P. A. Schaffer, S. K. Weller and D. M. Coen, Virology 173:276–283 (1989).
67. Jamieson, A. T., G. A. Gentry and J. H. Subak-Sharpe, J. Gen. Virol. 24:465–480 (1974).
68. Kalyanaraman V. S., Sarngadharan M. G., Robert-Guroff M., Miyoshi I., Blayney D., Golde D., and Gallo R. C., Science 218:571–573 (1982).
69. Kato, S., M. Takahashi, S. Kameyama and J. Kamahora, Biken's 2:353–363 (1959).
70. Kieny, M. P., Lathe, R., Drillien, R., Spehner, D., Skory, S., Schmitt, D., Wiktor, T., Koprowski, H., and Lecocq, J. P., Nature (London) 312:163–166 (1984).
71. Kiyokawa T., Seki M., Iwashita S., Imagawa K., Shimizu F., and Yoshida M., Proc. Acad. Sci. USA 82:8359–8363 (1985).
72. Klasse, P., Pipkorn, R. and Blomberg, J., Proc. Natl. Acad. Sci. USA 85:5225–5229 (1988).
73. Knauf, V. C., and Nester, E. W., Plasmid 8:45–54 (1982).
74. Komourian, F., Pelloquin, F., and de The, G., J. Virol. 65:3770–3778 (1991).
75. Koralnik, I. J., Fullen, J., and Franchini, G., J. Virol. 67:2360–2366 (1993).
76. Konishi et al., Virology 190:454–458 (1992).
77. Kotwal, G. J. and Moss, B., Nature (London) 335:176–178 (1988a).

78. Kotwal, G. J. and Moss, B., Virology 167:524–537 (1988b).
79. Kotwal, G. J., S. N. Isaacs, R. McKenzie, M. M. Frank and B. Moss, Science 250:827–830 (1990).
80. Kotwal, G. J., A. W. Hugin and B. Moss, Virology 171:579–587 (1989a).
81. Kotwal, G. J. and B. Moss, J. Virol. 63:600–606 (1989b).
82. Lai, C. K. and B. G. Pogo, Virus Res. 12:239–250 (1989).
83. LaRosa, G. L., Davide, J. P., Weinhold, K., Waterbury, J. A., Profy, A. T., Lewis, J. A., Langlois, A. J., Dreesman, G. R., Boswell, R. N., Shadduck, P., Holley, L. H., Karplus, M., Bpologneis, D. P., Matthews, T. J., Emini, E. A., and Putney, S. D., Science 249:932–935 (1990).
84. Le, L., R. Brasseur, C. Wemers, G. Meulemans, and A. Burny, Virus Genes 1:333–350 (1988).
85. Mandecki, W., Proc. Natl. Acad. Sci. USA 83:7177–7182 (1986).
86. Maniatis, T., Fritsch, E. F., and Sambrook, J., In Molecular cloning: a laboratory manual, (Cold Spring Harbor Laboratory, Cold Spring Harbor, N.Y.) (1982).
87. Matthews, R. E. F., Intervirology 17:42–44 (1982).
88. McGinnes, L. W., and T. G. Morrison, Virus Research 5:343–356 (1986).
89. Merz, D. C., A. Scheid, and P. Choppin, J. Exper. Med. 151:275–288 (1980).
90. Miller, M., Warmerdam, M., Gaston, I., Greene, W. and Feinberg, M., J. Exp. Med. 179:101–113 (1994).
91. Miyzawa, M., Nishio, J., and Cheesebro, B., J. Virol. 66:4497–4507 (1992).
92. Miyoshi, I., Kubonishi, I., Yoshimoto, S., Akagi, T., Ohtsuki, Y., Shiraishi, Y., Nagata, K., and Hinuma, Y., Nature 294:770–771 (1981).
93. Miyoshi, I., Yoshimoto, S., Kubonishi, I., Fujshita, M., Ohtsuki, Y., Yamashita, M., Yamato, K., Hiroswe, S., Taguchi, H., Niiya, K., and Kobayashi, M., Int. J. Canc. 35:81–85 (1985).
94. Morgan, A. J., M. Mackett, S. Finerty, J. R. Arrand, F. T. Scullion and M. A. Epstein, J. Med. Virol. 25:189–195 (1988).
95. Moss, B., E. Winters and J. A. Cooper, J. Virol. 40:387–395 (1981).
96. Nagai, Y., H. D. Klenk, and R. Rott, Virology 72:494–508 (1976).
97. Nagai, Y., T. Yoshida, M. Hamaguchi, H. Naruse, M. Iinuma, K. Maeno, and T. Matsumoto, Microbiol. Immunol. 24:173–177 (1980).
98. Nakamura S., Hayami M., Ohta Y., Ishikawa K., Tsujimoto H., Kiyokawa T., Yoshida M., Sasagawa A., and Honjo S., Int. J. Cancer 40:403–408 (1987).
99. Norrby, E., and Y. Gollmar, Infect. and Immun. 11:231–239 (1975).
100. Ogawa, R., N. Yanagida, S. Saeki, S. Saito, S. Ohkawa, H. Gotoh, K. Kodama, K. Kamogawa, K. Sawaguchi and Y. Iritani, Vaccine 8:486–490 (1990).
101. Paez, E., Dallo, S., and Esteban, M., Proc. Natl. Acad. Sci. USA 82:3365–3369 (1985).
102. Paine, E., Garcia, J., Philpott, T. C., Shaw, G., and Ratner, L., Virology 192:111–123 (1991).
103. Palumbo, G. J., Pickup, D. J., Fredrickson, T. N., Mcintyre, L. J., and Buller, R. M. L., Virology 172:262–273 (1989).
104. Panicali, D. and E. Paoletti, Proc. Natl. Acad. Sci. USA 79:4927–4931 (1982).
105. Panicali, D., Davis, S. W., Mercer, S. R., and Paoletti, E., J. Virol. 37:1000–1010 (1981).
106. Patel, D. D. and Pickup, D. J., EMBO 6:3787–3794 (1987).
107. Patel, D. D., Ray, C. A., Drucker, R. P., and Pickup, D. J., Proc. Natl. Acad. Sci. USA 85:9431–9435 (1988).
108. Pedersen, N. C., Johnson, L., Birch, D., and Theilen, G. H., Vet. Immunol. Immunopathol. 11:123–148 (1986).
109. Perkus, M. E., Goebel, S. J., Davis, S. W., Johnson, G. P., Limbach, K., Norton, E. K., and Paoletti, E., Virology 179:276–286 (1990).
110. Perkus, M. E., S. J. Goebel, S. W. Davis, G. P. Johnson, E. K. Norton and E. Paoletti, Virology 180:406–410 (1991).
111. Perkus, M. E., Limbach, K., and Paoletti, E., J. Virol. 63:3829–3836 (1989).
112. Perkus, M. E., A. Piccini, B. R. Lipinskas and E. Paoletti, Science 229:981–984 (1985).
113. Perkus, M. E., D. Panicali, S. Mercer and E. Paoletti, Virology 152:285–297 (1986).
114. Piccini, A., M. E. Perkus, and E. Paoletti, Methods in Enzymology 153:545–563 (1987).
115. Pickup, D. J., B. S. Ink, B. L. Parsons, W. Hu and W. K. Joklik, Proc. Natl. Acad. Sci. USA 81:6817–6821 (1984).
116. Pickup, D. J., B. S. Ink, W. Hu, C. A. Ray and W. K. Joklik, Proc. Natl. Acad. Sci. USA 83:7698–7702 (1986).
117. Poiesz, B. J., Ruscetti, F. W., Gazdar, A. F., Bunn, P. A., Minna, J. D., and Gallo, R. C., Proc. Natl. Acad. Sci. USA 77:7415–7419 (1980).
118. Popovic, M., Sarngadharan, M. G., Read, E., and Gallo, R. C., Science 224:497–500 (1984).
119. Reed, J. and Muench, H., Am. J. Hyg. 27:493–497 (1938).
120. Rickinson, A. B., Rowe, M., Hart, I. J., Yao, Q. Y., Henderson, L. E., Rabin, H., and Epstein, M. A., Cell Immunol. 87:649–658 (1984).
121. Robinson, W., Kawamura, T., Gorny, M., Lake, D., Xu, J.-Y., Matsumoto, Y., Sugano, T., Masuho, Y., Mitchell, W., Hersh, E. and Zolla-Pazner, S., Proc. Natl. Acad. Sci. USA 87:3185–3189 (1990).
122. Rusche, J. R., Javaherian, K., McDanal, C., Petro, J., Lynn, D. L., Grimaila, R., Langlois, A., Gallo, R. C., Arthur, L.O., Fischinger, P. J., Bolognesi, D. P., Putney S. D., Matthews, T. J., Proc. Natl. Acad. Sci. USA 85:3198–3202 (1988).
123. Sanger, F., Nickel, S. Coulson, A. R., Proc. Natl. Acad. Sci. 74:5463–5467 (1977).
124. Schmidtt, J. F. C. and H. G. Stunnenberg, J. Virol. 62:1889–1897 (1988).
125. Schultz, T. F., Calabro, M. L., Hoad, J. G., Carrington, C. V. F., Matutes, E., Catovsky D., Weiss R., Virology 184:483–491 (1991).
126. Seligmann, E. B., In Laboratory Techniques in Rabies, eds. M. M. Kaplan and H. Koprowski, (World Health Organization, Geneva) pp. 279–285 (1973).
127. Shafferman, A., Lennox, J., Grosfeld, H., Sadoff, J., Redfield, R. and Burke, D., AIDS Res. Hum. Retroviruses 5:33–39 (1989).
128. Shapira, S. K., Chou, J., Richaud, F. V. and Casadaban, M. J., Gene 25:71–82 (1983).
129. Sherman, M. P., Saksena, N. K., Dube, D. K., Yanagihara, R., Poiesz, B. J., J. Virol. 66:2556–2563 (1992).
130. Shida, H., Hinuma, Y., Hatanaka, M., Morita, M., Kidokoro, M., Suzuki, K., Maruyzam, T., Takahashi-Nishimaki, F., Sugimoto, M., Kitamura, R., Miyazawa, T., and Hayami, M., J. Virol. 62:4474–4480 (1988).
131. Shida, H., Virology 150:451–462 (1986).
132. Shida, H., T. Tochikura, T. Sato, T. Konno, K. Hirayoshi, M. Seki, Y. Ito, M. Hatanaka, Y. Hinuma, M.

Sugimoto, F. Takahashi-Nishimaki, T. Maruyama, K. Miki, K. Suzuki, M. Morita, H. Sashiyama and M. Hayami, EMBO 6:3379–3384 (1987).

133. Slabaugh, M., N. Roseman, R. Davis and C. Mathews, J. Virol. 62:519–527 (1988).

134. Smith, J. S., P. A. Yager and G. M. Baer, In Laboratory Techniques in Rabies, eds. M. M. Kaplan and H. Koprowski (WHO Geneva) pp. 354–357 (1973).

135. Spina, C., Kwoh, T., Chowers, M., Guatelli, J. and Richman, D., J. Exp. Med. 179:115–123 (1994).

136. Stanberry, L. R., Kit, S., Myers, M. G., J. Virol. 55:322–328 (1985).

137. Tabor, S. and C. C. Richardson, Proc. Natl. Acad. Sci. USA 84:4767–4771 (1987).

138. Tartaglia, J., Jarrett, O., Neil, J. C., Desmettre, P., Paoletti, E., J. Virol. 67:2370–2375 (1993).

139. Tartaglia, J. and Paoletti, E., In Immunochemistry of Viruses, II, eds. M. H. V. van Regenmortel & A. R. Neurath, (Elsevier Science Publishers, Amsterdam) pp. 125–151 (1990b).

140. Tartaglia, J., R. Gettig & E. Paoletti, Virology (In press).

141. Tartaglia, J., Perkus, M. E., Taylor, J., Norton, E. K., Audonnet, J.-C., Cox, W. I., Davis, S. W., Van Der Hoeven, J., Meignier, B., Riviere, M., Languet, B., Paoletti, E., Virology 188:217–232 (1992).

142. Tartaglia., J., Perkus, M. E., Taylor, J., Norton, E. K., Audonnet, J-C., Cox, W. I., Davis, S. W., Van der Hoeven, J., Meignier, B., Riviere, M., Languet, B., Paoletti, E., Virology 188:217–232 (1992).

143. Tartaglia, J., J. Taylor, W. I. Cox, J.-C. Audonnet, M. E. Perkus, A. Radaelli, C. de Giuli Morghen, B. Meignier, M. Riviere, K. Weinhold & E. Paoletti, In AIDS Research Reviews, eds. W. Koff, F. Wong-Staal & R. C. Kenedy, Vol. 3, (Marcel Dekker, N.Y.) pp. 361–378 (1993a).

144. Tartaglia, J., Jarrett, O., Desmettre, P., Paoletti, E. (1993b) J. Virol. 67:2370–2375 (1993b).

145. Tartaglia, J., Pincus, S., Paoletti, E., Critical Reviews in Immunology 10:13–30 (1990a).

146. Taylor, G., E. J. Stott, G. Wertz and A. Ball, J. Gen. Virol. 72:125–130 (1991a).

147. Taylor, J., C. Trimarchi, R. Weinberg, B. Languet, F. Guillemin, P. Desmettre and E. Paoletti, Vaccine 9:190–193 (1991b).

148. Taylor, J., Weinberg, R., Kawaoka, Y., Webster, R. G., and Paoletti, E., Vaccine 6:504–508 (1988a).

149. Taylor, J., R. Weinberg, B. Lanquet, P. Desmettre, and E. Paoletti, Vaccine 6:497–503 (1988b).

150. Taylor, J., R. Weinberg, J. Tartaglia, C. Richardson, G. Alkhatib, D. Briedis, M. Appel, E. Norton & E. Paoletti, Virology 187:321–328 (1992).

151. Taylor, J., Edbauer, C., Rey-Senelonge, A., Bouquet, J.-F., Norton, E., Goebel, S., Desmettre, P., Paoletti, E., J. Virol. 64:1441–1450 (1990).

152. Toyoda, T., T. Sakaguchi, K. Imai, N. M. Inocencio, B. Gotoh, M. Hamaguchi, and Y. Nagai, Virology 158:242–247 (1987).

153. Weir, J. P. and B. Moss, J. Virol. 46:530–537 (1983).

154. Yuen, L., and Moss, B., Proc. Natl. Acad. Sci. USA 84:6417–6421 (1987).

155. Zhou, J., L. Crawford, L. McLean, X. Sun, M. Stanley, N. Almond and G. L. Smith, J. Gen. Virol. 71:2185–2190 (1990).

---

What is claimed is:

1. A composition for inducing an immunological response comprising:
   (i) a recombinant ALVAC canarypox virus comprising exogenous DNA encoding at least one rabies virus antigen or a recombinant poxvirus having all of the identifying characteristics of ALVAC comprising exogenous DNA encoding at least one rabies virus antigen, wherein the at least one rabies virus antigen is expressed in vivo as a first antigen; and
   (ii) at least one second antigen; and optionally
   (iii) a suitable carrier.

2. The composition of claim 1 wherein the composition comprises the recombinant ALVAC canarypox virus comprising exogenous DNA encoding at least one rabies virus antigen and the at least one second antigen and optionally a suitable carrier.

3. The composition of claim 1 wherein the composition comprises the recombinant poxvirus having all of the identifying characteristics of ALVAC comprising exogenous DNA encoding at least one rabies antigen and the at least one second antigen and optionally a suitable carrier.

4. The composition of claim 2 wherein the ALVAC canarypox virus comprising exogenous DNA encoding at least one rabies antigen is vCP65.

5. The composition of any one of claims 1, 2, 3, or 4 wherein the second antigen is an antigen of a canine pathogen or a feline pathogen, where the antigen of a canine pathogen is selected from the group consisting of canine distemper virus (CDV) HA glycoprotein, CDV F glycoprotein, CDV HA and F glycoproteins, canine adenovirus type 2 antigen, canine coronavirus antigen, canine parainfluenza antigen, canine parvovirus antigen, Leptospira Canicola-Icterrohaemorrhagiae Bacterin antigen, and any combination of these antigens; and the antigen of a feline pathogen is selected from the group consisting of feline leukemia virus antigen, feline herpesvirus antigen, and a combination thereof.

6. The composition of claim 5 wherein the second antigen is provided from a lyophilized composition.

7. The composition of claim 5 wherein the second antigen is provided from another recombinant virus in the composition.

8. The composition of claim 5 wherein the second antigen is provided from DNA coding for the second antigen within the recombinant ALVAC canarypox virus or the recombinant poxvirus having all of the identifying characteristics of ALVAC, in addition to the DNA encoding at least one rabies antigen, which is also expressed in vivo.

9. The composition of claim 5 wherein the second antigen is provided from at least one poxvirus comprising DNA coding for the second antigen which expresses the DNA in vivo.

10. The composition of claim 5 wherein the second antigen is provided from in vitro expression of DNA coding for the second antigen by a vector comprising the DNA coding for the second.

11. A composition for inducing an immunological response comprising:

(i) as a first antigen at least one rabies virus antigen from in vitro expression thereof by a recombinant ALVAC canarypox virus comprising exogenous DNA encoding the at least one rabies virus antigen or a recombinant poxvirus having all of the identifying characteristics of ALVAC comprising exogenous DNA encoding the at least one rabies virus antigen; and (ii) at least one second antigen; and optionally (iii) a suitable carrier.

12. The composition of claim 11 wherein the composition comprises as a first antigen at least one rabies virus antigen from in vitro expression thereof by a recombinant ALVAC canarypox virus comprising exogenous DNA encoding the at least one rabies virus antigen and the at least one second antigen and optionally a suitable carrier.

13. The composition of claim 12 wherein the ALVAC canarypox virus comprising exogenous DNA encoding at least one rabies antigen is vCP65.

14. The composition of any one of claims 11, 12, or 13 wherein the second antigen is an antigen of a canine pathogen or a feline pathogen, where the antigen of a canine pathogen is selected from the group consisting of canine distemper virus (CDV) HA glycoprotein, CDV F glycoprotein, CDV HA and F glycoproteins, canine adenovirus type 2 antigen, canine coronavirus antigen, canine parainfluenza antigen, canine parvovirus antigen, Leptospira Canicola-Icterrohaemorrhagiae Bacterin antigen, and any combination of these antigens; and the antigen of a feline pathogen is selected from the group consisting of feline leukemia virus antigen, feline herpesvirus antigen, and a combination thereof.

15. The composition of claim 14 wherein the second antigen is provided from DNA coding for the second antigen within the recombinant ALVAC canarypox virus or the recombinant poxvirus having all of the identifying characteristics of ALVAC, in addition to the DNA encoding at least one rabies antigen, which is also expressed in vitro.

16. The composition of claim 14 wherein the second antigen is provided from at least one poxvirus comprising DNA coding for the second antigen which expresses the DNA in vivo.

17. The composition of claim 14 wherein the second antigen is provided from in vitro expression of DNA coding for the second antigen by a vector comprising the DNA coding for the second antigen.

18. A composition comprising (i) any one of Canine Distemper Virus antigen, Canine Adenovirus Type 2 antigen, Canine Coronavirus antigen, Canine Parainfluenza antigen, and Canine Parvovirus antigen; and (ii) vCP65.

19. The composition of claim 18 comprising (i) Canine Distemper Virus antigen, (ii) Canine Adenovirus Type 2 antigen, (iii) Canine Coronavirus antigen, (iv) Canine Parainfluenza antigen, (v) Canine Parvovirus antigen, and (vi) vCP65.

20. A composition comprising (i) any one of Canine Distemper Virus antigen, Canine Adenovirus Type 2 antigen, Canine Coronavirus antigen, Canine Parainfluenza antigen, and Canine Parvovirus antigen; and (ii) a rabies antigen from in vitro expression thereof by vCP65.

21. The composition of claim 20 comprising (i) Canine Distemper Virus antigen, (ii) Canine Adenovirus Type 2 antigen, (iii) Canine Coronavirus antigen, (iv) Canine Parainfluenza antigen, (v) Canine Parvovirus antigen, and (vi) a rabies antigen from in vitro expression thereof by vCP65.

22. A method for inducing an immunological response in an individual or animal comprising administering to said individual or animal a composition comprising a composition as claimed in any one of claims 1, 2, 3, or 4.

23. A method for inducing an immunological response in an individual or animal comprising administering to said individual or animal a composition as claimed in claim 5.

24. A method for inducing an immunological response in an individual or animal comprising administering to said individual or animal a composition as claimed in claim 6.

25. A method for inducing an immunological response in an individual or animal comprising administering to said individual or animal a composition as claimed in claim 7.

26. A method for inducing an immunological response in an individual or animal comprising administering to said individual or animal a composition as claimed in claim 8.

27. A method for inducing an immunological response in an individual or animal comprising administering to said individual or animal a composition as claimed in claim 9.

28. A method for inducing an immunological response in an individual or animal comprising administering to said individual or animal a composition as claimed in claim 10.

29. A method for inducing an immunological response in an individual or animal comprising administering to said individual or animal a composition comprising a composition as claimed in any one of claims 11, 12, or 13.

30. A method for inducing an immunological response in an individual or animal comprising administering to said individual or animal a composition as claimed in claim 14.

31. A method for inducing an immunological response in an individual or animal comprising administering to said individual or animal a composition as claimed in claim 15.

32. A method for inducing an immunological response in an individual or animal comprising administering to said individual or animal a composition as claimed in claim 16.

33. A method for inducing an immunological response in an individual or animal comprising administering to said individual or animal a composition as claimed in claim 17.

34. A method for of inducing an immunological response in an individual or animal comprising administering to said individual or animal a composition as claimed in any one of claims 26 or 18.

35. A method for of inducing an immunological response in an individual or animal comprising administering to said individual or animal a composition as claimed in any one of claims 20 or 21.

* * * * *